US009453235B2

(12) United States Patent
Kumar et al.

(10) Patent No.: US 9,453,235 B2
(45) Date of Patent: Sep. 27, 2016

(54) METHOD AND CONSTRUCT FOR SYNTHETIC BIDIRECTIONAL SCBV PLANT PROMOTER

(71) Applicant: Dow AgroSciences LLC, Indianapolis, IN (US)

(72) Inventors: Sandeep Kumar, Carmel, IN (US); Diaa Alabed, Carmel, IN (US); Sara Bennett, Indianapolis, IN (US); Manju Gupta, Carmel, IN (US); Susan Jayne, Zionsville, IN (US); Terry R. Wright, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 304 days.

(21) Appl. No.: 13/674,712

(22) Filed: Nov. 12, 2012

(65) Prior Publication Data

US 2013/0198898 A1 Aug. 1, 2013

Related U.S. Application Data

(60) Provisional application No. 61/582,148, filed on Dec. 30, 2011, provisional application No. 61/641,956, filed on May 3, 2012.

(51) Int. Cl.
*C12N 15/82* (2006.01)

(52) U.S. Cl.
CPC ....... *C12N 15/8216* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 6,093,569 | A * | 7/2000 | Olszewski | C07K 14/005 435/320.1 |
| 6,388,170 | B1 | 5/2002 | Gan et al. | |
| 7,235,652 | B2 | 6/2007 | Tuli et al. | |
| 2005/0188432 | A1 | 8/2005 | Li et al. | |
| 2006/0150282 | A1 | 7/2006 | Linemann et al. | |
| 2007/0033677 | A1 | 2/2007 | Lin | |
| 2009/0038025 | A1* | 2/2009 | Lai et al. | 800/268 |
| 2011/0041208 | A1 | 2/2011 | Pennell et al. | |
| 2011/0191899 | A1 | 8/2011 | Ainley et al. | |
| 2011/0252504 | A1 | 10/2011 | Fu et al. | |
| 2011/0283377 | A1* | 11/2011 | Mirkov et al. | 800/260 |

FOREIGN PATENT DOCUMENTS

| | | | |
|---|---|---|---|
| CN | 1230592 | | 10/1999 |
| EP | 1862552 | A2 | 12/2007 |
| EP | 2385129 | | 11/2011 |
| WO | 0242450 | A1 | 5/2002 |
| WO | 2007039424 | | 4/2007 |
| WO | 2010069950 | A1 | 6/2010 |
| WO | 2011022469 | | 2/2011 |

OTHER PUBLICATIONS

Xie_Nat_Biotech_19_677_2001.*
Christensen_S94464_1992.*
Kim_Plant Mol Biol_24_105_1994.*
Dolferus_Plant Phys_105_1075_1994.*
Donald_EMBO J_9_1717_1990.*
Christensen_Transgen Res_5_213_1996.*
Braithwaite_Plant Cell Rep_23_319_2004.*
Christensen et al., Plant Mol Biol 18:675-89 (1992).*
Christensen et al., Transgenic Res 5:213-18 (1996).*
Braithwaite et al., Plant Cell Rep 23:319-26 (2004).*
Xie et al., Nat Biotech 19:677-79 (2001).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Samac et al., Transgen Res 13:349-61 (2004).*
International Search Report and Written Opinion for PCT Application No. PCT/US2012/064699, mailed Jun. 2, 2013.
Barfield, D G., et al., "Gene-Transfer in Plants of Brassrca-Juncea Usrng Agrobacterium Tumefacriens-Mediated Transformation" Plant Cell Rep., 1991, pp. 308-314, vol. 10.
Bhullar, S. S., et al., "Strategies for development of functionally equivalent promoters with minimum sequence homology for transgene expression in plants: cis-elements in a novel DNA context versus domarn swappin" 2003, Plant Physiol. pp. 132988-132998.
Christensen, AH, et al., "Maize Polyubiquitin Genes: Structure, Thermal Perturbation of Expression and Transcript Splicing, and Promoter Activity Following Transfer to Protoplasts by Electroporation," 1992, Plant Mol Biology, pp. 675-689, vol. 18.
Langridge, W.H.R. et al., "Dual Promoter of Agrobacterium-Tumefaciens Mannopine Synthase Genes Is Regulated by Plant-Growth Honmones," 1989, P Nat/ Acad Sci USA pp. 3219-3223, vol. 86.
Mourrain, P., et al., "A single transgene locus triggers both transcriptional and post•transcriptional silencing through double-stranded RNA production," 2007, Planta. pp. 365-379, vol. 225.
Velten, J, L., et al. "Isolation of a Dual Plant Promoter Fragment from the Ti Plasmid of Agrobacterium• Tumefaciens," 1984,. Embo J, p. 2723-2730, vol. 3.
Xie, M.T.,et al., "Bidirectionalization of polar promoters in plants," 2001, Nat Biotechnol. pp. 19677-19679.
Al-Saady et al.; "Deletion Analysis of the Sugarcane bacilliform virus Promoter Activity in Monocot and Dicot Plants", Biotechnology, Asian Network for Scientific Information, PK, vol. 9, No. 3, Jan. 1, 2010, pp. 283-293.

* cited by examiner

*Primary Examiner* — Medina A Ibrahim
*Assistant Examiner* — Russell Boggs
(74) *Attorney, Agent, or Firm* — Yung H. Lee; Magleby Cataxinos & Greenwood

(57) ABSTRACT

Provided are constructs and methods for expressing multiple genes in plant cells and/or plant tissues. The constructs provided comprise at least one bi-directional promoter linked to multiple gene expression cassettes, wherein the bi-directional promoter comprises a functional promoter nucleotide sequence from Sugar Cane Bacilliform Virus promoter. In some embodiments, the constructs and methods provided employs a bi-directional promoter based on a minimal core promoter element from a *Zea mays* Ubiquitin-1 gene, or a functional equivalent thereof, and nucleotide sequence elements from a Sugar Cane Bacilliform Virus promoter. In some embodiments, the constructs and methods provided allow expression of genes between three and twenty.

2 Claims, 91 Drawing Sheets maize Ubi1 promoter synthetic bidirectional Ubi1 promoter 108708-bidirectional SCBV (promoter only)

GUS and yfp Expression Cassettes

SEQ ID NO: 1 shows a 215 bp region of a *Zea mays* Ubiquitin 1 minimal core promoter (minUbi1P):

CTGGACCCCTCTCGAGAGTTCCGCTCCACCGTTGGACTTGCTCCGCTGTCGGCATCCAG
AAATTGCGTGGCGGAGCGGCAGACGTGAGCCGGCACGGCAGGCGGCCTCCTCCTCCT
CTCACGGCACCGGCAGCTACGGGGGATTCCTTTCCCACCGCTCCTTCGCTTTCCCTTCC
TCGCCCGCCGTAATAAATAGACACCCCCTCCACACCCTCT

*FIG. 10A*

SEQ ID NO: 2 shows the reverse complement of a polynucleotide comprising a *Z. mays* minUbi1P minimal core promoter (underlined); a *Z. mays* Ubi1 leader (ZmUbi1 exon; bold font); and a *Z. mays* Ubi1 intron (lower case):

ctgcagaagtaacaccaaacaacagggtgagcatcgacaaaagaaacagtaccaagcaaataaatagcgtatgaaggcagggctaaaaaaat
ccacatatagctgctgcatatgccatcatccaagtatatcaagatcgaaataattataaaacatacttgtttattataatagataggtactcaaggttag
agcatatgaatagatgctgcatatgccatcatgtatatgcatcagtaaaacccacatcaacatgtatacctatcctagatcgatatttccatccatctta
aactcgtaactatgaagatgtatgacacacacatacagttccaaaattaataaatacaccaggtagtttgaaacagtattctactccgatctagaacg
aatgaacgaccgcccaaccacaccacatcatcacaaccaagcgaacaaaaagcatctctgtatatgcatcagtaaaacccgcatcaacatgtata
cctatcctagatcgatatttccatccatcatcttcaattcgtaactatgaatatgtatggcacacacatacagatccaaaattaataaatccaccaggta
gtttgaaacagaattctactccgatctagaacgaccgcccaaccagaccacatcatcacaaccaagacaaaaaaaagcatgaaaagatgaccc
gacaaacaagtgcacggcatatattgaaataaaggaaaagggcaaaccaaaccctatgcaacgaaacaaaaaaaatcatgaaatcgatcccgt
ctgcggaacggctagagccatcccaggattccccaaagagaaacactggcaagttagcaatcagaacgtgtctgacgtacaggtcgcatccgt
gtacgaacgctagcagcacggatctaacacaaacacggatctaacacaaacatgaacagaagtagaactaccgggccctaaccatgcatgga
ccggaacgccgatctagagaaggtagagaggggggggggggggaggacgagcggcgtac**CTTGAAGCGGAGGTGCC
GACGGGTGGATTTGGGGGAGATCTGGTTGTGTGTGTGTGCGCTCCGAACAACAC
GAGGTTGGGGA**GGTACCAAGAGGGTGTGGAGGGGGTGTCTATTTATTACGGCGGGC
GAGGAAGGGAAAGCGAAGGAGCGGTGGGAAAGGAATCCCCCGTAGCTGCCGGTGCC
GTGAGAGGAGGAGGAGGCCGCCTGCCGTGCCGGCTCACGTCTGCCGCTCCGCCACGC
AATTTCTGGATGCCGACAGCGGAGCAAGTCCAACGGTGGAGCGGAACTCTCGAGAGG
GGTCCAG

*FIG. 10B*

SEQ ID NO: 3 shows an exemplary synthetic Ubi1 bidirectional promoter, wherein the reverse complement of a first minUbi1P, and a second minUbi1P, are underlined:

CTGCAGAAGTAACACCAAACAACAGGGTGAGCATCGACAAAAGAAACAGTACCAAG
CAAATAAATAGCGTATGAAGGCAGGGCTAAAAAAATCCACATATAGCTGCTGCATAT
GCCATCATCCAAGTATATCAAGATCGAAATAATTATAAAACATACTTGTTTATTATAA
TAGATAGGTACTCAAGGTTAGAGCATATGAATAGATGCTGCATATGCCATCATGTATA
TGCATCAGTAAAACCCACATCAACATGTATACCTATCCTAGATCGATATTTCCATCCAT
CTTAAACTCGTAACTATGAAGATGTATGACACACACATACAGTTCCAAAATTAATAAA
TACACCAGGTAGTTTGAAACAGTATTCTACTCCGATCTAGAACGAATGAACGACCGCC
CAACCACACCACATCATCACAACCAAGCGAACAAAAAGCATCTCTGTATATGCATCAG
TAAAACCCGCATCAACATGTATACCTATCCTAGATCGATATTTCCATCCATCATCTTCA
ATTCGTAACTATGAATATGTATGGCACACACATACAGATCCAAAATTAATAAATCCAC
CAGGTAGTTTGAAACAGAATTCTACTCCGATCTAGAACGACCGCCCAACCAGACCACA
TCATCACAACCAAGACAAAAAAAAGCATGAAAAGATGACCCGACAAACAAGTGCAC
GGCATATATTGAAATAAAGGAAAAGGGCAAACCAAACCCTATGCAACGAAACAAAAA
AAATCATGAAATCGATCCCGTCTGCGGAACGGCTAGAGCCATCCCAGGATTCCCCAAA
GAGAAACACTGGCAAGTTAGCAATCAGAACGTGTCTGACGTACAGGTCGCATCCGTGT
ACGAACGCTAGCAGCACGGATCTAACACAAACACGGATCTAACACAAACATGAACAG
AAGTAGAACTACCGGGCCCTAACCATGCATGGACCGGAACGCCGATCTAGAGAAGGT
AGAGAGGGGGGGGGGGGGGAGGACGAGCGGCGTACCTTGAAGCGGAGGTGCCGACG
GGTGGATTTGGGGGAGATCTGGTTGTGTGTGTGTGCGCTCCGAACAACACGAGGTTGG
GGAGGTACCAAGAGGGTGTGGAGGGGGTGTCTATTTATTACGGCGGGCGAGGAAGGG
AAAGCGAAGGAGCGGTGGGAAAGGAATCCCCCGTAGCTGCCGGTGCCGTGAGAGGA
GGAGGAGGCCGCCTGCCGTGCCGGCTCACGTCTGCCGCTCCGCCACGCAATTTCTGGA
TGCCGACAGCGGAGCAAGTCCAACGGTGGAGCGGAACTCTCGAGAGGGGTCCAGCCG
CGGAGTGTGCAGCGTGACCCGGTCGTGCCCCTCTCTAGAGATAATGAGCATTGCATGT
CTAAGTTATAAAAAATTACCACATATTTTTTTTGTCACACTTGTTTGAAGTGCAGTTTA
TCTATCTTTATACATATATTTAAACTTTACTCTACGAATAATATAATCTATAGTACTAC
AATAATATCAGTGTTTTAGAGAATCATATAAATGAACAGTTAGACATGGTCTAAAGGA
CAATTGAGTATTTTGACAACAGGACTCTACAGTTTTATCTTTTTAGTGTGCATGTGTTC
TCCTTTTTTTTTGCAAATAGCTTCACCTATATAATACTTCATCCATTTTATTAGTACATC
CATTTAGGGTTTAGGGTTAATGGTTTTTATAGACTAATTTTTTTAGTACATCTATTTTAT
TCTATTTTAGCCTCTAAATTAAGAAAACTAAAACTCTATTTTAGTTTTTTTATTTAATAG
TTTAGATATAAAATAGAATAAAATAAAGTGACTAAAAATTAAACAAATACCCTTTAAG
AAATTAAAAAAACTAAGGAAACATTTTTCTTGTTTCGAGTAGATAATGCCAGCCTGTT
AAACGCCGTCGACGAGTCTAACGGACACCAACCAGCGAACCAGCAGCGTCGCGTCGG
GCCAAGCGAAGCAGACGGCACGGCATCTCTGTCGCTGCCTCTGGACCCCTCTCGAGAG
TTCCGCTCCACCGTTGGACTTGCTCCGCTGTCGGCATCCAGAAATTGCGTGGCGGAGC
GGCAGACGTGAGCCGGCACGGCAGGCGGCCTCCTCCTCCTCTCACGGCACCGGCAGCT
ACGGGGGATTCCTTTCCCACCGCTCCTTCGCTTTCCCTTCCTCGCCCGCCGTAATAAAT
AGACACCCCCTCCACACCCTCTTTCCCCAACCTCGTGTTGTTC

FIG. 11A

GGAGCGCACACACACACAACCAGATCTCCCCCAAATCCACCCGTCGGCACCTCCGCTT
CAAGGTACGCCGCTCGTCCTCCCCCCCCCCCCCCTCTCTACCTTCTCTAGATCGGCGT
TCCGGTCCATGCATGGTTAGGGCCCGGTAGTTCTACTTCTGTTCATGTTTGTGTTAGAT
CCGTGTTTGTGTTAGATCCGTGCTGCTAGCGTTCGTACACGGATGCGACCTGTACGTCA
GACACGTTCTGATTGCTAACTTGCCAGTGTTTCTCTTTGGGGAATCCTGGGATGGCTCT
AGCCGTTCCGCAGACGGGATCGATTTCATGATTTTTTTTGTTTCGTTGCATAGGGTTTG
GTTTGCCCTTTTCCTTTATTTCAATATATGCCGTGCACTTGTTTGTCGGGTCATCTTTTC
ATGCTTTTTTTTGTCTTGGTTGTGATGATGTGGTCTGGTTGGGCGGTCGTTCTAGATCG
GAGTAGAATTCTGTTTCAAACTACCTGGTGGATTTATTAATTTTGGATCTGTATGTGTG
TGCCATACATATTCATAGTTACGAATTGAAGATGATGGATGGAAATATCGATCTAGGA
TAGGTATACATGTTGATGCGGGTTTTACTGATGCATATACAGAGATGCTTTTTGTTCGC
TTGGTTGTGATGATGTGGTGTGGTTGGGCGGTCGTTCATTCGTTCTAGATCGGAGTAGA
ATACTGTTTCAAACTACCTGGTGTATTTATTAATTTTGGAACTGTATGTGTGTGTCATA
CATCTTCATAGTTACGAGTTTAAGATGGATGGAAATATCGATCTAGGATAGGTATACA
TGTTGATGTGGGTTTTACTGATGCATATACATGATGGCATATGCAGCATCTATTCATAT
GCTCTAACCTTGAGTACCTATCTATTATAATAAACAAGTATGTTTTATAATTATTTCGA
TCTTGATATACTTGGATGATGGCATATGCAGCAGCTATATGTGGATTTTTTTAGCCCTG
CCTTCATACGCTATTTATTTGCTTGGTACTGTTTCTTTTGTCGATGCTCACCCTGTTGTT
TGGTGTTACTTCTGCAG

FIG. 11B

SEQ ID NO: 4 shows an exemplary nucleic acid comprising *YFP* and *GUS* gene expression cassettes driven by a synthetic Ubi1 bidirectional promoter.

AGCACTTAAAGATCTTTAGAAGAAAGCAAAGCATTTATTAATACATAACAATGTCCAG
GTAGCCCAGCTGAATTACAATACGCAACTGCTCATAATAATTCAACAAACCCAAGTAG
TACACAACATCCAGAAGCAAATAAAGCCCATACGTACCAAAGCCTACACAAGCAGCA
ACACTCACTGCCAGTGCCGGTGGGTCTTTAAAGCACACGGGCCTTGACCACGCGATCC
ACCTTGAAACAAACTTGGTAAAATTAAAGCAAACCAGAAGCACACACACGCCAACGC
AACGCTTCTGATCGCGCGCCCAAGGCCCGGCCGGCCAGAACGTACGACGGACACGCA
CACGCTGCGACCGAGCTCTAGGTGATTAAGCTAACTACTCAAAGGTAGGTCTTGCGAC
AGTCAACAGCTCTGACAGTTTCTTTCAAGGACATGTTGTCTCTGTGGTCTGTCACATCT
TTGGAAAGTTTCACATGGTAAGACATGTGATGATACTCTGGAACATGAACTGGACCTC
CACCAATGGGAGTGTTCATCTGGGTGTGGTCAGCCACTATGAAGTCGCCTTTGCTGCC
AGTAATCTCATGACAGATCTTGAAGGCTGACTTGAGACCGTGGTTGGCTTGGTCACCC
CAGATGTAGAGGCAGTGGGGAGTGAAGTTGAACTCCAAGTTCTTTCCCAACACATGAC
CATCTTTCTTGAAGCCTTGACCATTGAGTTTGACCCTATTGTAGACAGACCCATTCTCA
AAGGTGACTTCAGCCCTAGTCTTGAAGTTGCCATCTCCTTCAAAGGTGATTGTGCGCTC
TTGCACATAGCCATCTGGCATACAGGACTTGTAGAAGTCCTTCAACTCTGGACCATAC
TTGGCAAAGCACTGTGCTCCATAGGTGAGAGTGGTGACAAGTGTGCTCCAAGGCACA
GGAACATCACCAGTTGTGCAGATGAACTGTGCATCAACCTTTCCCACTGAGGCATCTC
CGTAGCCTTTCCCACGTATGCTAAAGGTGTGGCCATCAACATTCCCTTCCATCTCCACA
ACGTAAGGAATCTTCCCATGAAAGAGAAGTGCTCCAGATGCCATGGTGTCGTGTGGAT
CCGGTACACACGTGCCTAGGACCGGTTCAACTAACTACTGCAGAAGTAACACCAAAC
AACAGGGTGAGCATCGACAAAAGAAACAGTACCAAGCAAATAAATAGCGTATGAAG
GCAGGGCTAAAAAAATCCACATATAGCTGCTGCATATGCCATCATCCAAGTATATCAA
GATCGAAATAATTATAAAACATACTTGTTTATTATAATAGATAGGTACTCAAGGTTAG
AGCATATGAATAGATGCTGCATATGCCATCATGTATATGCATCAGTAAAACCCACATC
AACATGTATACCTATCCTAGATCGATATTTCCATCCATCTTAAACTCGTAACTATGAAG
ATGTATGACACACACATACAGTTCCAAAATTAATAAATACACCAGGTAGTTTGAAACA
GTATTCTACTCCGATCTAGAACGAATGAACGACCGCCCAACCACACCACATCATCACA
ACCAAGCGAACAAAAAGCATCTCTGTATATGCATCAGTAAAACCCGCATCAACATGTA
TACCTATCCTAGATCGATATTTCCATCCATCATCTTCAATTCGTAACTATGAATATGTA
TGGCACACACATACAGATCCAAAATTAATAAATCCACCAGGTAGTTTGAAACAGAATT
CTACTCCGATCTAGAACGACCGCCCAACCAGACCACATCATCACAACCAAGACAAAA
AAAAGCATGAAAAGATGACCCGACAAACAAGTGCACGGCATATATTGAAATAAAGGA
AAAGGGCAAACCAAACCCTATGCAACGAAACAAAAAAAATCATGAAATCGATCCCGT
CTGCGGAACGGCTAGAGCCATCCCAGGATTCCCCAAAGAGAAACACTGGCAAGTTAG
CAATCAGAACGTGTCTGACGTACAGGTCGCATCCGTGTACGAACGCTAGCAGCACGG
ATCTAACACAAACACGGATCTAACACAAACATGAACAGAAGTAGAACTACCGGGCCC
TAACCATGCATGGACCGGAACGCCGATCTAGAGAAGGTAGAGAGGGGGGGGGGGGG
GAGGACGAGCGGCGTACCTTGAAGCGGAGGTGCCGACGGGTGGATTTGGGGGAGATC
TGGTTGTGTGTGTGTGCGCTCCGAACAACACGAGGTTGGGGAGGTACCAAGAGGGTGT
GGAGGGGGTGTCTATTTATTACGGCGGGCGAGGAAGGGAAAGCGAAGGAGCGGTGGG
AAAGGAATCCCCCGTAGCTGCCGGTGCCGTGAGAGGAGGAGGAGGCCGCCTGCCGTG
CCGGCTCACGTCTGCCGCTCCGCCACGCAATTTCTGGATGCCGACAGCGGAGCAAGTC
CAACGGTGGAGCGGAACTCTCGAGAGGGGTCCAGCCGCGGAGTGTGCAGCGTGACCC
GGTCGTGCCCCTCTCTAGAGATAATGAGCATTGCATGTCTAAGTTATAAAAAATTACC
ACATATTTTTTTTGTCACACTTGTTTGAAGTGCAG

*FIG. 12A*

TTTATCTATCTTTATACATATATTTAAACTTTACTCTACGAATAATATAATCTATAGTAC
TACAATAATATCAGTGTTTTAGAGAATCATATAAATGAACAGTTAGACATGGTCTAAA
GGACAATTGAGTATTTGACAACAGGACTCTACAGTTTTATCTTTTTAGTGTGCATGTG
TTCTCCTTTTTTTTTGCAAATAGCTTCACCTATATAATACTTCATCCATTTTATTAGTAC
ATCCATTTAGGGTTTAGGGTTAATGGTTTTTATAGACTAATTTTTTTAGTACATCTATTT
TATTCTATTTTAGCCTCTAAATTAAGAAAACTAAAACTCTATTTTAGTTTTTTTATTTAA
TAGTTTAGATATAAAATAGAATAAAATAAAGTGACTAAAAATTAAACAAATACCCTTT
AAGAAATTAAAAAAACTAAGGAAACATTTTTCTTGTTTCGAGTAGATAATGCCAGCCT
GTTAAACGCCGTCGACGAGTCTAACGGACACCAACCAGCGAACCAGCAGCGTCGCGT
CGGGCCAAGCGAAGCAGACGGCACGGCATCTCTGTCGCTGCCTCTGGACCCCTCTCGA
GAGTTCCGCTCCACCGTTGGACTTGCTCCGCTGTCGGCATCCAGAAATTGCGTGGCGG
AGCGGCAGACGTGAGCCGGCACGGCAGGCGGCCTCCTCCTCCTCTCACGGCACCGGC
AGCTACGGGGGATTCCTTTCCCACCGCTCCTTCGCTTTCCCTTCCTCGCCCGCCGTAAT
AAATAGACACCCCCTCCACACCCTCTTTCCCCAACCTCGTGTTGTTCGGAGCGCACAC
ACACACAACCAGATCTCCCCCAAATCCACCCGTCGGCACCTCCGCTTCAAGGTACGCC
GCTCGTCCTCCCCCCCCCCCCCCCTCTCTACCTTCTCTAGATCGGCGTTCCGGTCCATG
CATGGTTAGGGCCCGGTAGTTCTACTTCTGTTCATGTTTGTGTTAGATCCGTGTTTGTG
TTAGATCCGTGCTGCTAGCGTTCGTACACGGATGCGACCTGTACGTCAGACACGTTCT
GATTGCTAACTTGCCAGTGTTTCTCTTTGGGGAATCCTGGGATGGCTCTAGCCGTTCCG
CAGACGGGATCGATTTCATGATTTTTTTTGTTTCGTTGCATAGGGTTTGGTTTGCCCTTT
TCCTTTATTTCAATATATGCCGTGCACTTGTTTGTCGGGTCATCTTTTCATGCTTTTTTT
GTCTTGGTTGTGATGATGTGGTCTGGTTGGGCGGTCGTTCTAGATCGGAGTAGAATTCT
GTTTCAAACTACCTGGTGGATTTATTAATTTTGGATCTGTATGTGTGTGCCATACATAT
TCATAGTTACGAATTGAAGATGATGGATGGAAATATCGATCTAGGATAGGTATACATG
TTGATGCGGGTTTTACTGATGCATATACAGAGATGCTTTTTGTTCGCTTGGTTGTGATG
ATGTGGTGTGGTTGGGCGGTCGTTCATTCGTTCTAGATCGGAGTAGAATACTGTTTCAA
ACTACCTGGTGTATTTATTAATTTTGGAACTGTATGTGTGTGTCATACATCTTCATAGT
TACGAGTTTAAGATGGATGGAAATATCGATCTAGGATAGGTATACATGTTGATGTGGG
TTTTACTGATGCATATACATGATGGCATATGCAGCATCTATTCATATGCTCTAACCTTG
AGTACCTATCTATTATAATAAACAAGTATGTTTTATAATTATTTCGATCTTGATATACT
TGGATGATGGCATATGCAGCAGCTATATGTGGATTTTTTTAGCCCTGCCTTCATACGCT
ATTTATTTGCTTGGTACTGTTTCTTTTGTCGATGCTCACCCTGTTGTTTGGTGTTACTTCT
GCAGGTACAGTAGTTAGTTGAGGTACAGCGGCCGCAGGGCACCATGGTCCGTCCTGTA
GAAACCCCAACCCGTGAAATCAAAAAACTCGACGGCCTGTGGGCATTCAGTCTGGATC
GCGAAAACTGTGGAATTGATCAGCGTTGGTGGGAAAGCGCGTTACAAGAAAGCCGGG
CAATTGCTGTGCCAGGCAGTTTTAACGATCAGTTCGCCGATGCAGATATTCGTAATTAT
GCGGGCAACGTCTGGTATCAGCGCGAAGTCTTTATACCGAAAGGTTGGGCAGGCCAG
CGTATCGTGCTGCGTTTCGATGCGGTCACTCATTACGGCAAAGTGTGGGTCAATAATC
AGGAAGTGATGGAGCATCAGGGCGGCTATACGCCATTTGAAGCCGATGTCACGCCGT
ATGTTATTGCCGGGAAAAGTGTACGTATCACCGTTTGTGTGAACAACGAACTGAACTG
GCAGACTATCCCGCCGGGAATGGTGATTACCGACGAAAACGGCAAGAAAAAGCAGTC
TTACTTCCATGATTTCTTTAACTATGCCGGAATCCATCGCAGCGTAATGCTCTACACCA
CGCCGAACACCTGGGTGGACGATATCACCGTGGTGACGCATGTCGCGCAAGACTGTA
ACCACGCGTCTGTTGACTGGCAGGTGGTGGCCAATGGTGATGTCAGCGTTGAACTGCG
TGATGCGGATCAACAGGTGGTTGCAACTGGACAAGGCACTAGCGGGACTTTGCAAGT
GGTGAAT

*FIG. 12B*

CCGCACCTCTGGCAACCGGGTGAAGGTTATCTCTATGAACTGTGCGTCACAGCCAAAA
GCCAGACAGAGTGTGATATCTACCCGCTTCGCGTCGGCATCCGGTCAGTGGCAGTGAA
GGGCGAACAGTTCCTGATTAACCACAAACCGTTCTACTTTACTGGCTTTGGTCGTCATG
AAGATGCGGACTTGCGTGGCAAAGGATTCGATAACGTGCTGATGGTGCACGACCACG
CATTAATGGACTGGATTGGGGCCAACTCCTACCGTACCTCGCATTACCCTTACGCTGA
AGAGATGCTCGACTGGGCAGATGAACATGGCATCGTGGTGATTGATGAAACTGCTGCT
GTCGGCTTTAACCTCTCTTTAGGCATTGGTTTCGAAGCGGGCAACAAGCCGAAAGAAC
TGTACAGCGAAGAGGCAGTCAACGGGGAAACTCAGCAAGCGCACTTACAGGCGATTA
AAGAGCTGATAGCGCGTGACAAAAACCACCCAAGCGTGGTGATGTGGAGTATTGCCA
ACGAACCGGATACCCGTCCGCAAGGTGCACGGGAATATTTCGCGCCACTGGCGGAAG
CAACGCGTAAACTCGACCCGACGCGTCCGATCACCTGCGTCAATGTAATGTTCTGCGA
CGCTCACACCGATACCATCAGCGATCTCTTTGATGTGCTGTGCCTGAACCGTTATTACG
GATGGTATGTCCAAAGCGGCGATTTGGAAACGGCAGAGAAGGTACTGGAAAAAGAAC
TTCTGGCCTGGCAGGAGAAACTGCATCAGCCGATTATCATCACCGAATACGGCGTGGA
TACGTTAGCCGGGCTGCACTCAATGTACACCGACATGTGGAGTGAAGAGTATCAGTGT
GCATGGCTGGATATGTATCACCGCGTCTTTGATCGCGTCAGCGCCGTCGTCGGTGAAC
AGGTATGGAATTTCGCCGATTTTGCGACCTCGCAAGGCATATTGCGCGTTGGCGGTAA
CAAGAAAGGGATCTTCACTCGCGACCGCAAACCGAAGTCGGCGGCTTTTCTGCTGCAA
AAACGCTGGACTGGCATGAACTTCGGTGAAAAACCGCAGCAGGGAGGCAAACAATGA
GACGTCCGGTAACCTTTAAACTGAGGGCACTGAAGTCGCTTGATGTGCTGAATTGTTT
GTGATGTTGGTGGCGTATTTTGTTTAAATAAGTAAGCATGGCTGTGATTTTATCATATG
ATCGATCTTTGGGGTTTTATTTAACACATTGTAAAATGTGTATCTATTAATAACTCAAT
GTATAAGATGTGTTCATTCTTCGGTTGCCATAGATCTGCTTATTTGACCTGTGATGTTTT
GACTCCAAAAACCAAAATCACAACTCAATAAACTCATGGAATATGTCCACCTGTTTCT
TGAAGAGTTCATCTACCATTCCAGTTGGCATTTATCAGTGTTGCAGCGGCGCTGTGCTT
TGTAACATAACAATTGTTACGGCATATATCCAA

*FIG. 12C*

SEQ ID NO: 5 shows an exemplary SCBV bidirectional promoter comprising a minUbi1P minimal core promoter, wherein the reverse complement of the minUbi1P is underlined:

CTGCAGAAGTAACACCAAACAACAGGGTGAGCATCGACAAAAGAAACAGTACCAAG
CAAATAAATAGCGTATGAAGGCAGGGCTAAAAAAATCCACATATAGCTGCTGCATAT
GCCATCATCCAAGTATATCAAGATCGAAATAATTATAAAACATACTTGTTTATTATAA
TAGATAGGTACTCAAGGTTAGAGCATATGAATAGATGCTGCATATGCCATCATGTATA
TGCATCAGTAAAACCCACATCAACATGTATACCTATCCTAGATCGATATTTCCATCCAT
CTTAAACTCGTAACTATGAAGATGTATGACACACACATACAGTTCCAAAATTAATAAA
TACACCAGGTAGTTTGAAACAGTATTCTACTCCGATCTAGAACGAATGAACGACCGCC
CAACCACACCACATCATCACAACCAAGCGAACAAAAAGCATCTCTGTATATGCATCAG
TAAAACCCGCATCAACATGTATACCTATCCTAGATCGATATTTCCATCCATCATCTTCA
ATTCGTAACTATGAATATGTATGGCACACACATACAGATCCAAAATTAATAAATCCAC
CAGGTAGTTTGAAACAGAATTCTACTCCGATCTAGAACGACCGCCCAACCAGACCACA
TCATCACAACCAAGACAAAAAAAAGCATGAAAAGATGACCCGACAAACAAGTGCAC
GGCATATATTGAAATAAAGGAAAAGGGCAAACCAAACCCTATGCAACGAAACAAAAA
AAATCATGAAATCGATCCCGTCTGCGGAACGGCTAGAGCCATCCCAGGATTCCCCAAA
GAGAAACACTGGCAAGTTAGCAATCAGAACGTGTCTGACGTACAGGTCGCATCCGTGT
ACGAACGCTAGCAGCACGGATCTAACACAAACACGGATCTAACACAAACATGAACAG
AAGTAGAACTACCGGGCCCTAACCATGCATGGACCGGAACGCCGATCTAGAGAAGGT
AGAGAGGGGGGGGGGGGGAGGACGAGCGGCGTACCTTGAAGCGGAGGTGCCGACG
GGTGGATTTGGGGGAGATCTGGTTGTGTGTGTGCGCTCCGAACAACACGAGGTTGG
GGAGGTACCAAGAGGGTGTGGAGGGGGTGTCTATTTATTACGGCGGGCGAGGAAGGG
AAAGCGAAGGAGCGGTGGGAAAGGAATCCCCCGTAGCTGCCGGTGCCGTGAGAGGA
GGAGGAGGCCGCCTGCCGTGCCGGCTCACGTCTGCCGCTCCGCCACGCAATTTCTGGA
TGCCGACAGCGGAGCAAGTCCAACGGTGGAGCGGAACTCTCGAGAGGGGTCCAGCCG
CGGAGTATCGGAAGTTGAAGACAAAGAAGGTCTTAAATCCTGGCTAGCAACACTGAA
CTATGCCAGAAACCACATCAAAGCATATCGGCAAGCTTCTTGGCCCATTATATCCAAA
GACCTCAGAGAAAGGTGAGCGAAGGCTCAATTCAGAAGATTGGAAGCTGATCAATAG
GATCAAGACAATGGTGAGAACGCTTCCAAATCTCACTATTCCACCAGAAGATGCATAC
ATTATCATTGAAACAGATGCATGTGCAACTGGATGGGGAGCAGTATGCAAGTGGAAG
AAAAACAAGGCAGACCCAAGAAATACAGAGCAAATCTGTAGGTATGCCAGTGGAAAA
TTTGATAAGCCAAAAGGAACCTGTGATGCAGAAATCTATGGGGTTATGAATGGCTTAG
AAAAGATGAGATTGTTCTACTTGGACAAAAGAGAGATCACAGTCAGAACTGACAGTA
GTGCAATCGAAAGGTTCTACAACAAGAGTGCTGAACACAAGCCTTCTGAGATCAGAT
GGATCAGGTT

*FIG. 13A*

CATGGACTACATCACTGGTGCAGGACCAGAGATAGTCATTGAACACATAAAAGGGAA
GAGCAATGGTTTAGCTGACATCTTGTCCAGGCTCAAAGCCAAATTAGCTCAGAATGAA
CCAACGGAAGAGATGATCCTGCTTACACAAGCCATAAGGGAAGTAATTCCTTATCCAG
ATCATCCATACACTGAGCAACTCAGAGAATGGGGAAACAAAATTCTGGATCCATTCCC
CACATTCAAGAAGGACATGTTCGAAAGAACAGAGCAAGCTTTTATGCTAACAGAGGA
ACCAGTTCTACTCTGTGCATGCAGGAAGCCTGCAATTCAGTTAGTGTCCAGAACATCT
GCCAACCCAGGAAGGAAATTCTTCAAGTGCGCAATGAACAAATGCCATTGCTGGTACT
GGGCAGATCTCATTGAAGAACACATTCAAGACAGAATTGATGAATTTCTCAAGAATCT
TGAAGTTCTGAAGACCGGTGGCGTGCAAACAATGGAGGAGGAACTTATGAAGGAAGT
CACCAAGCTGAAGATAGAAGAGCAGGAGTTCGAGGAATACCAGGCCACACCAAGGG
CTATGTCGCCAGTAGCCGCAGAAGATGTGCTAGATCTCCAAGACGTAAGCAATGACG
ATTGAGGAGGCATTGACGTCAGGGATGACCGCAGCGGAGAGTACTGGGCCCATTCAG
TGGATGCTCCACTGAGTTGTATTATTGTGTGCTTTTCGGACAAGTGTGCTGTCCACTTT
CTTTTGGCACCTGTGCCACTTTATTCCTTGTCTGCCACGATGCCTTTGCTTAGCTTGTAA
GCAAGGATCGCAGTGCGTGTGTGACACCACCCCCCTTCCGACGCTCTGCCTATATAAG
GCACCGTCTGTAAGCTCTTACGATCATCGGTAGTTCACCAAGGCCCGGGGTCGGATCT
AGCTGAAGGCTCGACAAGGCAGTCCACGGAGGAGCTGATATTTGGTGGACAAGCTGT
GGATAGGAGCAACCCTATCCCTAATATACCAGCACCACCAAGTCAGGGCAATCCCCA
GATCACCCCAGCAGATTCGAAGAAGGTACAGTACACACACATGTATATATGTATGATG
TATCCCTTCGATCGAAGGCATGCCTTGGTATAATCACTGAGTAGTCATTTTATTACTTT
GTTTTGACAAGTCAGTAGTTCATCCATTTGTCCCATTTTTTCAGCTTGGAAGTTTGGTT
GCACTGGCCTTGGTCTAATAACTGAGTAGTCATTTTATTACGTTGTTTCGACAAGTCAG
TAGCTCATCCATCTGTCCCATTTTTTCAGCTAGGAAGTTTGGTTGCACTGGCCTTGGAC
TAATAACTGATTAGTCATTTTATTACATTGTTTCGACAAGTCAGTAGCTCATCCATCTG
TCCCATTTTTCAGCTAGGAAGTTC

*FIG. 13B*

SEQ ID NO: 6 shows a SCBV promoter containing ADH1 exon 6 (underlined), intron 6 (lower case font), and exon 7 (bold font).

ATCGGAAGTTGAAGACAAAGAAGGTCTTAAATCCTGGCTAGCAACACTGAACTATGC
CAGAAACCACATCAAAGCATATCGGCAAGCTTCTTGGCCCATTATATCCAAAGACCTC
AGAGAAAGGTGAGCGAAGGCTCAATTCAGAAGATTGGAAGCTGATCAATAGGATCAA
GACAATGGTGAGAACGCTTCCAAATCTCACTATTCCACCAGAAGATGCATACATTATC
ATTGAAACAGATGCATGTGCAACTGGATGGGGAGCAGTATGCAAGTGGAAGAAAAAC
AAGGCAGACCCAAGAAATACAGAGCAAATCTGTAGGTATGCCAGTGGAAAATTTGAT
AAGCCAAAAGGAACCTGTGATGCAGAAATCTATGGGGTTATGAATGGCTTAGAAAAG
ATGAGATTGTTCTACTTGGACAAAAGAGAGATCACAGTCAGAACTGACAGTAGTGCA
ATCGAAAGGTTCTACAACAAGAGTGCTGAACACAAGCCTTCTGAGATCAGATGGATC
AGGTTCATGGACTACATCACTGGTGCAGGACCAGAGATAGTCATTGAACACATAAAA
GGGAAGAGCAATGGTTTAGCTGACATCTTGTCCAGGCTCAAAGCCAAATTAGCTCAGA
ATGAACCAACGGAAGAGATGATCCTGCTTACACAAGCCATAAGGGAAGTAATTCCTT
ATCCAGATCATCCATACACTGAGCAACTCAGAGAATGGGGAAACAAAATTCTGGATC
CATTCCCCACATTCAAGAAGGACATGTTCGAAAGAACAGAGCAAGCTTTTATGCTAAC
AGAGGAACCAGTTCTACTCTGTGCATGCAGGAAGCCTGCAATTCAGTTAGTGTCCAGA
ACATCTGCCAACCCAGGAAGGAAATTCTTCAAGTGCGCAATGAACAAATGCCATTGCT
GGTACTGGGCAGATCTCATTGAAGAACACATTCAAGACAGAATTGATGAATTTCTCAA
GAATCTTGAAGTTCTGAAGACCGGTGGCGTGCAAACAATGGAGGAGGAACTTATGAA
GGAAGTCACCAAGCTGAAGATAGAAGAGCAGGAGTTCGAGGAATACCAGGCCACACC
AAGGGCTATGTCGCCAGTAGCCGCAGAAGATGTGCTAGATCTCCAAGACGTAAGCAA
TGACGATTGAGGAGGCATTGACGTCAGGGATGACCGCAGCGGAGAGTACTGGGCCCA
TTCAGTGGATGCTCCACTGAGTTGTATTATTGTGTGCTTTTCGGACAAGTGTGCTGTCC
ACTTTCTTTTGGCACCTGTGCCACTTTATTCCTTGTCTGCCACGATGCCTTTGCTTAGCT
TGTAAGCAAGGATCGCAGTGCGTGTGTGACACCACCCCCCTTCCGACGCTCTGCCTAT
ATAAGGCACCGTCTGTAAGCTCTTACGATCATCGGTAGTTCACCAAGGCCCGGGGTCG
GATCTAGCTGAAGGCTCGACAAGGCAGTCCACGGAGGAGCTGATATTTGGTGGACAA
GCTGTGGATAGGAGCAACCCTATCCCTAATATACCAGCACCACCAAGTCAGGGCAATC
CCCAGATCA<u>CCCCAGCAGATTCGAAGAAG</u>gtacagtacacacacatgtatatatgtatgatgtatcccttcgatcgaa
ggcatgccttggtataatcactgagtagtcattttattactttgttttgacaagtcagtagttcatccatttgtcccattttttcagcttggaagtttggttgc
actggccttggtctaataactgagtagtcattttattacgttgtttcgacaagtcagtagctcatccatctgtcccattttttcagctaggaagtttggttg
cactggccttggactaataactgattagtcattttattacattgtttcgacaagtcagtagctcatccatctgtcccattttttcag**CTAGGAAGT
TC**

FIG. 14

SEQ ID NO: 7 shows a nucleic acid comprising *YFP* and *GUS* gene expression cassettes driven by an exemplary SCBV bidirectional promoter.

AGCACTTAAAGATCTTTAGAAGAAAGCAAAGCATTTATTAATACATAACAATGTCCAG
GTAGCCCAGCTGAATTACAATACGCAACTGCTCATAATAATTCAACAAACCCAAGTAG
TACACAACATCCAGAAGCAAATAAAGCCCATACGTACCAAAGCCTACACAAGCAGCA
ACACTCACTGCCAGTGCCGGTGGGTCTTTAAAGCACACGGGCCTTGACCACGCGATCC
ACCTTGAAACAAACTTGGTAAAATTAAAGCAAACCAGAAGCACACACACGCCAACGC
AACGCTTCTGATCGCGCGCCCAAGGCCCGGCCGGCCAGAACGTACGACGGACACGCA
CACGCTGCGACCGAGCTCTAGGTGATTAAGCTAACTACTCAAAGGTAGGTCTTGCGAC
AGTCAACAGCTCTGACAGTTTCTTTCAAGGACATGTTGTCTCTGTGGTCTGTCACATCT
TTGGAAAGTTTCACATGGTAAGACATGTGATGATACTCTGGAACATGAACTGGACCTC
CACCAATGGGAGTGTTCATCTGGGTGTGGTCAGCCACTATGAAGTCGCCTTTGCTGCC
AGTAATCTCATGACAGATCTTGAAGGCTGACTTGAGACCGTGGTTGGCTTGGTCACCC
CAGATGTAGAGGCAGTGGGGAGTGAAGTTGAACTCCAAGTTCTTTCCCAACACATGAC
CATCTTTCTTGAAGCCTTGACCATTGAGTTTGACCCTATTGTAGACAGACCCATTCTCA
AAGGTGACTTCAGCCCTAGTCTTGAAGTTGCCATCTCCTTCAAAGGTGATTGTGCGCTC
TTGCACATAGCCATCTGGCATACAGGACTTGTAGAAGTCCTTCAACTCTGGACCATAC
TTGGCAAAGCACTGTGCTCCATAGGTGAGAGTGGTGACAAGTGTGCTCCAAGGCACA
GGAACATCACCAGTTGTGCAGATGAACTGTGCATCAACCTTTCCCACTGAGGCATCTC
CGTAGCCTTTCCCACGTATGCTAAAGGTGTGGCCATCAACATTCCCTTCCATCTCCACA
ACGTAAGGAATCTTCCCATGAAAGAGAAGTGCTCCAGATGCCATGGTGTCGTGTGGAT
CCGGTACACACGTGCCTAGGACCGGTTCAACTAACTACTGCAGAAGTAACACCAAAC
AACAGGGTGAGCATCGACAAAAGAAACAGTACCAAGCAAATAAATAGCGTATGAAG
GCAGGGCTAAAAAAATCCACATATAGCTGCTGCATATGCCATCATCCAAGTATATCAA
GATCGAAATAATTATAAAACATACTTGTTTATTATAATAGATAGGTACTCAAGGTTAG
AGCATATGAATAGATGCTGCATATGCCATCATGTATATGCATCAGTAAAACCCACATC
AACATGTATACCTATCCTAGATCGATATTTCCATCCATCTTAAACTCGTAACTATGAAG
ATGTATGACACACACATACAGTTCCAAAATTAATAAATACACCAGGTAGTTTGAAACA
GTATTCTACTCCGATCTAGAACGAATGAACGACCGCCCAACCACACCACATCATCACA
ACCAAGCGAACAAAAAGCATCTCTGTATATGCATCAGTAAAACCCGCATCAACATGTA
TACCTATCCTAGATCGATATTTCCATCCATCATCTTCAATTCGTAACTATGAATATGTA
TGGCACACACATACAGATCCAAAATTAATAAATCCACCAGGTAGTTTGAAACAGAATT
CTACTCCGATCTAGAACGACCGCCCAACCAGACCACATCATCACAACCAAGACAAAA
AAAAGCATGAAAAGATGACCCGACAAACAAGTGCACGGCATATATTGAAATAAAGGA
AAAGGGCAAACCAAACCCTATGCAACGAAACAAAAAAAATCATGAAATCGATCCCGT
CTGCGGAACGGCTAGAGCCATCCCAGGATTCCCCAAAGAGAAACACTGGCAAGTTAG
CAATCAGAACGTGTCTGACGTACAGGTCGCATCCGTGTACGAACGCTAGCAGCACGG
ATCTAACACAAACACGGATCTAACACAAACATGAACAGAAGTAGAACTACCGGGCCC
TAACCATGCATGGACCGGAACGCCGATCTAGAGAAGGTAGAGAGGGGGGGGGGGGG
GAGGACGAGCGGCGTACCTTGAAGCGGAGGTGCCGACGGGTGGATTTGGGGGAGATC
TGGTTGTGTGTGTGTGCGCTCCGAACAACACGAGGTTGGGGAGGTACCAAGAGGGTGT
GGAGGGGGTGTCTATTTATTACGGCGGGCGAGGAAGGGAAAGCGAAGGAGCGGTGGG
AAAGGAATCCCCCGTAGCTGCCGGTGCCGTGAGAGGAGGAGGAGGCCGCCTGCCGTG
CCGGCTCACGTCTGCCGCTCCGCCACGCAATTTCTGGATGCCGACAGCGGAGCAAGTC
CAACGGTGGAGCGGAACT

*FIG. 15A*

CTCGAGAGGGGTCCAGCCGCGGAGTATCGGAAGTTGAAGACAAAGAAGGTCTTAAAT
CCTGGCTAGCAACACTGAACTATGCCAGAAACCACATCAAAGCATATCGGCAAGCTTC
TTGGCCCATTATATCCAAAGACCTCAGAGAAAGGTGAGCGAAGGCTCAATTCAGAAG
ATTGGAAGCTGATCAATAGGATCAAGACAATGGTGAGAACGCTTCCAAATCTCACTAT
TCCACCAGAAGATGCATACATTATCATTGAAACAGATGCATGTGCAACTGGATGGGGA
GCAGTATGCAAGTGGAAGAAAAACAAGGCAGACCCAAGAAATACAGAGCAAATCTGT
AGGTATGCCAGTGGAAAATTTGATAAGCCAAAAGGAACCTGTGATGCAGAAATCTAT
GGGGTTATGAATGGCTTAGAAAAGATGAGATTGTTCTACTTGGACAAAAGAGAGATC
ACAGTCAGAACTGACAGTAGTGCAATCGAAAGGTTCTACAACAAGAGTGCTGAACAC
AAGCCTTCTGAGATCAGATGGATCAGGTTCATGGACTACATCACTGGTGCAGGACCAG
AGATAGTCATTGAACACATAAAAGGGAAGAGCAATGGTTTAGCTGACATCTTGTCCAG
GCTCAAAGCCAAATTAGCTCAGAATGAACCAACGGAAGAGATGATCCTGCTTACACA
AGCCATAAGGGAAGTAATTCCTTATCCAGATCATCCATACACTGAGCAACTCAGAGAA
TGGGGAAACAAAATTCTGGATCCATTCCCCACATTCAAGAAGGACATGTTCGAAAGA
ACAGAGCAAGCTTTTATGCTAACAGAGGAACCAGTTCTACTCTGTGCATGCAGGAAGC
CTGCAATTCAGTTAGTGTCCAGAACATCTGCCAACCCAGGAAGGAAATTCTTCAAGTG
CGCAATGAACAAATGCCATTGCTGGTACTGGGCAGATCTCATTGAAGAACACATTCAA
GACAGAATTGATGAATTTCTCAAGAATCTTGAAGTTCTGAAGACCGGTGGCGTGCAAA
CAATGGAGGAGGAACTTATGAAGGAAGTCACCAAGCTGAAGATAGAAGAGCAGGAG
TTCGAGGAATACCAGGCCACACCAAGGGCTATGTCGCCAGTAGCCGCAGAAGATGTG
CTAGATCTCCAAGACGTAAGCAATGACGATTGAGGAGGCATTGACGTCAGGGATGAC
CGCAGCGGAGAGTACTGGGCCCATTCAGTGGATGCTCCACTGAGTTGTATTATTGTGT
GCTTTTCGGACAAGTGTGCTGTCCACTTTCTTTTGGCACCTGTGCCACTTTATTCCTTGT
CTGCCACGATGCCTTTGCTTAGCTTGTAAGCAAGGATCGCAGTGCGTGTGTGACACCA
CCCCCCTTCCGACGCTCTGCCTATATAAGGCACCGTCTGTAAGCTCTTACGATCATCGG
TAGTTCACCAAGGCCCGGGGTCGGATCTAGCTGAAGGCTCGACAAGGCAGTCCACGG
AGGAGCTGATATTTGGTGGACAAGCTGTGGATAGGAGCAACCCTATCCCTAATATACC
AGCACCACCAAGTCAGGGCAATCCCCAGATCACCCCAGCAGATTCGAAGAAGGTACA
GTACACACACATGTATATATGTATGATGTATCCCTTCGATCGAAGGCATGCCTTGGTAT
AATCACTGAGTAGTCATTTTATTACTTTGTTTTGACAAGTCAGTAGTTCATCCATTTGT
CCCATTTTTTCAGCTTGGAAGTTTGGTTGCACTGGCCTTGGTCTAATAACTGAGTAGTC
ATTTTATTACGTTGTTTCGACAAGTCAGTAGCTCATCCATCTGTCCCATTTTTTCAGCTA
GGAAGTTTGGTTGCACTGGCCTTGGACTAATAACTGATTAGTCATTTTATTACATTGTT
TCGACAAGTCAGTAGCTCATCCATCTGTCCCATTTTTCAGCTAGGAAGTTCGCGGCCGC
AGGGCACCATGGTCCGTCCTGTAGAAACCCCAACCCGTGAAATCAAAAAACTCGACG
GCCTGTGGGCATTCAGTCTGGATCGCGAAAACTGTGGAATTGATCAGCGTTGGTGGGA
AAGCGCGTTACAAGAAAGCCGGGCAATTGCTGTGCCAGGCAGTTTTAACGATCAGTTC
GCCGATGCAGATATTCGTAATTATGCGGGCAACGTCTGGTATCAGCGCGAAGTCTTTA
TACCGAAAGGTTGGGCAGGCCAGCGTATCGTGCTGCGTTTCGATGCGGTCACTCATTA
CGGCAAAGTGTGGGTCAATAATCAGGAAGTGATGGAGCATCAGGGCGGCTATACGCC
ATTTGAAGCCGATGTCACGCCGTATGTTATTGCCGGGAAAAGTGTACGTATCACCGTT
TGTGTGAACAACGAACTGAACTGGCAGACTATCCCGCCGGGAATGGTGATTACCGAC
GAAAACGGCAAGAAAAAGCAGTCTTACTTCCATGATTTCTTTAACTATGCCGGAATCC
ATCGCAGCGTAATGCTCTACACCACGCCGAACACCTGGGTGGACGATATCACCGTGGT
GACGCATGTCGCGCAAGACTGTAACCACG

*FIG. 15B*

CGTCTGTTGACTGGCAGGTGGTGGCCAATGGTGATGTCAGCGTTGAACTGCGTGATGC
GGATCAACAGGTGGTTGCAACTGGACAAGGCACTAGCGGGACTTTGCAAGTGGTGAA
TCCGCACCTCTGGCAACCGGGTGAAGGTTATCTCTATGAACTGTGCGTCACAGCCAAA
AGCCAGACAGAGTGTGATATCTACCCGCTTCGCGTCGGCATCCGGTCAGTGGCAGTGA
AGGGCGAACAGTTCCTGATTAACCACAAACCGTTCTACTTTACTGGCTTTGGTCGTCAT
GAAGATGCGGACTTGCGTGGCAAAGGATTCGATAACGTGCTGATGGTGCACGACCAC
GCATTAATGGACTGGATTGGGGCCAACTCCTACCGTACCTCGCATTACCCTTACGCTG
AAGAGATGCTCGACTGGGCAGATGAACATGGCATCGTGGTGATTGATGAAACTGCTG
CTGTCGGCTTTAACCTCTCTTTAGGCATTGGTTTCGAAGCGGGCAACAAGCCGAAAGA
ACTGTACAGCGAAGAGGCAGTCAACGGGGAAACTCAGCAAGCGCACTTACAGGCGAT
TAAAGAGCTGATAGCGCGTGACAAAAACCACCCAAGCGTGGTGATGTGGAGTATTGC
CAACGAACCGGATACCCGTCCGCAAGGTGCACGGGAATATTTCGCGCCACTGGCGGA
AGCAACGCGTAAACTCGACCCGACGCGTCCGATCACCTGCGTCAATGTAATGTTCTGC
GACGCTCACACCGATACCATCAGCGATCTCTTTGATGTGCTGTGCCTGAACCGTTATTA
CGGATGGTATGTCCAAAGCGGCGATTTGGAAACGGCAGAGAAGGTACTGGAAAAAGA
ACTTCTGGCCTGGCAGGAGAAACTGCATCAGCCGATTATCATCACCGAATACGGCGTG
GATACGTTAGCCGGGCTGCACTCAATGTACACCGACATGTGGAGTGAAGAGTATCAGT
GTGCATGGCTGGATATGTATCACCGCGTCTTTGATCGCGTCAGCGCCGTCGTCGGTGA
ACAGGTATGGAATTTCGCCGATTTTGCGACCTCGCAAGGCATATTGCGCGTTGGCGGT
AACAAGAAAGGGATCTTCACTCGCGACCGCAAACCGAAGTCGGCGGCTTTTCTGCTGC
AAAAACGCTGGACTGGCATGAACTTCGGTGAAAAACCGCAGCAGGGAGGCAAACAAT
GAGACGTCCGGTAACCTTTAAACTGAGGGCACTGAAGTCGCTTGATGTGCTGAATTGT
TTGTGATGTTGGTGGCGTATTTTGTTTAAATAAGTAAGCATGGCTGTGATTTTATCATA
TGATCGATCTTTGGGGTTTTATTTAACACATTGTAAAATGTGTATCTATTAATAACTCA
ATGTATAAGATGTGTTCATTCTTCGGTTGCCATAGATCTGCTTATTTGACCTGTGATGT
TTTGACTCCAAAAACCAAAATCACAACTCAATAAACTCATGGAATATGTCCACCTGTT
TCTTGAAGAGTTCATCTACCATTCCAGTTGGCATTTATCAGTGTTGCAGCGGCGCTGTG
CTTTGTAACATAACAATTGTTACGGCATATATCCAA

*FIG. 15C*

SEQ ID NO: 16
CTGGACCCCTCTCGAGTGTTCCGCTTCACCGTTGGACTTGCTACGCTGTCAGCATCGA
GATGTTGCGTGGCGGAGCGGCAGACTTGAGCCGTCACGGCAGGCGGCCTCCTCCTCC
TCTCACGGCATCTGTAGCTACGGGGGATTCCTTTCGCACCGCTCGTTCGCTTTCCCTT
CCTCGTCTGCCGAAATAATGTTACACCCCCTCCACAGCCTCT

SEQ ID NO: 17
CTGGACCCCTCTCGAGAGTTCCGCTCCACCGTTGGACTAGCTCTGCTGTCGGCATCCA
GAAAATGCTTGGCAGTGCGGCAGACGTGAGCCGGCACGGCAGGGGGCCTCCTCCTG
CTCTCACGGCACATGAAGCTACGGGTGATAGCTTGCCCACCGCTCCAACGCTTTCCC
TTACTCTCACGCCGTAATAAATAGACACCCCTTCCACAACCTCT

SEQ ID NO: 18
CTGGACCTCTCTCGAGAGTTGCGCTCCACCGATGGACTTGCTCCGCTGTCGGCGTCC
ATAATTTGCGTGGCGGAGCGGCAGACGGGAGCCGGCACGGCAGGGAGCCTCGTCCT
CCTCTCACGGCACCTGCAACTACGGGGGATTCCTATCCCACCGCTCCTTCGCTTTCAC
TTCTTCGCCCTCCTTAATAAGTAGACACCCCATCCGAGCCCTCT

SEQ ID NO: 19
CAAGACCCCTCTCGAGAGTTCCGCACCACCGTTGGACGTGCTCCGCTATCTGCATCC
AGAAATTGCGTGGCGGAACGGTAAACGTGAGCCGTCACGGCAGGCGGCCTCCTCCT
CCTCTCACGACACCGGCAGCTACGGGGGATACCTGTCACACAGCTCCTTCGCTTTTCT
TTCCTCGCCCGCCGTAATATGTATACACTCCCTCCGCACCCTCT

SEQ ID NO: 20
CTGGACCCCTCTCGAGGGTTCCGTTCCACCGTTGGTCTTGGTCCGCTGTCGGGATCCA
GAAATAGCGTGGCGGAGCGGCAGACGTGATCCGGCACGGCATGCGGCCTCCTAGTC
CTATCACAGCACCGGCAGCTATGGGAGATTCCATTCCCACCGCTCCTGCGCTTTCACT
GGCTGGCCCGCCGTGATAGATAGACACCCCCTCCACACCCTCT

FIG. 21A

SEQ ID NO: 21
GTTGGCTTCTCTTGTGAGTTCTGCTTCACGGATGGACTTGGTCAACGGACGGCATCCA
GAATTTGCGTGGCGTAGCGGCGGACGTGATCCGGCGCGGCAGGCGGCTTCCTCCTCC
TCTCACTTAAGCGACAGCTACAGGGGATTCCTTTCCCACCGCTCCTTCGCTTGCCGTA
CCTCGCCCGCCGTAATAAATAGACACCCCTTCCACTCCCTCT

SEQ ID NO: 22
CTGGATCCCTCTCGAGAGTGCGGCTCCGACGTTGGACTTGCTCCGAAGTCGGCATCC
AAAAATTGCGTGGTGGAGAGGCAGACTTGAGCCGGCACGGCAGGAGGCCTCGTCCT
ACTCGCACGGTATCGGCAGCAACGGGAGAATCCTTGCACTCTGCTCCTTCGCTGTAC
CTTCCTCGCCCGCTGATATTGATAGACACCCCCTGCATACCCTCT

SEQ ID NO: 23
ATGGACCCTTCTCGAGTGTTCGGCTCCACCGTTAGACTTGCTCCACGATCGACATCA
AGAAATTGCGAGACGGAGCTACAAACGTAAGAAATCTCGGTAGGGGGCCTCCTCCT
CCTCTCACGGCACCGGCAGCTACGGGGGATTCCTGTCCCACCTCTCCTTCACGTTCCC
TACCTCGCCCGCCATAATTAATAAGCACCCCCTCCGCACCCTCT

SEQ ID NO: 24
CTGGACCCCTCTAAAGAGTTCCACGCCACCGTTATAATGGCTCCGCTGTCGGCATCC
AGAAATTACTTGGCGGATCAGCAGACGTGAGCCAGCATGGCTGGCGGCCTCCTCCTC
CTCTCACGATGCCGTCAGCTACGGGGGATTCCTTTCCCAACGCTCCTTCGCTTTCCTA
TGCGCGCCTGCCGGATTAAATAGGCAGCTTCTCGTCACCCTCT

SEQ ID NO: 25
CAAGACACCTCTCGATTGTTCCGCTTCACCGTTGGACTTTCTCCTCAGTCGGCATACA
GAAATTGCTTGGCGAAGCGGCAGACATGAGCCGGCACGACATGCGTCCTCATTCTCC
TCTCATGGCACCGGCAGTTACTGGTGAATCCTATCGCACCGCTCCTTCGCTGTCCCTT
AATCGCCCGCCGAAAATAATTGACACCCCATCCACACCCTCT

FIG. 21B

SEQ ID NO: 26
GAGGACCCCTCTCGTGTGTATCGCTCCACCTTTGGAGTTGGTCCACTATCGGCGTACA
GAAAATTCGTTGCGAAGCGGCAGACGTGAGCCTACACGGCAGTCGGCCTCTACCTCC
TGACAAGGCACGTGCAGCTACAGATGATGCCTTTCCCACCACTCCTTCGCGTTCCTTT
CCTCGCCATCAGTAATGAATGGACACGTCCTCCAGACTCTCT

SEQ ID NO: 27
CTGAACCCATCTCGAGTATGCCGCACGATCGATTGACATGCTCCACTGGCAGCATCC
AGAAATTGCATTGGGGAGCATCAGGCGTGAGCCTGCACGGCAGGCGGACTATTCCT
CCTCGCGCGGCACCGGCAACTACGGGGGATGCTTGACCGACCGCTCCATCGATTTCC
CAATCTCGCTTGCCGTATTAAATAGATAACCCCTTCACACCCTCT

SEQ ID NO: 28
CTGGACTCCTTACGGGAGATCCGCTCCACCGTTGGACTAGCTCCGTTTTCGGCTTCAA
TAAAGGGCGTGGGGGAGCGGCAGTCGGGGGCAGGCACGGCAGTGGTCCTCATCCAT
ATCTCACGGGGCCGGCAGTTGAGGGGGATTCCTGTCCCACCTCACCTACTCTTTCCCT
ACCTCGTCTGCCATATTAAATAGTCACCCCCTCCACAACCTTT

SEQ ID NO: 29
TTGGACCCCTCTCGAAAGTTAGGCTCCGCCGTTGGACTGGTTTCGCGGTCATCAATC
AGGAATTGCGGGGCGGAGGGTCAGACGTGTGCCGGCACAGCAGGTGGCCTCCTCAT
CGTCACAAGGCACTGGCAACTACGGGTGATTCATTTCCTTCAGCACCTACGCTTACC
CTGCCACGCCCTCCGTATTATAATGACACCCCCTCCACACCTTAT

SEQ ID NO: 30
CTGGACCCCACGCGGGGTTTTCGTTCCTCCGTTGGGATAGCTCCGGTGTCAGCATAC
AGAGAATATATGTCGGAGCGGAAGACGTGAGCCGACACGGCGGGCTGCCGCCTCCT
CCTGTCACGACACCGGCAGGTACGGGGGATTCCGTTCCCGCCGCACAGTCACTTTCG
CTTCCTTGCCGGTCGTATTAAATAGACACCGTGTCCACAGCCTCT

FIG. 21C

SEQ ID NO: 31
CTTGAGCCCACTCTAGAGTTCCGTTTCACCGAATGACTAGCTCCGCTGTCGGTATCCA
TTAAGTGGGAGGCAGAACGTCATATGAGAGTCGGCACGGGAGGCGTTCGCCACGTC
CGCGCACTACAGCGGGAGCTGCGGAATATACCTGTCCCAATGCTGCTACGCTTTCCC
TTCCGCGCCCACCGTAGAAAAATGACAGTCCCTTCACACCCTCT

SEQ ID NO: 32
TAGGAGGCCTCTCGAAAGGTCCGGAACTCCGTAGGACGTGCTCCGCTGACAGCATCC
AGGAATATCATGGGGGAGCTGCAGACGAGAGCCTGGACGACAAGGGGTCACCTCGG
CCGCTGACAGCTGCGGCAGCAACGGAGTATGCTTTTCTCACCGCTCCGGCGCTTTCC
CTTCGACGCAGGCCAGAATAAGTAGACATCAGCGCCACACCCTCT

SEQ ID NO: 33
CTTGTCTCCACTCTGATGTTCCGCTCCAACATTTGATTTGCTCCTCTGTAGGCATACA
GTTATTGGGGGACTGATCGGCAGACGTGAGCCAGCACTGCAAACGGCCAACTCCTCC
TCTCTCGACTAAGGGATTAATTAAGGATACCTTACCCGCGGCTCCTTCTCTTTCCCTA
CCTAGCCCGCCTTATTAAATAGAGACCGCCTCCACAGCCGCT

SEQ ID NO: 34
CTGTACCCTTCACAAGGGTTACACGCTACCGATGGACTTGCACCACTGTGGGGTTCC
AATAATTGCGTGGCTGGGCGTCAGACATATTCCGGCATGGCAAGCGGCCTGCTCCTC
CTCTGGGAGCACCGGCAACAATGGGGGATTCCAAGCCCGCAGGTCCTTCGTTTTACC
GTCCTCGCCCGCCGTAGTATGTAGGCATCCCAGAGACTACCTCT

SEQ ID NO: 35
CAGGAACCCTAACGAGGGTTCCGCACGACCAAATGACTTGATCTTCTGTCGGCATCC
AGAAATGGGGTGTCAGAGCGGCATGCGTGAGCCGGCGGGGCGTGCGGCCTCATGCT
GCTCTCGCGGGACTAGGAGTTACGGGGGATACCTGTATTGCCGCTCCGACACTGTAC
CATCCTCTCCCGCCGGAGTATAGAGACACCCCCTCGACGCCATAT

*FIG. 21D*

SEQ ID NO: 36
CTGTGCTCCTGTATGGGGTTCAACTCCACCGTGAAATTTGCGCCTCTGTCGTCATCCA
GAAATTGCGTGGTTGATCTGCTGACGTTAAAGGGCTCTGCAGGCGGCTTCCTTCGGC
TATGAAGGTACTGGCGTCTGCAAGTGATGCTTTTGCTAACTCGCCTTCGATGTCCCTT
CCTCGCGTGCTTTAATAGGTTGTCAGCCGCTCCAGACCATTT

SEQ ID NO: 37
CTGGTCCCATCGCTAGTGGTACGCTCCACCGGTGGAGTAGCTCAGATGTCTGAAGGG
TGGAATTTAGAGGTGGAGAGACAGACGTGAGCTAGAGCGGCATGGGACCTGGTCCA
CCGCTCGAGGCAATGGCAACGACTGTTGAAACCTTGCCCACCACTCCTGCAATTTTC
CATCCTCACCGGCCGGAATGAATTAAAACCCACGTCACAACCTCT

SEQ ID NO: 38
CGTGACAGGGCTCGGGTGTTCGGCTCCATCGTAGTGCATGCGCCGATGTAAGTATAC
AAGAAGTACGTGGCTTGGCGTCTGACGAGGGCCGTCAAGGCAGGCGGCCTCCTTCTA
AGCTTACGGCGCCGGCAGGTTCGTAGGTTACCTTACACTCAACTCATAGTCTATCTAT
TACTCGTACTGCGTTATAAATTGTCACCCCCTCCACACCCTCT

SEQ ID NO: 39
AGGAACGCTTCTCGATGGTTGCGCACATAGGAGGGACTTGATAGTCGGTGGAAATCT
AAGAATTGCATATCAGATCTGCAGACGTTAGCCGACATGGCTAGCAGACTACTCCGC
TTCACACGTCAGCGAAAGCGACGGAGGATTTCTTGCCAACGGCGCCTTCGCGAACCC
TTCCTCGCCCGTCGGAAGAAAGATACTCCCCTTGCACACCCTCT

SEQ ID NO: 40
CTTGACTTGGCTCGAGAGTTCTGCGCTTCCATTGTAGTTGCAGCGATGTCGGAGTCCG
AGGGTTGCGTGGCGGTGCGGCAGACGTGGGCAGATACGACTGTATGCCAGCACCTA
AACATACGGTACCAGAAGCTGCGGTGGATACCTTTCCCGACGCATATACGTTTTCCG
TGCCTCTCACGCCGTAGTAAATAAACTCCCCCTCCTGTTCCTTT

FIG. 21E

1 AATTACAACG GTATATATCC TGCCAGTCAG CATCATCACA CCAAAAGTTA GGCCCGAATA
61 GTTTGAAATT AGAAAGCTCG CAATTGAGGT CTACAGGCCA AATTCGCTCT TAGCCGTACA
121 ATATTACTCA CCAGATCCTA ACCGGTGTGA TCATGGGCCG CGATTAAAAA TCTCAATTAT
181 ATTTGGTCTA ATTTAGTTTG GTATTGAGTA AAACAAATTC GGCGCCATGC CCGGGCAAGC
241 GGCCGCACAA GTTTGTACAA AAAAGCAGGC TGAGTATTCA CTACAGTAGT GCATCGATGG
301 AGTCATCACG CAGACTATCT CAGCATGTGC GTAGCACGTC TAGACCTAGG TAGGTTAATT
361 AAGCTTGCAT GCCGGAGGAA ATATGAATTC AGCACTTAAA GATCTTTAGA AGAAAGCAAA

ZmLip 3' UTR v1

421 GCATTTATTA ATACATAACA ATGTCCAGGT AGCCCAGCTG AATTACAATA CGCAACTGCT

ZmLip 3' UTR v1

481 CATAATAATT CAACAAACCC AAGTAGTACA CAACATCCAG AAGCAAATAA AGCCCATACG

ZmLip 3' UTR v1

541 TACCAAAGCC TACACAAGCA GCAACACTCA CTGCCAGTGC CGGTGGGTCT TTAAAGCACA

ZmLip 3' UTR v1

601 CGGGCCTTGA CCACGCGATC CACCTTGAAA CAAACTTGGT AAAATTAAAG CAAACCAGAA

ZmLip 3' UTR v1

661 GCACACACAC GCCAACGCAA CGCTTCTGAT CGCGCGCCCA AGGCCCGGCC GGCCAGAACG

ZmLip 3' UTR v1

721 TACGACGGAC ACGCACACGC TGCGACCGAG CTCTCAAAGG TAGGTCTTGC GACAGTCAAC

ZmLip 3' UTR v1 PhiYFP v3 (with intron)

781 AGCTCTGACA GTTTCTTTCA AGCTCATGTT GTCTCTGTGG TCTGTCACAT CTTTGGAAAG

PhiYFP v3 (with intron)

841 TTTCACATGG TAAGACATAT GATGATACTC TGGAACATGA ACTGGACCTC CACCAATGGG

PhiYFP v3 (with intron)

901 AGTGTTCATC TGGGTGTGGT CAGCCACTAT GAAGTCGCCT TTGCTGCCAG TAATCTCATG

PhiYFP v3 (with intron)

961 ACATATCTTG AAGGCTGACT TGAGACCGTG GTTGGCTTGG TCTCCCCAGA TGTAGAGGCA

PhiYFP v3 (with intron)

1021 GTGGGGAGTG AAGTTGAACT CCAAGTTCTT TCCCAACACG TGACCATCTT TCTTGAAGCC

PhiYFP v3 (with intron)

1081 TTGACCATTG AGTTTGACCC TATTGTAGAC AGACCCATTC TCAAAGGTGA CTTCAGCCCT

PhiYFP v3 (with intron)

1141 AGTCTTGAAG TTGCCATCTC CTTCAAAGGT GATTGTGCGC TCTTGCACAT AGCCATCTGG

PhiYFP v3 (with intron)

1201 CATACAGGAC TTGTAGAAGT CCTTCAACTC TGGACCATAC TTGGCAAAGC ACTGTGCTCC

FIG. 27A

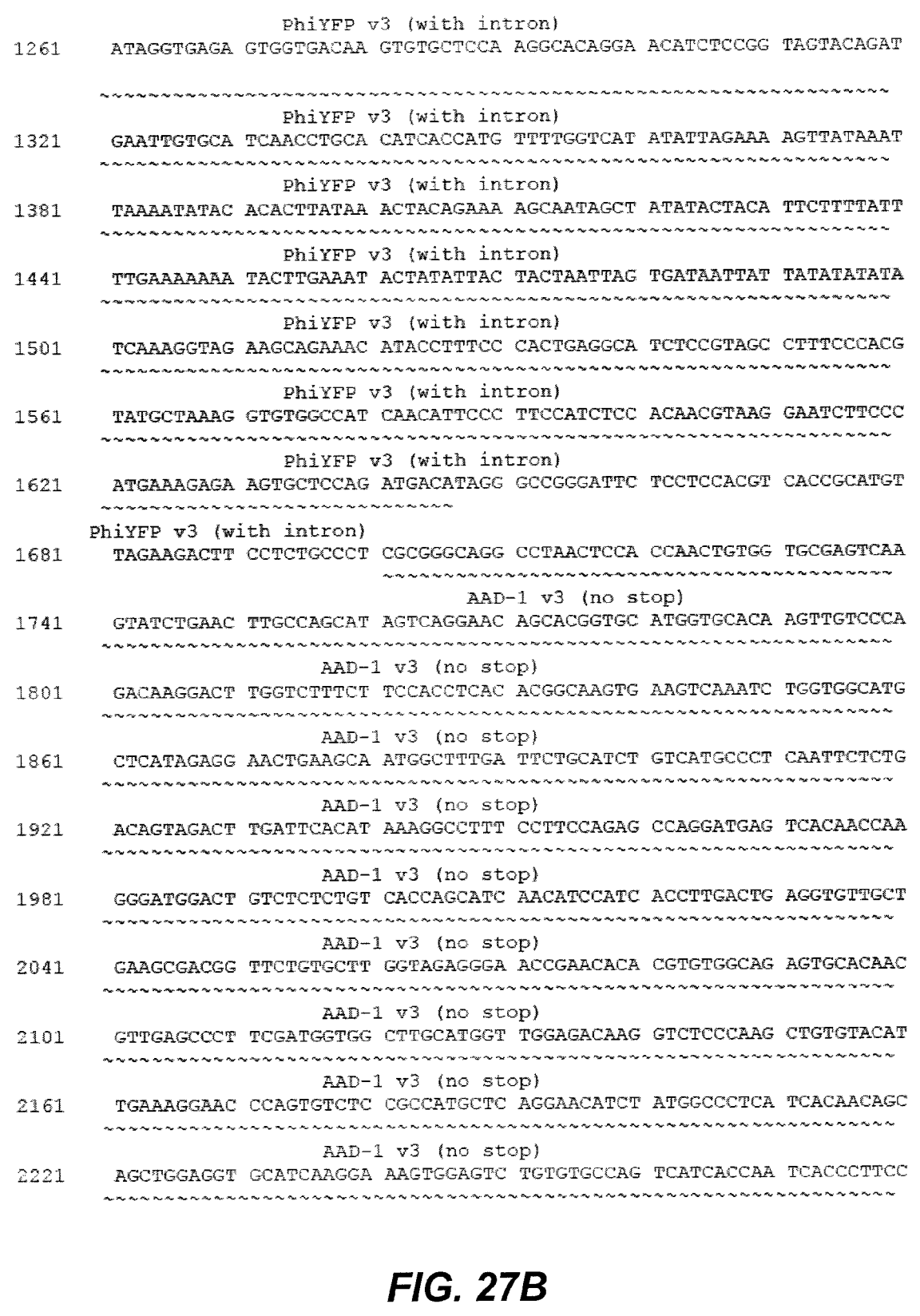

PhiYFP v3 (with intron)
1261 ATAGGTGAGA GTGGTGACAA GTGTGCTCCA AGGCACAGGA ACATCTCCGG TAGTACAGAT PhiYFP v3 (with intron)
1321 GAATTGTGCA TCAACCTGCA CATCACCATG TTTTGGTCAT ATATTAGAAA AGTTATAAAT PhiYFP v3 (with intron)
1381 TAAAATATAC ACACTTATAA ACTACAGAAA AGCAATAGCT ATATACTACA TTCTTTTATT PhiYFP v3 (with intron)
1441 TTGAAAAAAA TACTTGAAAT ACTATATTAC TACTAATTAG TGATAATTAT TATATATATA PhiYFP v3 (with intron)
1501 TCAAAGGTAG AAGCAGAAAC ATACCTTTCC CACTGAGGCA TCTCCGTAGC CTTTCCCACG PhiYFP v3 (with intron)
1561 TATGCTAAAG GTGTGGCCAT CAACATTCCC TTCCATCTCC ACAACGTAAG GAATCTTCCC PhiYFP v3 (with intron)
1621 ATGAAAGAGA AGTGCTCCAG ATGACATAGG GCCGGGATTC TCCTCCACGT CACCGCATGT PhiYFP v3 (with intron)
1681 TAGAAGACTT CCTCTGCCCT CGCGGGCAGG CCTAACTCCA CCAACTGTGG TGCGAGTCAA AAD-1 v3 (no stop)
1741 GTATCTGAAC TTGCCAGCAT AGTCAGGAAC AGCACGGTGC ATGGTGCACA AGTTGTCCCA AAD-1 v3 (no stop)
1801 GACAAGGACT TGGTCTTTCT TCCACCTCAC ACGGCAAGTG AAGTCAAATC TGGTGGCATG AAD-1 v3 (no stop)
1861 CTCATAGAGG AACTGAAGCA ATGGCTTTGA TTCTGCATCT GTCATGCCCT CAATTCTCTG AAD-1 v3 (no stop)
1921 ACAGTAGACT TGATTCACAT AAAGGCCTTT CCTTCCAGAG CCAGGATGAG TCACAACCAA AAD-1 v3 (no stop)
1981 GGGATGGACT GTCTCTCTGT CACCAGCATC AACATCCATC ACCTTGACTG AGGTGTTGCT AAD-1 v3 (no stop)
2041 GAAGCGACGG TTCTGTGCTT GGTAGAGGGA ACCGAACACA CGTGTGGCAG AGTGCACAAC AAD-1 v3 (no stop)
2101 GTTGAGCCCT TCGATGGTGG CTTGCATGGT TGGAGACAAG GTCTCCCAAG CTGTGTACAT AAD-1 v3 (no stop)
2161 TGAAAGGAAC CCAGTGTCTC CGCCATGCTC AGGAACATCT ATGGCCCTCA TCACAACAGC AAD-1 v3 (no stop)
2221 AGCTGGAGGT GCATCAAGGA AAGTGGAGTC TGTGTGCCAG TCATCACCAA TCACCCTTCC

FIG. 27B

```
                        AAD-1 v3 (no stop)
2281  AGACTCATTG GCTTCTCTGC GGATCATCTG AACCTCTGGA TAGCCTTCAA TGCTCTTGAG
      ~~~~~~~~~~~~~~~~~~~~~~~~~~~~~~~~~~~~~~~~~~~~~~~~~~~~~~~~~~~~~~~~
                        AAD-1 v3 (no stop)
2341  AAGAGGCACT GGATCAACTG GTCCAAACCT TCTTGAGAAT GCAATGTGCT GCTCATTGGT
      ~~~~~~~~~~~~~~~~~~~~~~~~~~~~~~~~~~~~~~~~~~~~~~~~~~~~~~~~~~~~~~~~
                        AAD-1 v3 (no stop)
2401  GATTGCTTGG CCAGGAAAGT AGATGACTTG GTAAGTGTGG AAGGCATCCA ATATCTCATT
      ~~~~~~~~~~~~~~~~~~~~~~~~~~~~~~~~~~~~~~~~~~~~~~~~~~~~~~~~~~~~~~~~
                        AAD-1 v3 (no stop)
2461  CCAGGTGCTG TCATCAAGTG GTTCCCTCAA GTCCACTCCA GTGATCTCAG CACCAAGGAC
      ~~~~~~~~~~~~~~~~~~~~~~~~~~~~~~~~~~~~~~~~~~~~~~~~~~~~~~~~~~~~~~~~
                        AAD-1 v3 (no stop)
2521  ACCAGTGAGT GGCTGGACAG CTATTCTCTC AAAGCGTTGG GAGAGAGGGC TGAGGGCAGC
      ~~~~~~~~~~~~~~~~~~~~~~~~~~~~~~~~~~~~~~~~~~~~~~~~~~~~~~~~~~~~~~~~
                        AAD-1 v3 (no stop)
2581  ATGAGCCATG GTGTCGTGTG GATCCCTGCA GAAGTAACAC CAAACAACAG GGTGAGCATC
      ~~~~~~~~~
2641  GACAAAAGAA ACAGTACCAA GCAAATAAAT AGCGTATGAA GGCAGGGCTA AAAAAATCCA
2701  CATATAGCTG CTGCATATGC CATCATCCAA GTATATCAAG ATCGAAATAA TTATAAAACA
2761  TACTTGTTTA TTATAATAGA TAGGTACTCA AGGTTAGAGC ATATGAATAG ATGCTGCATA
2821  TGCCATCATG TATATGCATC AGTAAAACCC ACATCAACAT GTATACCTAT CCTAGATCGA
2881  TATTTCCATC CATCTTAAAC TCGTAACTAT GAAGATGTAT GACACACACA TACAGTTCCA
2941  AAATTAATAA ATACACCAGG TAGTTTGAAA CAGTATTCTA CTCCGATCTA GAACGAATGA
3001  ACGACCGCCC AACCACACCA CATCATCACA ACCAAGCGAA CAAAAAGCAT CTCTGTATAT
3061  GCATCAGTAA AACCCGCATC AACATGTATA CCTATCCTAG ATCGATATTT CCATCCATCA
3121  TCTTCAATTC GTAACTATGA ATATGTATGG CACACACATA CAGATCCAAA ATTAATAAAT
3181  CCACCAGGTA GTTTGAAACA GAATTCTACT CCGATCTAGA ACGACCGCCC AACCAGACCA
3241  CATCATCACA ACCAAGACAA AAAAAAGCAT GAAAAGATGA CCCGACAAAC AAGTGCACGG
3301  CATATATTGA AATAAAGGAA AAGGGCAAAC CAAACCCTAT GCAACGAAAC AAAAAAAATC
3361  ATGAAATCGA TCCCGTCTGC GGAACGGCTA GAGCCATCCC AGGATTCCCC AAAGAGAAAC
3421  ACTGGCAAGT TAGCAATCAG AACGTGTCTG ACGTACAGGT CGCATCCGTG TACGAACGCT
3481  AGCAGCACGG ATCTAACACA AACACGGATC TAACACAAAC ATGAACAGAA GTAGAACTAC
3541  CGGGCCCTAA CCATGCATGG ACCGGAACGC CGATCTAGAG AAGGTAGAGA GGGGGGGGGG
3601  GGGGAGGACG AGCGGCGTAC CTTGAAGCGG AGGTGCCGAC GGGTGGATTT GGGGGAGATC
3661  TGGTTGTGTG TGTGTGCGCT CCGAACAACA CGAGGTTGGG GAGGTACCAA GAGGGTGTGG
                                                         ~~~~~~~~~~~~
                                                          MIn Ubi1P
3721  AGGGGGTGTC TATTTATTAC GGCGGGCGAG GAAGGGAAAG CGAAGGAGCG GTGGGAAAGG
      ~~~~~~~~~~~~~~~~~~~~~~~~~~~~~~~~~~~~~~~~~~~~~~~~~~~~~~~~~~~~~~~~
                           MIn Ubi1P
3781  AATCCCCCGT AGCTGCCGGT GCCGTGAGAG GAGGAGGAGG CCGCCTGCCG TGCCGGCTCA
      ~~~~~~~~~~~~~~~~~~~~~~~~~~~~~~~~~~~~~~~~~~~~~~~~~~~~~~~~~~~~~~~~
                           MIn Ubi1P
3841  CGTCTGCCGC TCCGCCACGC AATTTCTGGA TGCCGACAGC GGAGCAAGTC CAACGGTGGA
      ~~~~~~~~~~~~~~~~~~~~~~~~~~~~~~~~~~~~~~~~~~~~~~~~~~~~~~~~~~~~~~~~
                           MIn Ubi1P
                                          SCBV promoter v2
                                    ~~~~~~~~~~~~~~~~~~~~~~~~~~~~
3901  GCGGAACTCT CGAGAGGGGT CCAGCCGCGG AGTATCGGAA GTTGAAGACA AAGAAGGTCT
      ~~~~~~~~~~~~~~~~~~~~~~~~~~
        MIn Ubi1P
```

*FIG. 27C*

```
                    SCBV promoter v2
     ~~~~~~~~~~~~~~~~~~~~~~~~~~~~~~~~~~~~~~~~~~~~~~~~~~~~~~~~~~~~
3961 TAAATCCTGG CTAGCAACAC TGAACTATGC CAGAAACCAC ATCAAAGCAT ATCGGCAAGC
                    SCBV promoter v2
     ~~~~~~~~~~~~~~~~~~~~~~~~~~~~~~~~~~~~~~~~~~~~~~~~~~~~~~~~~~~~
4021 TTCTTGGCCC ATTATATCCA AAGACCTCAG AGAAAGGTGA GCGAAGGCTC AATTCAGAAG
                    SCBV promoter v2
     ~~~~~~~~~~~~~~~~~~~~~~~~~~~~~~~~~~~~~~~~~~~~~~~~~~~~~~~~~~~~
4081 ATTGGAAGCT GATCAATAGG ATCAAGACAA TGGTGAGAAC GCTTCCAAAT CTCACTATTC
                    SCBV promoter v2
     ~~~~~~~~~~~~~~~~~~~~~~~~~~~~~~~~~~~~~~~~~~~~~~~~~~~~~~~~~~~~
4141 CACCAGAAGA TGCATACATT ATCATTGAAA CAGATGCATG TGCAACTGGA TGGGGAGCAG
                    SCBV promoter v2
     ~~~~~~~~~~~~~~~~~~~~~~~~~~~~~~~~~~~~~~~~~~~~~~~~~~~~~~~~~~~~
4201 TATGCAAGTG GAAGAAAAAC AAGGCAGACC CAAGAAATAC AGAGCAAATC TGTAGGTATG
                    SCBV promoter v2
     ~~~~~~~~~~~~~~~~~~~~~~~~~~~~~~~~~~~~~~~~~~~~~~~~~~~~~~~~~~~~
4261 CCAGTGGAAA ATTTGATAAG CCAAAAGGAA CCTGTGATGC AGAAATCTAT GGGGTTATGA
                    SCBV promoter v2
     ~~~~~~~~~~~~~~~~~~~~~~~~~~~~~~~~~~~~~~~~~~~~~~~~~~~~~~~~~~~~
4321 ATGGCTTAGA AAAGATGAGA TTGTTCTACT TGGACAAAAG AGAGATCACA GTCAGAACTG
                    SCBV promoter v2
     ~~~~~~~~~~~~~~~~~~~~~~~~~~~~~~~~~~~~~~~~~~~~~~~~~~~~~~~~~~~~
4381 ACAGTAGTGC AATCGAAAGG TTCTACAACA AGAGTGCTGA ACACAAGCCT TCTGAGATCA
                    SCBV promoter v2
     ~~~~~~~~~~~~~~~~~~~~~~~~~~~~~~~~~~~~~~~~~~~~~~~~~~~~~~~~~~~~
4441 GATGGATCAG GTTCATGGAC TACATCACTG GTGCAGGACC AGAGATAGTC ATTGAACACA
                    SCBV promoter v2
     ~~~~~~~~~~~~~~~~~~~~~~~~~~~~~~~~~~~~~~~~~~~~~~~~~~~~~~~~~~~~
4501 TAAAAGGGAA GAGCAATGGT TTAGCTGACA TCTTGTCCAG GCTCAAAGCC AAATTAGCTC
                    SCBV promoter v2
     ~~~~~~~~~~~~~~~~~~~~~~~~~~~~~~~~~~~~~~~~~~~~~~~~~~~~~~~~~~~~
4561 AGAATGAACC AACGGAAGAG ATGATCCTGC TTACACAAGC CATAAGGGAA GTAATTCCTT
                    SCBV promoter v2
     ~~~~~~~~~~~~~~~~~~~~~~~~~~~~~~~~~~~~~~~~~~~~~~~~~~~~~~~~~~~~
4621 ATCCAGATCA TCCATACACT GAGCAACTCA GAGAATGGGG AAACAAAATT CTGGATCCAT
                    SCBV promoter v2
     ~~~~~~~~~~~~~~~~~~~~~~~~~~~~~~~~~~~~~~~~~~~~~~~~~~~~~~~~~~~~
4681 TCCCCACATT CAAGAAGGAC ATGTTCGAAA GAACAGAGCA AGCTTTTATG CTAACAGAGG
                    SCBV promoter v2
     ~~~~~~~~~~~~~~~~~~~~~~~~~~~~~~~~~~~~~~~~~~~~~~~~~~~~~~~~~~~~
4741 AACCAGTTCT ACTCTGTGCA TGCAGGAAGC CTGCAATTCA GTTAGTGTCC AGAACATCTG
                    SCBV promoter v2
     ~~~~~~~~~~~~~~~~~~~~~~~~~~~~~~~~~~~~~~~~~~~~~~~~~~~~~~~~~~~~
4801 CCAACCCAGG AAGGAAATTC TTCAAGTGCG CAATGAACAA ATGCCATTGC TGGTACTGGG
                    SCBV promoter v2
     ~~~~~~~~~~~~~~~~~~~~~~~~~~~~~~~~~~~~~~~~~~~~~~~~~~~~~~~~~~~~
4861 CAGATCTCAT TGAAGAACAC ATTCAAGACA GAATTGATGA ATTTCTCAAG AATCTTGAAG
                    SCBV promoter v2
     ~~~~~~~~~~~~~~~~~~~~~~~~~~~~~~~~~~~~~~~~~~~~~~~~~~~~~~~~~~~~
4921 TTCTGAAGAC CGGTGGCGTG CAAACAATGG AGGAGGAACT TATGAAGGAA GTCACCAAGC
```

*FIG. 27D*

```
                         SCBV promoter v2
      ~~~~~~~~~~~~~~~~~~~~~~~~~~~~~~~~~~~~~~~~~~~~~~~~~~~~~~~~~~~~~~~~
4981   TGAAGATAGA AGAGCAGGAG TTCGAGGAAT ACCAGGCCAC ACCAAGGGCT ATGTCGCCAG
                         SCBV promoter v2
      ~~~~~~~~~~~~~~~~~~~~~~~~~~~~~~~~~~~~~~~~~~~~~~~~~~~~~~~~~~~~~~~~
5041   TAGCCGCAGA AGATGTGCTA GATCTCCAAG ACGTAAGCAA TGACGATTGA GGAGGCATTG
                         SCBV promoter v2
      ~~~~~~~~~~~~~~~~~~~~~~~~~~~~~~~~~~~~~~~~~~~~~~~~~~~~~~~~~~~~~~~~
5101   ACGTCAGGGA TGACCGCAGC GGAGAGTACT GGGCCCATTC AGTGGATGCT CCACTGAGTT
                         SCBV promoter v2
      ~~~~~~~~~~~~~~~~~~~~~~~~~~~~~~~~~~~~~~~~~~~~~~~~~~~~~~~~~~~~~~~~
5161   GTATTATTGT GTGCTTTTCG GACAAGTGTG CTGTCCACTT TCTTTTGGCA CCTGTGCCAC
                         SCBV promoter v2
      ~~~~~~~~~~~~~~~~~~~~~~~~~~~~~~~~~~~~~~~~~~~~~~~~~~~~~~~~~~~~~~~~
5221   TTTATTCCTT GTCTGCCACG ATGCCTTTGC TTAGCTTGTA AGCAAGGATC GCAGTGCGTG
                         SCBV promoter v2
      ~~~~~~~~~~~~~~~~~~~~~~~~~~~~~~~~~~~~~~~~~~~~~~~~~~~~~~~~~~~~~~~~
5281   TGTGACACCA CCCCCCTTCC GACGCTCTGC CTATATAAGG CACCGTCTGT AAGCTCTTAC
      SCBV promoter v2
      ~~~~~~~~~~~~~~~~~~~~~~
5341   GATCATCGGT AGTTCACCAA GGCCCGGGGT CGGATCTAGC TGAAGGCTCG ACAAGGCAGT
5401   CCACGGAGGA GCTGATATTT GGTGGACAAG CTGTGGATAG GAGCAACCCT ATCCCTAATA
5461   TACCAGCACC ACCAAGTCAG GGCAATCCCC AGATCACCCC AGCAGATTCG AAGAAGGTAC
5521   AGTACACACA CATGTATATA TGTATGATGT ATCCCTTCGA TCGAAGGCAT GCCTTGGTAT
5581   AATCACTGAG TAGTCATTTT ATTACTTTGT TTTGACAAGT CAGTAGTTCA TCCATTTGTC
5641   CCATTTTTTC AGCTTGGAAG TTTGGTTGCA CTGGCCTTGG TCTAATAACT GAGTAGTCAT
5701   TTTATTACGT TGTTTCGACA AGTCAGTAGC TCATCCATCT GTCCCATTTT TTCAGCTAGG
5761   AAGTTTGGTT GCACTGGCCT TGGACTAATA ACTGATTAGT CATTTTATTA CATTGTTTCG
5821   ACAAGTCAGT AGCTCATCCA TCTGTCCCAT TTTTCAGCTA GGAAGTTCGC GGCCGCACAC
                              8V6 (no stop)
             ~~~~~~~~~~~~~~~~~~~~~~~~~~~~~~~~~~~~~~~~~~~~~~~~~~~~~~~~~~
5881   GACACCATGT CCGCCCGCGA GGTGCACATC GACGTGAACA ACAAGACCGG CCACACCCTC
                          8V6 (no stop)
      ~~~~~~~~~~~~~~~~~~~~~~~~~~~~~~~~~~~~~~~~~~~~~~~~~~~~~~~~~~~~~~~~
5941   CAGCTGGAGG ACAAGACCAA GCTCGACGGC GGCAGGTGGC GCACCTCCCC GACCAACGTG
                          8V6 (no stop)
      ~~~~~~~~~~~~~~~~~~~~~~~~~~~~~~~~~~~~~~~~~~~~~~~~~~~~~~~~~~~~~~~~
6001   GCCAACGACC AGATCAAGAC CTTCGTGGCC GAATCCAACG GCTTCATGAC CGGCACCGAG
                          8V6 (no stop)
      ~~~~~~~~~~~~~~~~~~~~~~~~~~~~~~~~~~~~~~~~~~~~~~~~~~~~~~~~~~~~~~~~
6061   GGCACCATCT ACTACTCCAT CAACGGCGAG GCCGAGATCA GCCTCTACTT CGACAACCCG
                          8V6 (no stop)
      ~~~~~~~~~~~~~~~~~~~~~~~~~~~~~~~~~~~~~~~~~~~~~~~~~~~~~~~~~~~~~~~~
6121   TTCGCCGGCT CCAACAAATA CGACGGCCAC TCCAACAAGT CCCAGTACGA GATCATCACC
                          8V6 (no stop)
      ~~~~~~~~~~~~~~~~~~~~~~~~~~~~~~~~~~~~~~~~~~~~~~~~~~~~~~~~~~~~~~~~
6181   CAGGGCGGCT CCGGCAACCA GTCCCACGTG ACCTACACCA TCCAGACCAC CTCCTCCCGC
    8V6 (no stop)
      ~~~~~~~~~~~~~~~
6241   TACGGCCACA AGTCCGAGGG CAGAGGAAGT CTTCTAACAT GCGGTGACGT GGAGGAGAAT
```

FIG. 27E

```
                         Cry35Ab1 v5
              ~~~~~~~~~~~~~~~~~~~~~~~~~~~~~~~~~~~~~~~~~~~~~~~~~~~~~~~~~~~
6301    CCCGGCCCTA TGCTCGACAC CAACAAGGTG TACGAGATCA GCAACCACGC CAACGGCCTC
                         Cry35Ab1 v5
        ~~~~~~~~~~~~~~~~~~~~~~~~~~~~~~~~~~~~~~~~~~~~~~~~~~~~~~~~~~~~~~~~~
6361    TACGCCGCCA CCTACCTCTC CCTCGACGAC TCCGGCGTGT CCCTCATGAA CAAGAACGAC
                         Cry35Ab1 v5
        ~~~~~~~~~~~~~~~~~~~~~~~~~~~~~~~~~~~~~~~~~~~~~~~~~~~~~~~~~~~~~~~~~
6421    GACGACATCG ACGACTACAA CCTCAAGTGG TTCCTCTTCC CGATCGACGA CGACCAGTAC
                         Cry35Ab1 v5
        ~~~~~~~~~~~~~~~~~~~~~~~~~~~~~~~~~~~~~~~~~~~~~~~~~~~~~~~~~~~~~~~~~
6481    ATCATCACCT CCTACGCCGC CAACAACTGC AAGGTGTGGA ACGTGAACAA CGACAAGATC
                         Cry35Ab1 v5
        ~~~~~~~~~~~~~~~~~~~~~~~~~~~~~~~~~~~~~~~~~~~~~~~~~~~~~~~~~~~~~~~~~
6541    AACGTGTCCA CCTACTCCTC CACCAACTCC ATCCAGAAGT GGCAGATCAA GGCCAACGGC
                         Cry35Ab1 v5
        ~~~~~~~~~~~~~~~~~~~~~~~~~~~~~~~~~~~~~~~~~~~~~~~~~~~~~~~~~~~~~~~~~
6601    TCCTCCTACG TGATCCAGTC CGACAACGGC AAGGTGCTCA CCGCCGGCAC CGGCCAGGCC
                         Cry35Ab1 v5
        ~~~~~~~~~~~~~~~~~~~~~~~~~~~~~~~~~~~~~~~~~~~~~~~~~~~~~~~~~~~~~~~~~
6661    CTCGGCCTCA TCCGCCTCAC CGACGAGTCC TCCAACAACC CGAACCAGCA GTGGAACCTG
                         Cry35Ab1 v5
        ~~~~~~~~~~~~~~~~~~~~~~~~~~~~~~~~~~~~~~~~~~~~~~~~~~~~~~~~~~~~~~~~~
6721    ACGTCCGTGC AGACCATCCA GCTCCCGCAG AAGCCGATCA TCGACACCAA GCTCAAGGAC
                         Cry35Ab1 v5
        ~~~~~~~~~~~~~~~~~~~~~~~~~~~~~~~~~~~~~~~~~~~~~~~~~~~~~~~~~~~~~~~~~
6781    TACCCGAAGT ACTCCCCGAC CGGCAACATC GACAACGGCA CCTCCCCGCA GCTCATGGGC
                         Cry35Ab1 v5
        ~~~~~~~~~~~~~~~~~~~~~~~~~~~~~~~~~~~~~~~~~~~~~~~~~~~~~~~~~~~~~~~~~
6841    TGGACCCTCG TGCCGTGCAT CATGGTGAAC GACCCGAACA TCGACAAGAA CACCCAGATC
                         Cry35Ab1 v5
        ~~~~~~~~~~~~~~~~~~~~~~~~~~~~~~~~~~~~~~~~~~~~~~~~~~~~~~~~~~~~~~~~~
6901    AAGACCACCC CGTACTACAT CCTCAAGAAG TACCAGTACT GGCAGAGGGC CGTGGGCTCC
                         Cry35Ab1 v5
        ~~~~~~~~~~~~~~~~~~~~~~~~~~~~~~~~~~~~~~~~~~~~~~~~~~~~~~~~~~~~~~~~~
6961    AACGTCGCGC TCCGCCCGCA CGAGAAGAAG TCCTACACCT ACGAGTGGGG CACCGAGATC
                         Cry35Ab1 v5
        ~~~~~~~~~~~~~~~~~~~~~~~~~~~~~~~~~~~~~~~~~~~~~~~~~~~~~~~~~~~~~~~~~
7021    GACCAGAAGA CCACCATCAT CAACACCCTC GGCTTCCAGA TCAACATCGA CAGCGGCATG
                         Cry35Ab1 v5
        ~~~~~~~~~~~~~~~~~~~~~~~~~~~~~~~~~~~~~~~~~~~~~~~~~~~~~~~~~~~~~~~~~
7081    AAGTTCGACA TCCCGGAGGT GGGCGGCGGT ACCGACGAGA TCAAGACCCA GCTCAACGAG
                         Cry35Ab1 v5
        ~~~~~~~~~~~~~~~~~~~~~~~~~~~~~~~~~~~~~~~~~~~~~~~~~~~~~~~~~~~~~~~~~
7141    GAGCTCAAGA TCGAGTACTC CCACGAGACG AAGATCATGG AGAAGTACCA GGAGCAGTCC
                         Cry35Ab1 v5
        ~~~~~~~~~~~~~~~~~~~~~~~~~~~~~~~~~~~~~~~~~~~~~~~~~~~~~~~~~~~~~~~~~
7201    GAGATCGACA ACCCGACCGA CCAGTCCATG AACTCCATCG GCTTCCTCAC CATCACCTCC
                         Cry35Ab1 v5
        ~~~~~~~~~~~~~~~~~~~~~~~~~~~~~~~~~~~~~~~~~~~~~~~~~~~~~~~~~~~~~~~~~
7261    CTGGAGCTCT ACCGCTACAA CGGCTCCGAG ATCCGCATCA TGCAGATCCA GACCTCCGAC
```

*FIG. 27F*

```
                 Cry35Ab1 v5
     ~~~~~~~~~~~~~~~~~~~~~~~~~~~~~~~~~~~~~~~~~~~~~~~~~~~~~~~~~~~~
7321 AACGACACCT ACAACGTGAC CTCCTACCCG AACCACCAGC AGGCCCTGCT GTGAGTAGTT
                                 StPinII 3' UTR v2
                      ~~~~~~~~~~~~~~~~~~~~~~~~~~~~~~~~~~~~~~~~~~~~~~~~~~
7381 AGCTTAATCA CCTAGAACCT AGACTTGTCC ATCTTCTGGA TTGGCCAACT TAATTAATGT
                 StPinII 3' UTR v2
     ~~~~~~~~~~~~~~~~~~~~~~~~~~~~~~~~~~~~~~~~~~~~~~~~~~~~~~~~~~~~~~~~~
7441 ATGAAATAAA AGGATGCACA CATAGTGACA TGCTAATCAC TATAATGTGG GCATCAAAGT
                 StPinII 3' UTR v2
     ~~~~~~~~~~~~~~~~~~~~~~~~~~~~~~~~~~~~~~~~~~~~~~~~~~~~~~~~~~~~~~~~~
7501 TGTGTGTTAT GTGTAATTAC TAGTTATCTG AATAAAAGAG AAAGAGATCA TCCATATTTC
                 StPinII 3' UTR v2
     ~~~~~~~~~~~~~~~~~~~~~~~~~~~~~~~~~~~~~~~~~~~~~~~~~~~~~~~~~~~~~~~~~
7561 TTATCCTAAA TGAATGTCAC GTGTCTTTAT AATTCTTTGA TGAACCAGAT GCATTTCATT
                 StPinII 3' UTR v2
     ~~~~~~~~~~~~~~~~~~~~~~~~~~~~~~~~~~~~~~~~~~~~~~~~~~~~~~~~~~~~~~~~~
7621 AACCAAATCC ATATACATAT AAATATTAAT CATATATAAT TAATATCAAT TGGGTTAGCA
      StPinII 3' UTR v2
     ~~~~~~~~~~~~~~~~~~~~~~~~~~~~~
7681 AAACAAATCT AGTCTAGGTG TGTTTTGCTC TAGTGCTAGC CTCGAGGTCG ACTCTGATCA
7741 TGGATGCTAC GTCACGGCAG TACAGGACTA TCATCTTGAA AGTCGATTGA GCATCGAAAC
7801 CCAGCTTTCT TGTACAAAGT GGTTGCGGCC GCTTAATTAA ATTTAAATGT TTGGGGATCC
                                 ZmUbi1 promoter v2
                      ~~~~~~~~~~~~~~~~~~~~~~~~~~~~~~~~~~~~~~~~~~~~~~~~~~
7861 TCTAGAGTCG ACCTGCAGTG CAGCGTGACC CGGTCGTGCC CCTCTCTAGA GATAATGAGC
                 ZmUbi1 promoter v2
     ~~~~~~~~~~~~~~~~~~~~~~~~~~~~~~~~~~~~~~~~~~~~~~~~~~~~~~~~~~~~~~~~~
7921 ATTGCATGTC TAAGTTATAA AAAATTACCA CATATTTTTT TTGTCACACT TGTTTGAAGT
                 ZmUbi1 promoter v2
     ~~~~~~~~~~~~~~~~~~~~~~~~~~~~~~~~~~~~~~~~~~~~~~~~~~~~~~~~~~~~~~~~~
7981 GCAGTTTATC TATCTTTATA CATATATTTA AACTTTACTC TACGAATAAT ATAATCTATA
                 ZmUbi1 promoter v2
     ~~~~~~~~~~~~~~~~~~~~~~~~~~~~~~~~~~~~~~~~~~~~~~~~~~~~~~~~~~~~~~~~~
8041 GTACTACAAT AATATCAGTG TTTTAGAGAA TCATATAAAT GAACAGTTAG ACATGGTCTA
                 ZmUbi1 promoter v2
     ~~~~~~~~~~~~~~~~~~~~~~~~~~~~~~~~~~~~~~~~~~~~~~~~~~~~~~~~~~~~~~~~~
8101 AAGGACAATT GAGTATTTTG ACAACAGGAC TCTACAGTTT TATCTTTTTA GTGTGCATGT
                 ZmUbi1 promoter v2
     ~~~~~~~~~~~~~~~~~~~~~~~~~~~~~~~~~~~~~~~~~~~~~~~~~~~~~~~~~~~~~~~~~
8161 GTTCTCCTTT TTTTTTGCAA ATAGCTTCAC CTATATAATA CTTCATCCAT TTTATTAGTA
                 ZmUbi1 promoter v2
     ~~~~~~~~~~~~~~~~~~~~~~~~~~~~~~~~~~~~~~~~~~~~~~~~~~~~~~~~~~~~~~~~~
8221 CATCCATTTA GGGTTTAGGG TTAATGGTTT TTATAGACTA ATTTTTTTAG TACATCTATT
                 ZmUbi1 promoter v2
     ~~~~~~~~~~~~~~~~~~~~~~~~~~~~~~~~~~~~~~~~~~~~~~~~~~~~~~~~~~~~~~~~~
8281 TTATTCTATT TTAGCCTCTA AATTAAGAAA ACTAAAACTC TATTTTAGTT TTTTTATTTA
                 ZmUbi1 promoter v2
     ~~~~~~~~~~~~~~~~~~~~~~~~~~~~~~~~~~~~~~~~~~~~~~~~~~~~~~~~~~~~~~~~~
8341 ATAGTTTAGA TATAAAATAG AATAAAATAA AGTGACTAAA AATTAAACAA ATACCCTTTA
```

*FIG. 27G*

```
                          ZmUbi1 promoter v2
           ~~~~~~~~~~~~~~~~~~~~~~~~~~~~~~~~~~~~~~~~~~~~~~~~~~~~~~~~~~~~~~
8401       AGAAATTAAA AAAACTAAGG AAACATTTTT CTTGTTTCGA GTAGATAATG CCAGCCTGTT
                          ZmUbi1 promoter v2
           ~~~~~~~~~~~~~~~~~~~~~~~~~~~~~~~~~~~~~~~~~~~~~~~~~~~~~~~~~~~~~~
8461       AAACGCCGTC GACGAGTCTA ACGGACACCA ACCAGCGAAC CAGCAGCGTC GCGTCGGGCC
                          ZmUbi1 promoter v2
           ~~~~~~~~~~~~~~~~~~~~~~~~~~~~~~~~~~~~~~~~~~~~~~~~~~~~~~~~~~~~~~
8521       AAGCGAAGCA GACGGCACGG CATCTCTGTC GCTGCCTCTG GACCCCTCTC GAGAGTTCCG
                          ZmUbi1 promoter v2
           ~~~~~~~~~~~~~~~~~~~~~~~~~~~~~~~~~~~~~~~~~~~~~~~~~~~~~~~~~~~~~~
8581       CTCCACCGTT GGACTTGCTC CGCTGTCGGC ATCCAGAAAT TGCGTGGCGG AGCGGCAGAC
                          ZmUbi1 promoter v2
           ~~~~~~~~~~~~~~~~~~~~~~~~~~~~~~~~~~~~~~~~~~~~~~~~~~~~~~~~~~~~~~
8641       GTGAGCCGGC ACGGCAGGCG GCCTCCTCCT CCTCTCACGG CACCGGCAGC TACGGGGGAT
                          ZmUbi1 promoter v2
           ~~~~~~~~~~~~~~~~~~~~~~~~~~~~~~~~~~~~~~~~~~~~~~~~~~~~~~~~~~~~~~
8701       TCCTTTCCCA CCGCTCCTTC GCTTTCCCTT CCTCGCCCGC CGTAATAAAT AGACACCCCC
                          ZmUbi1 promoter v2
           ~~~~~~~~~~~~~~~~~~~~~~~~~~~~~~~~~~~~~~~~~~~~~~~~~~~~~~~~~~~~~~
8761       TCCACACCCT CTTTCCCCAA CCTCGTGTTG TTCGGAGCGC ACACACACAC AACCAGATCT
                          ZmUbi1 promoter v2
           ~~~~~~~~~~~~~~~~~~~~~~~~~~~~~~~~~~~~~~~~~~~~~~~~~~~~~~~~~~~~~~
8821       CCCCCAAATC CACCCGTCGG CACCTCCGCT TCAAGGTACG CCGCTCGTCC TCCCCCCCCC
                          ZmUbi1 promoter v2
           ~~~~~~~~~~~~~~~~~~~~~~~~~~~~~~~~~~~~~~~~~~~~~~~~~~~~~~~~~~~~~~
8881       CCCCCCTCTC TACCTTCTCT AGATCGGCGT TCCGGTCCAT GCATGGTTAG GGCCCGGTAG
                          ZmUbi1 promoter v2
           ~~~~~~~~~~~~~~~~~~~~~~~~~~~~~~~~~~~~~~~~~~~~~~~~~~~~~~~~~~~~~~
8941       TTCTACTTCT GTTCATGTTT GTGTTAGATC CGTGTTTGTG TTAGATCCGT GCTGCTAGCG
                          ZmUbi1 promoter v2
           ~~~~~~~~~~~~~~~~~~~~~~~~~~~~~~~~~~~~~~~~~~~~~~~~~~~~~~~~~~~~~~
9001       TTCGTACACG GATGCGACCT GTACGTCAGA CACGTTCTGA TTGCTAACTT GCCAGTGTTT
                          ZmUbi1 promoter v2
           ~~~~~~~~~~~~~~~~~~~~~~~~~~~~~~~~~~~~~~~~~~~~~~~~~~~~~~~~~~~~~~
9061       CTCTTTGGGG AATCCTGGGA TGGCTCTAGC CGTTCCGCAG ACGGGATCGA TTTCATGATT
                          ZmUbi1 promoter v2
           ~~~~~~~~~~~~~~~~~~~~~~~~~~~~~~~~~~~~~~~~~~~~~~~~~~~~~~~~~~~~~~
9121       TTTTTTGTTT CGTTGCATAG GGTTTGGTTT GCCCTTTTCC TTTATTTCAA TATATGCCGT
                          ZmUbi1 promoter v2
           ~~~~~~~~~~~~~~~~~~~~~~~~~~~~~~~~~~~~~~~~~~~~~~~~~~~~~~~~~~~~~~
9181       GCACTTGTTT GTCGGGTCAT CTTTTCATGC TTTTTTTTGT CTTGGTTGTG ATGATGTGGT
                          ZmUbi1 promoter v2
           ~~~~~~~~~~~~~~~~~~~~~~~~~~~~~~~~~~~~~~~~~~~~~~~~~~~~~~~~~~~~~~
9241       CTGGTTGGGC GGTCGTTCTA GATCGGAGTA GAATTCTGTT TCAAACTACC TGGTGGATTT
                          ZmUbi1 promoter v2
           ~~~~~~~~~~~~~~~~~~~~~~~~~~~~~~~~~~~~~~~~~~~~~~~~~~~~~~~~~~~~~~
9301       ATTAATTTTG GATCTGTATG TGTGTGCCAT ACATATTCAT AGTTACGAAT TGAAGATGAT
                          ZmUbi1 promoter v2
           ~~~~~~~~~~~~~~~~~~~~~~~~~~~~~~~~~~~~~~~~~~~~~~~~~~~~~~~~~~~~~~
9361       GGATGGAAAT ATCGATCTAG GATAGGTATA CATGTTGATG CGGGTTTTAC TGATGCATAT
```

FIG. 27H

```
                    ZmUbi1 promoter v2
        ~~~~~~~~~~~~~~~~~~~~~~~~~~~~~~~~~~~~~~~~~~~~~~~~~~~~~~~~~~~~
9421    ACAGAGATGC TTTTTGTTCG CTTGGTTGTG ATGATGTGGT GTGGTTGGGC GGTCGTTCAT
                    ZmUbi1 promoter v2
        ~~~~~~~~~~~~~~~~~~~~~~~~~~~~~~~~~~~~~~~~~~~~~~~~~~~~~~~~~~~~
9481    TCGTTCTAGA TCGGAGTAGA ATACTGTTTC AAACTACCTG GTGTATTTAT TAATTTTGGA
                    ZmUbi1 promoter v2
        ~~~~~~~~~~~~~~~~~~~~~~~~~~~~~~~~~~~~~~~~~~~~~~~~~~~~~~~~~~~~
9541    ACTGTATGTG TGTGTCATAC ATCTTCATAG TTACGAGTTT AAGATGGATG GAAATATCGA
                    ZmUbi1 promoter v2
        ~~~~~~~~~~~~~~~~~~~~~~~~~~~~~~~~~~~~~~~~~~~~~~~~~~~~~~~~~~~~
9601    TCTAGGATAG GTATACATGT TGATGTGGGT TTTACTGATG CATATACATG ATGGCATATG
                    ZmUbi1 promoter v2
        ~~~~~~~~~~~~~~~~~~~~~~~~~~~~~~~~~~~~~~~~~~~~~~~~~~~~~~~~~~~~
9661    CAGCATCTAT TCATATGCTC TAACCTTGAG TACCTATCTA TTATAATAAA CAAGTATGTT
                    ZmUbi1 promoter v2
        ~~~~~~~~~~~~~~~~~~~~~~~~~~~~~~~~~~~~~~~~~~~~~~~~~~~~~~~~~~~~
9721    TTATAATTAT TTCGATCTTG ATATACTTGG ATGATGGCAT ATGCAGCAGC TATATGTGGA
                    ZmUbi1 promoter v2
        ~~~~~~~~~~~~~~~~~~~~~~~~~~~~~~~~~~~~~~~~~~~~~~~~~~~~~~~~~~~~
9781    TTTTTTTAGC CCTGCCTTCA TACGCTATTT ATTTGCTTGG TACTGTTTCT TTTGTCGATG
         ZmUbi1 promoter v2                                       PAT v9
        ~~~~~~~~~~~~~~~~~~~~~~~~~~~                                   ~
9841    CTCACCCTGT TGTTTGGTGT TACTTCTGCA GGGTACAGTA GTTAGTTGAC ACGACACCAT
                               PAT v9
        ~~~~~~~~~~~~~~~~~~~~~~~~~~~~~~~~~~~~~~~~~~~~~~~~~~~~~~~~~~~~
9901    GTCTCCGGAG AGGAGACCAG TTGAGATTAG GCCAGCTACA GCAGCTGATA TGGCCGCGGT
                               PAT v9
        ~~~~~~~~~~~~~~~~~~~~~~~~~~~~~~~~~~~~~~~~~~~~~~~~~~~~~~~~~~~~
9961    TTGTGATATC GTTAACCATT ACATTGAGAC GTCTACAGTG AACTTTAGGA CAGAGCCACA
                               PAT v9
        ~~~~~~~~~~~~~~~~~~~~~~~~~~~~~~~~~~~~~~~~~~~~~~~~~~~~~~~~~~~~
10021   AACACCACAA GAGTGGATTG ATGATCTAGA GAGGTTGCAA GATAGATACC CTTGGTTGGT
                               PAT v9
        ~~~~~~~~~~~~~~~~~~~~~~~~~~~~~~~~~~~~~~~~~~~~~~~~~~~~~~~~~~~~
10081   TGCTGAGGTT GAGGGTGTTG TGGCTGGTAT TGCTTACGCT GGGCCCTGGA AGGCTAGGAA
                               PAT v9
        ~~~~~~~~~~~~~~~~~~~~~~~~~~~~~~~~~~~~~~~~~~~~~~~~~~~~~~~~~~~~
10141   CGCTTACGAT TGGACAGTTG AGAGTACTGT TTACGTGTCA CATAGGCATC AAAGGTTGGG
                               PAT v9
        ~~~~~~~~~~~~~~~~~~~~~~~~~~~~~~~~~~~~~~~~~~~~~~~~~~~~~~~~~~~~
10201   CCTAGGATCC ACATTGTACA CACATTTGCT TAAGTCTATG GAGGCGCAAG GTTTTAAGTC
                               PAT v9
        ~~~~~~~~~~~~~~~~~~~~~~~~~~~~~~~~~~~~~~~~~~~~~~~~~~~~~~~~~~~~
10261   TGTGGTTGCT GTTATAGGCC TTCCAAACGA TCCATCTGTT AGGTTGCATG AGGCTTTGGG
                               PAT v9
        ~~~~~~~~~~~~~~~~~~~~~~~~~~~~~~~~~~~~~~~~~~~~~~~~~~~~~~~~~~~~
10321   ATACACAGCC CGTGGTACAT TGCGCGCAGC TGGATACAAG CATGGTGGAT GGCATGATGT
                               PAT v9
        ~~~~~~~~~~~~~~~~~~~~~~~~~~~~~~~~~~~~~~~~~~~~~~~~~~~~~~~~~~~~
10381   TGGTTTTTGG CAAAGGGATT TTGAGTTGCC AGCTCCTCCA AGGCCAGTTA GGCCAGTTAC
```

FIG. 27I

```
       PAT v9                                                    ZmLip 3' UTR v1
       ~~~~~~~~~~~                                                   ~~~~~~~~~~~~~~
10441  CCAGATCTGA CTGAGCTTGA GCTTATGAGC TTATGAGCTT AGAGCTCGGT CGCAGCGTGT
                          ZmLip 3' UTR v1
       ~~~~~~~~~~~~~~~~~~~~~~~~~~~~~~~~~~~~~~~~~~~~~~~~~~~~~~~~~~~~~~~~~
10501  GCGTGTCCGT CGTACGTTCT GGCCGGCCGG GCCTTGGGCG CGCGATCAGA AGCGTTGCGT
                          ZmLip 3' UTR v1
       ~~~~~~~~~~~~~~~~~~~~~~~~~~~~~~~~~~~~~~~~~~~~~~~~~~~~~~~~~~~~~~~~~
10561  TGGCGTGTGT GTGCTTCTGG TTTGCTTTAA TTTTACCAAG TTTGTTTCAA GGTGGATCGC
                          ZmLip 3' UTR v1
       ~~~~~~~~~~~~~~~~~~~~~~~~~~~~~~~~~~~~~~~~~~~~~~~~~~~~~~~~~~~~~~~~~
10621  GTGGTCAAGG CCCGTGTGCT TTAAAGACCC ACCGGCACTG GCAGTGAGTG TTGCTGCTTG
                          ZmLip 3' UTR v1
       ~~~~~~~~~~~~~~~~~~~~~~~~~~~~~~~~~~~~~~~~~~~~~~~~~~~~~~~~~~~~~~~~~
10681  TGTAGGCTTT GGTACGTATG GGCTTTATTT GCTTCTGGAT GTTGTGTACT ACTTGGGTTT
                          ZmLip 3' UTR v1
       ~~~~~~~~~~~~~~~~~~~~~~~~~~~~~~~~~~~~~~~~~~~~~~~~~~~~~~~~~~~~~~~~~
10741  GTTGAATTAT TATGAGCAGT TGCGTATTGT AATTCAGCTG GGCTACCTGG ACATTGTTAT
                ZmLip 3' UTR v1
       ~~~~~~~~~~~~~~~~~~~~~~~~~~~~~~~~~~~~~~~~~~~~
10801  GTATTAATAA ATGCTTTGCT TTCTTCTAAA GATCTTTAAG TGCTTCTAGA GCATGCACAT
10861  AGACACACAC ATCATCTCAT TGATGCTTGG TAATAATTGT CATTAGATTG TTTTTATGCA
10921  TAGATGCACT CGAAATCAGC CAATTTTAGA CAAGTATCAA ACGGATGTGA CTTCAGTACA
10981  TTAAAAACGT CCGCAATGTG TTATTAAGTT GTCTAAGCGT CAATTTGATT TACAATTGAA
11041  TATATCCTGC CCCAGCCAGC CAACAGCTCG ATTTACAATT GAATATATCC TGCCGGCCGG
11101  CCCACGCGTG TCGAGGAATT CTGATCTGGC CCCCATTTGG ACGTGAATGT AGACACGTCG
11161  AAATAAAGAT TTCCGAATTA GAATAATTTG TTTATTGCTT TCGCCTATAA ATACGACGGA
11221  TCGTAATTTG TCGTTTTATC AAAATGTACT TTCATTTTAT AATAACGCTG CGGACATCTA
11281  CATTTTTGAA TTGAAAAAAA ATTGGTAATT ACTCTTTCTT TTTCTCCATA TTGACCATCA
11341  TACTCATTGC TGATCCATGT AGATTTCCCG GACATGAAGC CATTTACAAT TGAATATATC
11401  CTGCCG
```

*FIG. 27J*

| Level | | | Mean |
|---|---|---|---|
| 108717 | A | | 82.50000 |
| 108718 | | B | 28.08333 |
| 105818 | | B | 23.52500 |
| 108719 | | B | -3.00000 |
| 105748 | | B | -6.50000 |
| 108720 | | B | -6.70000 |

| Level | | | Mean |
|---|---|---|---|
| 108717 | A | | 82.50000 |
| 108718 | | B | 28.08333 |
| 105818 | | B | 23.52500 |
| 108719 | | B | -3.00000 |
| 105748 | | B | -6.50000 |
| 108720 | | B | -6.70000 |

| Level | | | Mean |
|---|---|---|---|
| 108717 | A | | 229.97704 |
| 108718 | A | | 164.67868 |
| 105818 | | B | 24.20925 |
| 108720 | | B | 8.36888 |
| 108719 | | B | 1.99869 |
| 105748 | | B | 0.98761 |

SEQ ID NO: 51: yellow fluorescent protein from Phialidium sp. SL-2003 (PhiYFP; 234 a.a.; GenBank: AAR85349.1):
MSSGALLFHG KIPYVVEMEG NVDGHTFSIR GKGYGDASVG KVDAQFICTT
GDVPVPWSTL VTTLTYGAQC FAKYGPELKD FYKSCMPEGY VQERTITFEG
DGVFKTRAEV TFENGSVYNR VKLNGQGFKK DGHVLGKNLE FNFTPHCLYI
WGDQANHGLK SAFKIMHEIT GSKEDFIVAD HTQMNTPIGG GPVHVPEYHH
ITYHVTLSKD VTDHRDNMSL VETVRAVDCR KTYL SEQ ID NO: 52: PhiYFPv3; 234 a.a.

MSSGALLFHG KIPYVVEMEG NVDGHTFSIR GKGYGDASVG KVDAQFICTT
GDVPVPWSTL VTTLTYGAQC FAKYGPELKD FYKSCMPDGY VQERTITFEG
DGNFKTRAEV TFENGSVYNR VKLNGQGFKK DGHVLGKNLE FNFTPHCLYI
WGDQANHGLK SAFKICHEIT GSKGDFIVAD HTQMNTPIGG GPVHVPEYHH
MSYHVKLSKD VTDHRDNMSL KETVRAVDCR KTYL

FIG. 29

| | | |
|---|---|---|
| 108708 A | | 328.3276 |
| 108709 A | | 267.6876 |
| 108707 | B | 57.63336 |
| 108706 | B | 52.6654 |
| 101556 | B | 49.75972 |
| 108715 | B | 10.63202 |
| 108716 | B | 0 |

Levels not connected by same letter are significantly different.

| | | | | |
|---|---|---|---|---|
| 108708 | A | | | 31.02019 |
| 108709 | B | | | 23.68044 |
| 108706 | | C | | 9.966029 |
| 108707 | | C | | 8.0728 |
| 101556 | | C | | 6.954422 |
| 108716 | | C | D | 1.01158 |
| 108715 | | | D | 0.767854 |

| Level | | | | Mean |
|---|---|---|---|---|
| 108709 | A | | | 282.22909 |
| 108708 | | B | | 228.17205 |
| 108716 | A | B | C | 213.97739 |
| 108715 | | | C | 166.52102 |
| 108706 | | | C | 151.27776 |
| 108707 | | | C | 143.22297 |
| 101556 | | | D | 0.00000 |

Levels not connected by same letter are significantly different.

| | | | |
|---|---|---|---|
| 108709 | A | | 3.14136 |
| 108716 | A | | 3.0266 |
| 108715 | A | | 2.949466 |
| 108708 | A | | 2.851752 |
| 108707 | B | | 0.784242 |
| 108706 | B | C | 0.647211 |
| 101556 | | C | 0 |

| Level | | | | | Mean |
|---|---|---|---|---|---|
| 108716 | A | | | | 1795.4332 |
| 108708 | A | B | | | 1574.8654 |
| 108709 | | B | C | | 1437.2658 |
| 108707 | | | C | | 1417.0101 |
| 108715 | | | C | | 1325.8135 |
| 101556 | | | | D | 856.5800 |
| 108706 | | | | D | 710.8802 |

Levels not connected by same letter are significantly different.

| | | | | | |
|---|---|---|---|---|---|
| 108716 | A | | | | 2.9338 |
| 101556 | B | | | | 1.936933 |
| 108708 | B | C | | | 1.752869 |
| 108707 | | C | D | | 1.368713 |
| 108706 | | | D | E | 1.333686 |
| 108715 | | | D | E | 1.11043 |
| 108709 | | | | E | 0.937108 |

| Level | | Mean |
|---|---|---|
| 108708 | A | 105.53451 |
| 108709 | A | 89.43307 |
| 108707 | A | 81.80872 |
| 108706 | A B | 71.76678 |
| 101556 | A B | 49.58332 |
| 108716 | A B | 23.01201 |
| 108715 | B | 19.94290 |

Levels not connected by same letter are significantly different.

| Level | | | | Mean |
|---|---|---|---|---|
| 108709 | A | | | 206.13021 |
| 108715 | A | B | | 153.06273 |
| 108716 | A | B | | 138.02009 |
| 108708 | | B | | 125.00936 |
| 108706 | | B | | 109.63065 |
| 108707 | | B | | 98.24549 |
| 101556 | | | C | 0.00000 |

Levels not connected by same letter are significantly different.

| Level | | | | | Mean |
|---|---|---|---|---|---|
| 108716 | A | | | | 1002.8448 |
| 101556 | | B | | | 715.1248 |
| 108706 | | B | C | | 666.1088 |
| 108707 | | | C | D | 597.8005 |
| 108715 | | | C | D | 578.7276 |
| 108708 | | | C | D | 574.1088 |
| 108709 | | | | D | 530.3379 |

Levels not connected by same letter are significantly different.

| Level | | Mean |
|---|---|---|
| 108706 | A | 91.380952 |
| 108708 | A B | 63.222222 |
| 108707 | A B | 49.185185 |
| 108709 | B C | 43.600000 |
| 101556 | B C | 21.666667 |
| 108715 | C | 3.000000 |
| 108716 | B C | 0.400000 |

| Level | | | | | Mean |
|---|---|---|---|---|---|
| 108709 | A | | | | 91.200000 |
| 108716 | | B | C | | 46.600000 |
| 108715 | | B | | | 42.766667 |
| 108708 | | B | | | 40.629630 |
| 108707 | | | C | D | 16.814815 |
| 108706 | | | | D | 5.523810 |
| 101556 | | | | D | 1.066667 |

| Level | | | | | Mean |
|---|---|---|---|---|---|
| 108716 | A | | | | 197.80000 |
| 108709 | A | B | | | 178.00000 |
| 108715 | A | B | C | | 173.30000 |
| 101556 | | B | C | D | 165.40000 |
| 108708 | | | C | D | 158.33333 |
| 108706 | | | | D | 156.71429 |
| 108707 | | | | D | 153.44444 |

| Level | | Mean |
|---|---|---|
| 108717 | A | 2.6770370 |
| 105818 | A B | 2.4213333 |
| 108718 | A B | 2.2554545 |
| 108720 | B C | 1.9048980 |
| 108719 | C | 1.6506329 |
| 105748 | D | 0.0000000 |

| Level | | Mean |
|---|---|---|
| 108717 | A | 2044.7248 |
| 108718 | B | 719.1750 |
| 105818 | B C | 596.9441 |
| 108719 | C | 66.9930 |
| 105748 | B C | 0.0000 |
| 108720 | C | 0.0000 |

| Level | | Mean |
|---|---|---|
| 108717 | A | 2.6842593 |
| 108718 | B | 2.0268182 |
| 105818 | A B | 1.9756667 |
| 108719 | B | 1.8015190 |
| 108720 | B | 1.4540816 |
| 105748 | C | 0.0000000 |

| Level | | | | Mean |
|---|---|---|---|---|
| 108717 | A | | | 5763.8761 |
| 108718 | | B | | 2379.1465 |
| 105818 | | B | | 2237.5350 |
| 108720 | | | C | 315.9063 |
| 108719 | | | C | 34.4708 |
| 105748 | | | C | 0.0000 |

| Level | | Mean |
|---|---|---|
| 105748 | A | 3.5986364 |
| 108717 | A | 2.7827778 |
| 108718 | B | 1.9533333 |
| 108719 | B | 1.8054430 |
| 108720 | B | 1.4918367 |
| 105818 | C | 0.0000000 |

| Level | | | Mean |
|---|---|---|---|
| 105748 | A | | 1420.6883 |
| 108717 | A | B | 1154.0353 |
| 108718 | | B C | 706.0426 |
| 108720 | | C | 381.0429 |
| 108719 | | C | 283.5958 |
| 105818 | | C | 251.6821 |

| Level | | Mean |
|---|---|---|
| 108717 | A | 3.7442593 |
| 108718 | A | 3.2030303 |
| 108720 | B | 2.1365306 |
| 108719 | B | 1.9309302 |
| 105818 | C | 1.1190000 |
| 105748 | D | 0.0000000 |

Levels not connected by same letter are significantly different.

| Level | | Mean |
|---|---|---|
| 108717 | A | 635.82520 |
| 105818 | B | 283.54176 |
| 108718 | C | 90.97016 |
| 108719 | C | 4.91214 |
| 105748 | C | 0.00000 |
| 108720 | C | 0.00000 |

| Level | | Mean |
|---|---|---|
| 105748 | A | 1.5627273 |
| 108717 | A | 1.4614815 |
| 108718 | B | 1.0131818 |
| 108720 | B | 0.9251020 |
| 108719 | C | 0.5496203 |
| 105818 | D | 0.0706667 |

| Level | | Mean |
|---|---|---|
| 105748 | A | 1033.4667 |
| 108719 | B | 169.8439 |
| 108717 | B | 136.1815 |
| 108718 | B | 119.0613 |
| 105818 | B | 27.5133 |
| 108720 | B | 22.4840 |

| Level | | Mean |
|---|---|---|
| 108717 | A | 1544.6963 |
| 105818 | A | 1323.8000 |
| 108718 | B | 802.5000 |
| 105748 | C | 80.8917 |
| 108719 | C | 46.4927 |
| 108720 | C | 0.0000 |

| Level | | Mean |
|---|---|---|
| 108717 | A | 1089.1778 |
| 108718 | A | 769.8065 |
| 105818 | B | 246.0533 |
| 105748 | B | 0.0000 |
| 108719 | B | 0.0000 |
| 108720 | B | 0.0000 |

| Level | | Mean |
|---|---|---|
| 108717 | A | 106.08519 |
| 105818 | A | 90.74667 |
| 108718 | A | 88.80323 |
| 105748 | B | 0.00000 |
| 108719 | B | 0.00000 |
| 108720 | B | 0.00000 |

| Level | | Mean |
|---|---|---|
| 105748 | A | 2589.6333 |
| 108718 | B | 1721.9581 |
| 108717 | B | 1305.2741 |
| 108719 | C | 438.8829 |
| 105818 | C | 43.6267 |
| 108720 | C | 37.4400 |

Levels not connected by same letter are significantly different.

| Level | Mean |
|---|---|
| 105818 A | 1803.9867 |
| 108717 A | 1642.4370 |
| 108718 A B | 1279.1677 |
| 108719 B | 869.0707 |
| 105748 C | 244.4083 |
| 108720 C | 0.0000 |

Levels not connected by same letter are significantly different.

| Level | | | | Mean |
|---|---|---|---|---|
| 108717 | A | | | 9285.7370 |
| 108718 | | B | | 7544.7484 |
| 105818 | A | B | | 7258.1533 |
| 108719 | | | C | 950.5341 |
| 105748 | | | C | 422.4500 |
| 108720 | | | C | 247.9240 |

Levels not connected by same letter are significantly different.

| Level | | Mean |
|---|---|---|
| 108717 | A | 441.10741 |
| 105818 | A | 373.34667 |
| 108718 | A | 348.44839 |
| 108719 | B | 83.04634 |
| 108720 | B | 71.80800 |
| 105748 | B | 0.00000 |

Levels not connected by same letter are significantly different.

METHOD AND CONSTRUCT FOR SYNTHETIC BIDIRECTIONAL SCBV PLANT PROMOTER

CROSS-REFERENCE TO RELATED APPLICATIONS

This application claims priority under 35 U.S.C. §119 to U.S. Provisional Patent Application Ser. No. 61/582,148 filed Dec. 30, 2011, which application is hereby incorporated by reference in its entirety. This application also claims priority to U.S. Provisional Patent Application Ser. No. 61/641,956 filed May 3, 2012, which application is hereby incorporated by reference in its entirety.

TECHNICAL FIELD

This invention is generally related to the field of plant molecular biology, and more specifically the field of stable expression of multiple genes in transgenic plants.

BACKGROUND

Many plant species are capable of being transformed with transgenes from other species to introduce agronomically desirable traits or characteristics, for example, improving nutritional value quality, increasing yield, conferring pest or disease resistance, increasing drought and stress tolerance, improving horticultural qualities (such as pigmentation and growth), imparting herbicide resistance, enabling the production of industrially useful compounds and/or materials from the plant, and/or enabling the production of pharmaceuticals. The introduction of transgenes into plant cells and the subsequent recovery of fertile transgenic plants that contain a stably integrated copy of the transgene can be used to produce transgenic plants that possess the desirable traits.

Control and regulation of gene expression can occur through numerous mechanisms. Transcription initiation of a gene is a predominant controlling mechanism of gene expression. Initiation of transcription is generally controlled by polynucleotide sequences located in the 5'-flanking or upstream region of the transcribed gene. These sequences are collectively referred to as promoters. Promoters generally contain signals for RNA polymerase to begin transcription so that messenger RNA (mRNA) can be produced. Mature mRNA is translated by ribosome, thereby synthesizing proteins. DNA-binding proteins interact specifically with promoter DNA sequences to promote the formation of a transcriptional complex and initiate the gene expression process. There are a variety of eukaryotic promoters isolated and characterized from plants that are functional for driving the expression of a transgene in plants. Promoters that affect gene expression in response to environmental stimuli, nutrient availability, or adverse conditions including heat shock, anaerobiosis, or the presence of heavy metals have been isolated and characterized. There are also promoters that control gene expression during development or in a tissue, or organ specific fashion. In addition, prokaryotic promoters isolated from bacteria and virus have been isolated and characterized that are functional for driving the expression of a transgene in plants.

A typical eukaryotic promoter consists of a minimal promoter and other cis-elements. The minimal promoter is essentially a TATA box region where RNA polymerase II (polII), TATA-binding protein (TBP), and TBP-associated factors (TAFs) may bind to initiate transcription. However in most instances, sequence elements other than the TATA motif are required for accurate transcription. Such sequence elements (e.g., enhancers) have been found to elevate the overall level of expression of the nearby genes, often in a position- and/or orientation-independent manner. Other sequences near the transcription start site (e.g., INR sequences) of some polII genes may provide an alternate binding site for factors that also contribute to transcriptional activation, even alternatively providing the core promoter binding sites for transcription in promoters that lack functional TATA elements. See e.g., Zenzie-Gregory et al. (1992) *J. Biol. Chem.* 267: 2823-30.

Other gene regulatory elements include sequences that interact with specific DNA-binding factors. These sequence motifs are sometimes referred to as cis-elements, and are usually position- and orientation-dependent, though they may be found 5' or 3' to a gene's coding sequence, or in an intron. Such cis-elements, to which tissue-specific or development-specific transcription factors bind, individually or in combination, may determine the spatiotemporal expression pattern of a promoter at the transcriptional level. The arrangement of upstream cis-elements, followed by a minimal promoter, typically establishes the polarity of a particular promoter. Promoters in plants that have been cloned and widely used for both basic research and biotechnological application are generally unidirectional, directing only one gene that has been fused at its 3' end (i.e., downstream). See, for example, Xie et al. (2001) *Nat. Biotechnol.* 19(7):677-9; U.S. Pat. No. 6,388,170.

Many cis-elements (or "upstream regulatory sequences") have been identified in plant promoters. These cis-elements vary widely in the type of control they exert on operably linked genes. Some elements act to increase the transcription of operably linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al. (1989) *Proc. Natl. Acad. Sci. USA* 86:3219-23. The type of control of specific promoter elements is typically an intrinsic quality of the promoter; i.e., a heterologous gene under the control of such a promoter is likely to be expressed according to the control of the native gene from which the promoter element was isolated. These elements also typically may be exchanged with other elements and maintain their characteristic intrinsic control over gene expression.

It is often necessary to introduce multiple genes into plants for metabolic engineering and trait stacking, which genes are frequently controlled by identical or homologous promoters. However, homology-based gene silencing (HBGS) is likely to arise when multiple introduced transgenes have homologous promoters driving them. See, e.g., Mol et al. (1989) *Plant Mol. Biol.* 13:287-94. HBGS has been reported to occur extensively in transgenic plants. See, e.g., Vaucheret and Fagard (2001) *Trends Genet.* 17:29-35. Several mechanisms have been suggested to explain the phenomena of HBGS, all of which include the feature that sequence homology in the promoter triggers cellular recognition mechanisms that result in silencing of the repeated genes. See, e.g., Matzke and Matzke (1995) *Plant Physiol.* 107:679-85; Meyer and Saedler (1996) *Ann. Rev. Plant Physiol. Plant Mol. Biol.* 47:23-48; Fire (1999) *Trends Genet.* 15:358-63; Hamilton and Baulcombe (1999) *Science* 286:950-2; and Steimer et al. (2000) *Plant Cell* 12:1165-78.

Strategies to avoid HBGS in transgenic plants frequently involve the development of synthetic promoters that are functionally equivalent but have minimal sequence homology. When such synthetic promoters are used for expressing transgenes in crop plants, they may aid in avoiding or reducing HBGS. See, e.g., Mourrain et al. (2007) *Planta* 225(2):365-79; Bhullar et al. (2003) *Plant Physiol.* 132:988-98. Such promoters can be generated by introducing known cis-elements in a novel or synthetic stretch of DNA, or alternatively by "domain swapping," wherein domains of one promoter are replaced with functionally equivalent domains from other heterologous promoters.

Thus, there remains a need for constructs and methods for stable expression of multiple transgenes effectively with minimum risk for recombination or loss of transgenes through breeding or multiple generations in transgenic plants.

DISCLOSURE

Described herein are particular synthetic promoters comprising a Ubi1 minimal promoter. In embodiments, a synthetic promoter comprising a Ubi1 minimal promoter further comprises at least one sequence element of a SCBV promoter or functional equivalent thereof. In some examples, such a synthetic promoter (a "synthetic SCBV promoter") can be a promoter that is able to control transcription of an operably linked nucleotide sequence in a plant cell. In other examples, a synthetic SCBV promoter may be a synthetic bidirectional SCBV promoter, for example, a nucleic acid comprising a minimal Ubi1 promoter element nucleotide sequences oriented in the opposite direction with respect to the SCBV promoter elements that is able to control transcription in a plant cell of two operably linked nucleotide sequences that flank the promoter. Additional elements that may be engineered to be included in a synthetic SCBV bidirectional promoter include introns (e.g., an alcohol dehydrogenase (ADH) intron), exons, and/or all or part of an upstream promoter region. In certain examples, a synthetic bidirectional promoter may comprise more than one of any of the foregoing.

Particular embodiments of the invention include cells (e.g., plant cells) comprising a synthetic SCBV promoter or functional equivalent thereof. For example, specific embodiments may include a cell comprising a synthetic bidirectional SCBV promoter or functional equivalent thereof. Plant cells according to particular embodiments may be present in a cell culture, a tissue, a plant part, and/or a whole plant. Thus, a plant (e.g., a monocot or dicot) comprising a cell having a synthetic SCBV promoter or functional equivalent thereof are included in some embodiments.

Other embodiments of the invention include a means for initiating transcription of two operably linked nucleotide sequences of interest. Means for initiating transcription of two operably linked nucleotide sequences of interest include the synthetic bidirectional SCBV promoter of SEQ ID NO: 5.

Also provided are constructs and methods for expressing multiple genes in plant cells and/or plant tissues. The constructs provided comprise at least one bidirectional promoter linked to multiple gene expression cassettes, wherein the bidirectional promoter comprises a functional promoter nucleotide sequence from Sugar Cane Bacilliform Virus (SCBV) promoter. In some embodiments, the constructs and methods provided employs a bidirectional promoter based on a minimal core promoter element from a *Zea mays* Ubiquitin-1 gene, or a functional equivalent thereof, and nucleotide sequence elements from a Sugar Cane Bacilliform Virus promoter. In some embodiments, the constructs and methods provided allow expression of genes between three and twenty.

In one aspect, provided is a synthetic polynucleotide comprising a minimal core promoter element from an Ubiquitin-1 gene of *Zea mays* or *Zea luxurians* and a functional promoter nucleotide sequence from a Sugar Cane Bacilliform Virus promoter. In one embodiment, the minimal core promoter element comprises a polynucleotide sequence that is at least 65%, 70%, 75%, 80%, 85%, 90%, 95%, or 100% identical to SEQ ID NO: 1 or its complement. In a further or alternative embodiment, the minimal core promoter element comprises a polynucleotide sequence selected from the group consisting of SEQ ID NOs: 1 and 16-40. In a further embodiment, the minimal core promoter element comprises SEQ ID NO: 1 or its complement. In a further embodiment, the minimal core promoter element consists essentially of SEQ ID NO: 1 or its complement. In another embodiment, the synthetic polynucleotide provided further comprises an exon from an Ubiquitin-1 gene and an intron from an Ubiquitin-1 gene. In a further embodiment, the exon is from an Ubiquitin-1 gene of *Zea mays* or *Zea luxurians*. In another embodiment, the synthetic polynucleotide provided further comprises an intron from an alcohol dehydrogenase gene. In another embodiment, the synthetic polynucleotide provided further comprises an upstream regulatory sequence from the Sugar Cane Bacilliform Virus promoter. In another embodiment, the functional promoter nucleotide sequence from a Sugar Cane Bacilliform Virus promoter and the alcohol dehydrogenase gene a polynucleotide sequence that is at least 65%, 70%, 75%, 80%, 85%, 90%, 95%, or 100% identical to SEQ ID NO: 6 or its complement. In a further or alternative embodiment, the functional promoter nucleotide sequence from a Sugar Cane Bacilliform Virus promoter and the alcohol dehydrogenase gene comprises SEQ ID NO: 6 its complement. In a further embodiment, the functional promoter nucleotide sequence from a Sugar Cane Bacilliform Virus promoter and the alcohol dehydrogenase gene consists essentially of SEQ ID NO: 6 or its complement.

In one embodiment, the synthetic polynucleotide provided further comprises at least one element selected from a list comprising an upstream regulatory sequence (URS), an enhancer element, an exon, an intron, a transcription start site, a TATA box, a heat shock consensus element, and a translation START and/or STOP nucleotide sequence. In another embodiment, the synthetic polynucleotide provided further comprises an element selected from the group consisting of an upstream regulatory sequence (URS), an enhancer element, an exon, an intron, a transcription start site, a TATA box, a heat shock consensus element, a translation START and/or STOP nucleotide sequence, and combinations thereof. In another embodiment, the synthetic polynucleotide provided further comprises a nucleotide sequence of interest operably linked to the minimal core promoter element. In another embodiment, the minimal core promoter element from a *Zea mays* Ubiquitin-1 gene and the functional promoter nucleotide sequence from a Sugar Cane Bacilliform Virus promoter are in reverse complimentary orientation with respect to each other in the polynucleotide.

In another embodiment, the synthetic polynucleotide provided comprises an exon from an Ubiquitin-1 gene, an intron from an Ubiquitin-1 gene, and an intron from an alcohol dehydrogenase gene. In a further or alternative embodiment, the synthetic polynucleotide provided comprises a second coding nucleotide sequence of interest operably linked to the functional promoter nucleotide sequence from a Sugar Cane Bacilliform Virus promoter. In a further embodiment, the synthetic polynucleotide provided comprises a polynucleotide sequence that is at least 65%, 70%, 75%, 80%, 85%, 90%, 95%, or 100% identical to SEQ ID NO: 5 or its complement. In a further embodiment, the synthetic polynucleotide provided comprises SEQ ID NO: 5 or its complement. In a further embodiment, the synthetic polynucleotide provided consists essentially of SEQ ID NO: 5 or its complement. In a further embodiment, the exon or intron is from an Ubiquitin-1 gene of *Zea mays* or *Zea luxurians.*

In a further embodiment, the synthetic polynucleotide provided comprises a first coding nucleotide sequence of interest operably linked to the minimal core promoter element from a *Zea mays* Ubiquitin-1 gene. In another further embodiment, the synthetic polynucleotide provided comprises a second coding nucleotide sequence of interest operably linked to the functional promoter nucleotide sequence from a Sugar Cane Bacilliform Virus promoter.

In another aspect, provided is a method for producing a transgenic cell, the method comprising transforming the cell with the polynucleotide provided herein. In one embodiment, the cell is a plant cell. In another aspect, provided is a plant cell comprising the polynucleotide provided herein. In another aspect, provided is a plant comprising the plant cell provided herein.

In another aspect, provided is a method for expressing a nucleotide sequence of interest in a plant cell, the method comprising introducing into the plant cell the nucleotide sequence of interest operably linked to a means for initiating transcription of two operably linked nucleotide sequences of interest. In one embodiment, the method provided comprises introducing into the plant cell a nucleic acid comprising (a) the nucleotide sequence of interest operably linked to the means for initiating transcription of two operably linked nucleotide sequences of interest; and (b) a second nucleotide sequence of interest operably linked to the means for initiating transcription of two operably linked nucleotide sequences of interest.

In one embodiment, the means for initiating transcription of two operably linked nucleotide sequences of interest comprises SEQ ID NO: 5 or its complement. In another embodiment, the means for initiating transcription of two operably linked nucleotide sequences of interest comprises SEQ ID NO: 5. In another embodiment, the means for initiating transcription of two operably linked nucleotide sequences of interest comprises the reverse complement of SEQ ID NO: 5. In another embodiment, the nucleic acid is introduced into the plant cell so as to target to a predetermined site in the DNA of the plant cell the nucleotide sequence of interest operably linked to the means for initiating transcription of two operably linked nucleotide sequences of interest. In a further or alternative embodiment, the nucleotide sequence of interest operably linked to the means for initiating transcription of two operably linked nucleotide sequences of interest is targeted to the predetermined site utilizing Zinc finger nuclease-mediated recombination.

In some embodiments, the exon is from an Ubiquitin-1 gene of a *Zea* spp. In some embodiments, the intron is from an Ubiquitin-1 gene of a *Zea* spp. In some embodiments, the *Zea* spp. is *Zea mays* or *Zea luxurians.*

In another aspect, provided is a nucleic acid construct for expressing multiple genes in plant cells and/or tissues. The nucleic acid construct comprises (a) a bidirectional promoter, wherein the bidirectional promoter comprises a functional promoter nucleotide sequence from Sugar Cane Bacilliform Virus (SCBV) promoter; and (b) two gene expression cassettes on opposite ends of the bidirectional promoter; wherein at least one of the gene expression cassettes comprises two or more genes linked via a translation switch.

In one embodiment, the bidirectional promoter comprises at least one enhancer. In another embodiment, the bidirectional promoter does not comprise an enhancer. In another embodiment, the nucleic acid construct comprises a binary vector for *Agrobacterium*-mediated transformation. In one embodiment, the bidirectional promoter comprises an element selected from the group consisting of an upstream regulatory sequence (URS), an enhancer element, an exon, an intron, a transcription start site, a TATA box, a heat shock consensus element, and combinations thereof. In another embodiment, the bidirectional promoter comprises a minimal core promoter element from an Ubiquitin-1 gene of *Zea mays* or *Zea luxurians*. In another embodiment, the core promoter element from an Ubiquitin-1 gene and the promoter nucleotide sequence from Sugar Cane Bacilliform Virus (SCBV) promoter are in reverse complimentary orientation with respect to each other. In a further or alternative embodiment, the minimal core promoter element comprises a polynucleotide sequence at least 65%, 70%, 75%, 80%, 85%, 90%, 95%, or 100% identical to SEQ ID NO: 1 or its complement. In a further or alternative embodiment, the minimal core promoter element comprises a polynucleotide sequence selected from the group consisting of SEQ ID NOs: 1 and 16-40. In a further embodiment, the minimal core promoter element comprises a polynucleotide sequence selected from the group consisting of SEQ ID NOs: 1 and 16-35. In a further embodiment, the minimal core promoter element comprises a polynucleotide sequence selected from the group consisting of SEQ ID NOs: 1 and 16-30. In a further embodiment, the minimal core promoter element comprises a polynucleotide sequence selected from the group consisting of SEQ ID NOs: 1 and 16-25. In a further embodiment, the minimal core promoter element comprises a polynucleotide sequence selected from the group consisting of SEQ ID NOs: 1 and 16-20. In a further embodiment, the minimal core promoter element comprises a polynucleotide sequence of SEQ ID NO: 1.

In a further or alternative embodiment, the bidirectional promoter comprises an exon from an Ubiquitin-1 gene and/or an intron from an Ubiquitin gene. In another embodiment, the bidirectional promoter comprises an intron from an alcohol dehydrogenase gene. In one embodiment, the nucleic acid construct is stably transformed into transgenic plants. In one embodiment, the plants are monocotyledons plants. In another embodiment, the plants are dicotyledons plants. In another embodiment, the plants are not monocotyledons plants. In another embodiment, the plants are not dicotyledons plants.

In a further or alternative embodiment, the bidirectional promoter comprises an upstream regulatory sequence from an Ubiquitin gene or the Sugar Cane Bacilliform Virus (SCBV) promoter. In a further embodiment, the bidirectional promoter comprises an upstream regulatory sequence from an Ubiquitin gene. In another embodiment, the bidirectional promoter comprises an upstream regulatory sequence from an Ubiquitin gene or the Sugar Cane Bacilliform Virus (SCBV) promoter.

In a further embodiment, the bidirectional promoter comprises a polynucleotide of at least 75%, 80%, 85%, 90%, 95% or 100% identical to SEQ ID NO: 5 or its complement. In a further embodiment, the bidirectional promoter comprises a polynucleotide of SEQ ID NO: 5 or its complement. In a further embodiment, the bidirectional promoter comprises a polynucleotide of at least 75%, 80%, 85%, 90%, 95% or 100% identical to SEQ ID NO: 6 or its complement.

In a further embodiment, the bidirectional promoter comprises a polynucleotide of SEQ ID NO: 6 or its complement.

In one embodiment, both the gene expression cassettes comprise two or more genes linked via a translation switch. In a further or alternative embodiment, the translation switch is selected from the group consisting of an internal ribosome entry site (IRES), an alternative splicing site, a ribozyme cleavage site, a polynucleotide sequence coding a 2A peptide, a polynucleotide sequence coding a 2A-like peptide, a polynucleotide sequence coding an intein, a polynucleotide sequence coding a protease cleavage site, and combinations thereof. In a further or alternative embodiment, the translation switch comprises a cis-acting hydrolase element (CHYSEL). In a further embodiment, the CHYSEL is a 2A or 2A-like peptide sequence. In another embodiment, a gene upstream of the translational switch does not comprise a translation stop codon. In another embodiment, the nucleic acid construct enables or allows expression of at least four genes. In a further embodiment, all four genes are transgenes. In another embodiment, the nucleic acid construct enables expression of genes between three and twenty. In another embodiment, the nucleic acid construct enables expression of genes between four and eight. In a further or alternative embodiment, the genes are transgenes. In another embodiment, at least one gene expression cassette comprises a polynucleotide sequence encoding a fusion protein. In a further embodiment, the fusion protein comprises three to five genes.

In some embodiments, expression of genes from the bidirectional promoter is at least four-fold higher as compared to a uni-directional promoter. In some embodiments, expression of genes from the bidirectional promoter is from three to ten folds higher as compared to a uni-directional promoter. In some embodiments, expression of genes from the bidirectional promoter is from four to eight folds higher as compared to a uni-directional promoter. In some embodiments, a selection marker gene is placed at far end from the promoter (i.e., at the 3' end of a gene expression cassette downstream of another gene).

In another aspect, provided is a method for generating a transgenic plant comprising transforming a plant cell with the nucleic acid construct provided herein. In another aspect, provided is a method for generating a transgenic cell comprising transforming the cell with the nucleic acid construct provided herein. In another aspect, provided is a plant cell comprising the nucleic acid construct provided herein. In a further or alternative embodiment, the nucleic acid construct is stably transformed into the plant cell. In another aspect, provided is a transgenic plant comprising the nucleic acid construct provided herein. In a further or alternative embodiment, the nucleic acid construct is stably transformed into cells of the transgenic plant. In another aspect, provide is a method for expressing multiple genes in plant cells and/or tissues, comprising introducing into the plant cells and/or tissues the nucleic acid construct provided herein. In a further or alternative embodiment, the plant cells and/or tissues are stably transformed with the nucleic acid construct provided herein. In another aspect, provided is a binary vector for *Agrobacterium*-mediated transformation. In one embodiment, the binary vector comprises the nucleic acid construct provided herein. In another embodiment, the binary vector comprises the synthetic polynucleotide provided herein. In another aspect, provided is the use of the bidirectional promoter provided herein for multiple-transgenes expression in plants.

BRIEF DESCRIPTION OF THE DRAWINGS AND SEQUENCES

FIG. 1 shows an exemplary (not to scale) maize Ubi1 (ZmUbi1) promoter, which comprises an approximately 900 bp Upstream Element located 5' of the transcription start site (TSS). The upstream element contains a TATA box (located approximately −30 bp of the TSS), and two overlapping heat shock consensus elements (located approximately −200 bp of the TSS). This promoter also comprises about 1100 bp 3' of the TSS region. This 3' region contains an adjacent leader sequence (ZmUbi1 exon), and an intron.

FIG. 10A shows SEQ ID NO: 1, which comprises a 215 bp region of a *Zea mays* Ubiquitin 1 minimal core promoter (minUbi1P). FIG. 10B shows SEQ ID NO: 2, which comprises the reverse complement of a polynucleotide comprising a *Z. mays* minUbi1P minimal core promoter (underlined); a *Z. mays* Ubi1 leader (ZmUbi1 exon; bold font); and a *Z. mays* Ubi1 intron (lower case).

FIGS. 11A and 11B show SEQ ID NO: 3, which comprises an exemplary synthetic Ubi1 bidirectional promoter, wherein the reverse complement of a first minUbi1P, and a second minUbi1P, are underlined.

FIGS. 12A and 12B and 12C show SEQ ID NO: 4, which comprises an exemplary nucleic acid comprising YFP and GUS gene expression cassettes driven by a synthetic Ubi1 bidirectional promoter.

FIGS. 13A and 13B show SEQ ID NO: 5, which comprises an exemplary SCBV bidirectional promoter comprising a minUbi1P minimal core promoter, wherein the reverse complement of the minUbi1P is underlined.

FIG. 14 shows SEQ ID NO: 6, which comprises a SCBV promoter containing ADH1 exon 6 (underlined), intron 6 (lower case font), and exon 7 (bold font).

FIGS. 15A through 15C show SEQ ID NO: 7, which comprises a nucleic acid comprising YFP and GUS gene expression cassettes driven by an exemplary SCBV bidirectional promoter.

SEQ ID NO: 8 shows the YFP Forward Primer: 5'-GATGCCTCAG TGGGAAAGG-3'. SEQ ID NO: 9 comprises a YFP Reverse Primer: 5'-CCATAGGTGA GAGTGGTGAC AA-3'. SEQ ID NO: 10 comprises an Invertase Forward Primer: 5'-TGGCGGACGA CGACTTGT-3'. SEQ ID NO: 11 comprises an Invertase Reverse Primer:

5'-AAAGTTTGGA GGCTGCCGT-3'. SEQ ID NO: 12 comprises an Invertase Probe: 5'-CGAGCAGACC GCCGT-GTACT TCTACC-3'. SEQ ID NO: 13 comprises an AAD1 Forward Primer: 5'-TGTTCGGTTC CCTCTACCAA-3'. SEQ ID NO: 14 comprises an AAD1 Reverse Primer: 5'-CAACATCCAT CACCTTGACT GA-3'. SEQ ID NO: 15 comprises an AAD1 Probe: 5'-CACAGAACCG TCGCT-TCAGC AACA-3' (see also Table 7).

Figure 16:
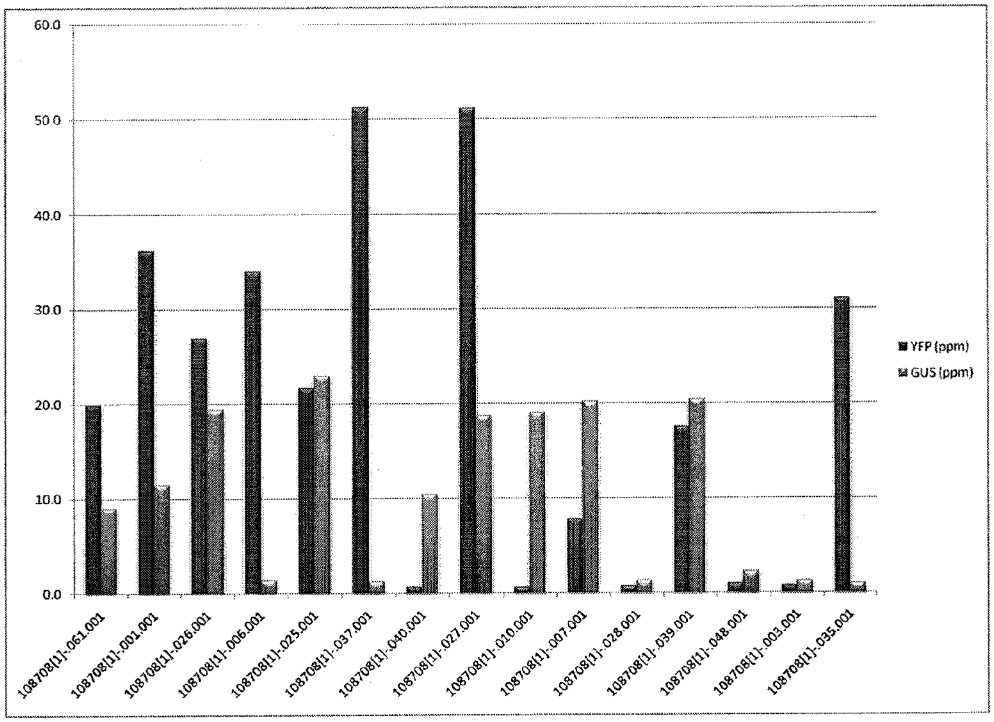

FIG. 16 shows a Western blot analysis for stable YFP expression driven by a bidirectional SCBV Promoter construct (pDAB108708) in maize $T_0$ plants. Representative plants showed stable YFP expression in leaf driven by the Min-Ubi1P minimal core promoter element. The amount of protein which is produced is indicated as parts per million (ppm).

Figure 17:
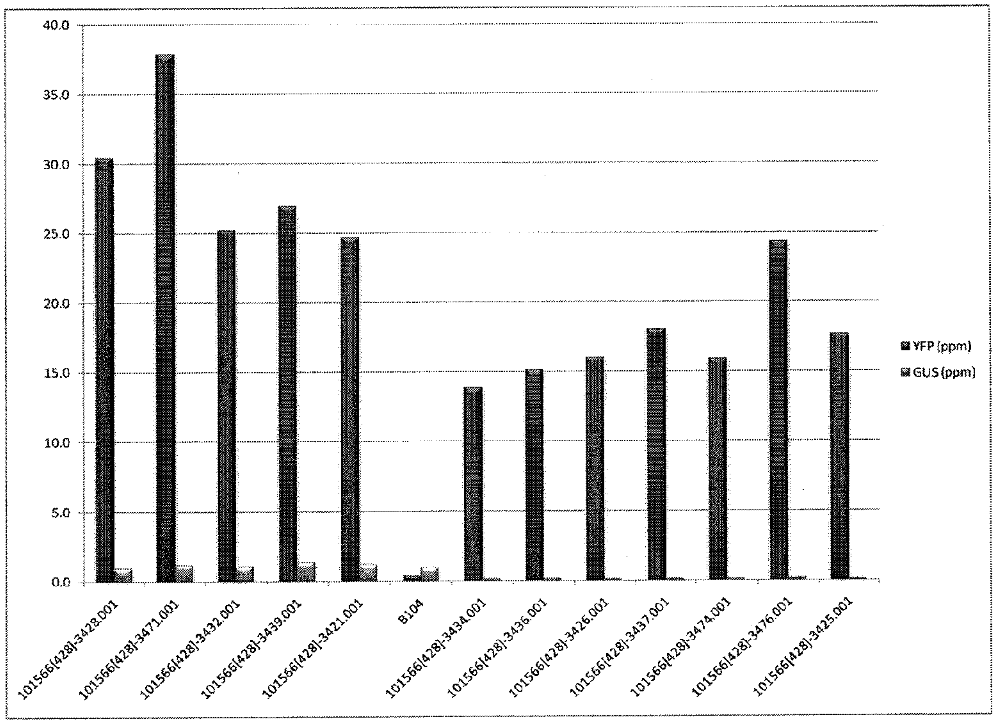

FIG. 17 shows a Western blot analysis for stable YFP expression from the control construct containing a ZmUbi1 promoter that only drives expression of YFP (pDAB101556); a GUS coding sequence is not contained in this construct. The amount of protein which is produced is indicated as parts per million (ppm).

Figure 18:
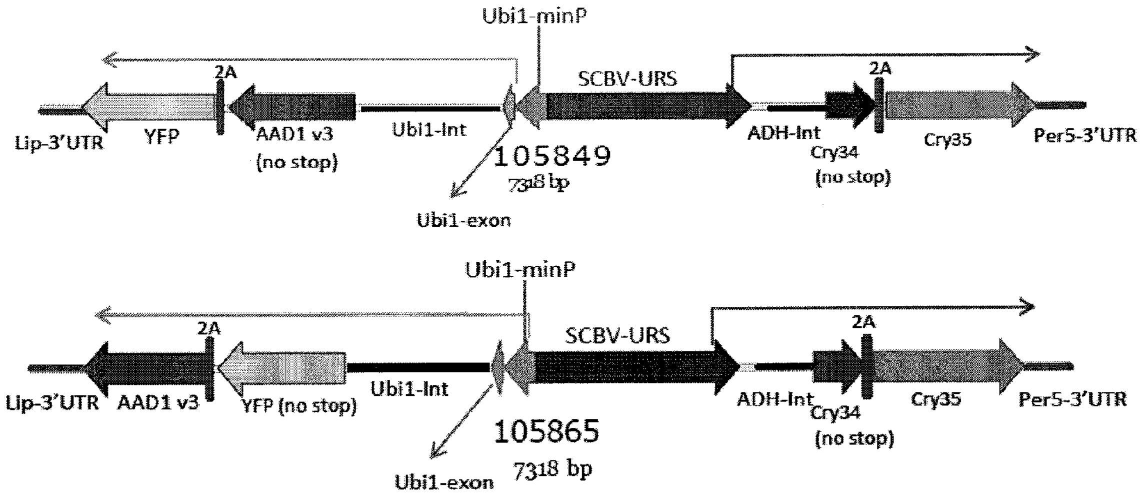

FIG. 18 shows exemplary constructs of four-gene cassette stacks pDAB105849 (AAD1-2A-YFP plus Cry34-2A-Cry35) and pDAB105865 (YFP-2A-AAD1 plus Cry34-2A-Cry35). Shaded arrows indicate direction of transcription from the bidirectional promoter. Ubi1-mimP comprises 200 nt sequence upstream of transcriptional start site of maize Ubi1 promoter. SCBV-URS comprises upstream regulatory sequence of SCBV promoter excluding the core promoter (shown as arrow). Ubi1-Int comprises an intron of maize Ubi1 promoter.

Figure 19:
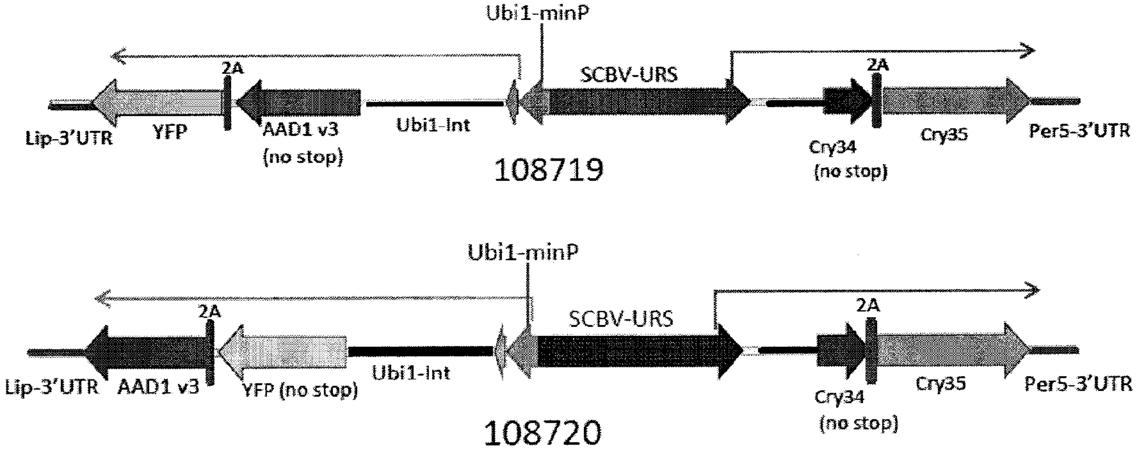

FIG. 19 shows two additional exemplary constructs of four-gene cassette stacks.

Figure 20A:
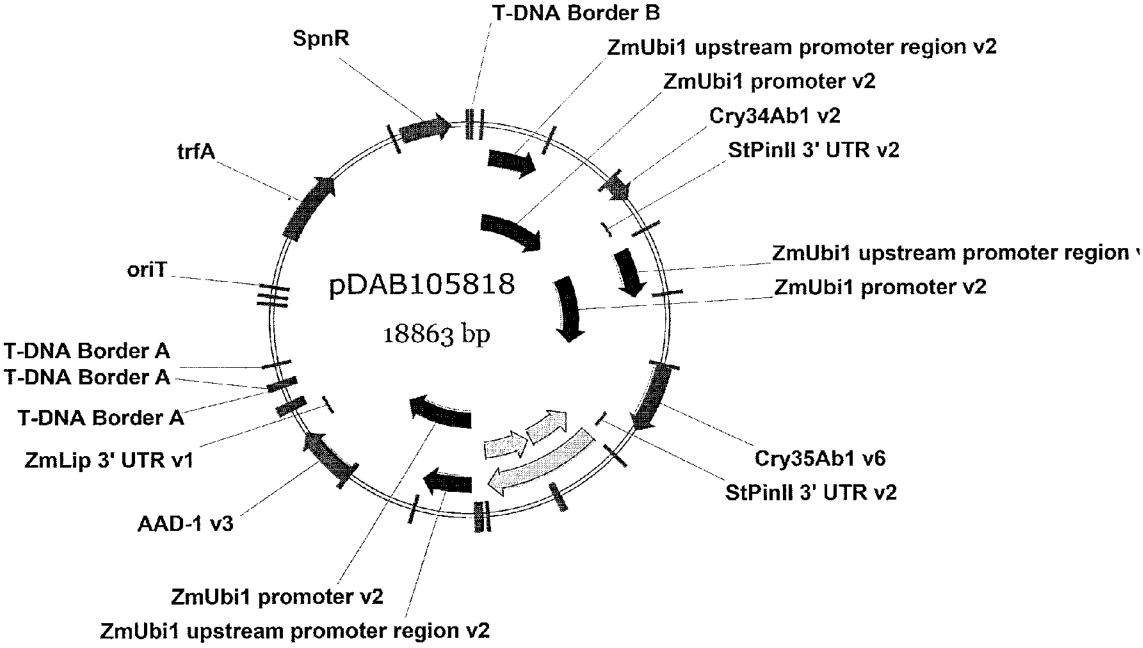
Figure 20B:
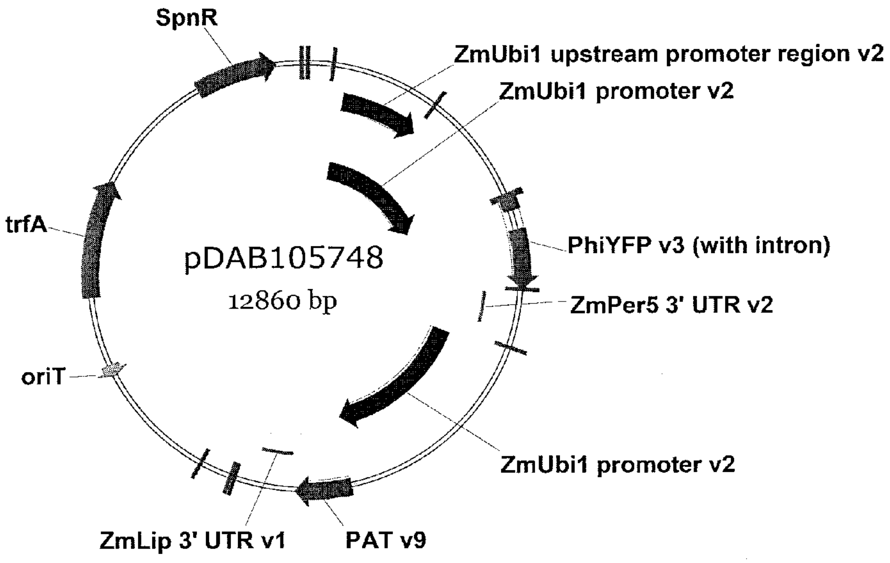

FIGS. 20A and 20B show representative maps for plasmids pDAB105818 and pDAB105748.

FIGS. 21A-21E shows additional minimal core promoters (min-Ubi1P or Ubi1-minP) of SEQ ID NOs: 16-40.

Figure 22A:
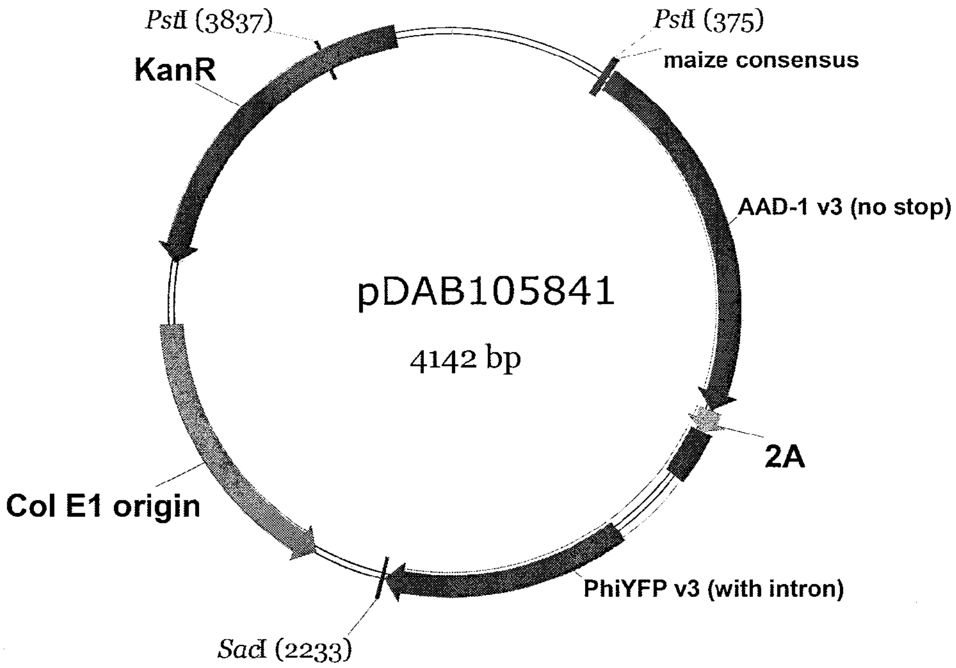
Figure 22B:
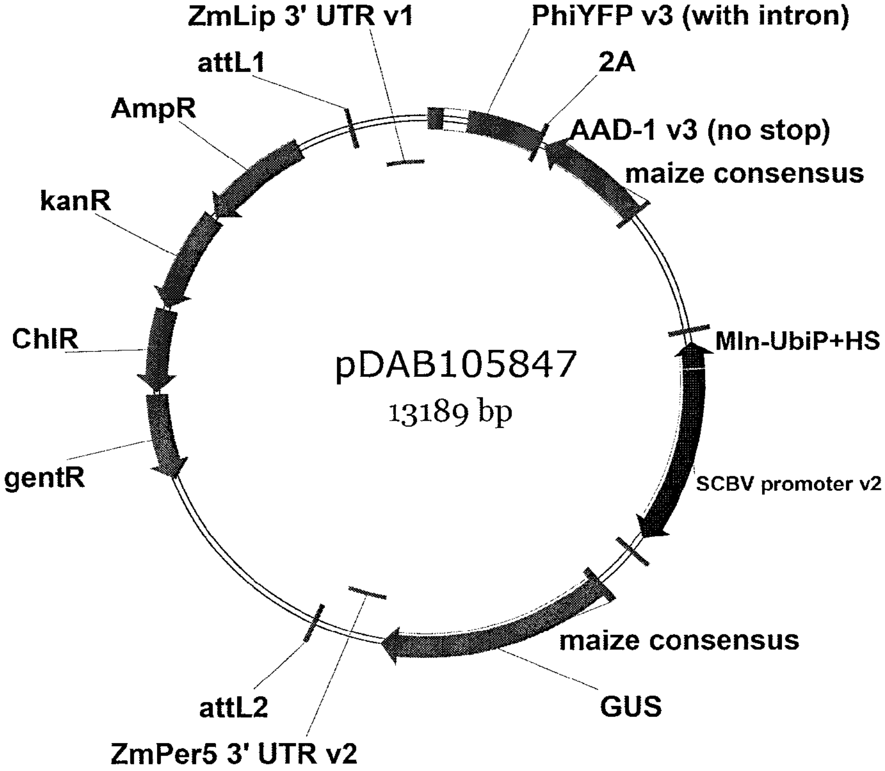

FIGS. 22A and 22B show representative maps for plasmids pDAB105841 and pDAB105847.

Figure 23A:
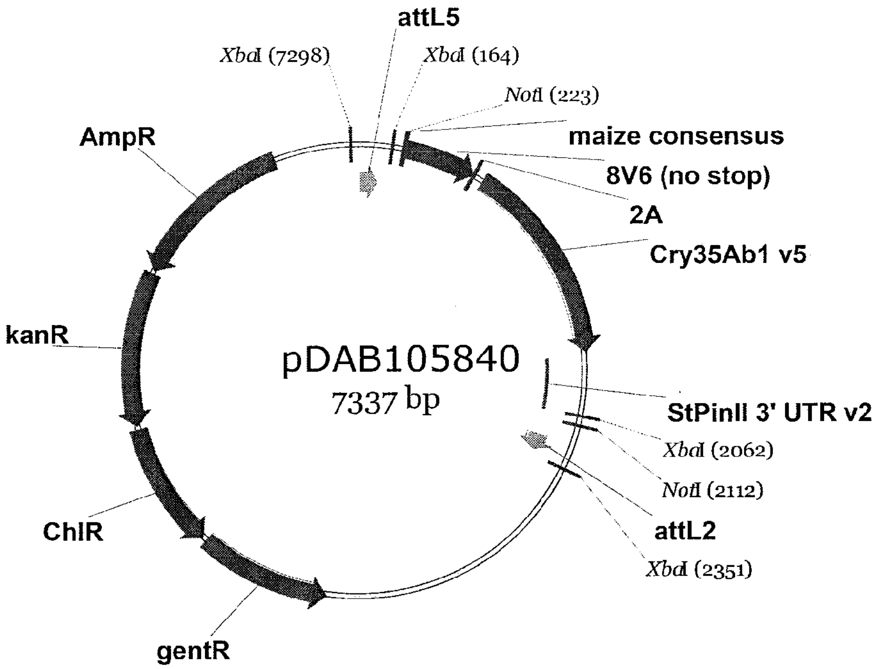
Figure 23B:
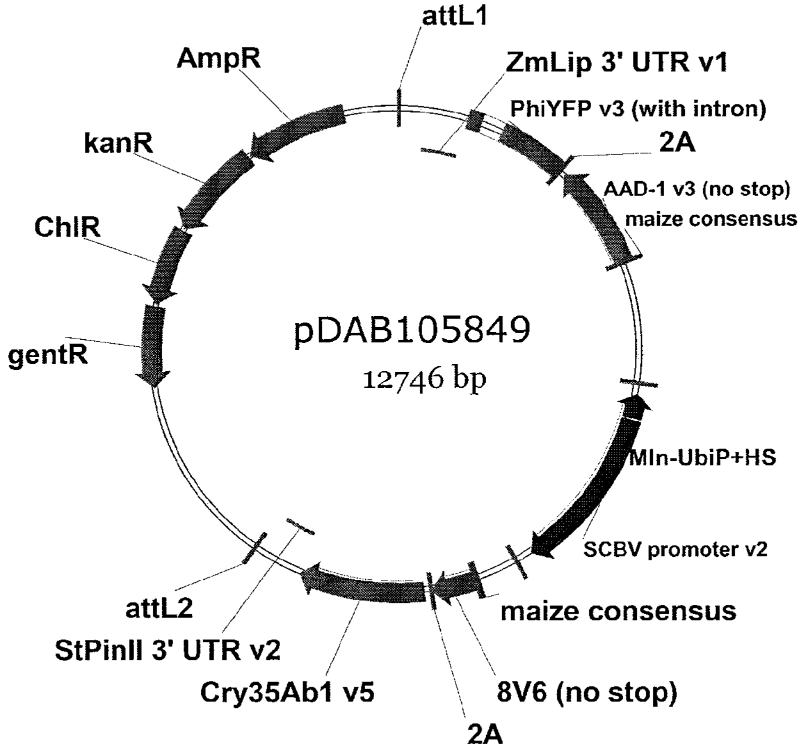

FIGS. 23A and 23B show representative maps for plasmids pDAB105840 and pDAB105849.

Figure 24A:
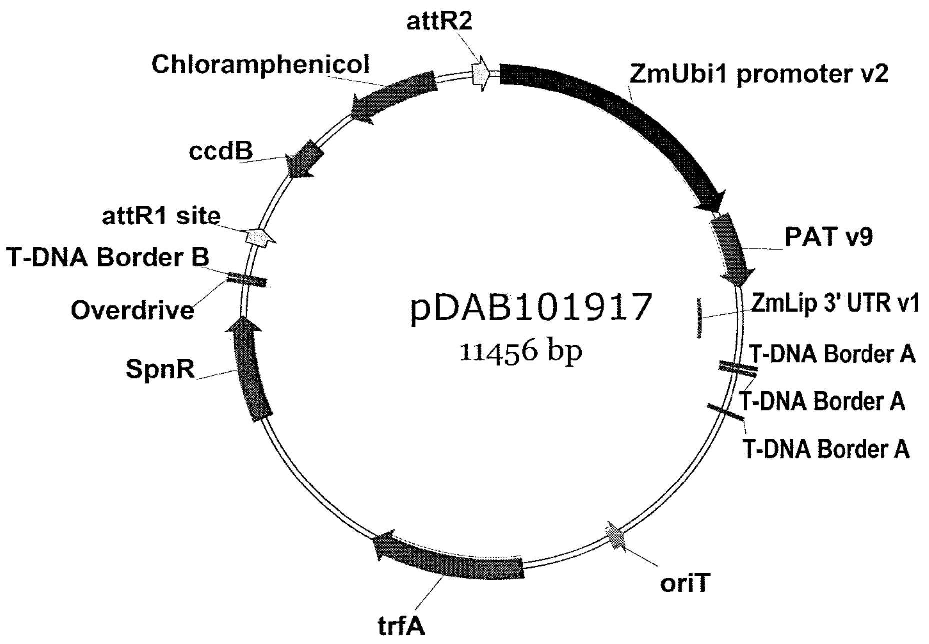
Figure 24B:
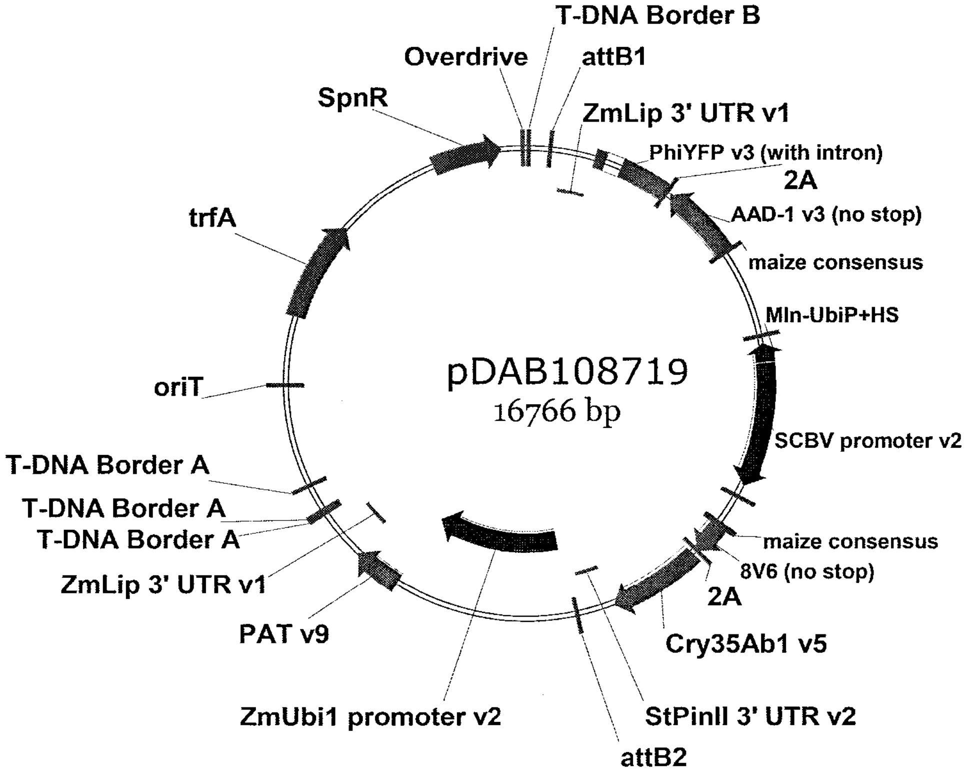

FIGS. 24A and 24B show representative maps for plasmids pDAB101917 and pDAB108719.

Figure 25A:
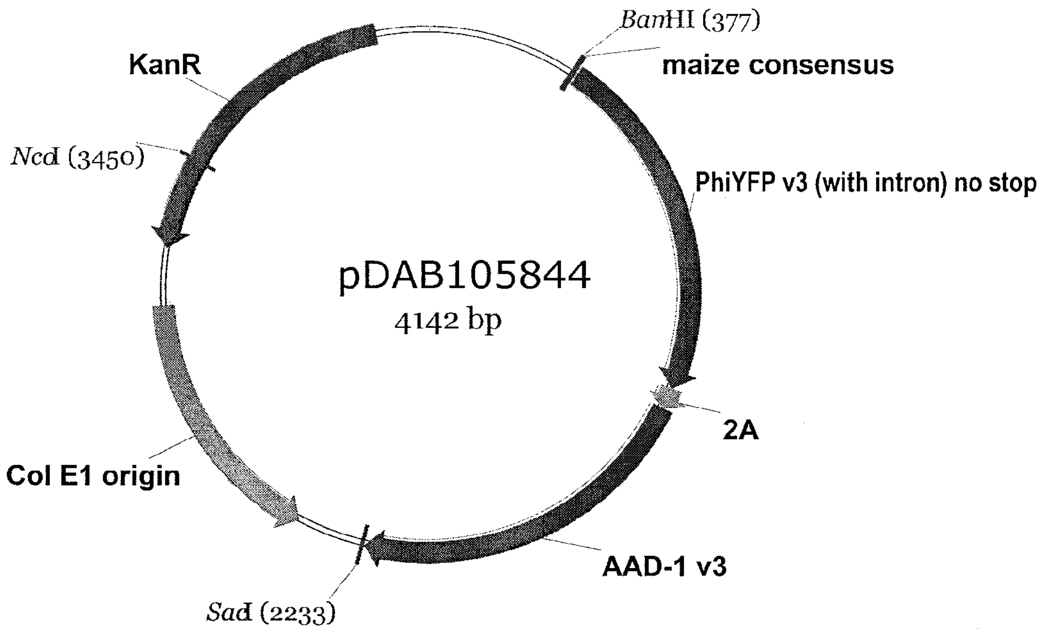
Figure 25B:
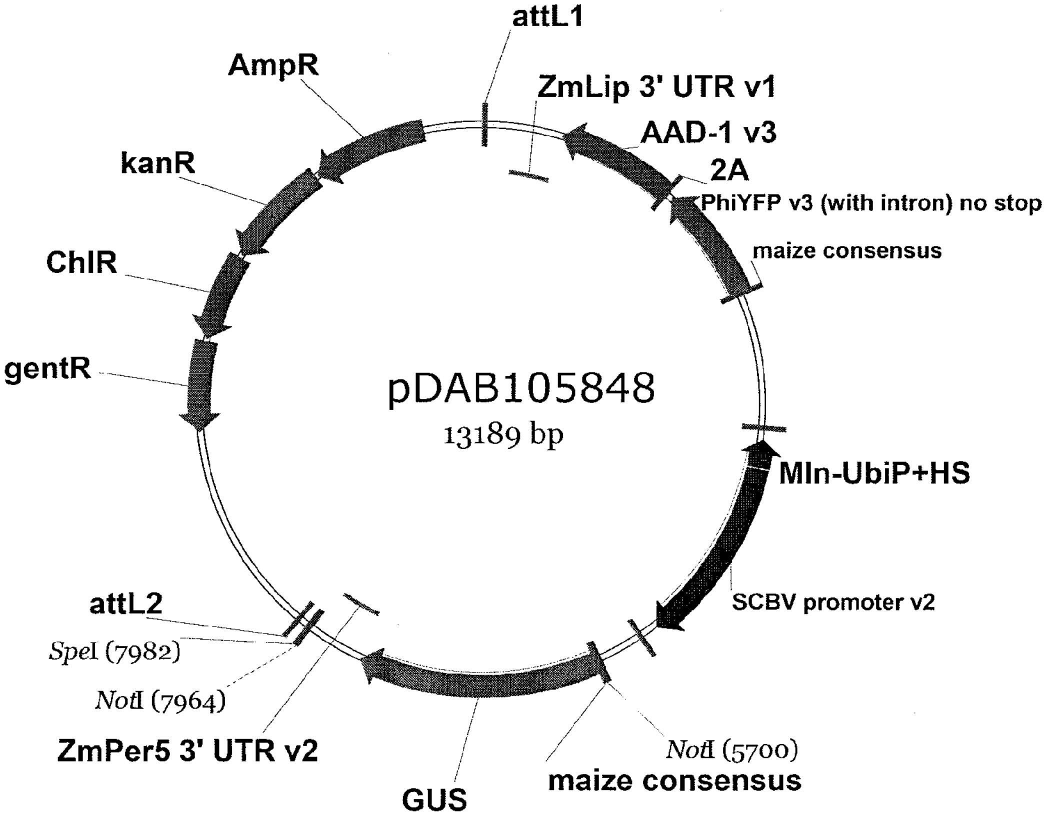

FIGS. 25A and 25B show representative maps for plasmids pDAB105844 and pDAB105848.

Figure 26A:
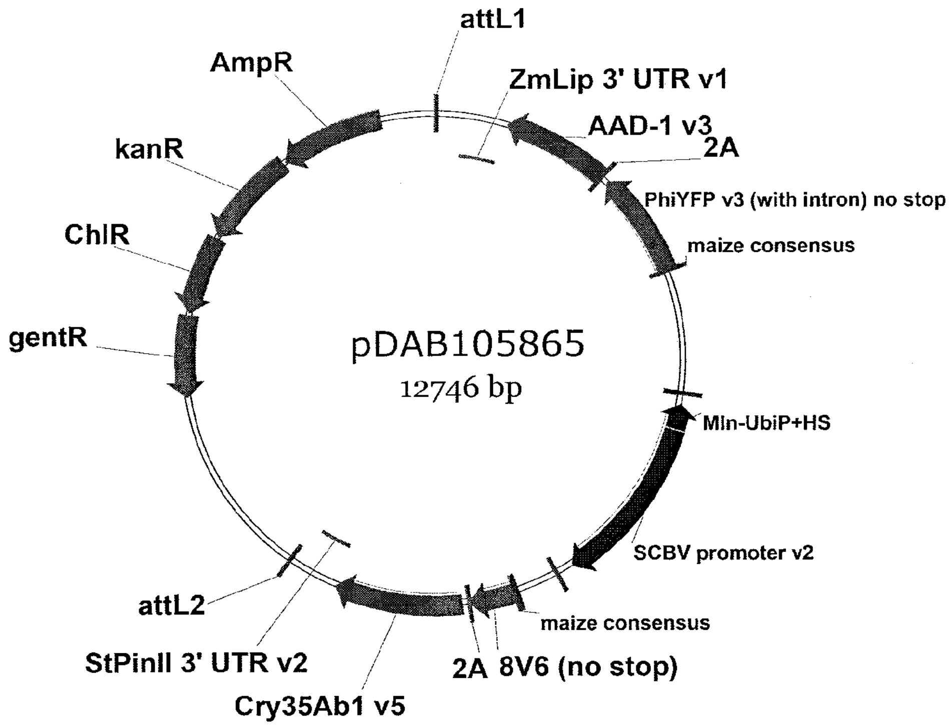
Figure 26B:
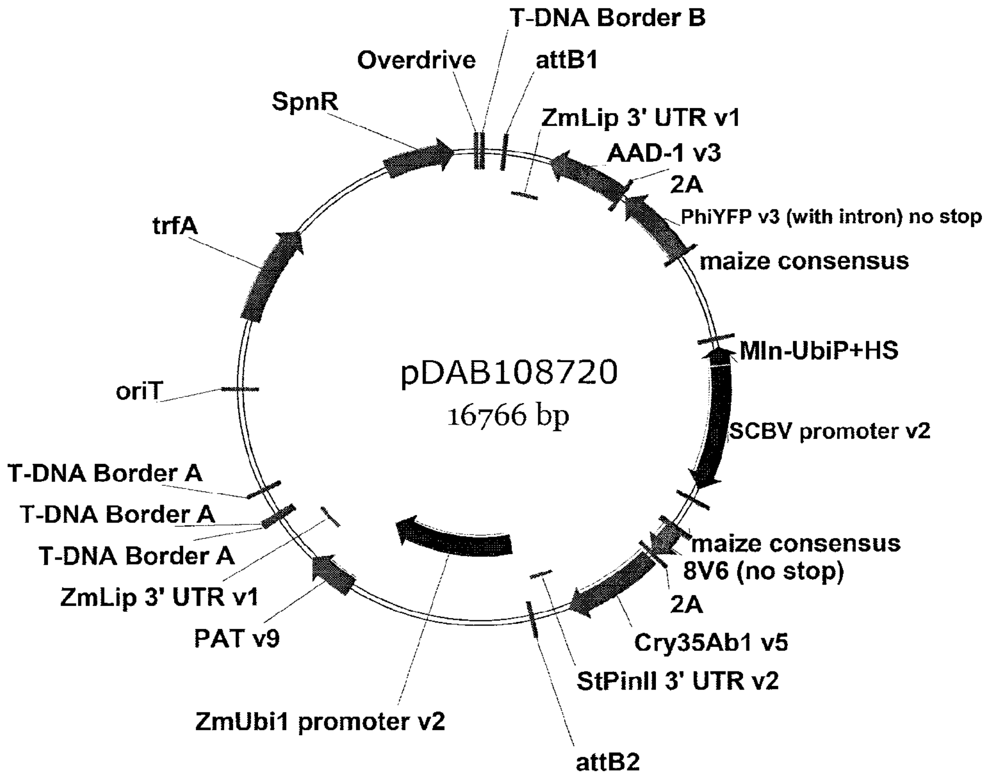

FIGS. 26A and 26B show representative maps for plasmids pDAB105865 and pDAB108720.

FIGS. 27A through 27J show a nucleic acid sequence for gene expression cassettes of pDAB108719 (SEQ ID NO:53), where each gene and element is illustrated.

Figure 28A:
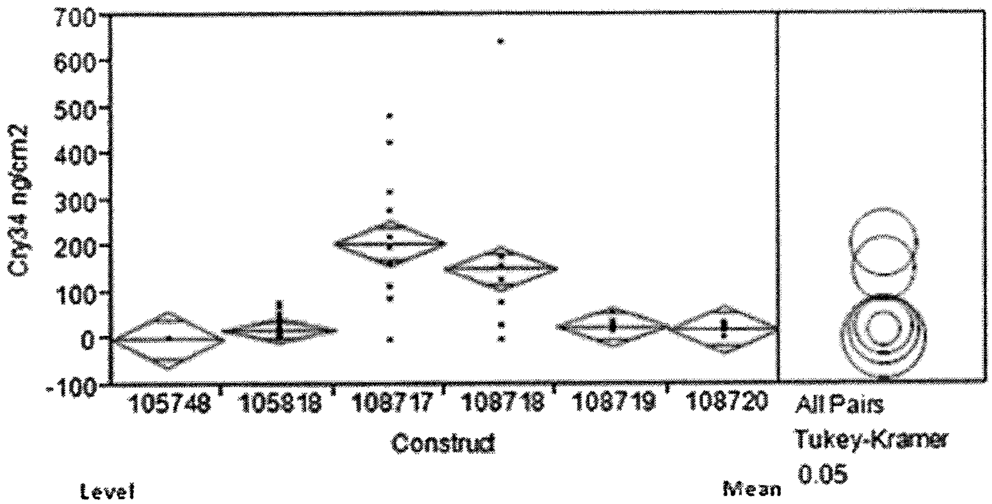
Figure 28B:
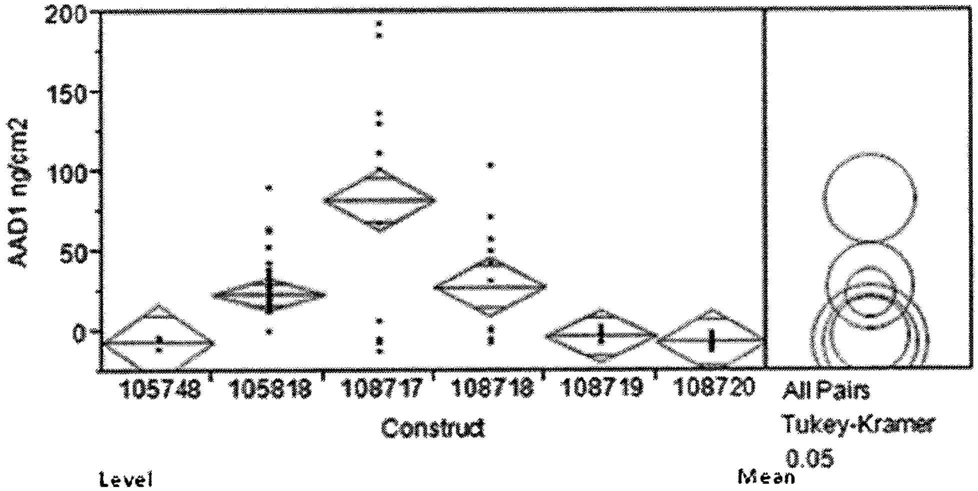
Figure 28C:
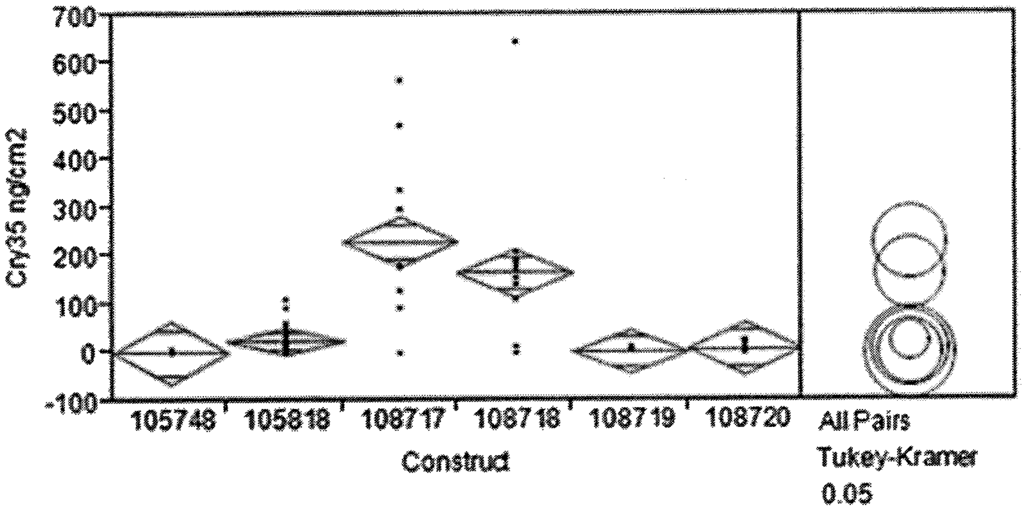

FIG. 28 shows exemplary protein expression data among various constructs tested for Cry34 (FIG. 28A), AAD-1 (FIG. 28B), and Cry35 (FIG. 28C).

FIG. 29 shows two exemplary sequences for yellow fluorescent proteins from *Phialidium* sp. SL-2003 (PhiYFP, SEQ ID NO: 51; and PhiYFPv3, SEQ ID NO: 52).

Figure 30:
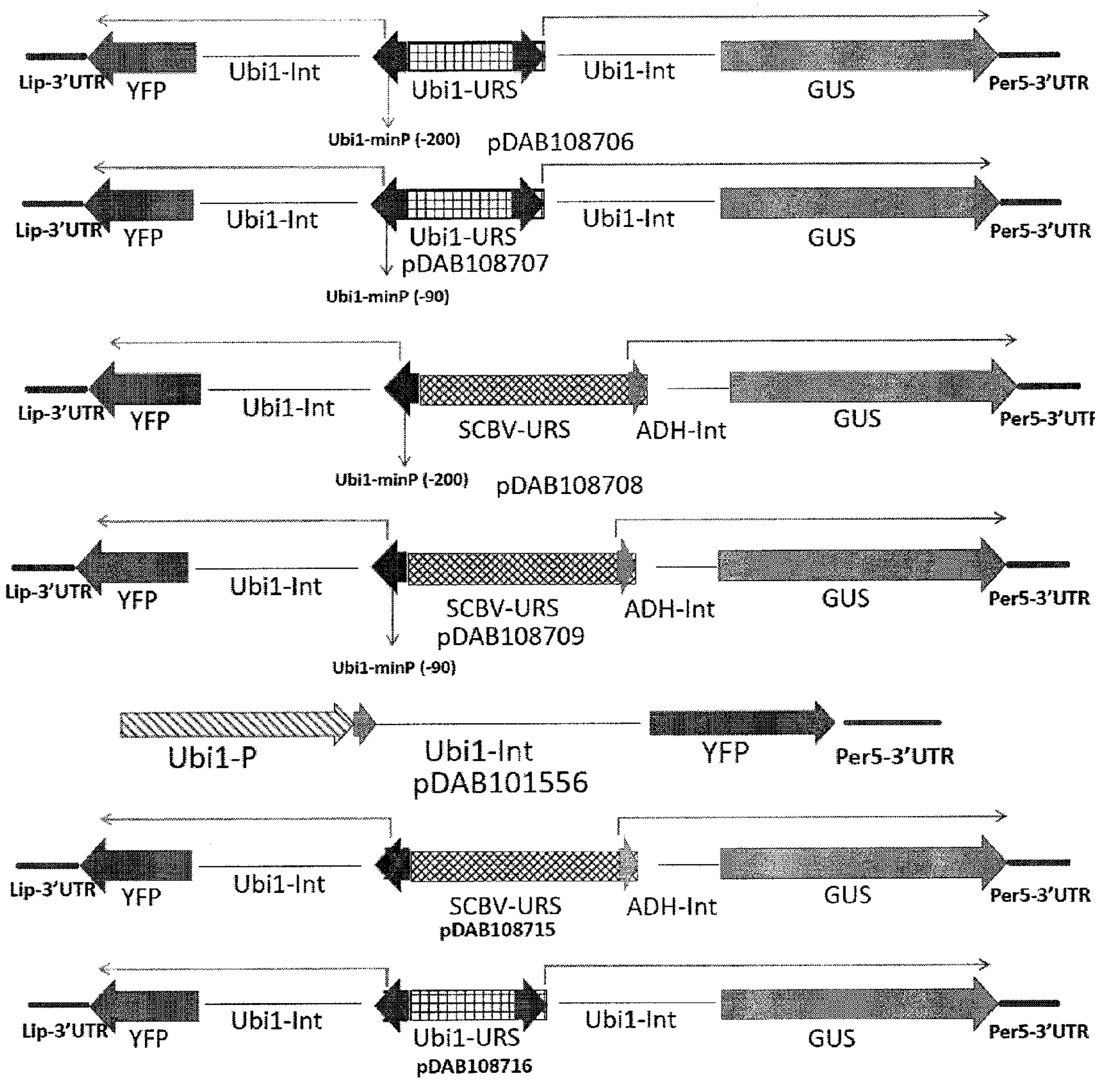

FIG. 30 shows exemplary embodiments of the synthetic Ubi1 bidirectional promoter and constructs provided, including pDAB108706 (ZMUbi bidirectional (−200)), pDAB108707 (ZMUbi bidirectional (−90)), pDAB108708 (SCBV bidirectional (−200)), and pDAB108709 (SCBV bidirectional (−90)). pDAB101556 (ZmUbi1-YFP control), pDAB108715 (SCBV without minimal promoter), and pDAB108716 (ZMUbi1 without minimal promoter) serve as control constructs with uni-directional promoters.

Figure 31A:
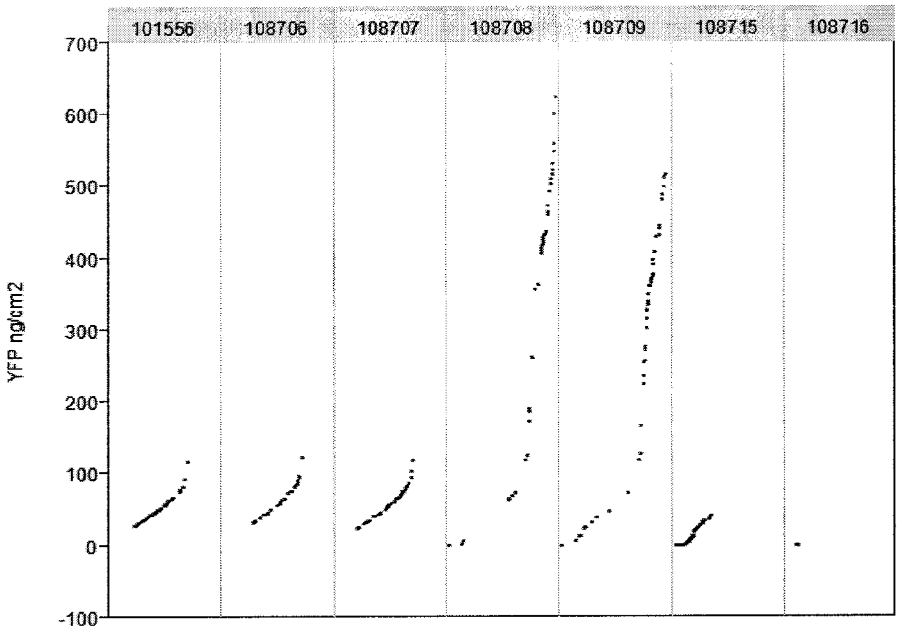
Figure 31B:
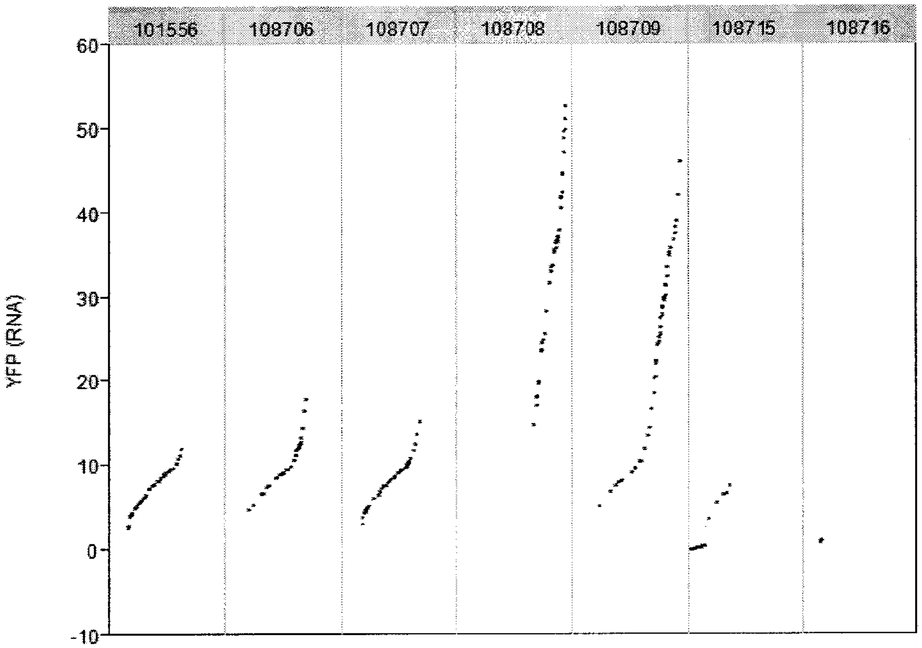

FIG. 31A shows exemplary expression results (V6) from the seven constructs shown in FIG. 30 for YFP protein (LCMS) in ng/$cm^2$. FIG. 31B shows exemplary relative expression results (V6) from the seven constructs shown in FIG. 30 for YFP RNA.

Figure 32A:
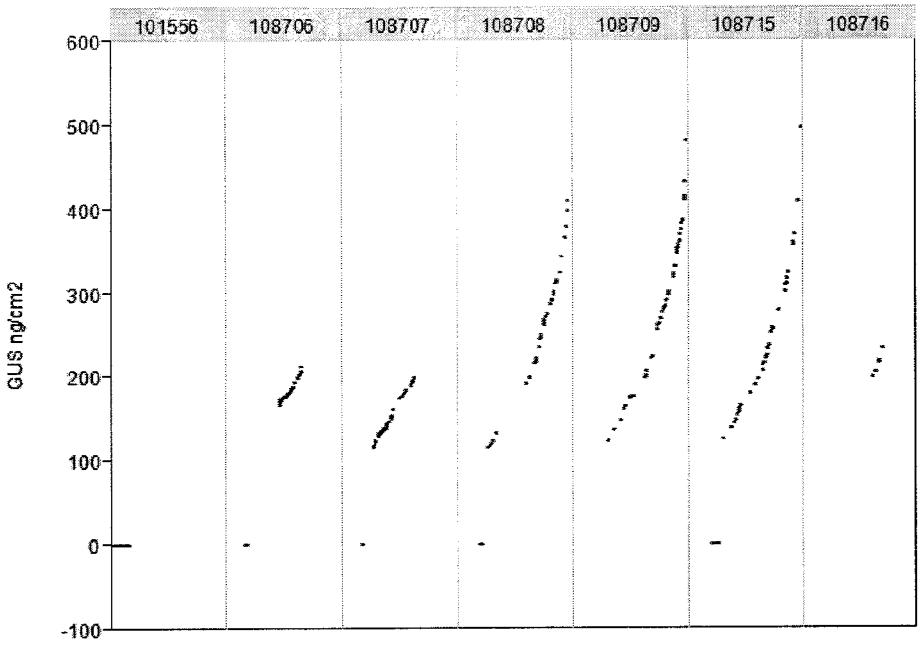
Figure 32B:
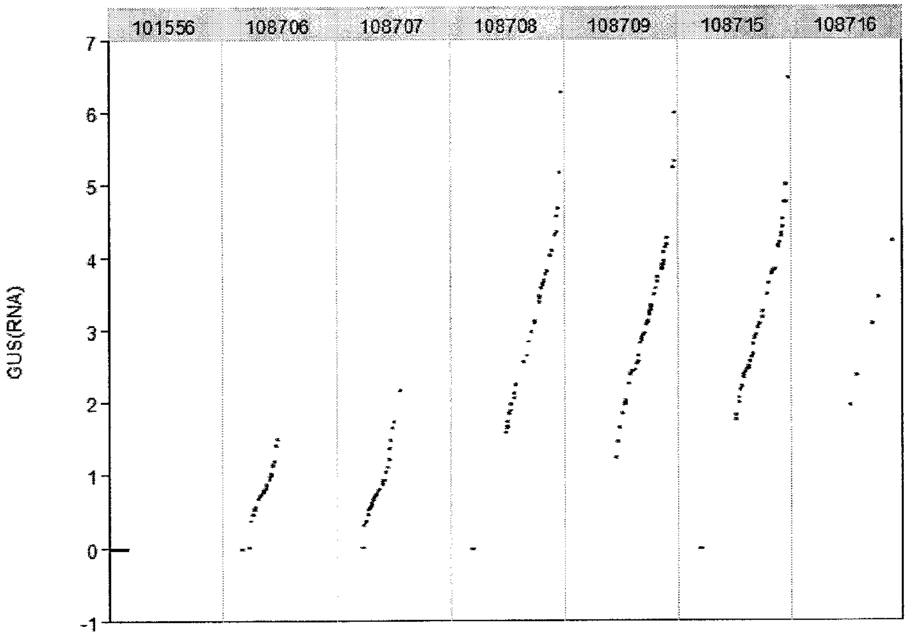

FIG. 32A shows exemplary expression results (V6) from the seven constructs shown in FIG. 30 for GUS protein (LCMS) in ng/$cm^2$. FIG. 32B shows exemplary relative expression results (V6) from the seven constructs shown in FIG. 30 for GUS RNA.

Figure 33A:
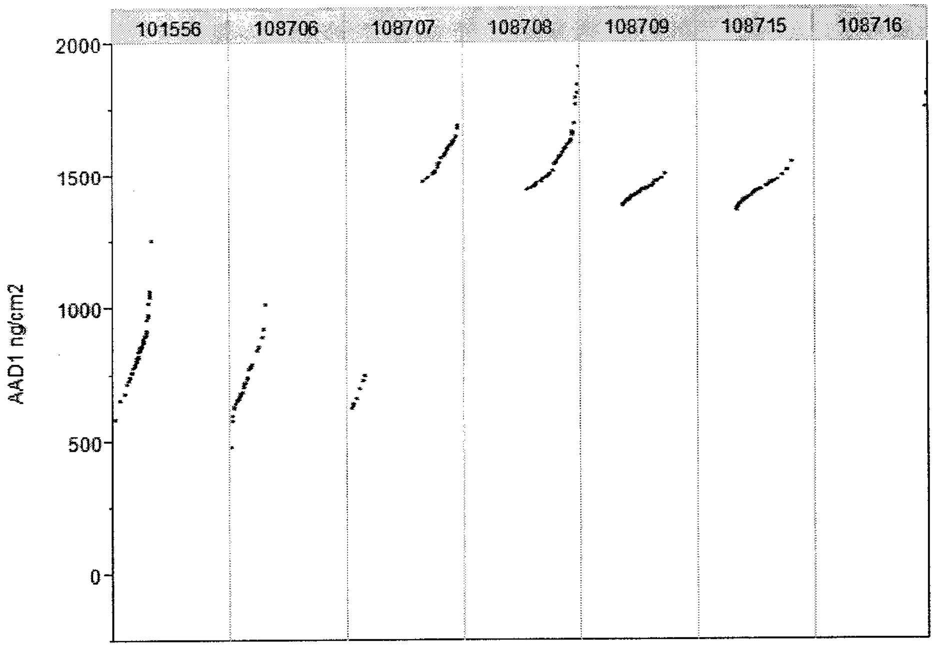
Figure 33B:
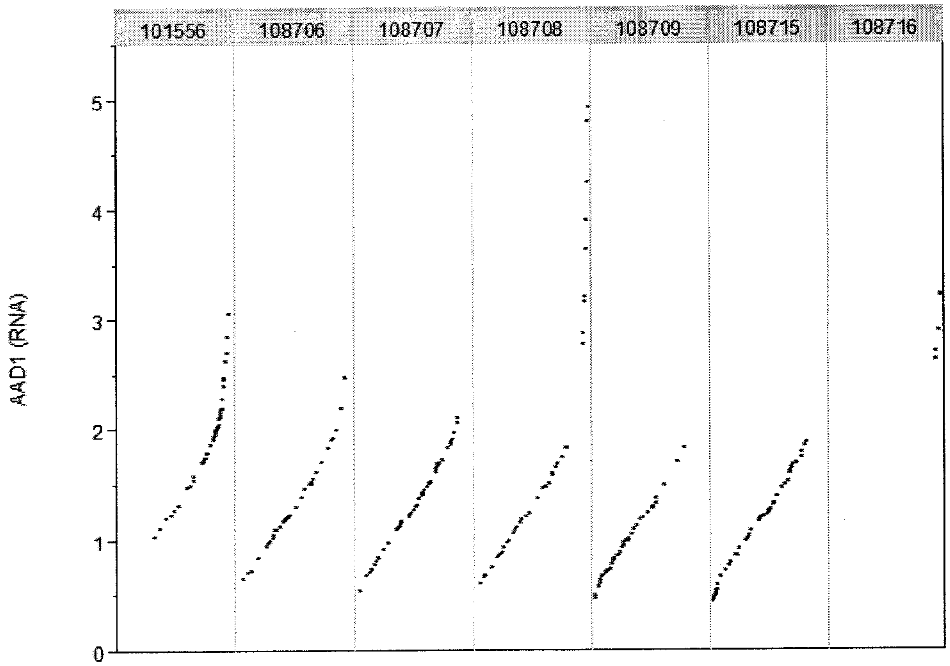

FIG. 33A shows exemplary expression results (V6) from the seven constructs shown in FIG. 30 for AAD1 protein (LCMS) in ng/$cm^2$. FIG. 33B shows exemplary relative expression results (V6) from the seven constructs shown in FIG. 30 for AAD1 RNA.

Figure 34A:
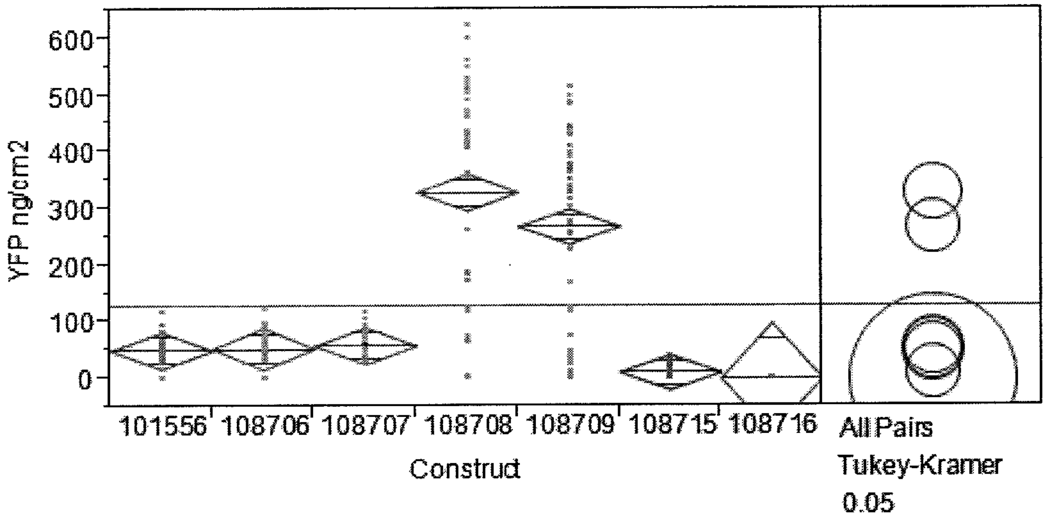
Figure 34B:
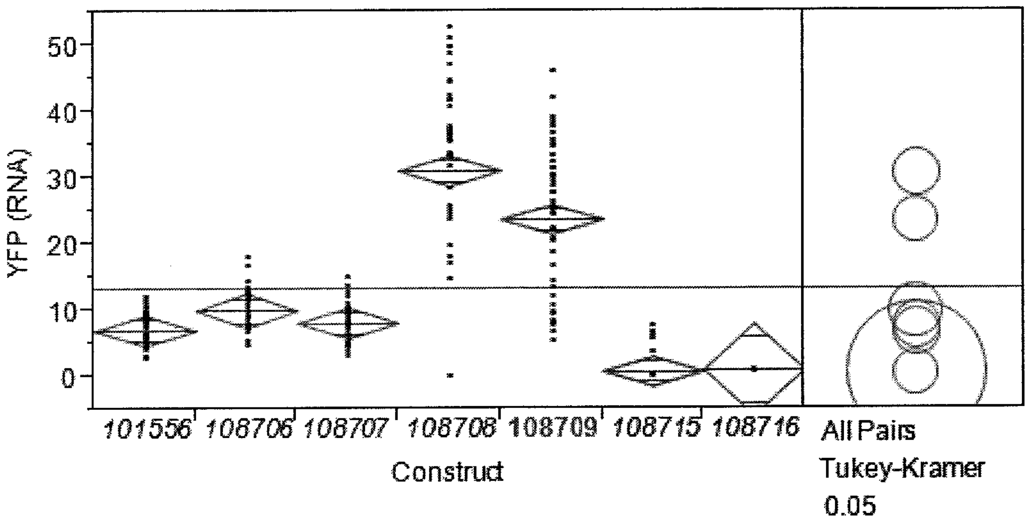

FIG. 34A shows a statistical analysis of expression results (V6) from the seven constructs shown in FIG. 30 for YFP protein (LCMS) in ng/$cm^2$. FIG. 34B shows a statistical analysis of relative expression results (V6) from the seven constructs shown in FIG. 30 for YFP RNA. The mean values and statistical results are listed.

Figure 35A:
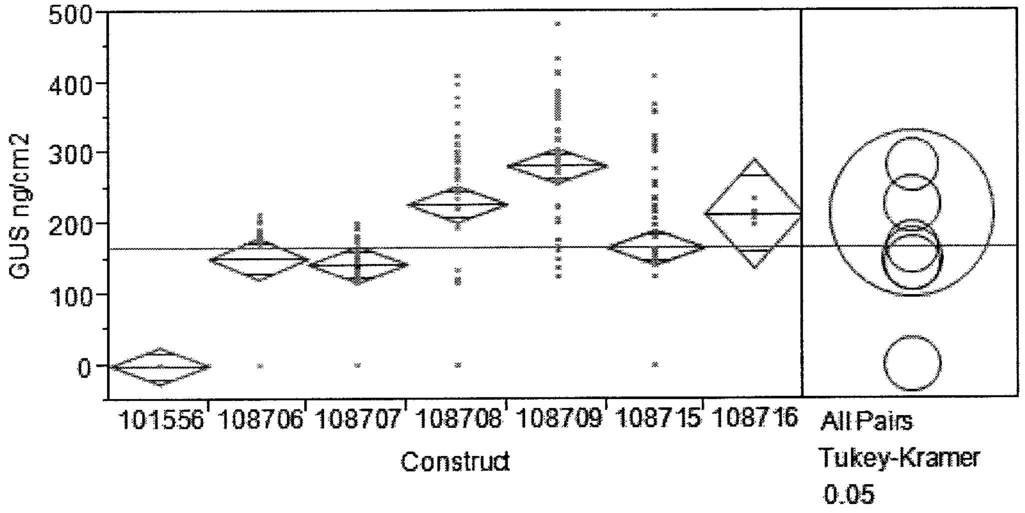
Figure 35B:
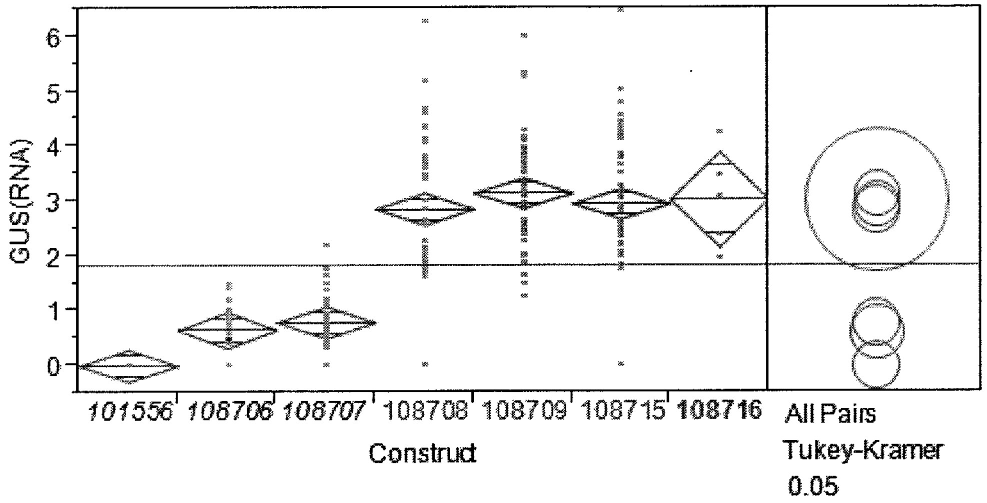

FIG. 35A shows a statistical analysis of expression results (V6) from the seven constructs shown in FIG. 30 for GUS protein (LCMS) in ng/$cm^2$. FIG. 35B shows a statistical analysis of relative expression results (V6) from the seven constructs shown in FIG. 30 for GUS RNA. The mean values and statistical results are listed.

Figure 36A:
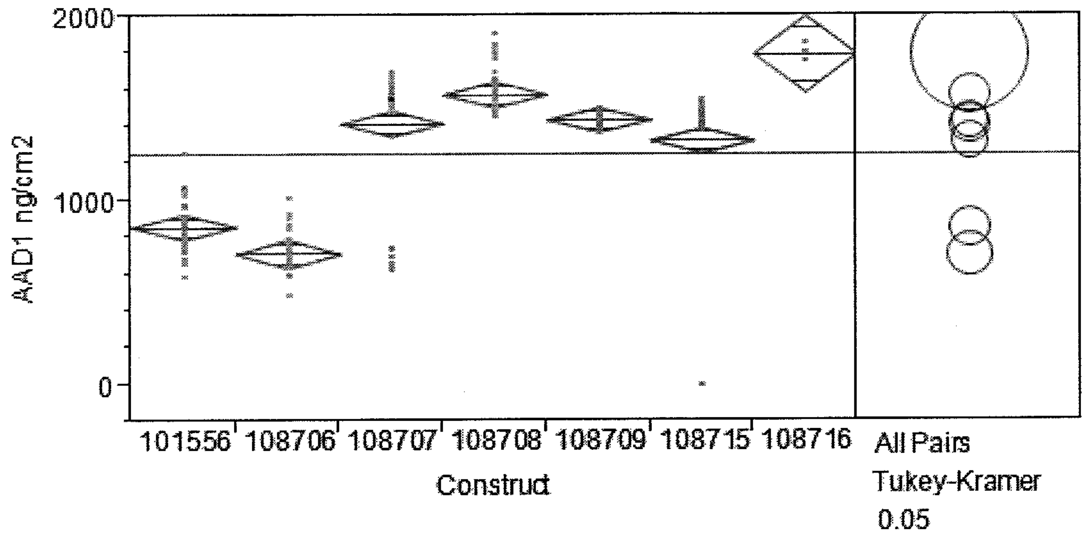
Figure 36B:
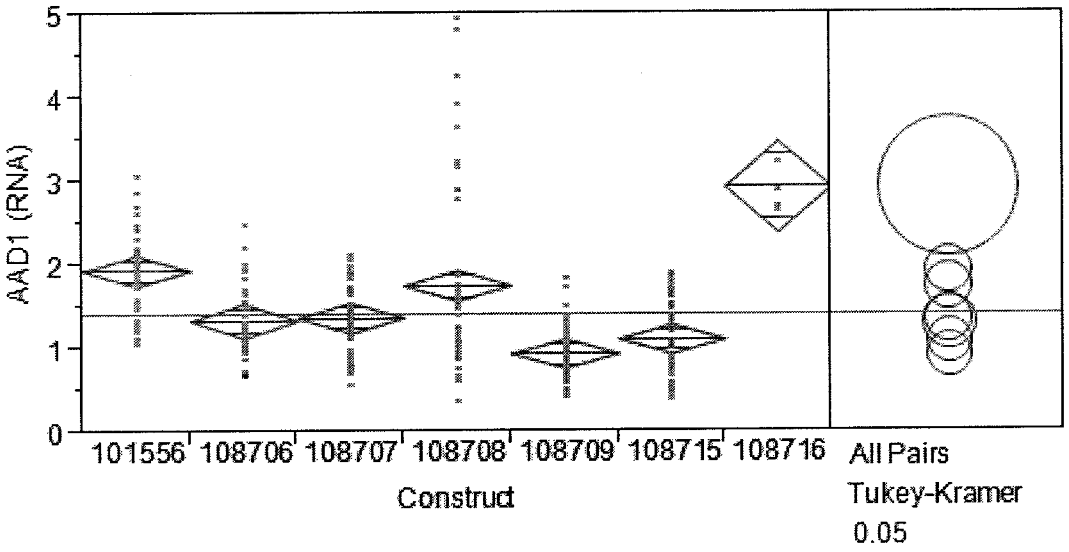

FIG. 36A shows a statistical analysis of expression results (V6) from the seven constructs shown in FIG. 30 for AAD1 protein (LCMS) in ng/$cm^2$. FIG. 36B shows a statistical analysis of relative expression results (V6) from the seven constructs shown in FIG. 30 for AAD1 RNA. The mean values and statistical results are listed.

Figure 37A:
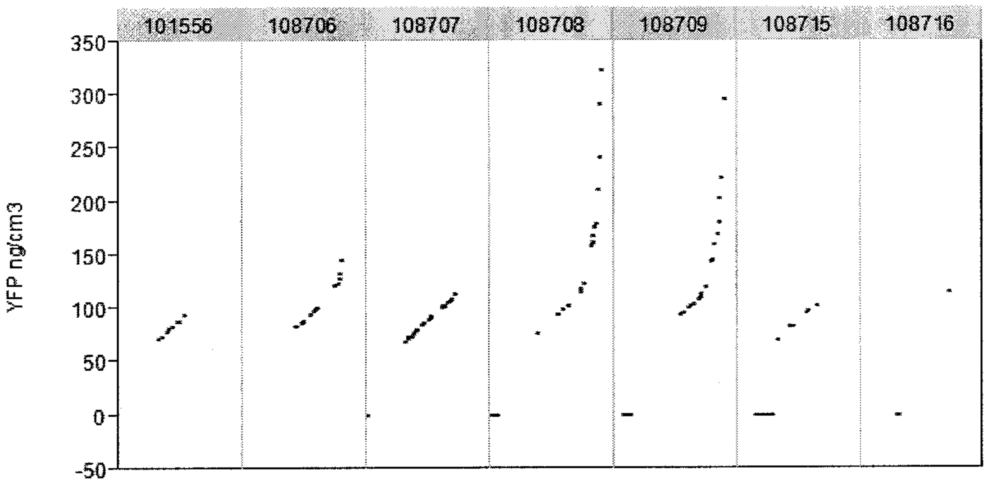
Figure 37B:
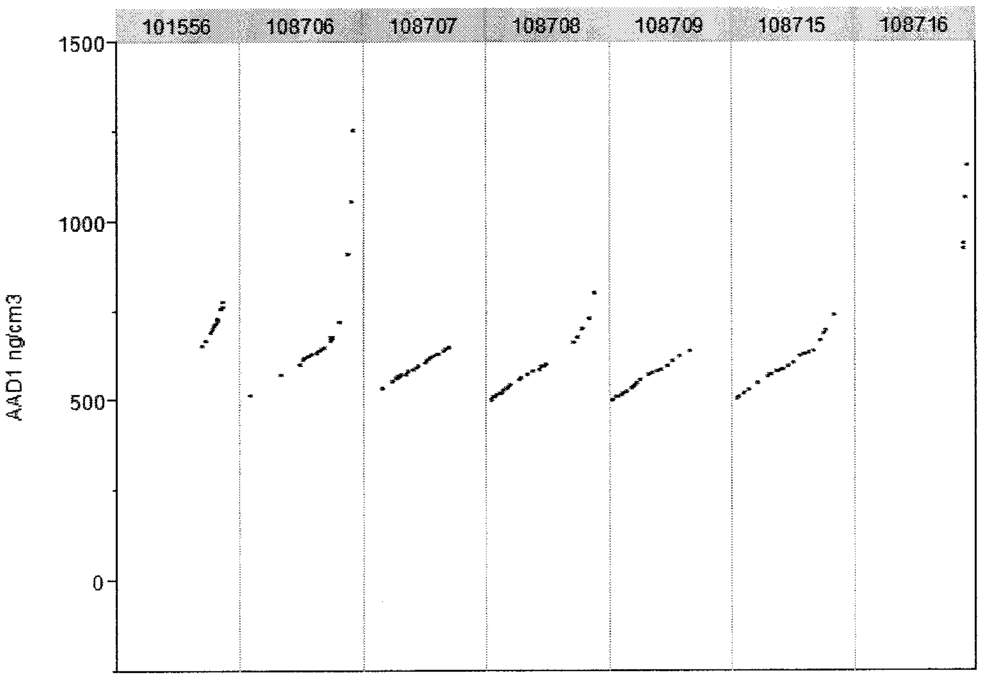
Figure 37C:
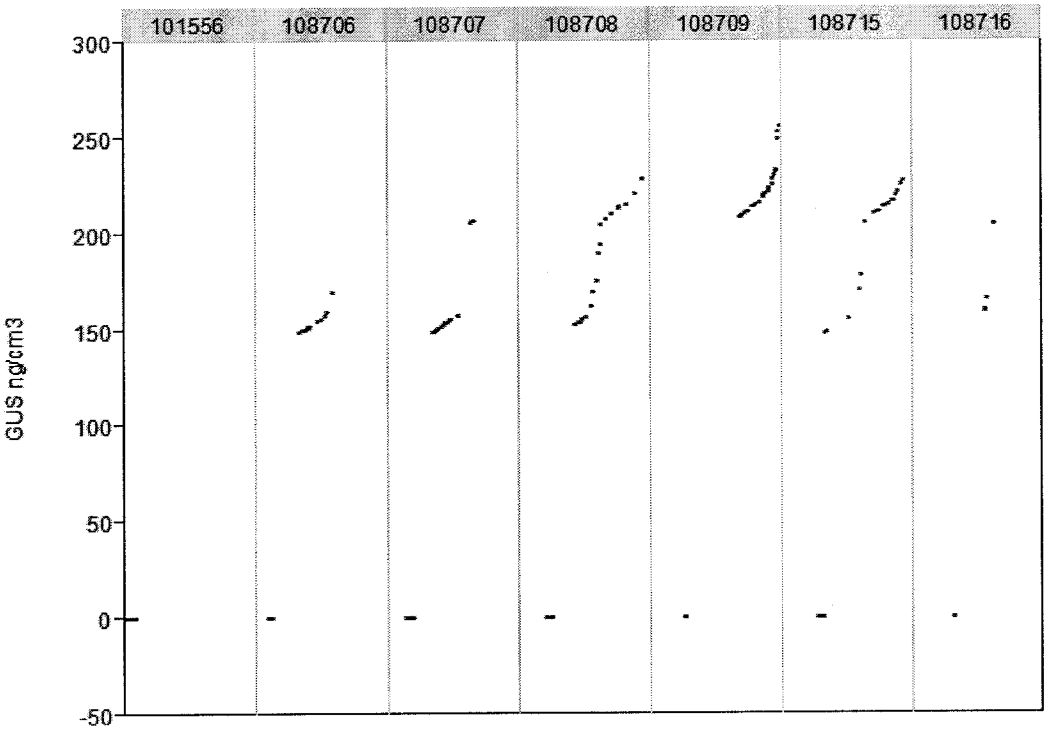

FIGS. 37A, 37B, and 37C show exemplary expression results (V10) from the seven constructs shown in FIG. 30 for YFP, AAD1, and GUS protein (LCMS) in ng/$cm^2$ respectively.

Figure 38A:
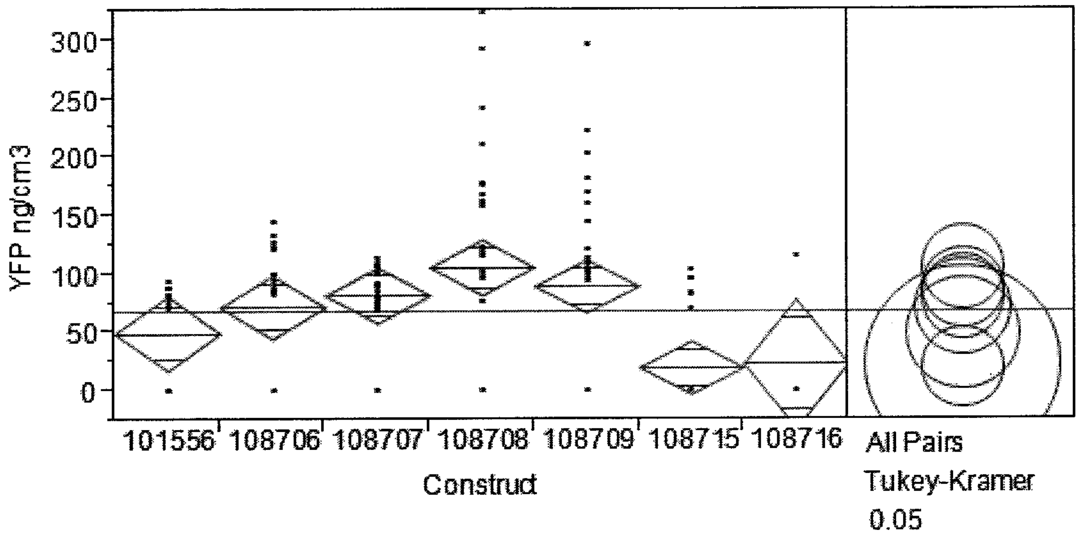
Figure 38B:
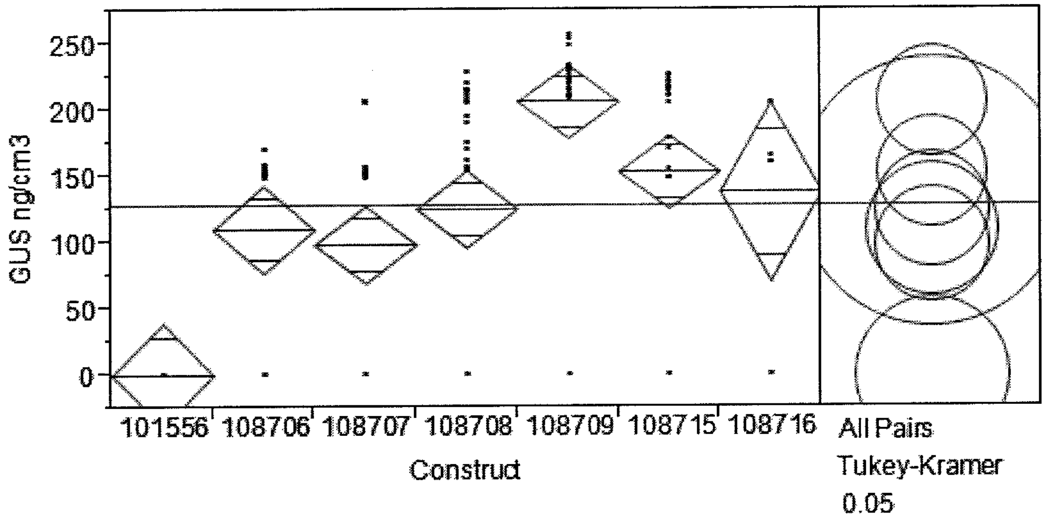
Figure 38C:
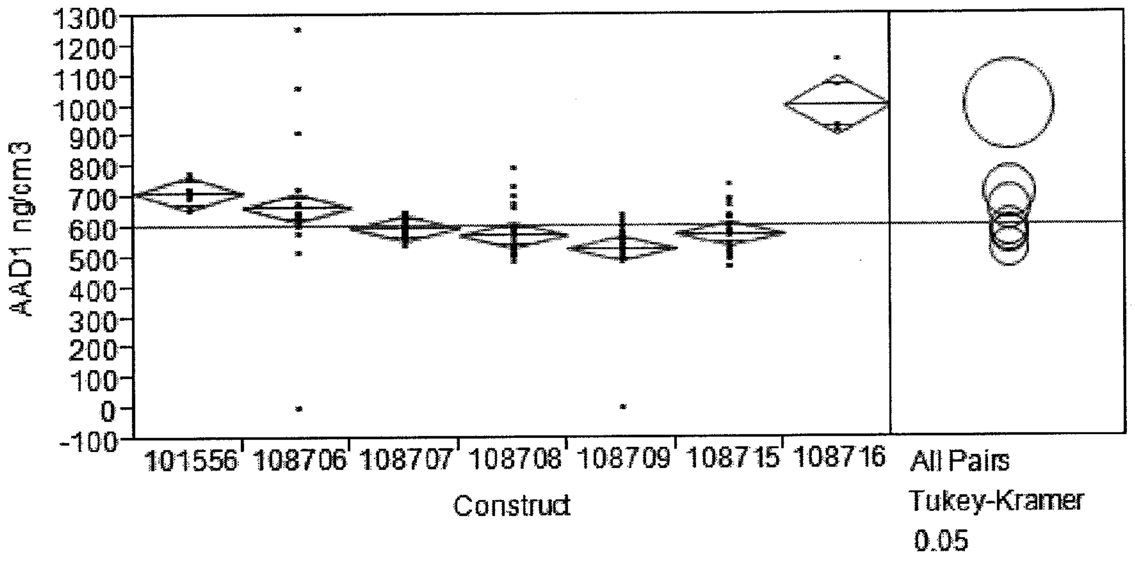

FIGS. 38A, 38B, and 38C show statistical analysis of expression results (V10) from the seven constructs shown in FIG. 30 for YFP, GUS, and AAD1 protein (LCMS) in ng/$cm^2$ respectively. The mean values and statistical results are listed.

Figure 39A:
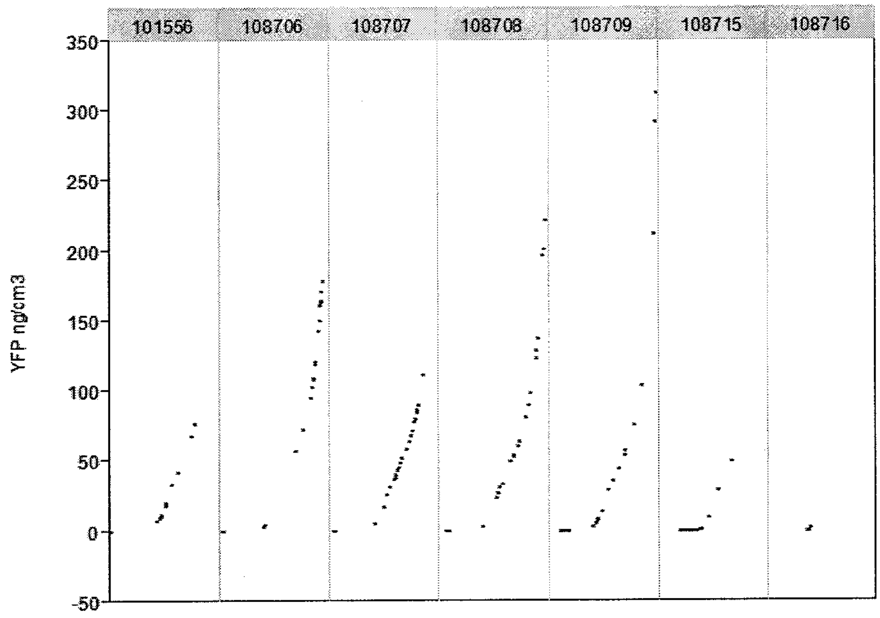
Figure 39B:
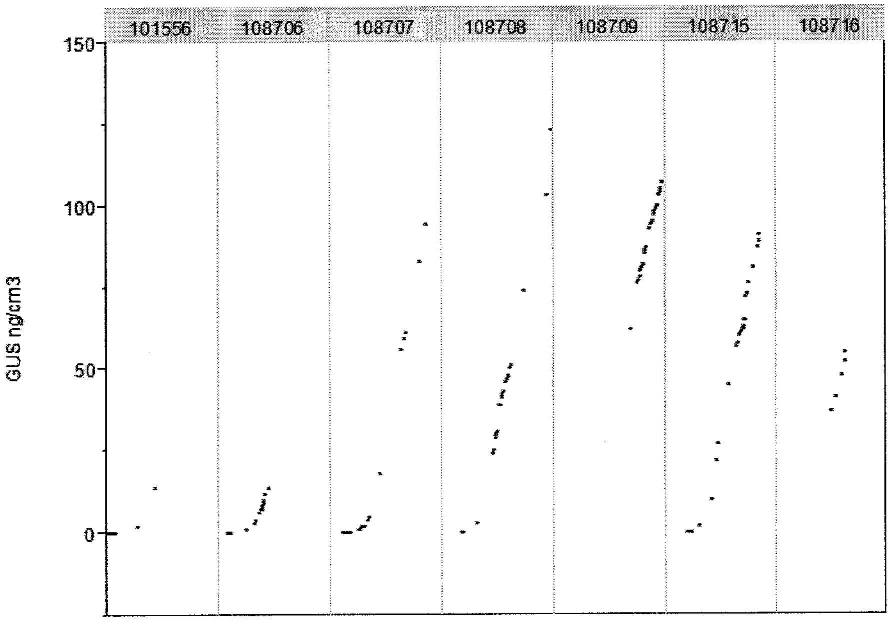
Figure 39C:
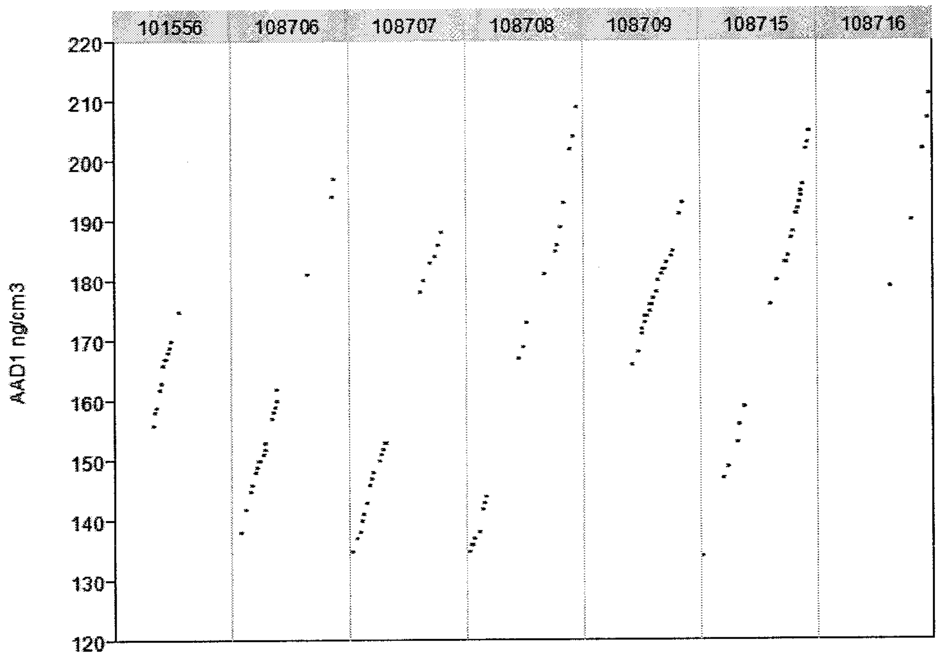

FIGS. 39A, 39B, and 39C show exemplary expression results (R3) from the seven constructs shown in FIG. 30 for YFP, GUS, and AAD1 protein (LCMS) in ng/$cm^2$, respectively.

Figure 40A:
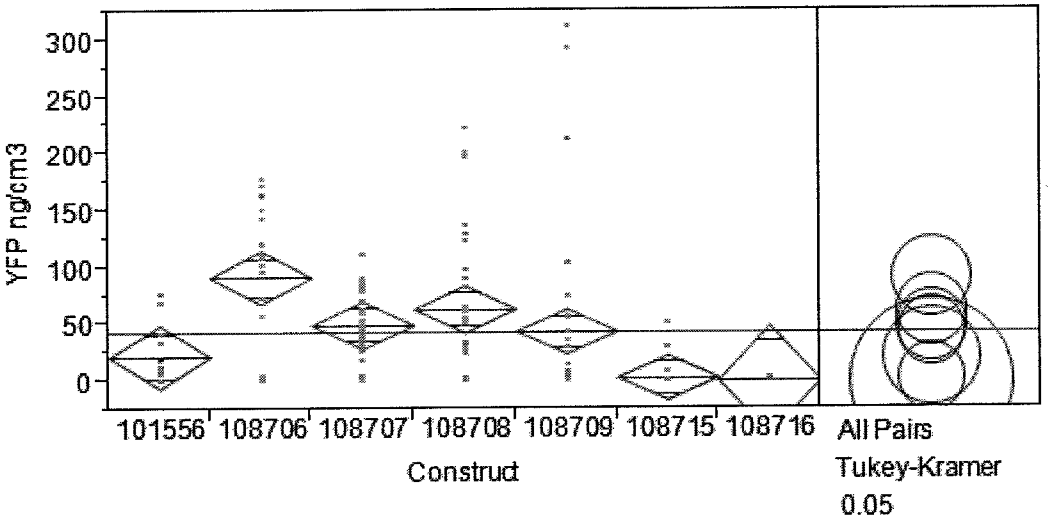
Figure 40B:
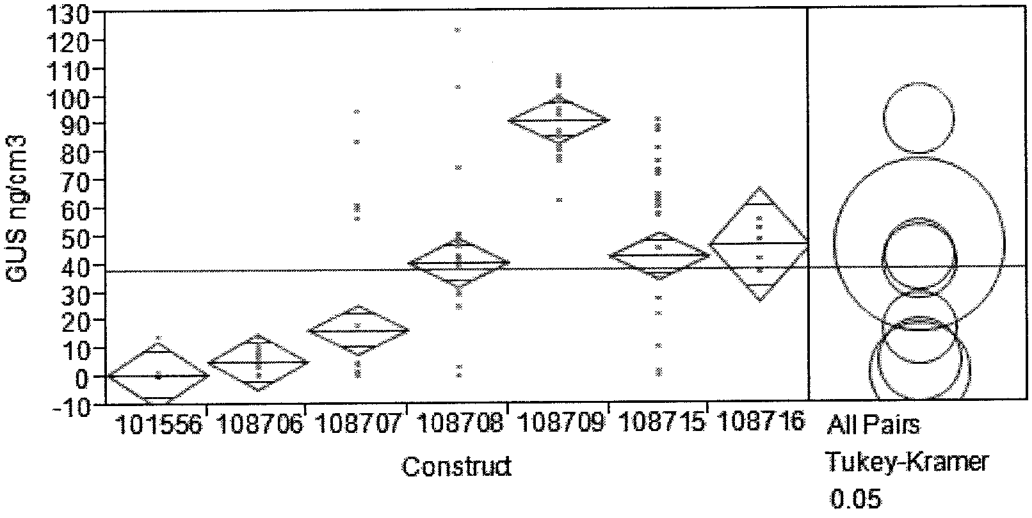
Figure 40C:
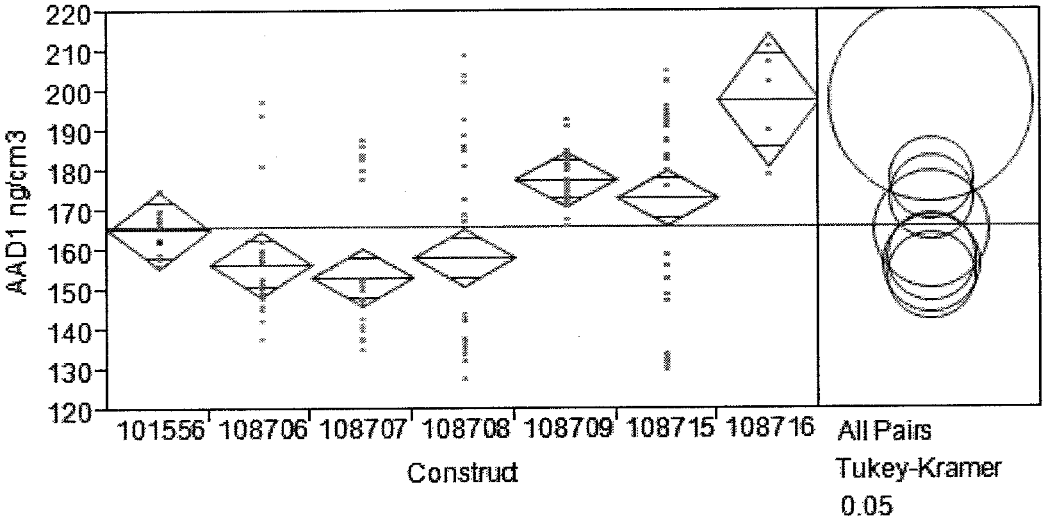

FIGS. 40A, 40B, and 40C show statistical analysis of expression results (R3) from the seven constructs shown in FIG. 30 for YFP, GUS, and AAD1 protein (LCMS) in ng/$cm^2$, respectively. The mean values and statistical results are listed.

Figure 41:
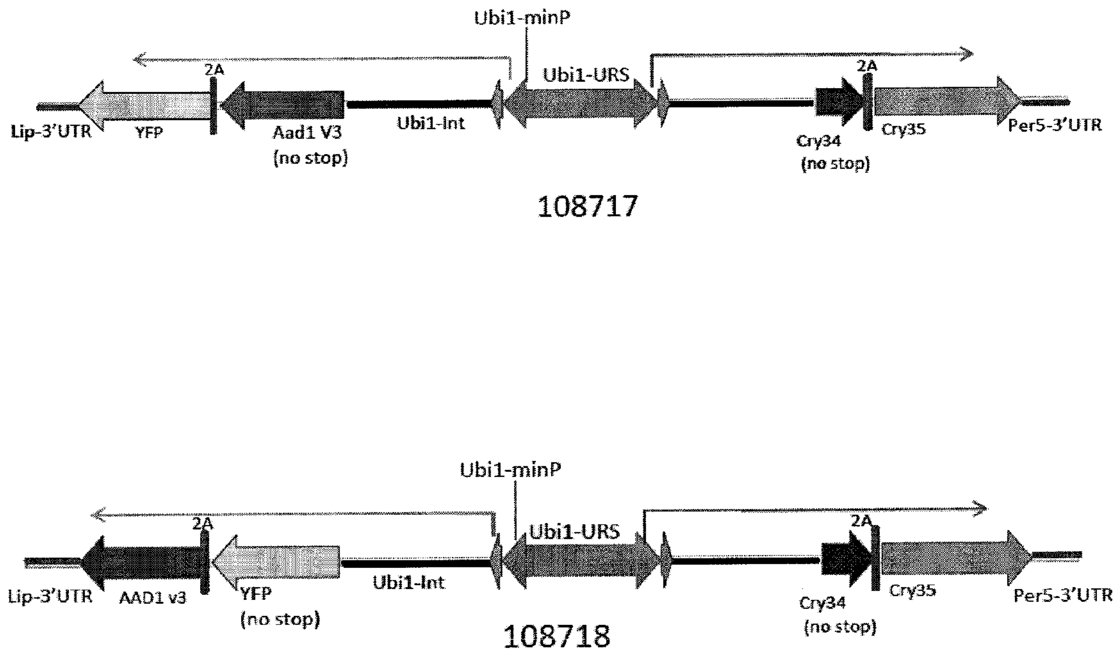

FIG. 41 shows additional multi-transgene constructs using Ubi1 promoter, including pDAB108717 and pDAB108718.

Figure 42A:
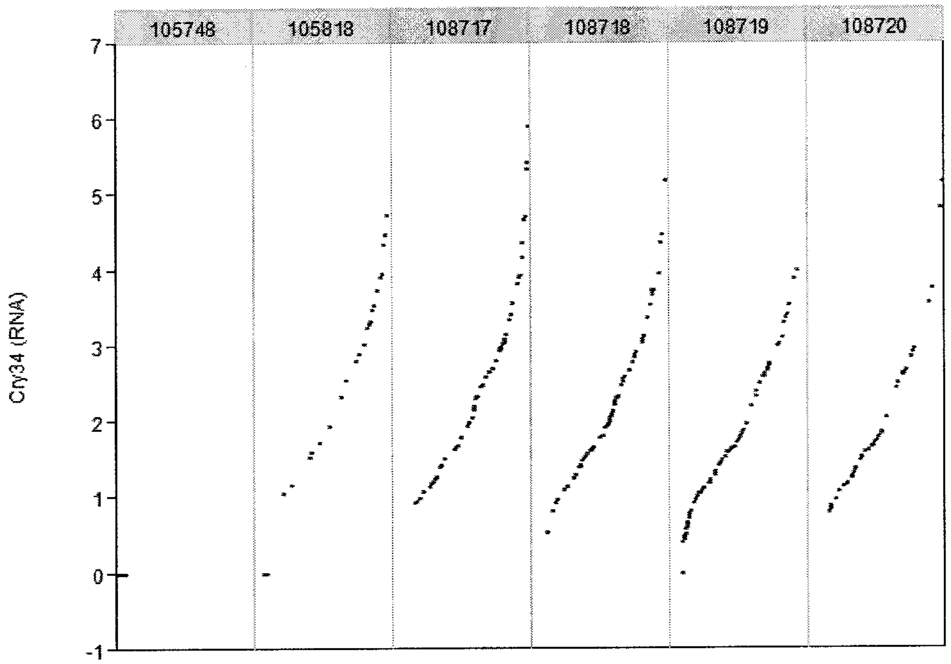
Figure 42B:
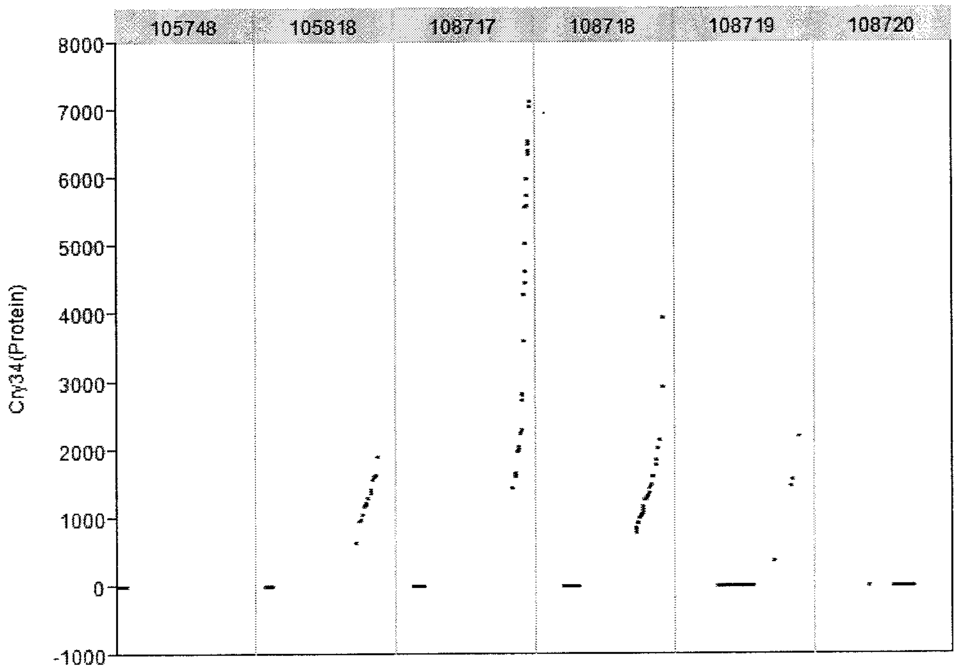

FIG. 42A shows exemplary relative expression results (V6) of Cry34 RNA from six constructs pDAB105748 (ZMUbi1-YFP), pDAB105818 (ZMUbi1-Cry34/ZMUbi1-Cry35/ZMUbi1-AAD1), pDAB108717 (YFP/AAD-1-ZMUbi1 bidirectional-Cry34-Cry35), pDAB108718 (AAD1/YFP-ZMUbi1 bidirectinal-Cry34-Cry35), pDAB108719 (YFP/AAD1-SCBV bidirectional-Cry34-Cry35), and pDAB108720 (AAD1/YFP-SCBV bidirectional-Cry34-Cry35). FIG. 42B shows exemplary relative expression results (V6) of Cry34 protein (LCMS) from the same six constructs pDAB105748, pDAB105818, pDAB108717, pDAB108718, pDAB108719, and pDAB108720.

Figure 43A:
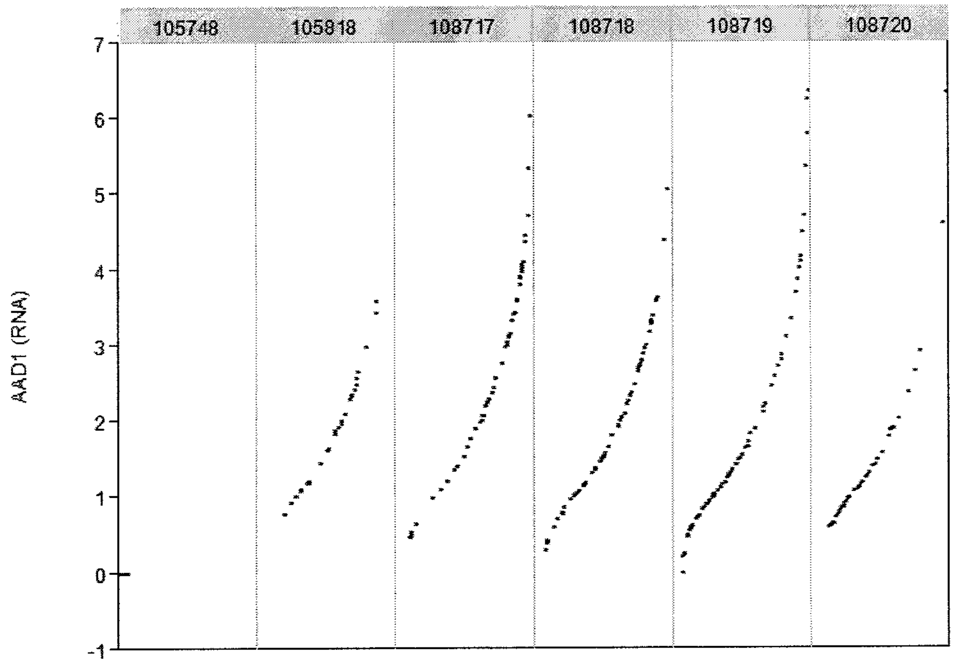
Figure 43B:
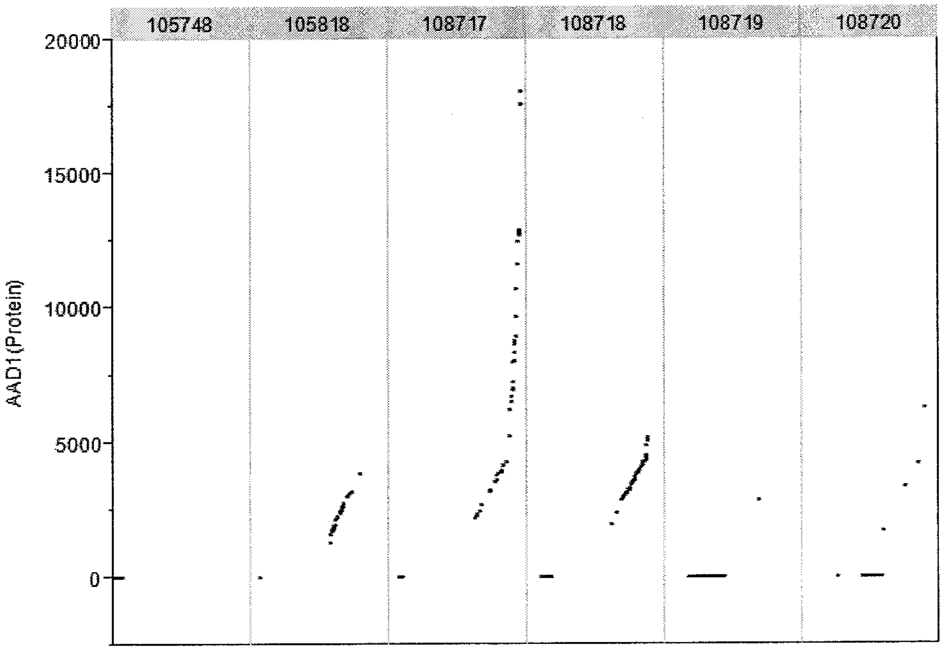

FIG. 43A shows exemplary relative expression results (V6) of AAD1 RNA from the six constructs pDAB105748, pDAB105818, pDAB108717, pDAB108718, pDAB108719, and pDAB108720. FIG. 43B shows exemplary relative expression results (V6) of AAD1 protein (LCMS) from the same six constructs pDAB105748, pDAB105818, pDAB108717, pDAB108718, pDAB108719, and pDAB108720.

Figure 44A:
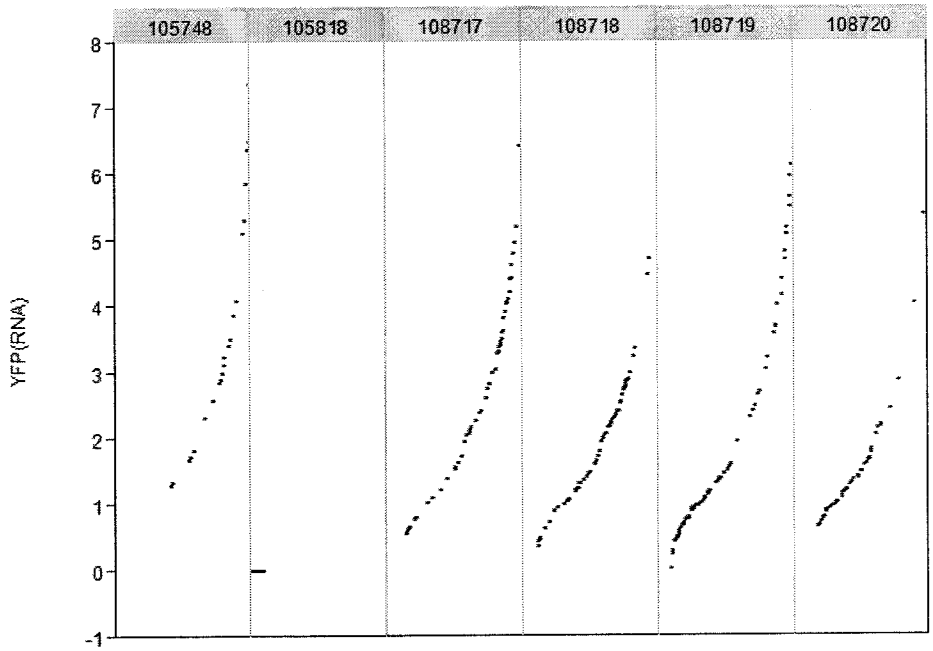
Figure 44B:
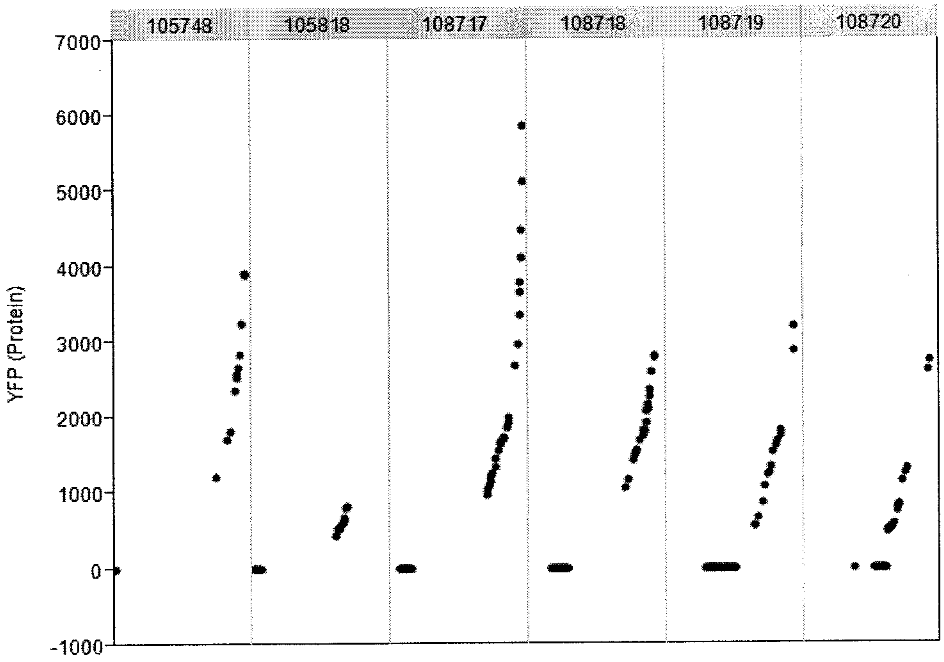

FIG. 44A shows exemplary relative expression results (V6) of YFP RNA from the six constructs pDAB105748, pDAB105818, pDAB108717, pDAB108718, pDAB108719, and pDAB108720. FIG. 44B shows exemplary relative expression results (V6) of YFP protein (LCMS) from the same six constructs pDAB105748, pDAB105818, pDAB108717, pDAB108718, pDAB108719, and pDAB108720.

Figure 45A:
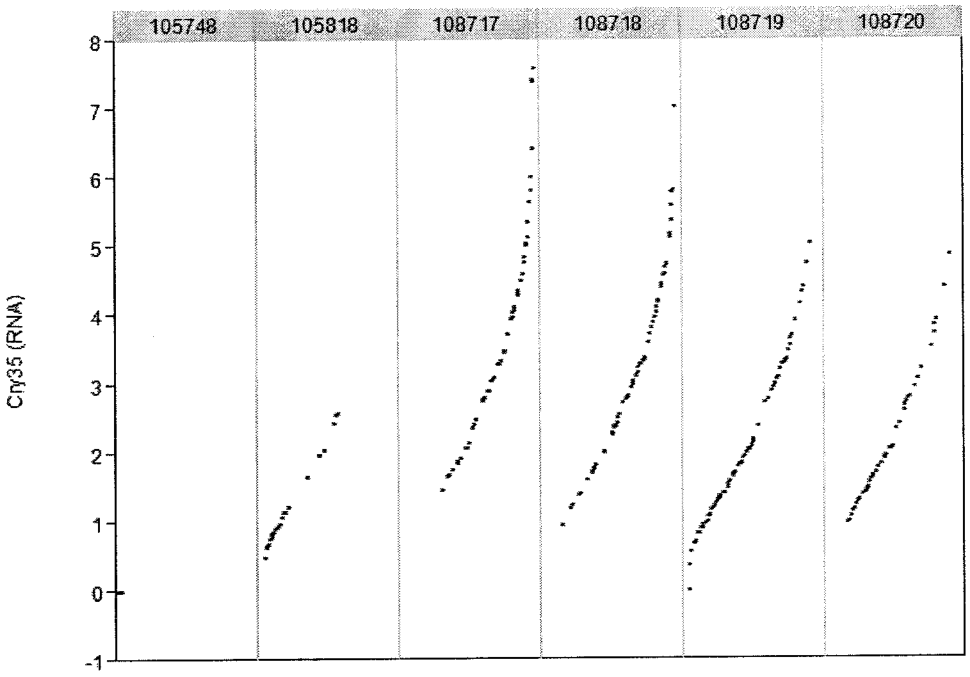
Figure 45B:
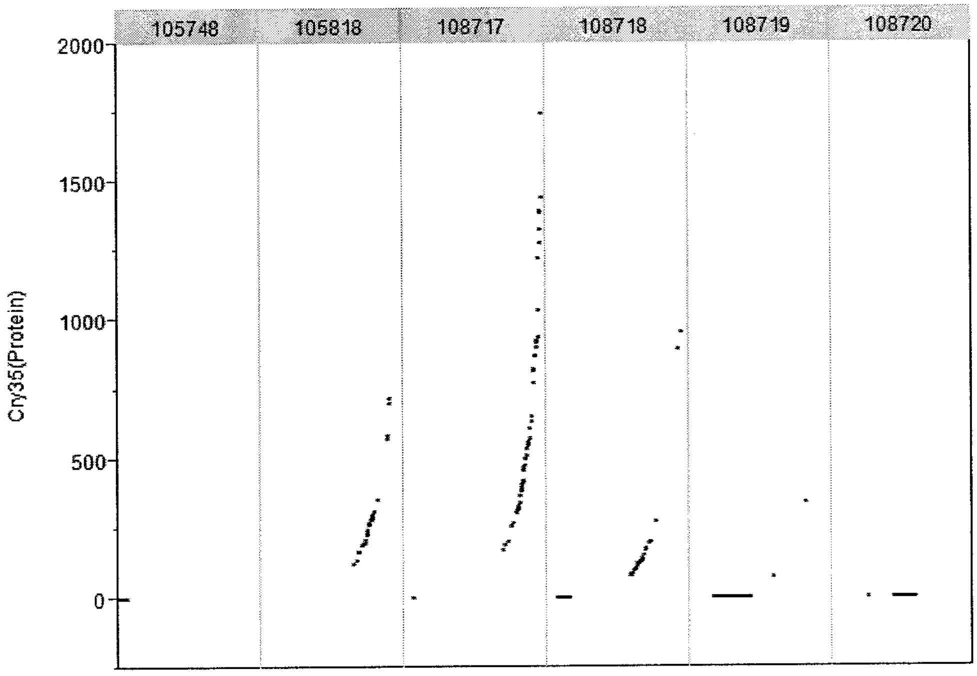

FIG. 45A shows exemplary relative expression results (V6) of Cry35 RNA from the six constructs pDAB105748, pDAB105818, pDAB108717, pDAB108718, pDAB108719, and pDAB108720. FIG. 45B shows exemplary relative expression results (V6) of Cry35 protein (ELISA) from the same six constructs pDAB105748, pDAB105818, pDAB108717, pDAB108718, pDAB108719, and pDAB108720.

Figure 46:
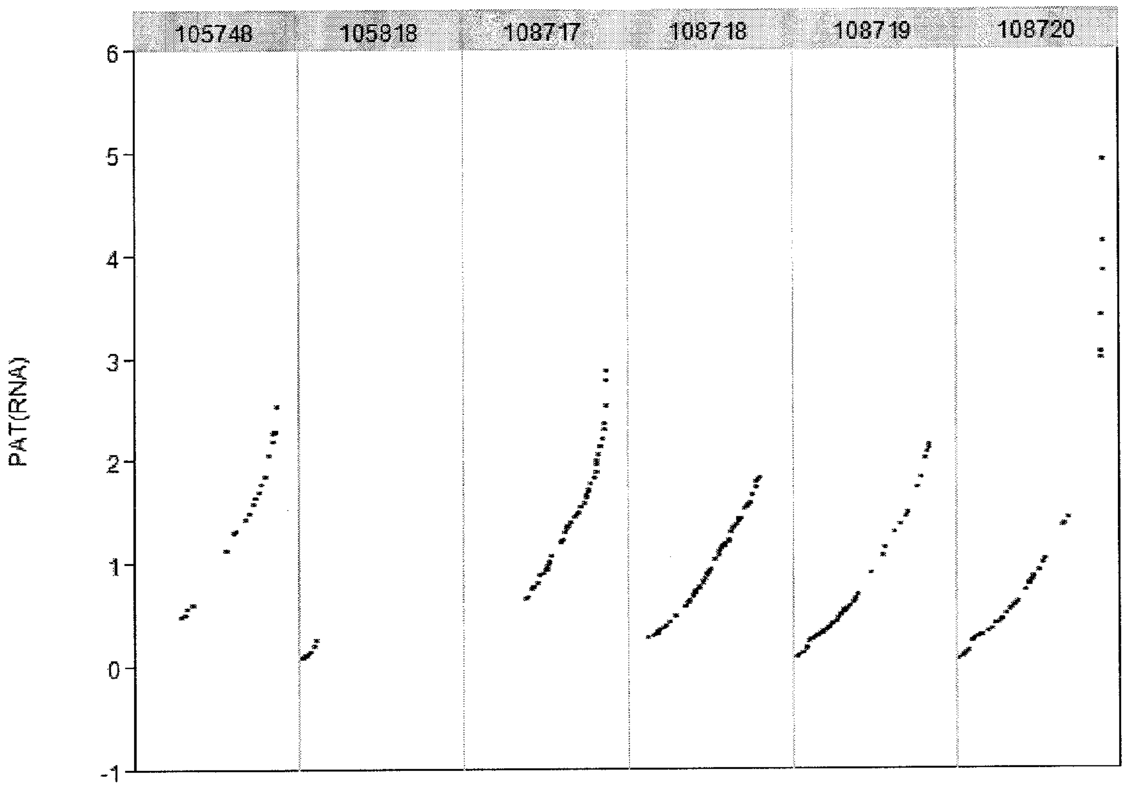

FIG. 46 shows exemplary relative expression results (V6) of PAT RNA from the six constructs pDAB105748, pDAB105818, pDAB108717, pDAB108718, pDAB108719, and pDAB108720.

Figure 47A:
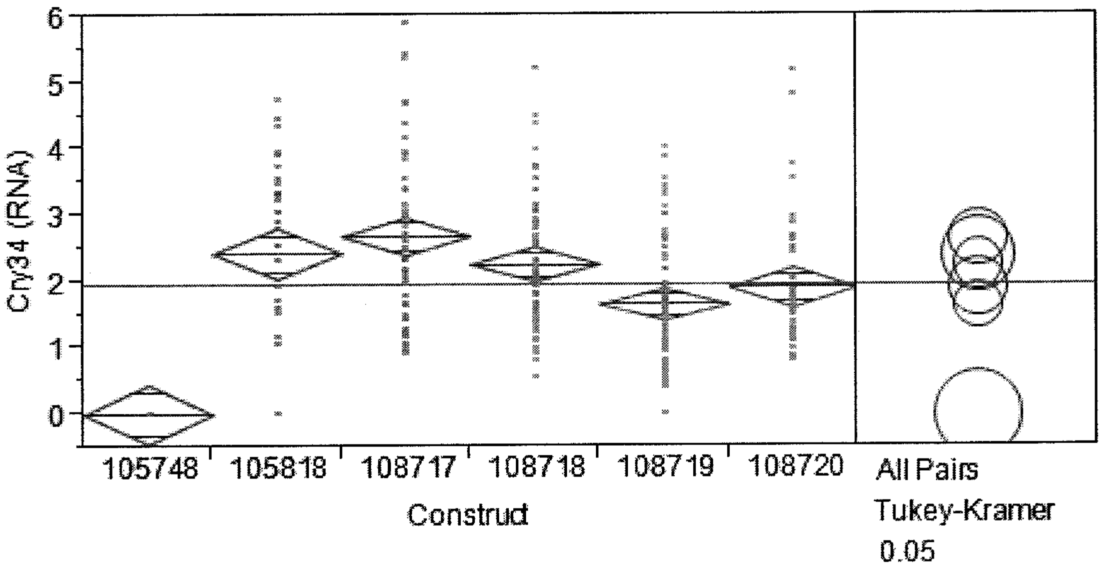
Figure 47B:
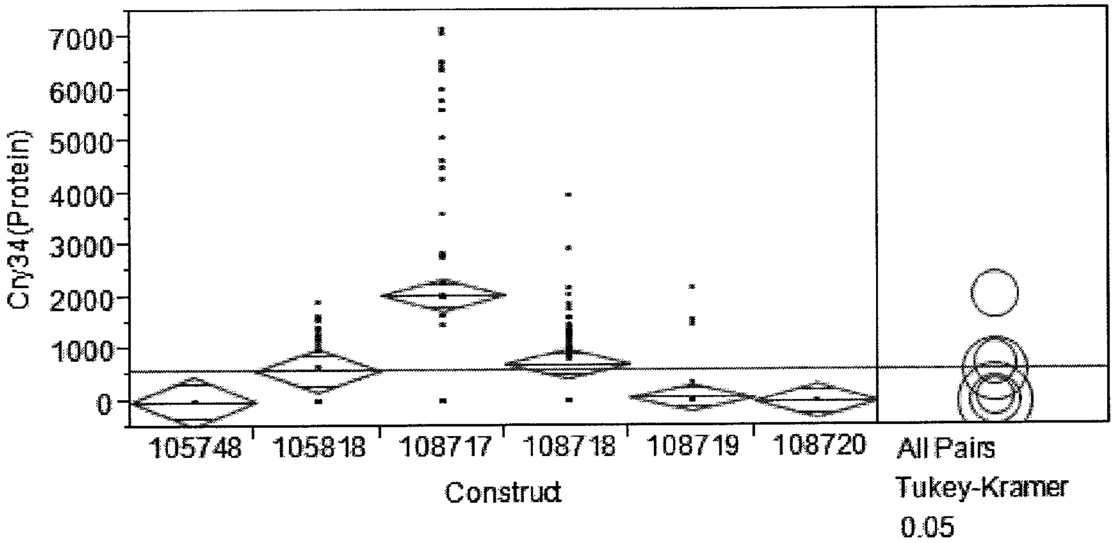

FIG. 47A shows a statistical analysis of expression results (V6) of Cry34 RNA from the six constructs pDAB105748, pDAB105818, pDAB108717, pDAB108718, pDAB108719, and pDAB108720. FIG. 47B shows a statistical analysis of expression results (V6) of Cry34 protein from the same six constructs pDAB105748, pDAB105818, pDAB108717, pDAB108718, pDAB108719, and pDAB108720. The mean values and statistical results are listed.

Figure 48A:
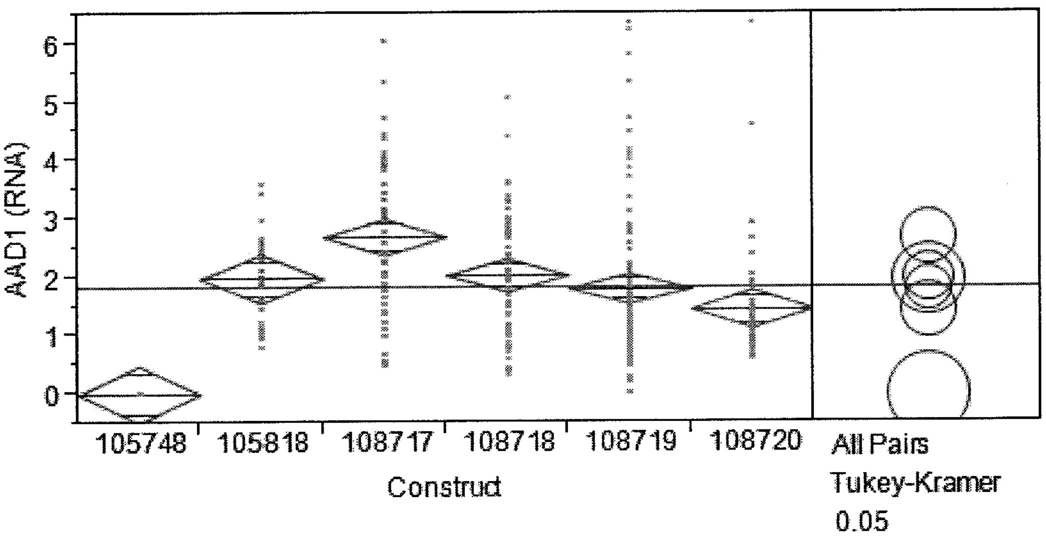
Figure 48B:
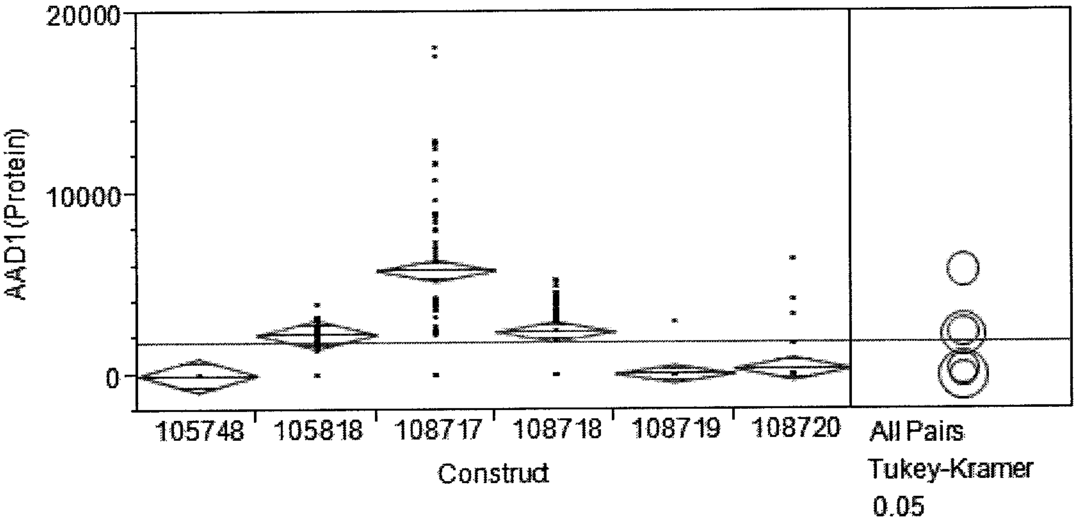

FIG. 48A shows a statistical analysis of expression results (V6) of AAD1 RNA from the six constructs pDAB105748, pDAB105818, pDAB108717, pDAB108718, pDAB108719, and pDAB108720. FIG. 48B shows a statistical analysis of expression results (V6) of AAD1 protein from the same six constructs pDAB105748, pDAB105818, pDAB108717, pDAB108718, pDAB108719, and pDAB108720. The mean values and statistical results are listed.

Figure 49A:
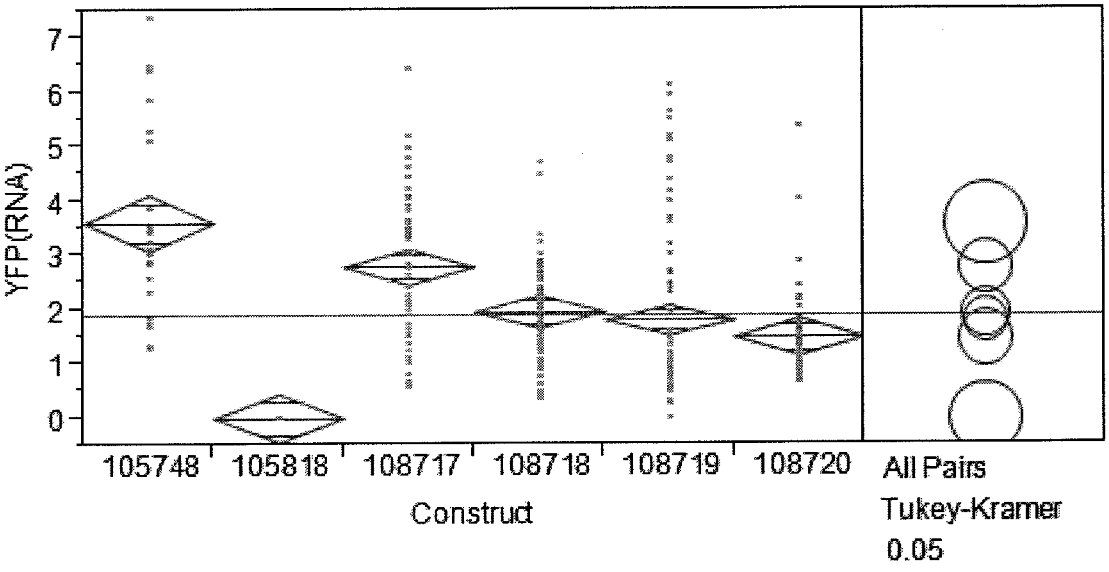
Figure 49B:
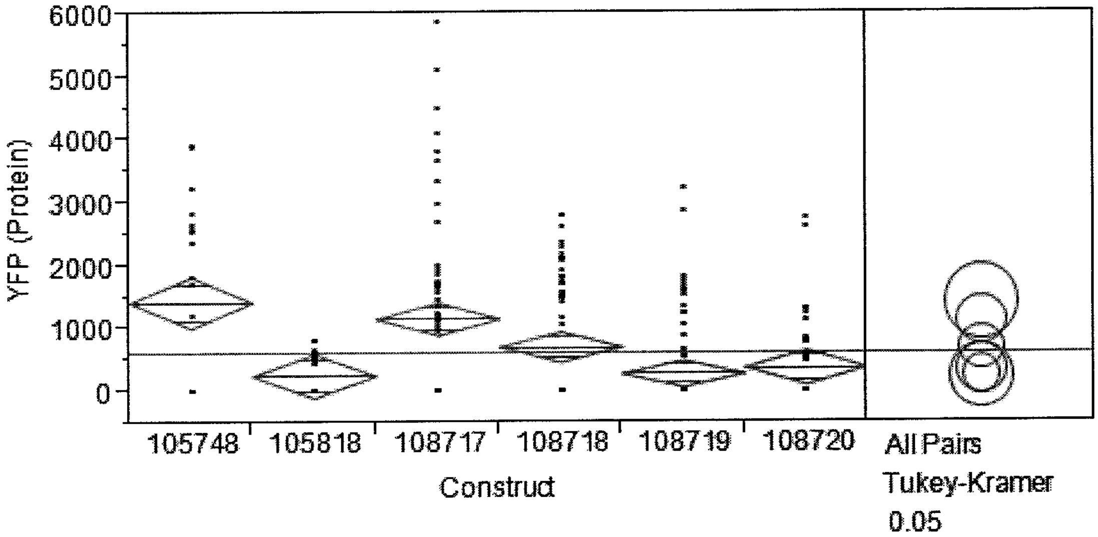

FIG. 49A shows a statistical analysis of expression results (V6) of YFP RNA from the six constructs pDAB105748, pDAB105818, pDAB108717, pDAB108718, pDAB108719, and pDAB108720. FIG. 49B shows a statistical analysis of expression results (V6) of YFP protein from the same six constructs pDAB105748, pDAB105818, pDAB108717, pDAB108718, pDAB108719, and pDAB108720. The mean values and statistical results are listed.

Figure 50A:
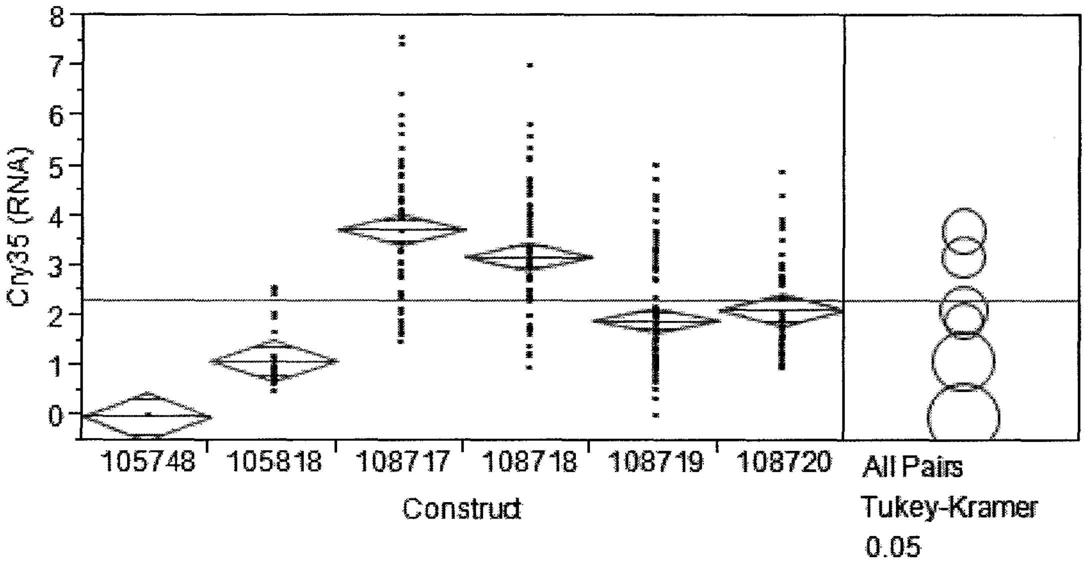
Figure 50B:
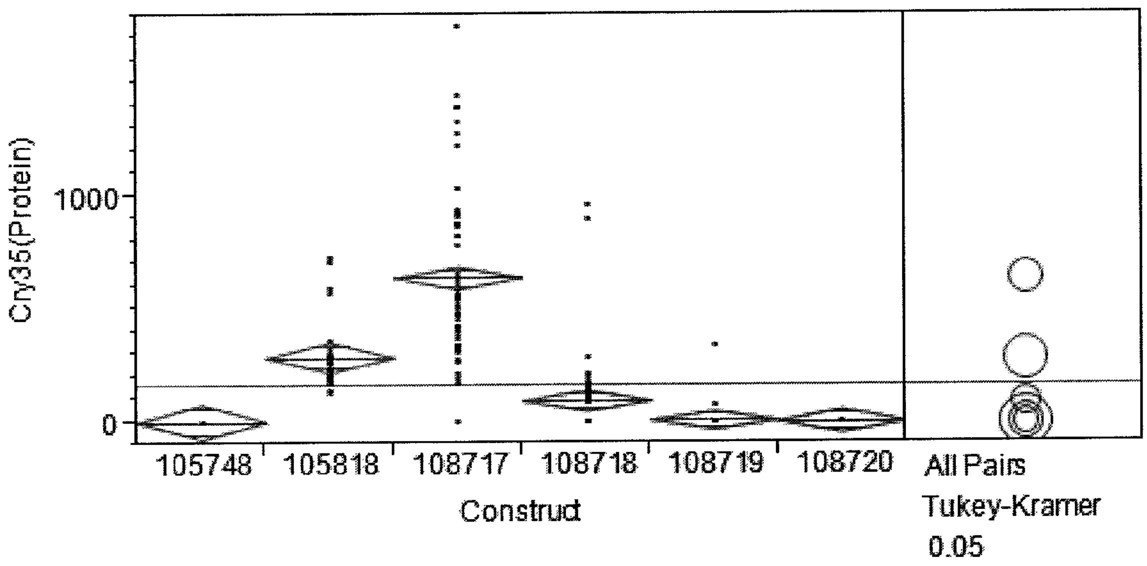

FIG. 50A shows a statistical analysis of expression results (V6) of Cry35 RNA from the six constructs pDAB105748, pDAB105818, pDAB108717, pDAB108718, pDAB108719, and pDAB108720. FIG. 50B shows a statistical analysis of expression results (V6) of Cry35 protein from the same six constructs pDAB105748, pDAB105818, pDAB108717, pDAB108718, pDAB108719, and pDAB108720. The mean values and statistical results are listed.

Figure 51:
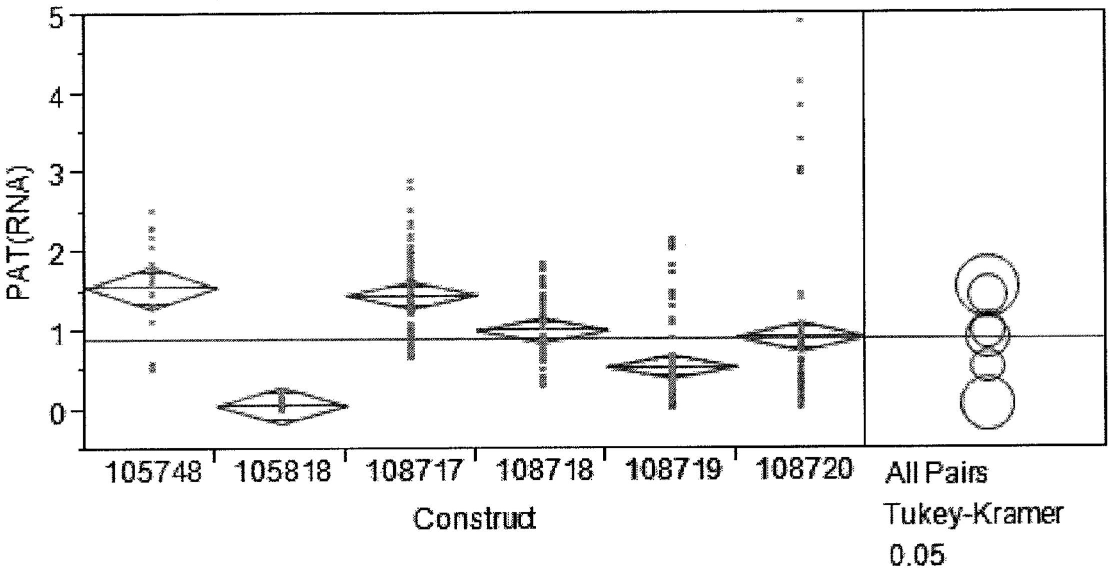
Figure 52A:
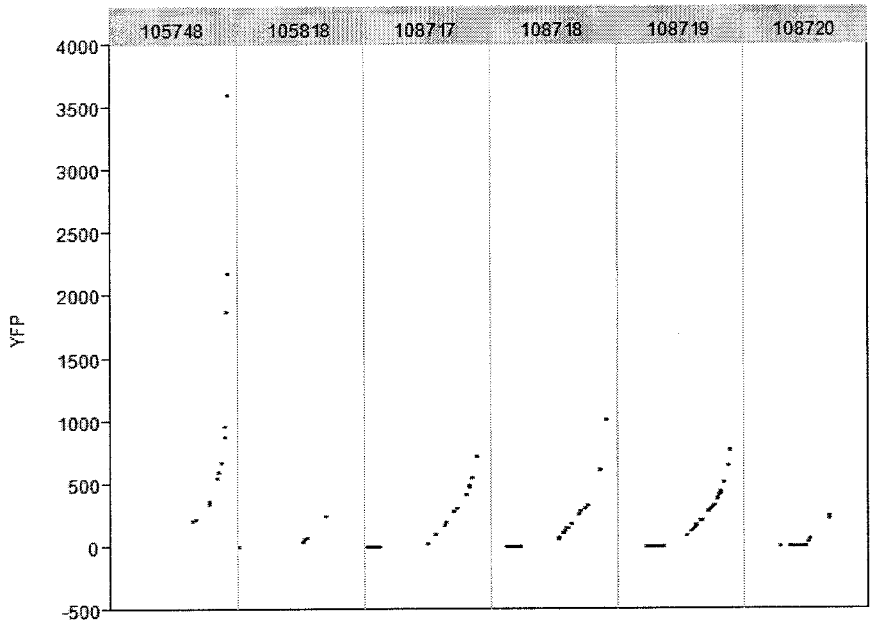
Figure 52B:
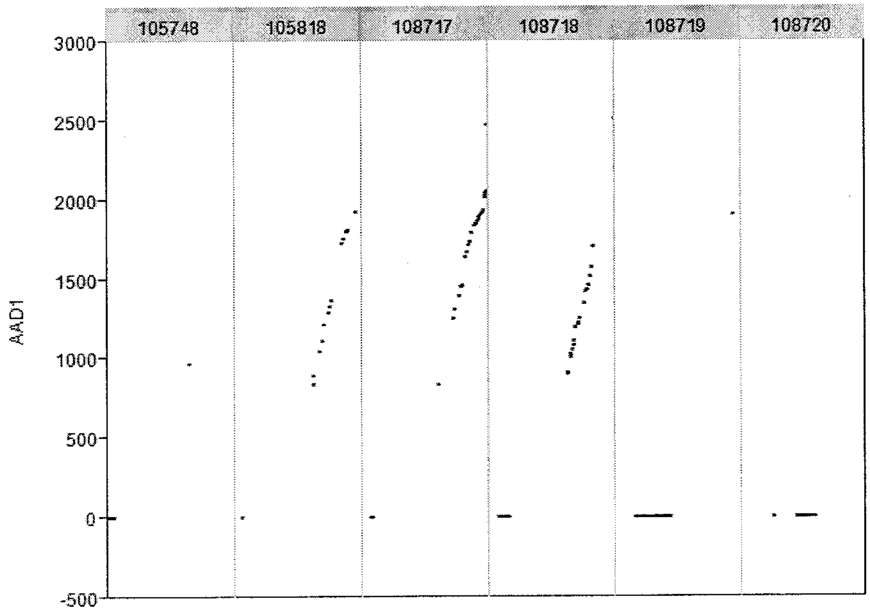
Figure 52C:
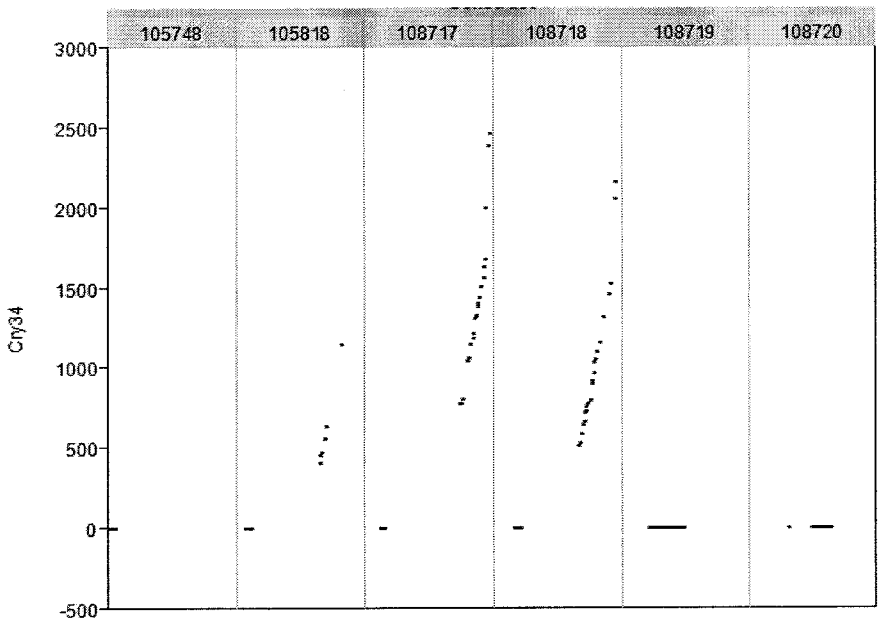
Figure 52D:
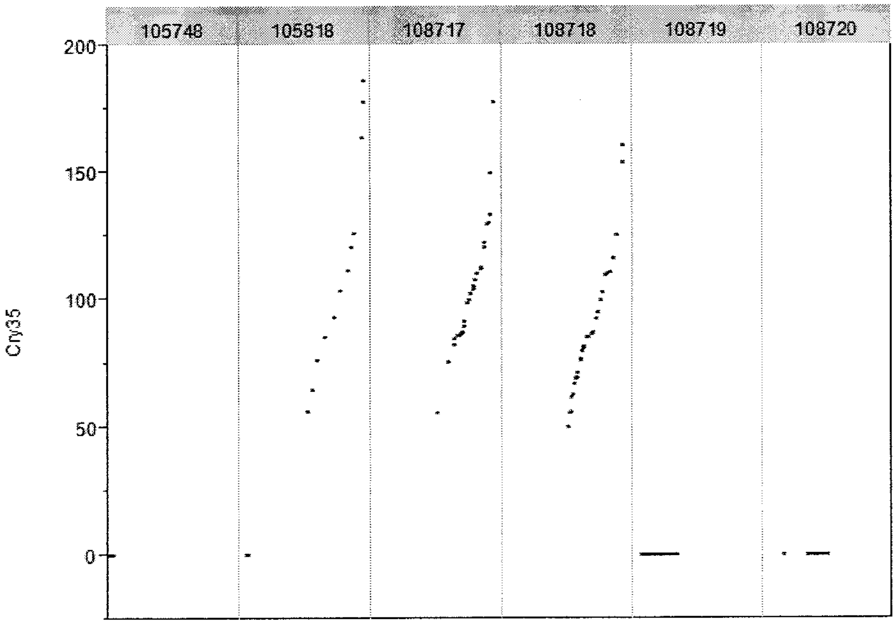
Figure 53A:
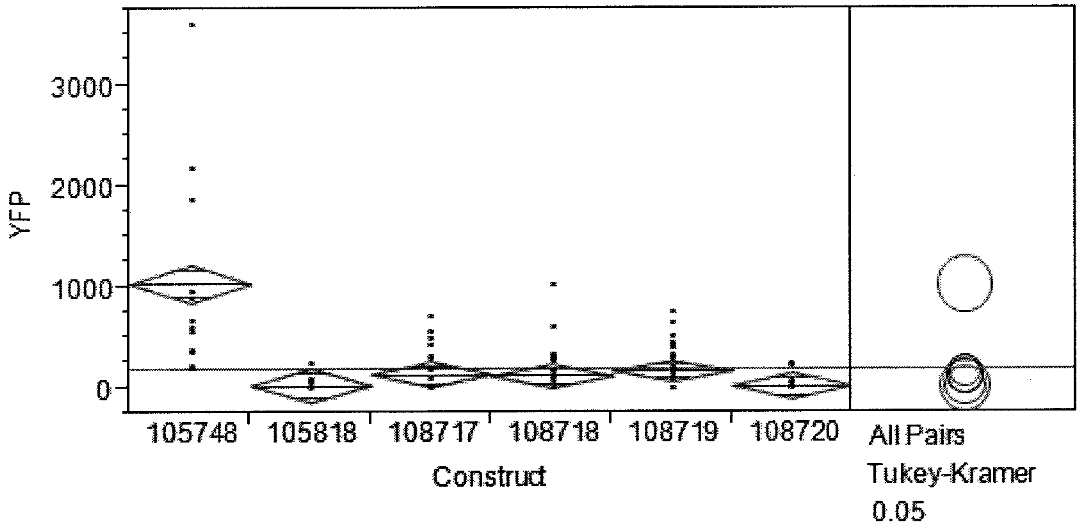
Figure 53B:
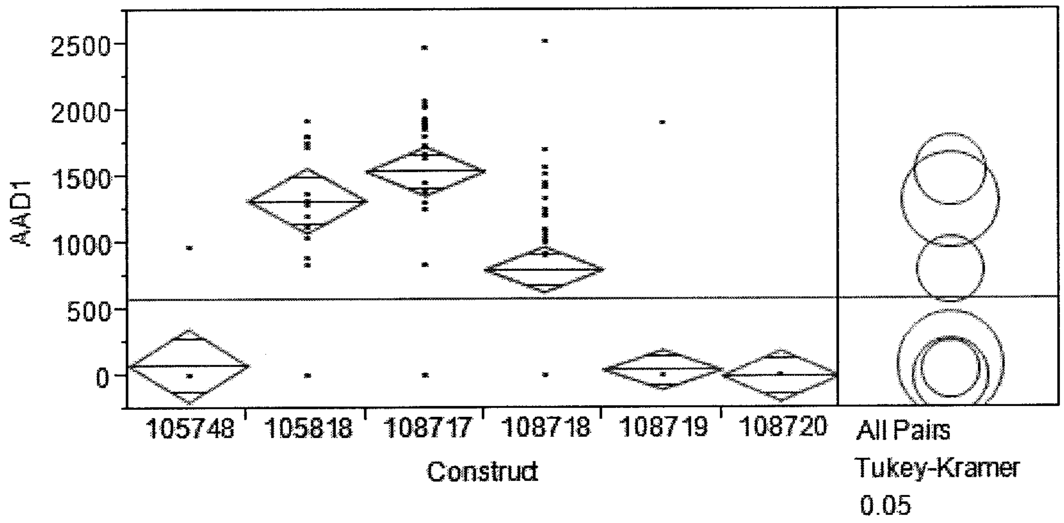
Figure 53C:
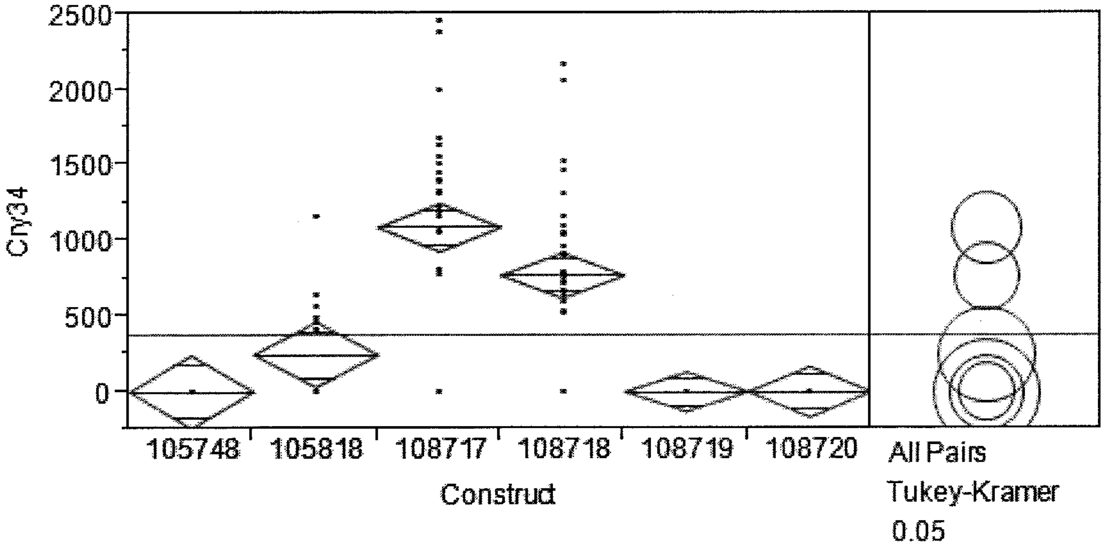
Figure 53D:
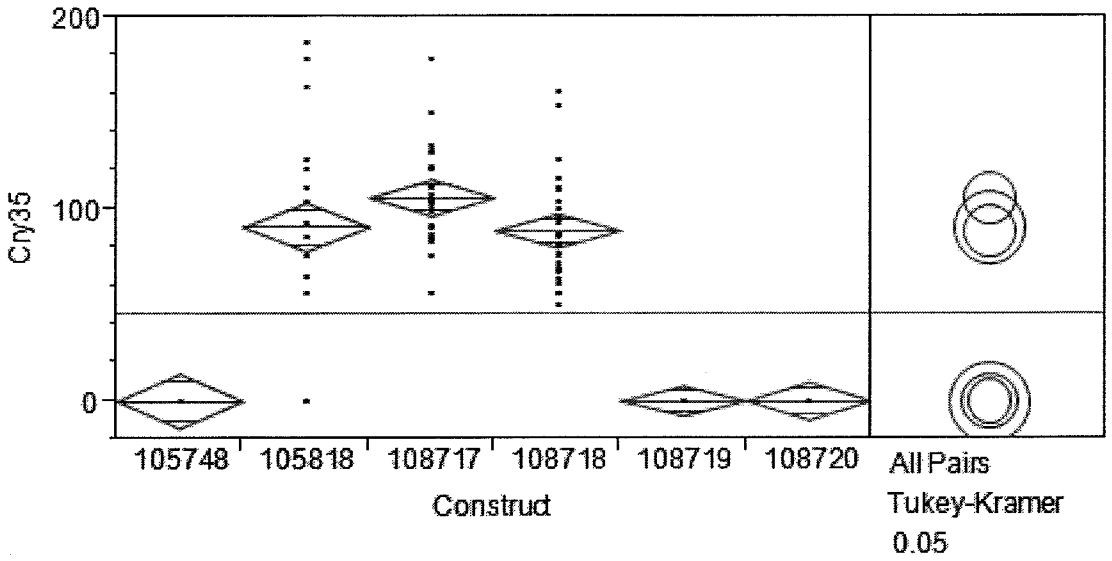
Figure 54A:
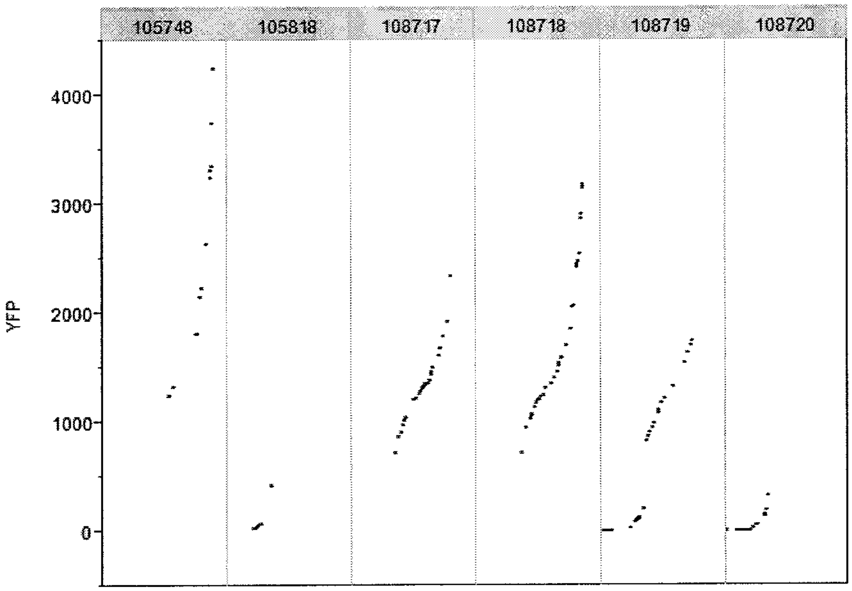
Figure 54B:
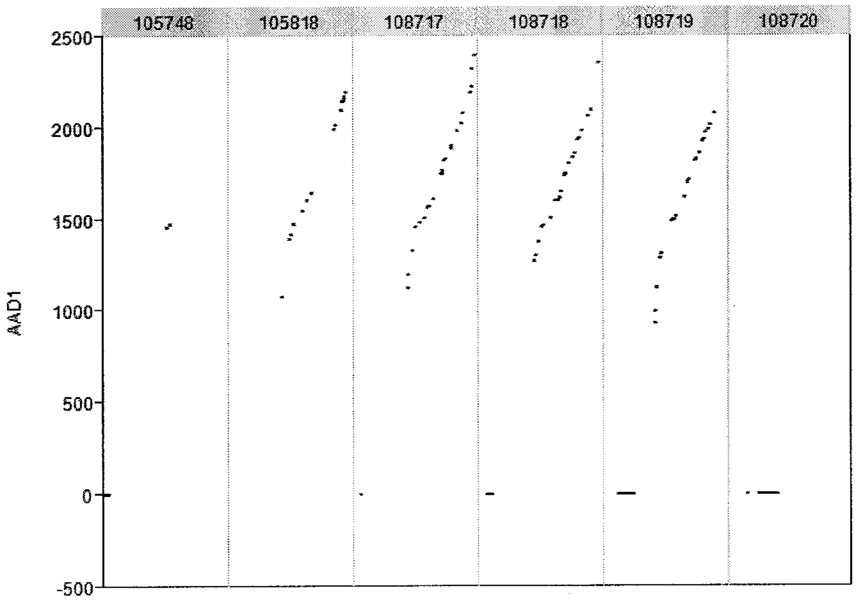
Figure 54C:
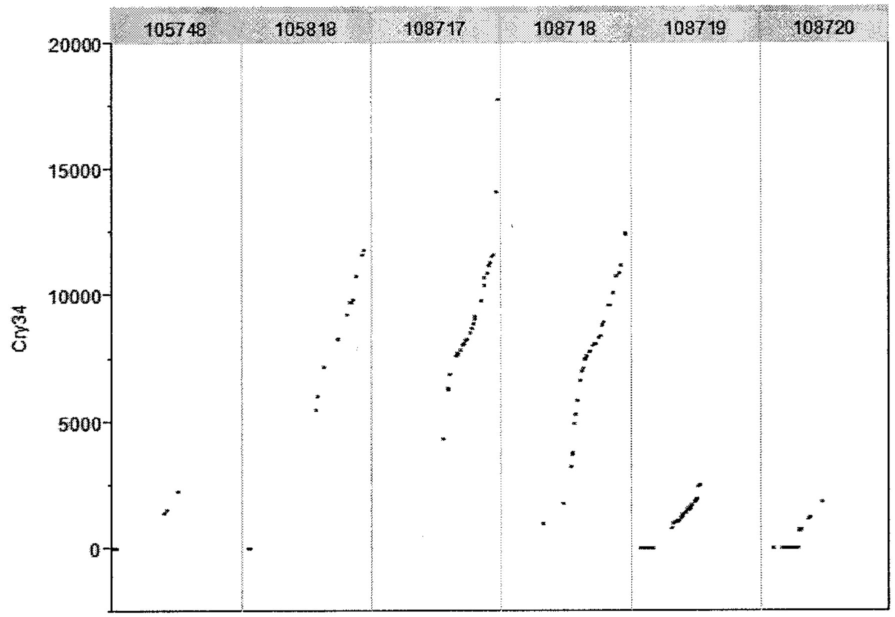
Figure 54D:
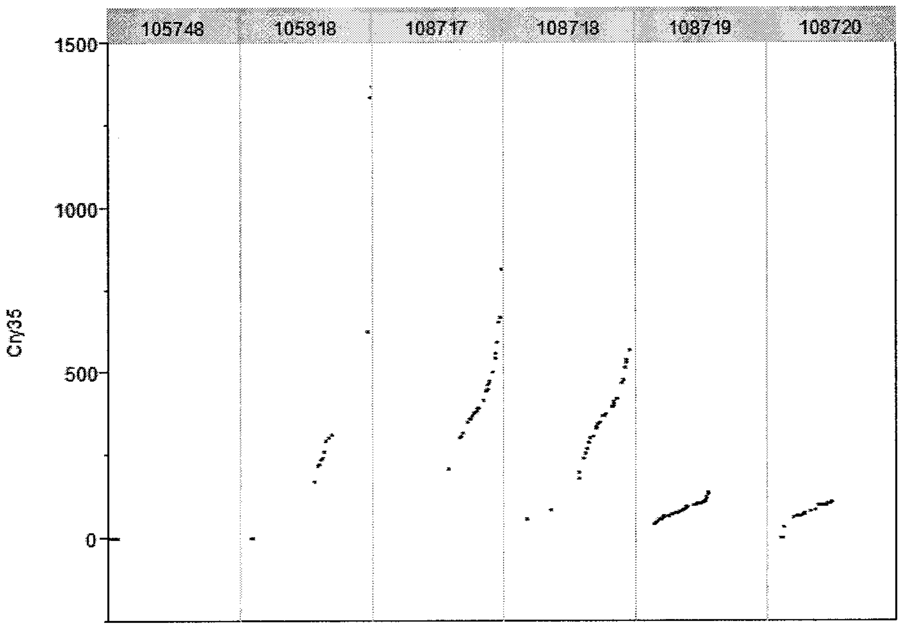
Figure 55A:
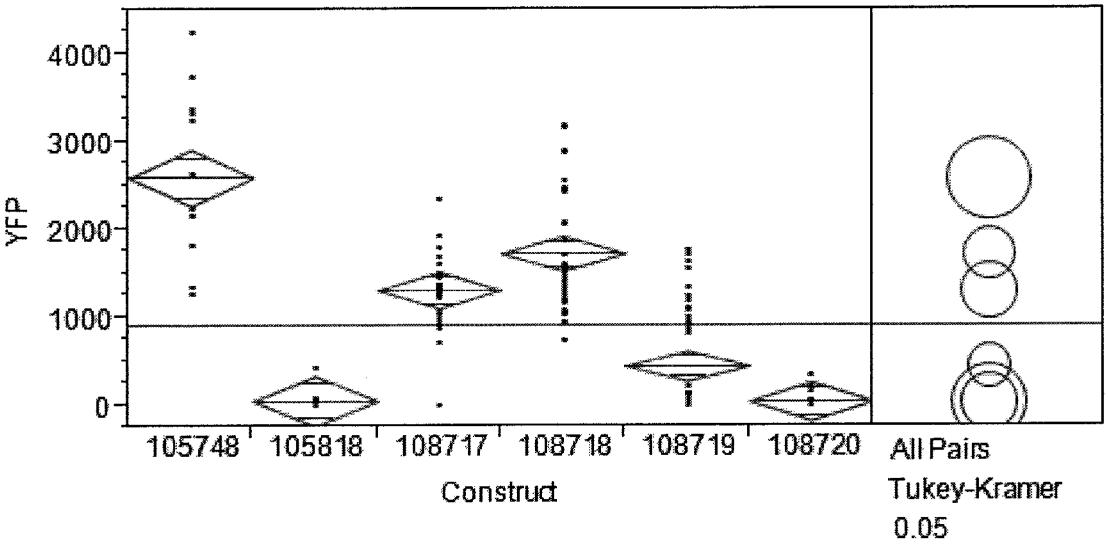
Figure 55B:
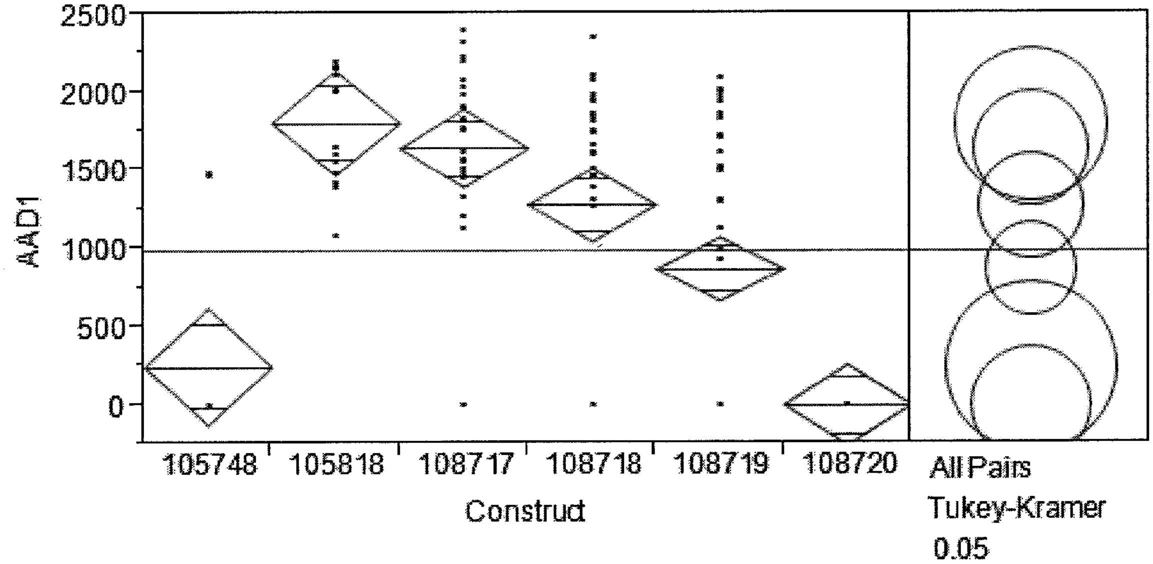
Figure 55C:
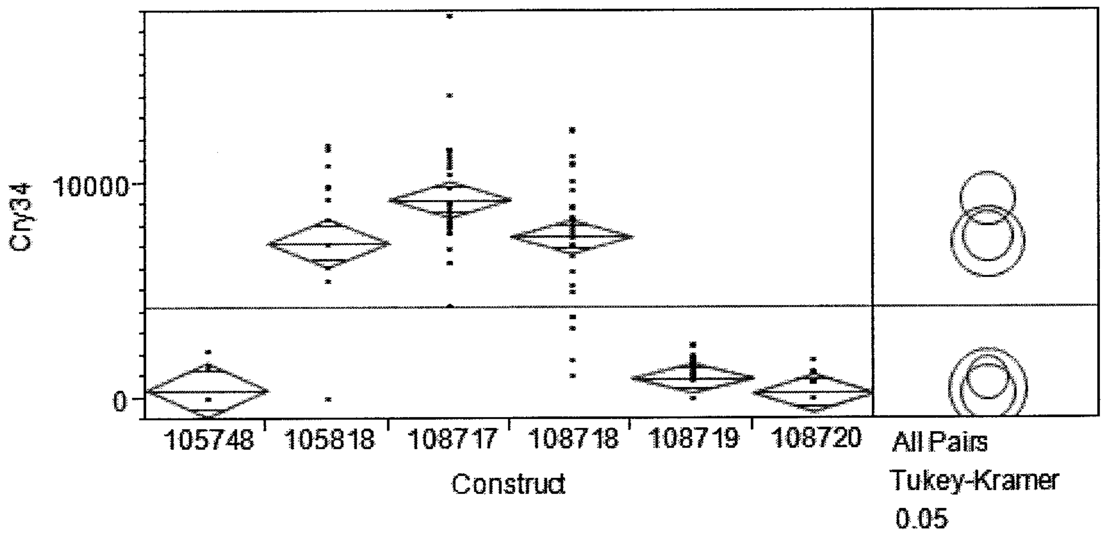
Figure 55D:
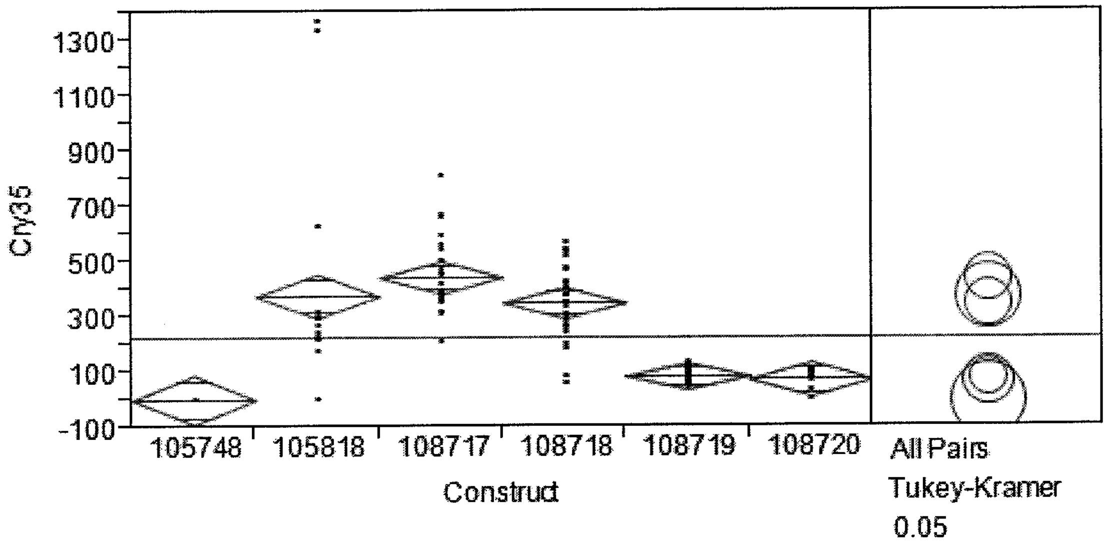

FIG. 51 shows a statistical analysis of expression results (V6) of PAT RNA from the six constructs pDAB105748, pDAB105818, pDAB108717, pDAB108718, pDAB108719, and pDAB108720. The mean values and statistical results are listed.

FIGS. 52A, 52B, 52C, and 52D show exemplary protein expression results (V10) of YFP, AAD1, Cry34, and Cry35 respectively from the six constructs pDAB105748, pDAB105818, pDAB108717, pDAB108718, pDAB108719, and pDAB108720.

FIGS. 53A, 53B, 53C, and 53D show statistical analysis of protein expression results (V10) of YFP, AAD1, Cry34, and Cry35 respectively from the six constructs pDAB105748, pDAB105818, pDAB108717, pDAB108718, pDAB108719, and pDAB108720. The mean values and statistical results are listed.

FIGS. 54A, 54B, 54C, and 54D show exemplary protein expression results (R3) of YFP, AAD1, Cry34, and Cry35 respectively from the six constructs pDAB105748, pDAB105818, pDAB108717, pDAB108718, pDAB108719, and pDAB108720.

FIGS. 55A, 55B, 55C, and 55D show statistical analysis of protein expression results (R3) of YFP, AAD1, Cry34, and Cry35 respectively from the six constructs pDAB105748, pDAB105818, pDAB108717, pDAB108718, pDAB108719, and pDAB108720. The mean values and statistical results are listed.

Figure 56:
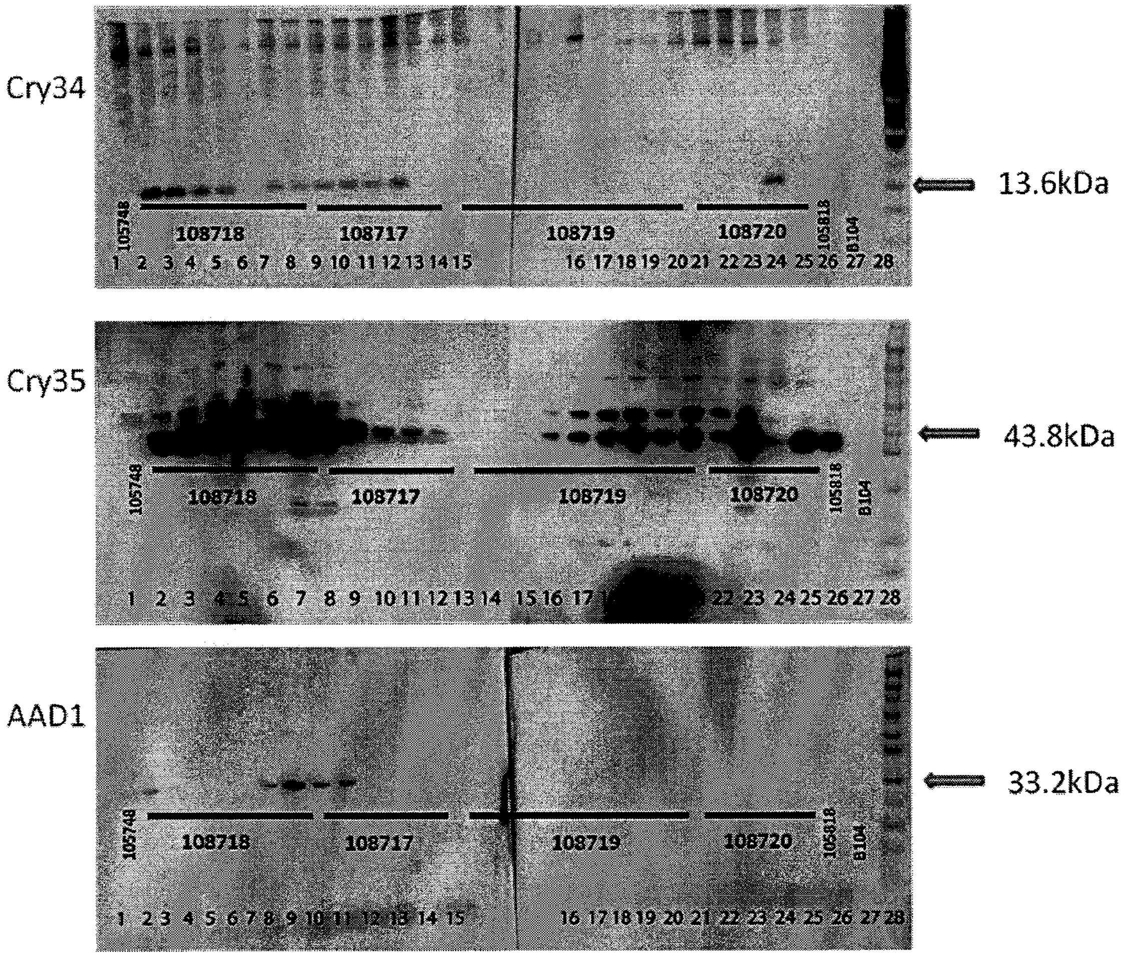

FIG. 56 shows exemplary results of Western blot for protein expression of Cry34, Cry35, and AAD1 from pDAB108718, pDAB108717, pDAB108719, and pDAB108720.

DETAILED DESCRIPTION OF THE INVENTION

Development of transgenic products is becoming increasingly complex, which requires pyramiding multiple transgenes into a single locus. Traditionally each transgene usually requires a unique promoter for expression, so multiple promoters are required to express different transgenes within one gene stack. In addition to increasing the size of the gene stack, this frequently leads to repeated use of the same promoter to obtain similar levels of expression patterns of different transgenes controlling the same trait. Multi-gene constructs driven by the same promoter are known to cause gene silencing, thus making transgenic products less efficacious in the field. Excess of transcription factor (TF)-binding sites due to promoter repetition can cause depletion of endogenous TFs leading to transcriptional inactivation. The silencing of transgenes will likely undesirably affect the performance of a transgenic plant produced to express the transgenes. Repetitive sequences within a transgene may lead to gene intra-locus homologous recombination resulting in polynucleotide rearrangements.

Provided are methods and constructs combining the bidirectional promoter system with bicistronic organization of genes on either one or both ends of the promoter, for example with the use of a 2A sequence from Thosea asigna virus. The 2A protein, which is only 16-20 amino acids long, cleaves the polyprotein at its own carboxyl-terminus. This "self-cleavage" or "ribosome skip" property of the 2A or 2A-like peptide can be used to process artificial polyproteins produced in transgenic plants. In one embodiment, Cry34 and Cry35 genes are fused in one gene expression cassette, while YFP (or PhiYFP) and AAD1 genes are fused into another gene expression cassette (with a single open reading frame (ORF) with a copy of the 2A protein gene placed between the two genes in each combination). For example, each of these gene expression cassettes (or gene pairs) can be placed on the either end of the bidirectional promoter to drive 4 transgenes using a single promoter. Thus, the constructs and methods provided herein are useful to avoid repeated use of the same promoter and significantly reduce the size of commercial constructs. In addition, driving four or more genes with one promoter also provides ability to co-express genes controlling a single trait.

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in future transgenic crops to drive the expression of multiple genes. It is desirable to design strategies that can save the number of promoters deployed and allow simultaneous co-regulated expression for gene pyramiding. In some embodiment, the bidirectional promoters provided can drive transcription of multiple transcription units, including RNAi, artificial miRNA, or haipin-loop RNA sequences.

Embodiments herein utilize a process wherein a unidirectional promoter from a maize ubiquitin-1 gene (e.g., ZmUbi1) and a SCBV promoter to design a synthetic bidirectional promoter, such that one promoter can direct the expression of two genes, one on each end of the promoter. Synthetic bidirectional promoters may allow those in the art to stack transgenes in plant cells and plants while lessening the repeated use of the same promoter and reducing the size of transgenic constructs. Furthermore, regulating the expression of two genes with a single synthetic bidirectional promoter may also provide the ability to co-express the two genes under the same conditions, such as may be useful, for example, when the two genes each contribute to a single trait in the host. The use of bidirectional function of promoters in plants has been reported in some cases, including the CaMV 35 promoters (Barfield and Pua (1991) *Plant Cell Rep.* 10(6-7):308-14; Xie et al. (2001)), and the mannopine synthase promoter (mas) promoters (Velten et al. (1984) *EMBO J.* 3(12):2723-30; Langridge et al. (1989) *Proc. Natl. Acad. Sci. USA* 86:3219-23).

Transcription initiation and modulation of gene expression in plant genes is directed by a variety of DNA sequence elements that are collectively arranged within the promoter. Eukaryotic promoters consist of minimal core promoter element (minP), and further upstream regulatory sequences (URSs). The core promoter element is a minimal stretch of contiguous DNA sequence that is sufficient to direct accurate initiation of transcription. Core promoters in plants also comprise canonical regions associated with the initiation of transcription, such as CAAT and TATA boxes. The TATA box element is usually located approximately 20 to 35 nucleotides upstream of the initiation site of transcription.

The activation of the minP is dependent upon the URS, to which various proteins bind and subsequently interact with the transcription initiation complex. URSs comprise of DNA sequences, which determine the spatiotemporal expression pattern of a promoter comprising the URS. The polarity of a promoter is often determined by the orientation of the minP, while the URS is bipolar (i.e., it functions independent of its orientation). For example, the CaMV 35S synthetic unidirectional polar promoter may be converted to a bidirectional promoter by fusing a minP at the 5' end of the promoter in the opposite orientation. See, for example, Xie et al. (2001) *Nat. Biotechnol.* 19(7):677-9.

In specific examples of some embodiments, a minimal core promoter element (minUbi1P) of a modified maize Ubi1 promoter (ZmUbi1) originally derived from the *Z. mays* inbred line, B73, is used to engineer a synthetic bidirectional SCBV promoter that may function in plants to provide expression control characteristics that are unique with respect to previously available bidirectional promoters. Embodiments include a synthetic bidirectional SCBV promoter that further includes nucleotide sequence derived from a native SCBV promoter. Particular embodiments may further include a synthetic bidirectional SCBV promoter comprising an intron (e.g., an ADH intron) in close proximity to SCBV and minUbi1P sequence elements in the synthetic bidirectional SCBV promoter.

The ZmUbi1 promoter originally derived from B73 comprises sequences located in the maize genome within about 899 bases 5' of the transcription start site, and further within about 1093 bases 3' of the transcription start site. Christensen et al. (1992) *Plant Mol. Biol.* 18(4):675-89 (describing a B73 ZmUbi1 gene). A modified ZmUbi1 promoter derived from B73 that is used in some examples is an approximately 2 kb promoter that contains a TATA box; two overlapping heat shock consensus elements; an 82 or 83 nucleotide (depending on the reference strand) leader sequence immediately adjacent to the transcription start site, which is referred to herein as ZmUbi1 exon; and a 1015-1016 nucleotide intron (see FIG. 1 for example). Other maize ubiquitin promoter variants derived from *Zea* species and *Zea mays* genotypes may exhibit high sequence conservation around the minP element consisting of the TATA element and the upstream heat shock consensus elements. Thus, embodiments of the invention are exemplified by the use of this short (~200 nt) highly conserved region (e.g., SEQ ID NO: 1) of a ZmUbi1 promoter as a minimal core promoter element for constructing synthetic bidirectional plant promoters.

Certain abbreviations disclosed are listed in Table 1.

TABLE 1

Abbreviations used in the disclosure

| Phrase | Abbreviation |
|---|---|
| bicinchoninic acid | BCA |
| cauliflower mosaic virus | CaMV |
| chloroplast transit peptide | CTP |
| homology-based gene silencing | HBGS |
| ZmUbi1 minimal core promoter | minUbi1P |
| oligo ligation amplification | OLA |
| phosphate buffered saline | PBS |
| phosphate buffered saline with 0.05% Tween 20 | PBST |
| polymerase chain reaction | PCR |
| rolling circle amplification | RCA |
| reverse transcriptase PCR | RT-PCR |
| single nucleotide primer extension | SNuPE |
| upstream regulatory sequence | URS |
| *Zea mays* Ubiquitin-1 gene | ZmUbi1 |

As used herein, the articles, “a,” “an,” and “the” include plural references unless the context clearly and unambiguously dictates otherwise.

As used herein, the phrase “backcrossing” refers to a process in which a breeder crosses hybrid progeny back to one of the parents, for example, a first generation hybrid$_{F1}$ with one of the parental genotypes of the F1 hybrid.

As used herein, the phrase “intron” refers to any nucleic acid sequence comprised in a gene (or expressed nucleotide sequence of interest) that is transcribed but not translated. Introns include untranslated nucleic acid sequence within an expressed sequence of DNA, as well as the corresponding sequence in RNA molecules transcribed therefrom.

As used herein, the phrase “isolated” refers to biological component (including a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The phrase "isolated" also embraces nucleic acids and proteins prepared by recombinant expression in a host cell, as well as chemically synthesized nucleic acid molecules, proteins, and peptides.

As used herein, the phrase "gene expression" refers to a process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the phrase "homology-based gene silencing" (HBGS) refers to a generic term that includes both transcriptional gene silencing and posttranscriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes. See, for example, Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the phrase "nucleic acid molecule" (or "nucleic acid" or "polynucleotide") refers to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the phrase "base position," refers to the location of a given base or nucleotide residue within a designated nucleic acid. The designated nucleic acid may be defined by alignment (see below) with a reference nucleic acid.

As used herein, the phrase "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the phrases "specifically hybridizable" and "specifically complementary" refers to a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, N.Y., 1989, chs. 9 and 11.

As used herein, the phrase "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5× SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

As used herein, the phrase "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

As used herein, the phrase "sequence identity" or "identity," refers to a context where two nucleic acid or polypeptide sequences, may refer to the residues in the two sequences that are the same when aligned for maximum correspondence over a specified comparison window.

As used herein, the phrase "percentage of sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the phrase "operably linked" refers to a context where the first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the phrase "promoter" refers to a region of DNA that generally is located upstream (towards the 5' region of a gene) that is needed for transcription. Promoters may permit the proper activation or repression of the gene which they control. A promoter may contain specific sequences that are recognized by transcription factors. These factors may bind to the promoter DNA sequences and result in the recruitment of RNA polymerase, an enzyme that synthesizes RNA from the coding region of the gene.

As used herein, the phrase "transforms" or "transduces" refers to a process where a virus or vector transfers nucleic acid molecules into a cell. A cell is "transformed" by a nucleic acid molecule "transduced" into the cell when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) *Nature* 319:791-3); lipofection (Feigner et al. (1987) *Proc. Natl. Acad. Sci. USA* 84:7413-7); microinjection (Mueller et al. (1978) *Cell* 15:579-85); *Agrobacterium*-mediated transfer (Fraley et al. (1983) *Proc. Natl. Acad. Sci. USA* 80:4803-7); direct DNA uptake; whiskers-mediated transformation; and microprojectile bombardment (Klein et al. (1987) *Nature* 327:70).

As used herein, the phrase "transgene" refers to an exogenous nucleic acid sequence. In one example, a transgene is a gene sequence (e.g., a herbicide-resistant gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a nucleic acid sequence of interest is a transgene. However, in other embodiments, a nucleic acid sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the phrase "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the phrase "plant" includes plants and plant parts including but not limited to plant cells and plant tissues such as leaves, stems, roots, flowers, pollen, and seeds. The class of plants that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicotyledons plants and monocotyledons plants. Examples of dicotyledons plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledons plants include corn, rice, wheat, sugarcane, barley, rye, sorghum, orchids, bamboo, banana, cattails, lilies, oat, onion, millet, and triticale.

As used herein, the phrase "plant material" refers to leaves, stems, roots, flowers or flower parts, fruits, pollen, egg cells, zygotes, seeds, cuttings, cell or tissue cultures, or any other part or product of a plant. In some embodiment, plant material includes cotyledon and leaf.

As used herein, the phrase "translation switch" refers to a mechanism at end of a gene allowing translation of an immediate downstream gene. The mechanism of translation switch can function at nucleic acid level (for example, viral or eukaryotic internal ribosome entry site (IRES), an alternative splicing site, or a ribozyme cleavage site) or at peptide/protein level (for example, a 2A peptide, a 2A-like peptide, an intein peptide, or a protease cleavage site).

These mechanisms of translation switch at nucleic acid level or at peptide/protein level are well known in the art. See, e.g., Z. Li, H. M. Schumacher, et al. (2010) *J. Biotechnol.* 145(1): 9-16; Y. Chen, K. Perumal, et al. (2000) *Gene Expr.* 9(3):133-143; T. D. Dinkova, H. Zepeda, et al. (2005) *Plant J.* 41(5): 722-731; Y. L. Dorokhov, M. V. Skulachev, et al. (2002) *Proc. Natl. Acad. Sci. U.S.A* 99(8): 5301-5306; O. Fernandez-Miragall and C. Hernandez (2011) *PLoS One* 6(7): e22617; E. Groppelli, G. J. Belsham, et al. (2007) *J. Gen. Virol.* 88(Pt 5): 1583-1588; S. H. Ha, Y. S. Liang, et al. (2010) *Plant Biotechnol J.* 8(8): 928-938; A. Karetnikov and K. Lehto (2007) *J. Gen. Virol.* 88(Pt 1): 286-297; A. Karetnikov and K. Lehto (2008) *Virology* 371(2): 292-308; M. A. Khan, H. Yumak, et al. (2009) *J. Biol. Chem.* 284(51): 35461-35470; and D. C. Koh, S. M. Wong, et al. (2003) *J. Biol. Chem.* 278(23): 20565-20573, the content of which are hereby incorporated by reference in their entireties. Multigene expression constructs containing modified inteins have been disclosed in U.S. Pat. Nos. 7,026,526 and 7,741,530, as well as U.S. Patent application 2008/0115243, the content of which are hereby incorporated by reference in their entireties.

As used herein, the phrase "selectable marker" or "selectable marker gene" refers to a gene that is optionally used in plant transformation to, for example, protect the plant cells from a selective agent or provide resistance/tolerance to a selective agent. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include gene for neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including Bar (resistance against BASTA® (glufosinate ammonium), or phosphinothricin (PPT)), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. The phrase "marker-positive" refers to plants that have been transformed to include the selectable marker gene.

Various selectable or detectable markers can be incorporated into the chosen expression vector to allow identification and selection of transformed plants, or transformants. Many methods are available to confirm the expression of selection markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or other proteins such as reporter genes β-glucuronidase (GUS), luciferase, green fluorescent protein (GFP), DsRed, β-galactosidase, chloramphenicol acetyltransferase (CAT), alkaline phosphatase, and the like (see Sambrook, et al., *Molecular Cloning: A Laboratory Manual*, Third Edition, Cold Spring Harbor Press, N.Y., 2001, the content of which is incorporated herein by reference in its entirety).

Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate or has been obtained by using genes coding for the mutant target enzymes, 5-enolpyruvylshikimate-3-phosphate synthase (EPSPS). Genes and mutants for EPSPS have been disclosed in U.S. Pat. Nos. 4,940,835, 5,188,642, 5,310,667, 5,633,435, 5,633,448, and 6,566,587, the contents of which are incorporated by reference in their entireties. Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides. Enzymes/genes for glufosinate resistance/tolerance have been disclosed in U.S. Pat. Nos. 5,273,894, 5,276,268, 5,550,318, and 5,561,236, the contents of which are incorporated by reference in their entireties. Enzymes/genes for 2,4-D resistance have been previously disclosed in U.S. Pat. Nos. 6,100,446 and 6,153,401, as well as patent applications US 2009/0093366 and WO 2007/053482, the contents of which are hereby incorporated by reference in their entireties. Enzymes/genes for nitrilase has been previously disclosed in U.S. Pat. No. 4,810,648, the content of which is incorporated by reference in its entirety.

Other herbicides can inhibit the growing point or meristem, including imidazolinone or sulfonylurea, and genes for resistance/tolerance of acetohydroxyacid synthase (AHAS) and acetolactate synthase (ALS) for these herbicides have been described. Genes and mutants for AHAS and mutants have been disclosed in U.S. Pat. Nos. 4,761,373, 5,304,732, 5,331,107, 5,853,973, and 5,928,937, the contents of which are incorporated by reference in their entireties. Genes and mutants for ALS have been disclosed in U.S. Pat. Nos. 5,013,659 and 5,141,870, the contents of which are incorporated by reference in their entireties.

Glyphosate resistance genes include mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (ACCase inhibitor-encoding genes). Herbicide resistance/tolerance genes of acetyl coemzyme A carboxylase (ACCase) have been described in U.S. Pat. Nos. 5,162,602 and 5,498,544, the contents of which are incorporated by reference in their entireties.

A DNA molecule encoding a mutant aroA gene can be obtained under ATCC accession number 39256, and the nucleotide sequence of the mutant gene is disclosed in U.S. Pat. No. 4,769,061 to Comai, European patent application No. 0 333 033 to Kumada et al., and U.S. Pat. No. 4,975,374 to Goodman et al., disclosing nucleotide sequences of glutamine synthetase genes which confer resistance to herbicides such as L-phosphinothricin. The nucleotide sequence of a PAT gene is provided in European application No. 0 242 246 to Leemans et al. Also DeGreef et al., *Bio/Technology* 7:61 (1989), describes the production of transgenic plants that express chimeric bar genes coding for PAT activity. Exemplary of genes conferring resistance to phenoxy proprionic acids and cyclohexones, including sethoxydim and haloxyfop, are the Accl-S1, Accl-S2 and Accl-S3 genes described by Marshall et al., *Theon. Appl. Genet.* 83:435 (1992). GAT genes capable of conferring glyphosate resistance are described in WO 2005012515 to Castle et al. Genes conferring resistance to 2,4-D, fop and pyridyloxy auxin herbicides are described in WO 2005107437 and U.S. patent application Ser. No. 11/587,893.

Other herbicides can inhibit photosynthesis, including triazine (psbA and 1 s+ genes) or benzonitrile (nitrilase gene). Przibila et al., *Plant Cell* 3:169 (1991), describes the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

For purposes of the present invention, selectable marker genes include, but are not limited to genes encoding: neomycin phosphotransferase II (Fraley et al. (1986) *CRC Critical Reviews in Plant Science* 4:1-25); cyanamide hydratase (Maier-Greiner et al. (1991) *Proc. Natl. Acad. Sci. USA* 88:4250-4264); aspartate kinase; dihydrodipicolinate synthase (Perl et al. (1993) *Bio/Technology* 11:715-718); tryptophan decarboxylase (Goddijn et al. (1993) *Plant Mol. Bio.* 22:907-912); dihydrodipicolinate synthase and desensitized aspartade kinase (Perl et al. (1993) *Bio/Technology* 11:715-718); bar gene (Toki et al. (1992) *Plant Physiol.* 100:1503-1507; and Meagher et al. (1996), *Crop Sci.* 36:1367); tryptophan decarboxylase (Goddijn et al. (1993) *Plant Mol. Biol.* 22:907-912); neomycin phosphotransferase (NEO) (Southern et al. (1982) *J. Mol. Appl. Gen.* 1:327; hygromycin phosphotransferase (HPT or HYG) (Shimizu et al. (1986) *Mol. Cell Biol.* 6:1074); dihydrofolate reductase (DHFR) (Kwok et al. (1986) *PNAS* USA 4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (Anderson et al., U.S. Pat. No. 4,761,373; Haughn et al. (1988) *Mol. Gen. Genet.* 221:266); 5-enolpyruvyl-shikimate-phosphate synthase (aroA) (Comai et al. (1985) *Nature* 317:741); haloarylnitrilase (Stalker et al., published PCT application WO87/04181); acetyl-coenzyme A carboxylase (Parker et al. (1990) *Plant Physiol.* 92:1220); dihydropteroate synthase (sul I) (Guerineau et al.

(1990) *Plant Mol. Biol.* 15:127); and 32 kD photosystem II polypeptide (psbA) (Hirschberg et al. (1983) *Science* 222: 1346).

Also included are genes encoding resistance to: chloramphenicol (Herrera-Estrella et al. (1983) *EMBO J.* 2:987-992); methotrexate (Herrera-Estrella et al. (1983) *Nature* 303:209-213; Meijer et al. (1991) *Plant Mol Bio.* 16:807-820 (1991); hygromycin (Waldron et al. (1985) *Plant Mol. Biol.* 5:103-108; Zhijian et al. (1995) *Plant Science* 108: 219-227; and Meijer et al. (1991) *Plant Mol. Bio.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1986) *Plant Mol. Biol.* 7:171-176); sulfonamide (Guerineau et al. (1990) *Plant Mol. Bio.* 15:127-136); bromoxynil (Stalker et al. (1988) *Science* 242:419-423); 2,4-D (Streber et al. (1989) *Bio/Technology* 7:811-816); glyphosate (Shaw et al. (1986) *Science* 233:478-481); and phosphinothricin (DeBlock et al. (1987) *EMBO J.* 6:2513-2518). All references recited in the disclosure are hereby incorporated by reference in their entireties unless stated otherwise.

The above list of selectable marker and reporter genes are not meant to be limiting. Any reporter or selectable marker gene are encompassed by the present invention. If necessary, such genes can be sequenced by methods known in the art.

The reporter and selectable marker genes are synthesized for optimal expression in the plant. That is, the coding sequence of the gene has been modified to enhance expression in plants. The synthetic marker gene is designed to be expressed in plants at a higher level resulting in higher transformation efficiency. Methods for synthetic optimization of genes are available in the art. In fact, several genes have been optimized to increase expression of the gene product in plants.

The marker gene sequence can be optimized for expression in a particular plant species or alternatively can be modified for optimal expression in plant families. The plant preferred codons may be determined from the codons of highest frequency in the proteins expressed in the largest amount in the particular plant species of interest. See, for example, EPA 0359472; EPA 0385962; WO 91/16432; Perlak et al. (1991) *Proc. Natl. Acad. Sci. USA* 88:3324-3328; and Murray et al. (1989) *Nucleic Acids Research* 17: 477-498; U.S. Pat. No. 5,380,831; and U.S. Pat. No. 5,436,391, herein incorporated by reference. In this manner, the nucleotide sequences can be optimized for expression in any plant. It is recognized that all or any part of the gene sequence may be optimized or synthetic. That is, fully optimized or partially optimized sequences may also be used.

Genes that Confer Resistance to an Herbicide:

A. Resistance/tolerance of acetohydroxyacid synthase (AHAS) and acetolactate synthase (ALS) against herbicides imidazolinone or sulfonylurea. Genes and mutants for AHAS and mutants have been disclosed in U.S. Pat. Nos. 4,761,373, 5,304,732, 5,331,107, 5,853,973, and 5,928,937. Genes and mutants for ALS have been disclosed in U.S. Pat. Nos. 5,013,659 and 5,141,870.

B. Resistance/tolerance genes of acetyl coemzyme A carboxylase (ACCase) against herbicides cyclohexanediones and/or aryloxyphenoxypropanoic acid (including Haloxyfop, Diclofop, Fenoxyprop, Fluazifop, Quizalofop) have been described in U.S. Pat. Nos. 5,162,602 and 5,498,544.

C. Genes for glyphosate resistance/tolerance. Gene of 5-enolpyruvyl-3-phosphoshikimate synthase (ES3P synthase) has been described in U.S. Pat. No. 4,769,601. Genes of 5-enolpyruvylshikimate-3-phosphate synthase (EPSPS) and mutants have been described in U.S. Pat. Nos. 4,940,835, 5,188,642, 5,310,667, 5,633,435, 5,633,448, and 6,566,587.

D. Genes for glufosinate (bialaphos, phosphinothricin (PPT)) resistance/tolerance. Gene for phosphinothricin acetyltransferase (Pat) has been described in U.S. Pat. Nos. 5,273,894, 5,276,268, and 5,550,318; and gene for bialaphos resistance gene (Bar) has been described in U.S. Pat. Nos. 5,561,236 and 5,646,024, 5,648,477, and 7,112,665. Gene for glutamine synthetase (GS) has been described in U.S. Pat. No. 4,975,372 and European patent application EP 0333033 A1.

E. Resistance/tolerance genes of hydroxy phenyl pyruvate dioxygenase (HPPD) against herbicides isoxazole, diketonitriles, and/or triketones including sulcotrione and mesotrione have been described in U.S. Pat. Nos. 6,268,549 and 6,069,115.

F. Genes for 2,4-D resistance/tolerance. Gene of 2,4-D-monooxygenase has been described in U.S. Pat. Nos. 6,100,446 and 6,153,401. Additional genes for 2,4-D resistance/tolerance are disclosed in US 2009/0093366 and WO 2007/053482.

G. Gene of imidazoleglycerol phosphate dehydratase (IGPD) against herbicides imidazole and/or triazole has been described in U.S. Pat. No. 5,541,310. Genes of Dicamba degrading enzymes (oxygenase, ferredoxin, and reductase) against herbicide Dicamba have been disclosed in U.S. Pat. Nos. 7,022,896 and 7,105,724.

H. Genes for herbicides that inhibit photosynthesis, including triazine (psbA and 1s+ genes) or a benzonitrile (nitrilase gene). See, e.g., Przibila et al., *Plant Cell* 3:169 (1991) disclosing transformation of *Chlamydomonas* with plasmids encoding mutant psbA genes. Nucleotide sequences for nitrilase genes are disclosed in U.S. Pat. No. 4,810,648 and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

Unless otherwise specifically explained, all technical and scientific terms used herein have the same meaning as commonly understood by those of ordinary skill in the art to which this disclosure belongs. Definitions of common terms in molecular biology can be found in, for example: Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

This disclosure provides nucleic acid molecules comprising a synthetic nucleotide sequence that may function as a bidirectional promoter. In some embodiments, a synthetic bidirectional promoter may be operably linked to one or two nucleotide sequence(s) of interest. For example, a synthetic bidirectional promoter may be operably linked to one or two nucleotide sequence(s) of interest (e.g., two genes, one on each end of the promoter), so as to regulate transcription of at least one (e.g., one or both) of the nucleotide sequence(s) of interest. By incorporating a URS from a SCBV promoter in the synthetic bidirectional promoter, particular expression and regulatory patterns (e.g., such as are exhibited by genes under the control of the SCBV promoter) may be achieved with regard to a nucleotide sequence of interest that is operably linked to the synthetic bidirectional promoter.

Some embodiments of the invention are exemplified herein by incorporating a minimal core promoter element from a unidirectional maize ubiquitin-1 gene (ZmUbi1) promoter into a molecular context different from that of the native promoter to engineer a synthetic bidirectional promoter. This minimal core promoter element is referred to herein as "minUbi1P," and is approximately 200 nt in length. Sequencing and analysis of minUbi1P elements from multiple *Zea* species and *Z. mays* genotypes has revealed that functional minUbi1P elements are highly conserved, such that a minUbi1P element may element may preserve its function as an initiator of transcription if it shares, for example, at least about 75%; at least about 80%; at least about 85%; at least about 90%; at least about 91%; at least about 92%; at least about 93%; at least about 94%; at least about 95%; at least about 96%; at least about 97%; at least about 98%; at least about 99%; and/or at least about 100% sequence identity to the minUbi1P element of SEQ ID NO:1. Characteristics of minUbi1P elements that may be useful in some embodiments of the invention may include, for example and without limitation, the aforementioned high conservation of nucleotide sequence; the presence of at least one TATA box; and/or the presence of at least one (e.g., two) heat shock consensus element(s). In particular minUbi1P elements, more than one heat shock consensus elements may be overlapping within the minUbi1P sequence.

In some embodiments, the process of incorporating a minUbi1P element into a molecular context different from that of a native promoter to engineer a synthetic bidirectional promoter may comprise incorporating the minUbi1P element into a SCBV promoter nucleic acid, while reversing the orientation of the minUbi1P element with respect to the remaining sequence of the SCBV promoter. Thus, a synthetic SCBV bidirectional promoter may comprise a minUbi1P minimal core promoter element located 3' of, and in reverse orientation with respect to, a SCBV promoter nucleotide sequence, such that it may be operably linked to a nucleotide sequence of interest located 3' of the SCBV promoter nucleotide sequence. For example, the minUbi1P element may be incorporated at the 3' end of a SCBV promoter in reverse orientation.

A synthetic bidirectional SCBV promoter may also comprise one or more additional sequence elements in addition to a minUbi1P element and elements of a native SCBV promoter. In some embodiments, a synthetic bidirectional SCBV promoter may comprise a promoter URS; an exon (e.g., a leader or signal peptide); an intron; a spacer sequence; and or combinations of one or more of any of the foregoing. For example and without limitation, a synthetic bidirectional SCBV promoter may comprise a URS sequence from a SCBV promoter; an intron from a ADH gene; an exon encoding a leader peptide from a Ubi1 gene; an intron from a Ubi1 gene; and combinations of these.

In some of those examples comprising a synthetic bidirectional SCBV promoter comprising a promoter URS, the URS may be selected to confer particular regulatory properties on the synthetic promoter. Known promoters vary widely in the type of control they exert on operably linked genes (e.g., environmental responses, developmental cues, and spatial information), and a URS incorporated into a heterologous promoter typically maintains the type of control the URS exhibits with regard to its native promoter and operably linked gene(s). Langridge et al. (1989), supra. Examples of eukaryotic promoters that have been characterized and may contain a URS comprised within a synthetic bidirectional Ubi1 promoter according to some embodiments include, for example and without limitation: those promoters described in U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. No. 6,433,252 (maize L3 oleosin promoter); U.S. Pat. No. 6,429,357 (rice actin 2 promoter, and rice actin 2 intron); U.S. Pat. No. 5,837,848 (root-specific promoter); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter).

Additional exemplary prokaryotic promoters include the nopaline synthase (NOS) promoter (Ebert et al. (1987) *Proc. Natl. Acad. Sci. USA* 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) *Plant Mol. Biol.* 9:315-24); the CaMV 35S promoter (Odell et al. (1985) *Nature* 313:810-2; the figwort mosaic virus 35S-promoter (Walker et al. (1987) *Proc. Natl. Acad. Sci. USA* 84(19):6624-8); the sucrose synthase promoter (Yang and Russell (1990) *Proc. Natl. Acad. Sci. USA* 87:4144-8); the R gene complex promoter (Chandler et al. (1989) *Plant Cell* 1:1175-83); CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) *J. Mol. Appl. Genet.* 1:561-73; Bevan et al. (1983) *Nature* 304:184-7), and the like.

In some embodiments, a synthetic bidirectional SCBV promoter may further comprise an exon. For example, in examples it may be desirable to target or traffic a polypeptide encoded by a nucleotide sequence of interest operably linked to the promoter to a particular subcellular location and/or compartment. In these and other embodiments, a coding sequence (exon) may be incorporated into a nucleic acid molecule between the remaining synthetic bidirectional SCBV promoter sequence and a nucleotide sequence encoding a polypeptide. These elements may be arranged according to the discretion of the skilled practitioner such that the synthetic bidirectional SCBV promoter promotes the expression of a polypeptide (or one or both of two polypeptide-encoding sequences that are operably linked to the promoter) comprising the peptide encoded by the incorporated coding sequence in a functional relationship with the remainder of the polypeptide. In particular examples, an exon encoding a leader, transit, or signal peptide (e.g., a Ubi1 leader peptide) may be incorporated.

Peptides that may be encoded by an exon incorporated into a synthetic bidirectional Ubi1 promoter include, for example and without limitation: a Ubiquitin (e.g., Ubi1) leader peptide; a chloroplast transit peptide (CTP) (e.g., the *A. thaliana* EPSPS CTP (Klee et al. (1987) *Mol. Gen. Genet.* 210:437-42), and the *Petunia hybrida* EPSPS CTP (della-Cioppa et al. (1986) *Proc. Natl. Acad. Sci. USA* 83:6873-7)), as exemplified for the chloroplast targeting of dicamba monooxygenase (DMO) in International PCT Publication No. WO 2008/105890.

Introns may also be incorporated in a synthetic bidirectional SCBV promoter in some embodiments of the invention, for example, between the remaining synthetic bidirectional SCBV promoter sequence and a nucleotide sequence of interest that is operably linked to the promoter. In some examples, an intron incorporated into a synthetic bidirectional SCBV promoter may be, without limitation, a 5' UTR that functions as a translation leader sequence that is present in a fully processed mRNA upstream of the translation start sequence (such a translation leader sequence may affect processing of a primary transcript to mRNA, mRNA stability, and/or translation efficiency). Examples of translation leader sequences include maize and *petunia* heat shock protein leaders (U.S. Pat. No. 5,362,865), plant virus coat protein leaders, plant rubisco leaders, and others. See, e.g., Turner and Foster (1995) *Molecular Biotech.* 3(3):225-36. Non-limiting examples of 5' UTRs include GmHsp (U.S. Pat. No. 5,659,122); PhDnaK (U.S. Pat. No. 5,362,865); AtAnt1; TEV (Carrington and Freed (1990) *J. Virol.* 64:1590-7); and AGRtunos (GenBank Accession No. V00087; and Bevan et al. (1983) *Nature* 304:184-7). In particular examples, a Ubi1 and/or ADH intron(s) may be incorporated in a synthetic bidirectional SCBV promoter.

Additional sequences that may optionally be incorporated into a synthetic bidirectional SCBV promoter include, for example and without limitation: 3' non-translated sequences; 3' transcription termination regions; and polyadenylation regions. These are genetic elements located downstream of a nucleotide sequence of interest (e.g., a sequence of interest that is operably linked to a synthetic bidirectional SCBV promoter), and include polynucleotides that provide polyadenylation signal, and/or other regulatory signals capable of affecting transcription, mRNA processing, or gene expression. A polyadenylation signal may function in plants to cause the addition of polyadenylate nucleotides to the 3' end of a mRNA precursor. The polyadenylation sequence may be derived from the natural gene, from a variety of plant genes, or from T-DNA genes. A non-limiting example of a 3' transcription termination region is the nopaline synthase 3' region (nos 3'; Fraley et al. (1983) *Proc. Natl. Acad. Sci. USA* 80:4803-7). An example of the use of different 3' nontranslated regions is provided in Ingelbrecht et al. (1989), *Plant Cell* 1:671-80. Non-limiting examples of polyadenylation signals include one from a *Pisum sativum* RbcS2 gene (Ps.RbcS2-E9; Coruzzi et al. (1984) *EMBO J.* 3:1671-9) and AGRtu.nos (GenBank Accession No. E01312).

In some embodiments, a synthetic bidirectional SCBV promoter comprises one or more nucleotide sequence(s) that facilitate targeting of a nucleic acid comprising the promoter to a particular locus in the genome of a target organism. For example, one or more sequences may be included that are homologous to segments of genomic DNA sequence in the host (e.g., rare or unique genomic DNA sequences). In some examples, these homologous sequences may guide recombination and integration of a nucleic acid comprising a synthetic bidirectional SCBV promoter at the site of the homologous DNA in the host genome. In particular examples, a synthetic bidirectional SCBV promoter comprises one or more nucleotide sequences that facilitate targeting of a nucleic acid comprising the promoter to a rare or unique location in a host genome utilizing engineered nuclease enzymes that recognize sequence at the rare or unique location and facilitate integration at that rare or unique location. Such a targeted integration system employing zinc-finger endonucleases as the nuclease enzyme is described in U.S. patent application Ser. No. 13/011,735, the contents of the entirety of which are incorporated herein by this reference.

Nucleic acids comprising a synthetic bidirectional SCBV promoter may be produced using any technique known in the art, including for example and without limitation: RCA; PCR amplification; RT-PCR amplification; OLA; and SNuPE. These and other equivalent techniques are well known to those of skill in the art, and are further described in detail in, for example and without limitation: Sambrook et al., *Molecular Cloning: A Laboratory Manual,* 3$^{rd}$ Ed., Cold Spring Harbor Laboratory, 2001; and Ausubel et al., *Current Protocols in Molecular Biology, John* Wiley & Sons, 1998. All of the references cited above, including both of the foregoing manuals, are incorporated herein by this reference in their entirety, including any drawings, figures, and/or tables provided therein.

Delivery and/or transformation: The present disclosure also provides methods for transforming a cell with a nucleic acid molecule comprising a synthetic bidirectional SCBV promoter. Any of the large number of techniques known in the art for introduction of nucleic acid molecules into plants may be used to transform a plant with a nucleic acid molecule comprising a synthetic bidirectional SCBV promoter according to some embodiments, for example, to introduce one or more synthetic bidirectional SCBV promoters into the host plant genome, and/or to further introduce one or more nucleic acid molecule(s) of interest operably linked to the promoter.

Suitable methods for transformation of plants include any method by which DNA can be introduced into a cell, for example and without limitation: electroporation (see, e.g., U.S. Pat. No. 5,384,253); microprojectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184). Through the application of techniques such as the foregoing, the cells of virtually any plant species may be stably transformed, and these cells may be developed into transgenic plants by techniques known to those of skill in the art. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soya are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, the transformed cell is generally identified for further culturing and plant regeneration. In order to improve the ability to identify transformants, one may desire to employ a selectable or screenable marker gene with the transformation vector used to generate the transformant. In this case, the potentially transformed cell population can be assayed by exposing the cells to a selective agent or agents, or the cells can be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of the desired nucleic acid molecule comprising a synthetic bidirectional SCBV promoter in the regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002), *Plant J.* 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

Some embodiments of the present invention also provide cells comprising a synthetic bidirectional SCBV promoter, for example, as may be present in a nucleic acid construct. In particular examples, a synthetic bidirectional SCBV promoter according to some embodiments may be utilized as a regulatory sequence to regulate the expression of transgenes in plant cells and plants. In some such examples, the use of a synthetic bidirectional SCBV promoter operably linked to a nucleotide sequence of interest (e.g., a transgene) may reduce the number of homologous promoters needed to regulate expression of a given number of nucleotide sequences of interest, and/or reduce the size of the nucleic acid construct(s) required to introduce a given number of nucleotide sequences of interest. Furthermore, use of a synthetic bidirectional SCBV promoter may allow co-expression of two operably linked nucleotide sequence of interest under the same conditions (i.e., the conditions under which the SCBV promoter is active). Such examples may be particularly useful, e.g., when the two operably linked nucleotide sequences of interest each contribute to a single trait in a transgenic host comprising the nucleotide sequences of interest, and co-expression of the nucleotide sequences of interest advantageously impacts expression of the trait in the transgenic host.

In some embodiments, a transgenic plant comprising one or more synthetic bidirectional SCBV promoter(s) and/or nucleotide sequence(s) of interest may have one or more desirable traits conferred (e.g., introduced, enhanced, or contributed to) by expression of the nucleotide sequence(s) of interest in the plant. Such traits may include, for example and without limitation: resistance to insects, other pests, and disease-causing agents; tolerances to herbicides; enhanced stability, yield, or shelf-life; environmental tolerances; pharmaceutical production; industrial product production; and nutritional enhancements. In some examples, a desirable trait may be conferred by transformation of a plant with a nucleic acid molecule comprising a synthetic bidirectional SCBV promoter operably linked to a nucleotide sequence of interest. In some examples, a desirable trait may be conferred to a plant produced as a progeny plant via breeding, which trait may be conferred by one or more nucleotide sequences of interest operably linked to a synthetic bidirectional SCBV promoter that is/are passed to the plant from a parent plant comprising a nucleotide sequence of interest operably linked to a synthetic bidirectional SCBV promoter.

A transgenic plant according to some embodiments may be any plant capable of being transformed with a nucleic acid molecule of the invention, or of being bred with a plant transformed with a nucleic acid molecule of the invention. Accordingly, the plant may be a dicot or monocot. Non-limiting examples of dicotyledonous plants for use in some examples include: alfalfa; beans; broccoli; cabbage; canola, carrot; cauliflower; celery; Chinese cabbage; cotton; cucumber; eggplant; lettuce; melon; pea; pepper; peanut; potato; pumpkin; radish; rapeseed; spinach; soybean; squash; sugarbeet; sunflower; tobacco; tomato; and watermelon. Non-limiting examples of monocotyledonous plants for use in some examples include: corn; onion; rice; sorghum; wheat; rye; millet; sugarcane; oat; triticale; switchgrass; and turfgrass.

In some embodiments, a transgenic plant may be used or cultivated in any manner, wherein presence a synthetic bidirectional SCBV promoter and/or operably linked nucleotide sequence of interest is desirable. Accordingly, such transgenic plants may be engineered to, inter alia, have one or more desired traits, by being transformed with nucleic acid molecules according to the invention, and may be cropped and/or cultivated by any method known to those of skill in the art.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

The following examples are provided to illustrate certain particular features and/or embodiments. The examples should not be construed to limit the disclosure to the particular features or embodiments exemplified.

EXAMPLES

Example 1

Transformation and Expression

Transformation of *Agrobacterium tumefaciens*: The pDAB108706 binary vector was transformed into *Agrobacterium tumefaciens* strain DAt13192 ternary (U.S. Prov. Pat. No. 61/368,965). Bacterial colonies were isolated and binary plasmid DNA was isolated and confirmed via restriction enzyme digestion.

Corn Transformation: Ear Sterilization and Embryo Isolation. To obtain maize immature embryos, plants of *Zea mays* (c.v. B104) were grown in the greenhouse and self or sib-pollinated to produce ears. The ears were harvested approximately 9-12 days post-pollination. On the day of the experiment, ears were surface-sterilized by immersion in a 20% solution of household bleach, which contained 5% sodium hypochlorite, and shaken for 20-30 minutes, followed by three rinses in sterile water. After sterilization, immature zygotic embryos (1.5-2.2 mm) were aseptically dissected from each ear and randomly distributed into micro-centrifuge tubes containing liquid infection media (LS Basal Medium, 4.43 gm/L; N6 Vitamin Solution [1000×], 1.00 mL/L; L-proline, 700.0 mg/L; sucrose, 68.5 gm/L; glucose, 36.0 gm/L; 2,4-D, 1.50 mg/L. For a given set of experiments, pooled embryos from 2-3 ears were used for each treatment.

*Agrobacterium* Culture Initiation: Glycerol stocks of *Agrobacterium* containing the binary vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-cultivation: On the day of the experiment, *Agrobacterium* colonies were taken from the YEP plate, suspended in 10 mL of infection medium in a 50 ml, disposable tube, and the cell density was adjusted to OD600=0.2-0.4 nm using a spectrophotometer. The *Agrobacterium* cultures were placed on a rotary shaker at 100 rpm, room temperature, while embryo dissection was performed. Immature zygotic embryos between 1.5-2.2 mm in size were isolated from the sterilized maize kernels and placed in 1 mL of the infection medium and washed once in the same medium. The *Agrobacterium* suspension (2 mL) was added to each tube and the tubes were inverted for about 20 times then shaken for 10-15 minutes. The embryos were transferred onto co-cultivation media (MS Salts, 4.33 gm/L; L-proline, 700.0 mg/L; myo-inositol, 100.0 mg/L; casein enzymatic hydrolysate 100.0 mg/L; Dicamba-3.30 mg/L; sucrose, 30.0 gm/L; Gelzan™, 3.00 gm/L; modified MS-Vitamin [1000×], 1.00 ml/L, $AgNo_3$, 15.0 mg/L; Acetosyringone, 100 μM), oriented with the scutellum facing up, and incubated for 3-4 days in the light at 25° C.

GUS and YFP/PhiYFP Transient expression: Transient YFP/PhiYFP and GUS expression could be observed in transformed embryos and after 3 days of co-cultivation with *Agrobacterium*. The embryos were observed under a stereomicroscope (Leica Microsystems, Buffalo Grove, Ill.) using YFP filter and 500 nm light source. Embryos showing YFP/PhiYFP expression were selected for GUS histochemical assay. GUS staining solution was prepared as described in Maniatis et al. (1989) and embryos were incubated in 1 mL solution for 24 hours at 37° C. The embryos were observed for GUS transient expression under the microscope.

Callus Selection and Regeneration of Putative Events: Following the co-cultivation period, embryos were transferred to resting media (MS salts, 4.33 gm/L; L-proline, 700.0 mg/L; myo-inositol, 100.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan 2.30 gm/L; modified MS-Vitamin [1000×], 1.00 ml/L; $AgNo_3$, 15.0 mg/L; Carbenicillin, 250.0 mg/L) without selective agent and incubated in the light for 7 days at 28° C. Embryos were transferred onto Selection 1 media (MS salts, 4.33 gm/L; L-proline, 700.0 mg/L; myo-inositol, 100.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan™ 2.30 gm/L; modified MS-Vitamin [1000×], 1.00 ml/L; $AgNo_3$, 15.0 mg/L; Carbenicillin, 250.0 mg/L) containing 100 nM haloxyfop and incubated in 24 hours light with light intensity of 50 $\mu mol\ m^{-2}s^{-1}$ for 7 days at 28° C.

Embryos with proliferating embryogenic calli were transferred onto Selection 2 media (MS salts, 4.33 gm/L; myo-inositol, 100.0 mg/L; L-proline, 700.0 mg/L; MES [(2-(n-morpholino)-ethanesulfonic acid), free acid] 500.0 mg/L; casein enzymatic hydrolysate 100.0 mg/L; Dicamba, 3.30 mg/L; sucrose, 30.0 gm/L; Gelzan™ 2.30 gm/L; modified MS-Vitamin [1000×], 1.00 ml/L; $AgNo_3$, 15.0 mg/L; Carbenicillin, 250.0 mg/L) containing 500 nM haloxyfop and were incubated in 24 hours light with light intensity of 50 $\mu mol\ m^{-2}s^{-1}$ for another 14 days at 28° C. This selection step allowed transgenic callus to further proliferate and differentiate. The callus selection period lasted for three weeks. Proliferating, embryogenic calli were transferred onto Regeneration 1 media (MS salts, 4.33 gm/L; myo-inositol, 100.0 mg/L; L-proline, 350.0 mg/L; MES [(2-(n-morpholino)-ethanesulfonic acid), free acid] 250.0 mg/L; casein enzymatic hydrolysate 50.0 mg/L; NAA 0.500 mg/L; ABA 2.50 mg/L; BA 1.00 mg/L; sucrose, 45.0 gm/L; Gelzan™ 2.50 gm/L; modified MS-Vitamin [1000×], 1.00 ml/L; $AgNo_3$, 1.00 mg/L; Carbenicillin, 250.0 mg/L) containing 500 nM haloxyfop and cultured in 24 hours light with light intensity of 50 $\mu mol\ m^{-2}s^{-1}$ for 7 days at 28° C. Embryogenic calli with shoot-like buds were transferred onto Regeneration 2 media (MS salts, 4.33 gm/L; modified MS-Vitamin [1000×], 1.00 ml/L; myo-inositol, 100.0 mg/L; sucrose, 60.0 gm/L; Gellan Gum G434™ 3.00 gm/L; Carbenicillin, 250.0 mg/L) containing 500 nM haloxyfop. The cultures were incubated under 24 hours light with light intensity of 50 $\mu mol\ m^{-2}s^{-1}$ for 7-10 days at 28° C. Small shoots with primary roots were transferred to shoot elongation and rooting media (MS salts, 4.33 gm/L; modified MS-Vitamin [1000×], 1.00 ml/L; myo-inositol, 100.0 mg/L; sucrose, 60.0 gm/L; Gellan Gum G434™ 3.00 gm/L; Carbenicillin, 250.0 mg/L) in MAGENTA™ boxes (Sigma-Aldrich, St. Louis, Mo.), and were incubated under 16/8 hours light/dark for 7 days at 28° C. Putative transgenic plantlets were analyzed for transgene copy number and transferred to the greenhouse.

Example 2

Construction of a Synthetic Bidirectional SCBV Promoter and pDAB108708 Vector

Figure 1:
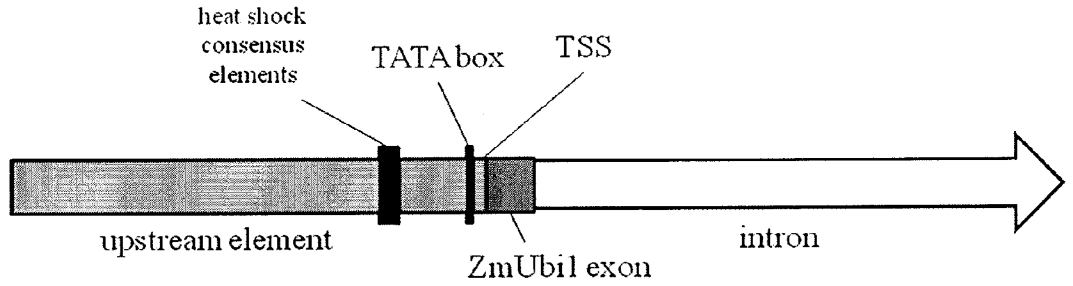
Figure 2:
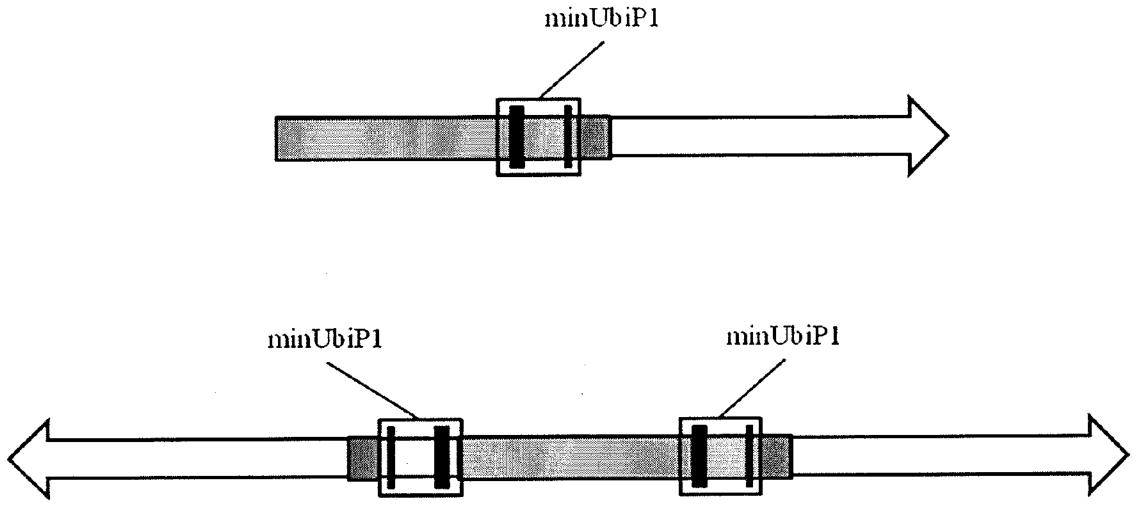
FIG. 2 shows an exemplary embodiment of the synthetic Ubi1 bidirectional promoter provided, which includes a minUbi1P minimal core element cloned upstream of a ZmUbi1 promoter.
Figure 3:
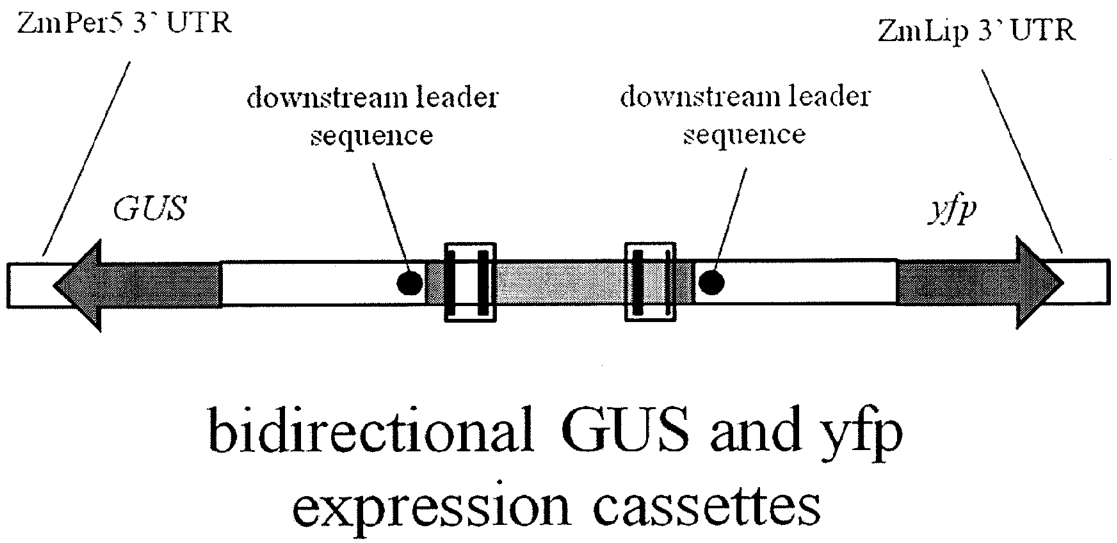
FIG. 3 shows an exemplary schematic drawing of YFP and GUS gene expression cassettes, which are each operably linked to the synthetic Ubi1 bidirectional promoter.

An exemplary schematic drawing of the maize Ubiquitin-1 promoter (Ubi1) is shown in FIG. 1. An Ubi1 promoter was cloned from maize. A plasmid which contained the promoter was PCR amplified using a high-fidelity PCR amplification system. An approximately 200 nt region of the maize Ubi1 promoter was identified as a *Zea mays* Ubi1 minimal core promoter (minUbi1P) (SEQ ID NO: 1). The minUbi1P of SEQ ID NO: 1 was then added to a polynucleotide comprising a *Zea mays* Ubiquitin-1 exon (ZmUbi1 exon) and a *Zea mays* Ubiquitin-1 intron (ZmUbi1 intron) using cloning methods commonly known in the art to produce the polynucleotide of SEQ ID NO: 2. The resulting polynucleotide was then cloned upstream in reverse orientation of a nucleic acid comprising the maize Ubi1 promoter (including the Ubi1 URS) to produce the synthetic bidirectional Ubi1 promoter of SEQ ID NO: 3.

Figure 4:
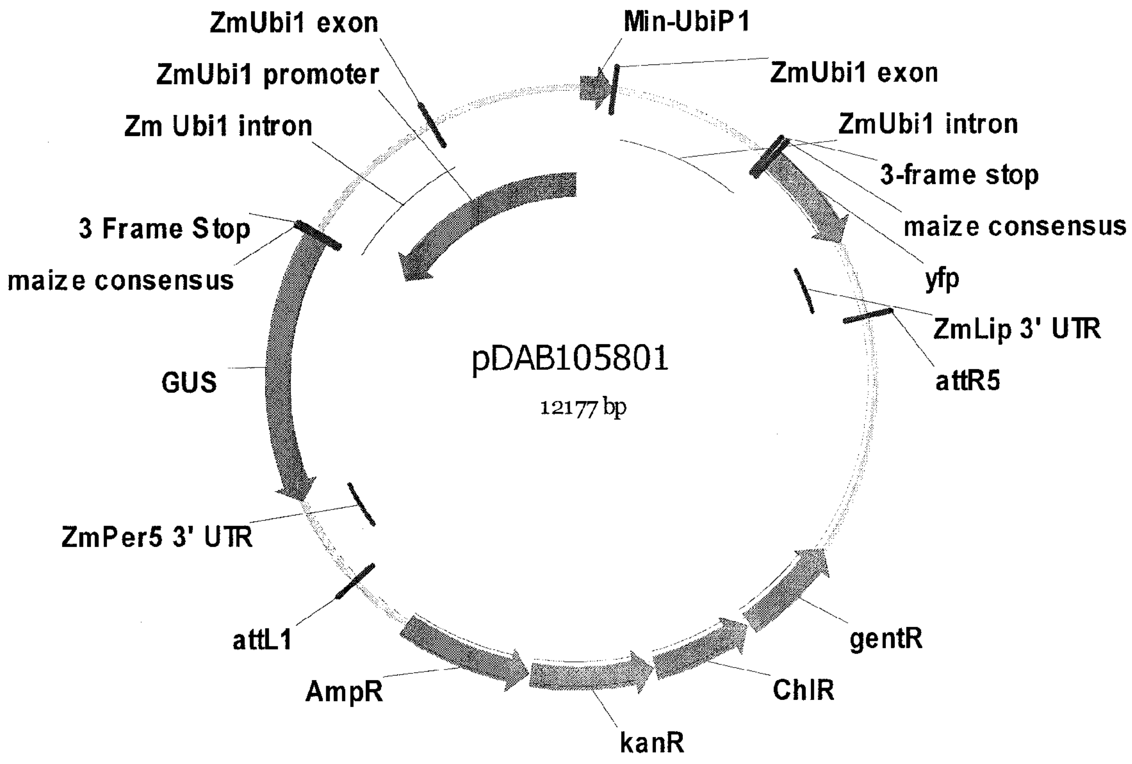
FIG. 4 shows a representative plasmid map of pDAB105801.

Reporter gene coding sequences were cloned downstream of each end of the synthetic bidirectional Ubi1 promoter. A yellow fluorescence protein (YFP) coding sequence was inserted downstream of the polynucleotide fragment, which contained the minUbi1P, ZmUbi1 exon, and ZmUbi1 intron promoter elements. In addition, a downstream leader sequence containing a 3-frame stop polynucleotide sequence and the maize consensus polynucleotide sequence was added to the minUbi1P, ZmUbi1, exon and ZmUbi1 intron promoter elements fragment. A uidA (GUS) coding sequence was also inserted downstream of the synthetic bidirectional Ubi1 promoter in reverse orientation with respect to the YFP sequence to produce the nucleic acid of SEQ ID NO: 4. The resulting polynucleotide comprising the synthetic bidirectional Ubi1 promoter operably linked to the YFP and GUS genes was cloned into plasmid pDAB105801. FIG. 4 shows the orientation of the YFP and GUS expression cassette in relation to the synthetic bidirectional Ubi1 promoter in plasmid pDAB105801.

Figure 5:
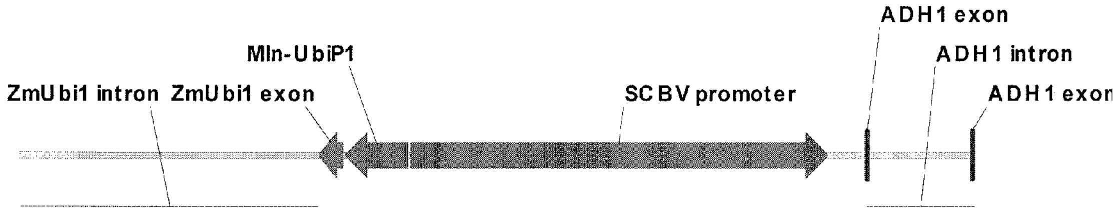
FIG. 5 shows a schematic drawing of an exemplary Sugar Cane Bacilliform Virus (SCBV) bidirectional promoter, which includes a Min-Ubi1Pminimal core element cloned upstream of a SCBV promoter.
Figure 6:
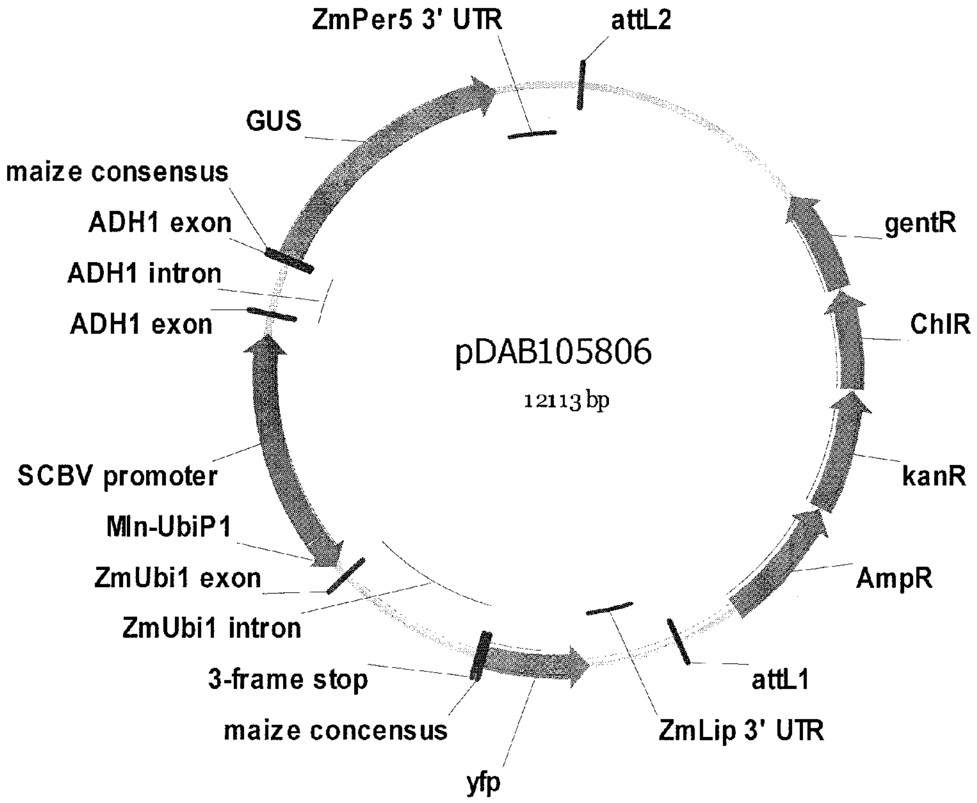
FIG. 6 shows a representative plasmid map of pDAB105806.
Figure 7:
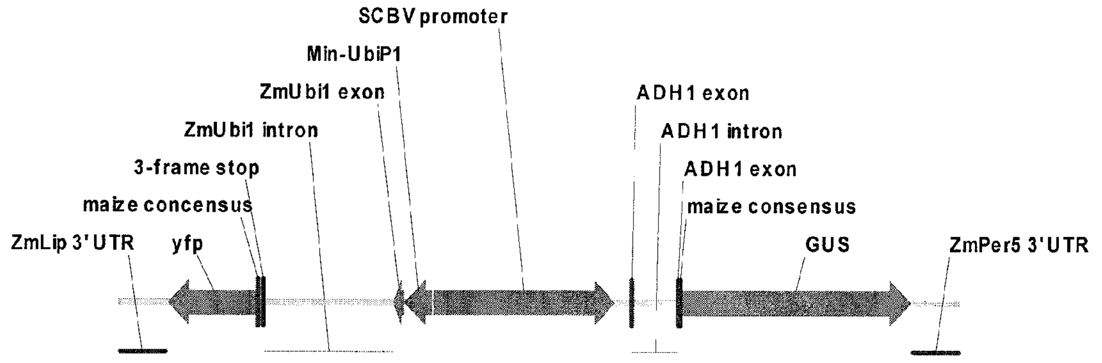
FIG. 7 shows an exemplary schematic drawing of YFP and GUS gene expression cassettes, which are each operably linked to a synthetic SCBV bidirectional promoter.
Figure 8:
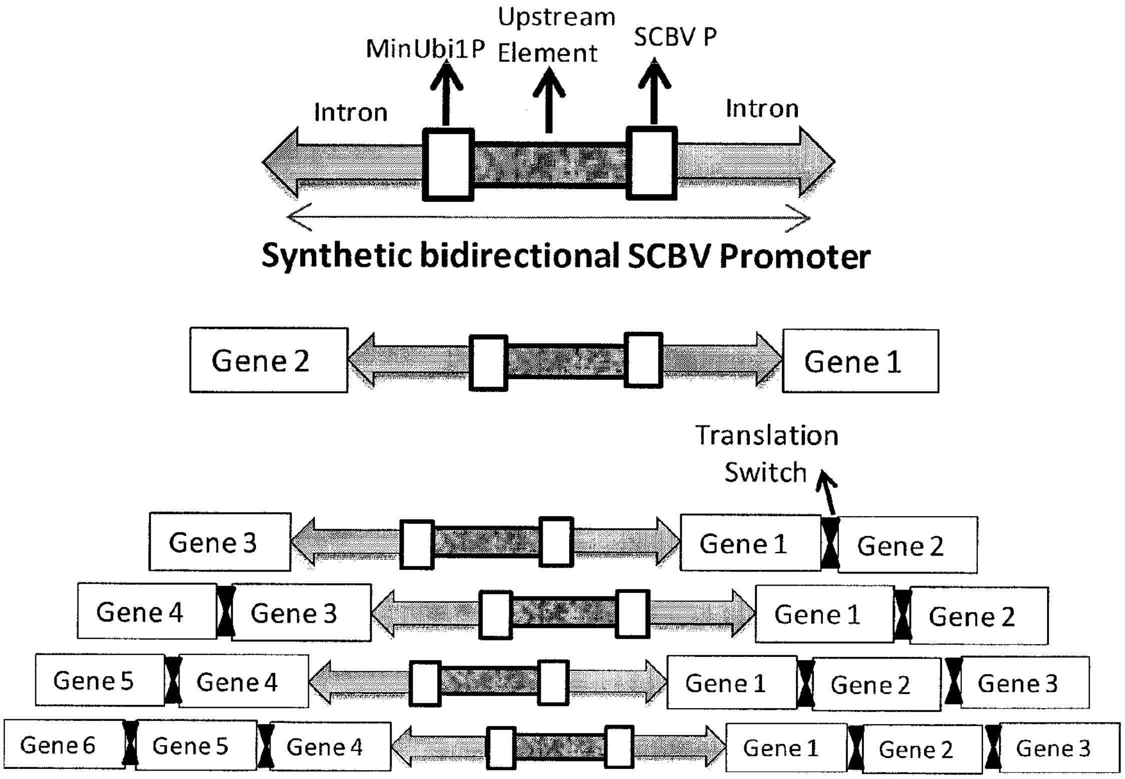
FIG. 8 shows exemplary schematic presentations of multi-gene constructs provided herein. Translation switches are shown using a special (vertical dumbbell) symbol.

The native Ubi1 promoter sequence was removed from the bidirectional Ubi1 promoter of plasmid pDAB105801 and replaced with a PCR amplified fragment containing the SCBV promoter and ADH intron (SEQ ID NO: 6). The resulting exemplary synthetic bidirectional SCBV promoter is set forth as SEQ ID NO: 5 (also see FIG. 5). The addition of this SCBV promoter resulted in the completion of vector pDAB105806 (FIG. 6). This vector contained the YFP and GUS gene expression cassettes which were driven by the SCBV bidirectional promoter (SEQ ID NO: 7; also see FIG. 7).

Figure 9A:
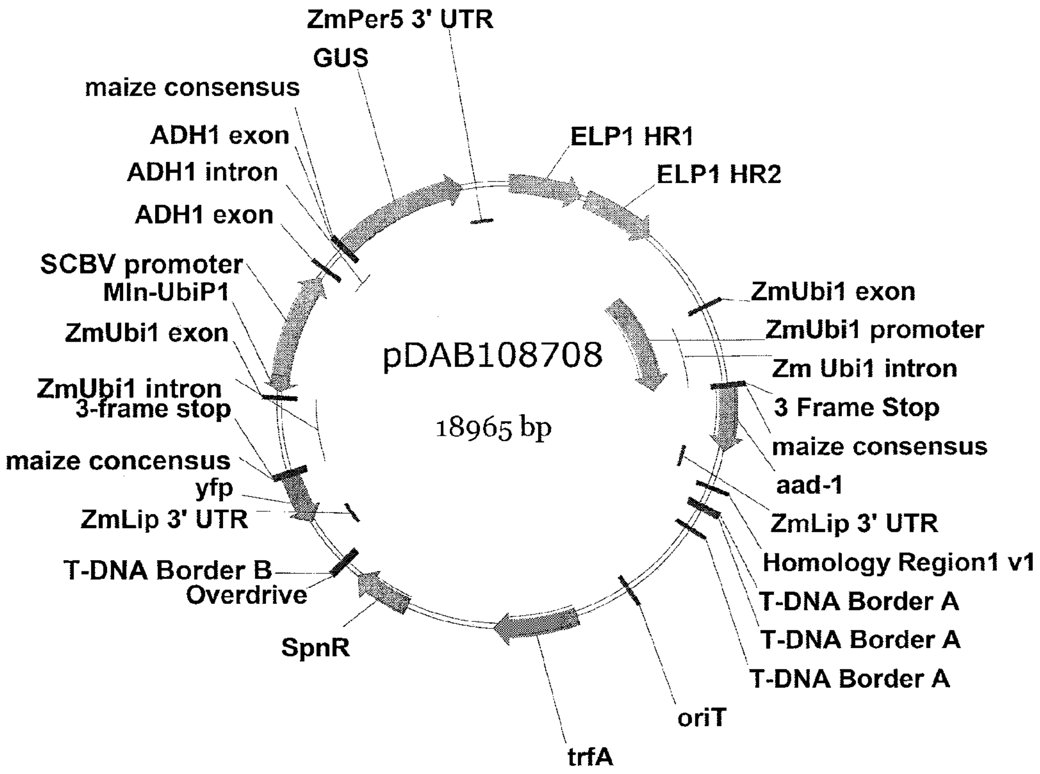
FIGS. 9A and 9B show representative plasmid maps of pDAB108708 and pDAB101556, respectively.
Figure 9B:
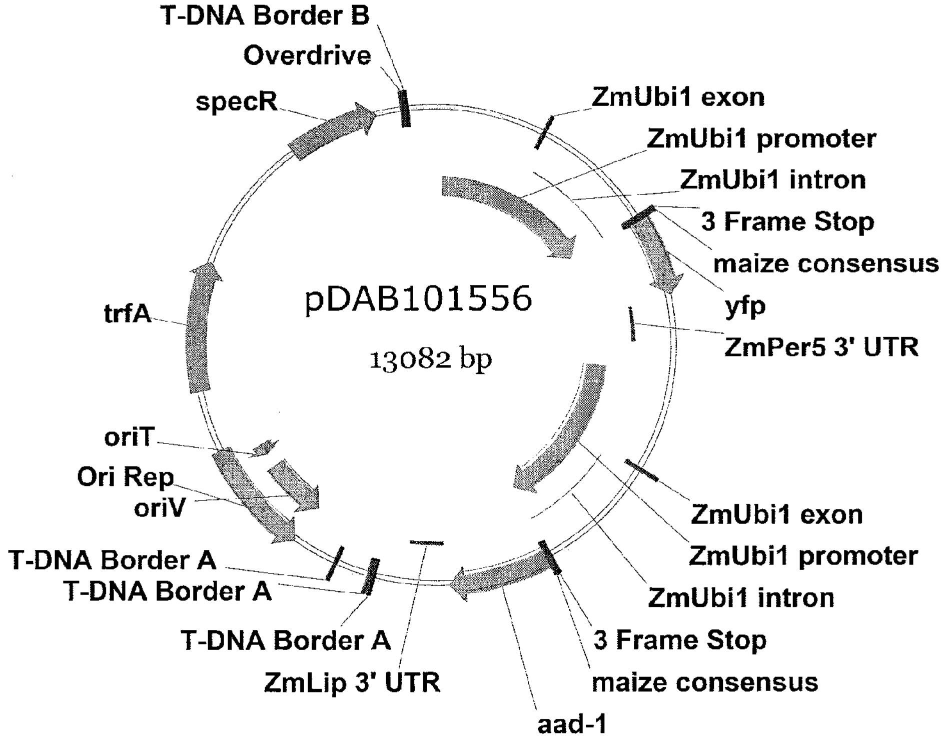

A binary vector which contained the GUS and YFP gene expression cassettes from plasmid pDAB105806 was completed via a GATEWAY L-R CLONASE reaction (Invitrogen, Carlsbad, Calif.). The resulting vector, pDAB108708, contained the GUS, YFP, and AAD-1 gene expression cassettes within the T-strand region (see FIG. 9).

Example 3

Expression of Genes Operably Linked to a Synthetic Bidirectional SCBV Promoter

Representative examples of YFP and GUS transient expression in *Zea mays* embryos transformed with pDAB108708 were imaged. Both sides of the bidirectional SCBV promoter drove robust expression of the operably linked YFP and GUS coding sequences. The YFP expression levels were comparable to the GUS expression levels. These observations confirmed that both sides of the bidirectional SCBV promoter are biologically functional. Moreover, the minUbi1P element of the synthetic bidirectional SCBV promoter could express YFP at similar expression levels as compared to *Zea mays* callus transformed with a binary plasmid (pDAB101556) that contained only a unidirectional ZmUbi1 promoter driving the YFP coding sequence. Expression of YFP or GUS was not detected in negative control immature embryos which were not transformed with a binary construct, and did not contain the YFP or GUS coding sequences.

Example 4

Stable Expression of Genes Operably Linked to a Synthetic Bidirectional SCBV Promoter Images of *Zea mays* callus cells that are stably transformed with the pDAB108708 binary vector, which contains a YFP coding sequence, were observed. These cells were obtained from *Z. mays* embryos that have been propagating on Selection 2 medium. The bidirectional SCBV promoter drove robust expression of the YFP coding sequences. These results confirmed that the Min-Ubi1P minimal promoter element of the bidirectional SCBV promoter was capable of expressing a reporter gene in stably transformed *Z. mays* callus cells. The levels of expression of the YFP protein were similar as compared to YFP expression in *Z. mays* callus transformed with a control binary vector that contained the unidirectional ZmUbi1 promoter driving the YFP coding sequence (pDAB101556). Expression of YFP was not detected in the negative control callus that was not transformed with a binary construct and did not contain a YFP or GUS coding sequence.

Example 5

Transgene Copy Number Estimation Using Real Time TaqMan™ PCR

*Zea mays* embryos were transformed with a binary vector containing a bidirectional SCBV promoter, pDAB108708, and other plants were transformed with a control binary vector, pDAB101556. The presence of YFP transgenes within the genome of both set of *Z. mays* plants was confirmed via a hydrolysis probe assay. Stably transformed transgenic *Z. mays* plantlets that developed from the callus were obtained and analyzed to identify events that contain a low copy number (1-2 copies) of full-length T-strand inserts from the pDAB108708 binary vector and pDAB101556 control binary vector. Identified plantlets were advanced to the green house and grown.

The Roche Light Cycler 480™ system was used to determine the transgene copy number for events that were transformed with the pDAB108708 binary vector. The method utilizes a biplex TAQMAN® reaction that employs oligonucleotides specific to the YFP gene and to the endogenous *Z. mays* reference gene, invertase (Genbank Accession No: U16123.1), in a single assay. Copy number and zygosity were determined by measuring the intensity of YFP-specific fluorescence, relative to the invertase-specific fluorescence, as compared to known copy number standards.

In *Z. mays* transformed with the pDAB108708 binary vector, a YFP gene-specific DNA fragment was amplified with one TAQMAN® primer/probe set containing a probe labeled with FAM fluorescent dye, and invertase was amplified with a second TAQMAN® primer/probe set containing a probe labeled with HEX fluorescence (Table 2). The PCR reaction mixture was prepared as set forth in Table 3, and the gene-specific DNA fragments were amplified according to the conditions set forth in Table 4. Copy number and zygosity of the samples was determined by measuring the relative intensity of fluorescence specific for the reporter gene, YFP, to fluorescence specific for the reference gene, invertase, as compared to known copy number standards.

TABLE 2

Forward and reverse nucleotide primer and fluorescent probes (synthesized by Integrated DNA Technologies, Coralville, IA)

| Primer Name | SEQ ID NO: | Primer Sequence |
|---|---|---|
| YFP Forward Primer | SEQ ID NO: 8 | GATGCCTCAGTGGGAAAGG |
| YFP Reverse Primer | SEQ ID NO: 9 | CCATAGGTGAGAGTGGTGACAA |
| YFP Probe | SEQ ID NO: 41 | ROCHE UPL Probe #125 CTTGGAGC<br>Cat # 04693604001 (Roche, Indianapolis, IN) |
| Invertase Forward Primer | SEQ ID NO: 10 | TGGCGGACGACGACTTGT |
| Invertase Reverse Primer | SEQ ID NO: 11 | AAAGTTTGGAGGCTGCCGT |
| Invertase Probe | SEQ ID NO: 12 | 5'HEX/CGAGCAGACCGCCGTGTACTTCT<br>ACC/3BHQ_1/3' |
| AAD1 Forward Primer | SEQ ID NO: 13 | TGTTCGGTTCCCTCTACCAA |
| AAD1 Reverse Primer | SEQ ID NO: 14 | CAACATCCATCACCTTGACTGA |
| AAD1 Probe | SEQ ID NO: 15 | CACAGAACCGTCGCTTCAGCAACA |

TABLE 3

TAQMAN ® PCR reaction mixture.

| Number of Reactions | μl each | Final Concentration |
|---|---|---|
| $H_2O$ | 0.5 μL | — |
| PVP (10%) | 0.1 μL | 0.1% |
| ROCHE 2X Master Mix | 5 μL | 1X |
| YFP Forward Primer (10 μM) | 0.4 μL | 0.4 μM |
| YFP Reverse Primer (10 μM) | 0.4 μL | 0.4 μM |
| YFP Probe UPL#125 (5 μM) | 0.4 μL | 0.2 μM |
| Invertase Forward Primer (10 μM) | 0.4 μL | 0.4 μM |
| Invertase Reverse Primer (10 μM) | 0.4 μL | 0.4 μM |
| Invertase Probe (5 μM) | 0.4 μL | 0.2 μM |
| DNA Template | 2.0 μL | — |
| Total reaction volume | 10 μL | — |

Standards were created by diluting the vector, pDAB108708, into *Z. mays* B104 genomic DNA (gDNA) to obtain standards with a known relationship of pDAB108706:gDNA. For example, samples having one; two; and four cop(ies) of vector DNA per one copy of the *Z. mays* B104 gDNA were prepared. One and two copy dilutions of the pDAB108706 mixed with the *Z. mays* B104 gDNA standard were validated against a control *Z. mays* event that is known to be hemizygous, and a control *Z. mays* event that is known to be homozygous (*Z. mays* event 278; see PCT International Patent Publication No. WO 2011/022469 A2). A TAQMAN® biplex assay which utilizes oligonucleotides specific to the AAD1 gene and oligonucleotides specific to the endogenous *Z. mays* reference gene, invertase, was performed by amplifying and detecting a gene-specific DNA fragment for AAD1 with one TAQMAN® primer/probe set containing a probe labeled with FAM fluorescent dye, and by amplifying and detecting a gene-specific DNA fragment for invertase with a second TAQMAN® primer/probe set containing a probe labeled with HEX fluorescence (Table 2). The AAD1 TAQMAN® reaction mixture was prepared as set forth in Table 3 and the specific fragments were amplified according to the conditions set forth in Table 4.

The level of fluorescence that was generated for each reaction was analyzed using the Roche LightCycler 480™ Thermocycler according to the manufacturer's directions. The FAM fluorescent moiety was excited at an optical density of 465/510 nm, and the HEX fluorescent moiety was excited at an optical density of 533/580 nm. The copy number was determined by comparison of Target/Reference values for unknown samples (output by the LightCycler 480™) to Target/Reference values of four known copy number standards (Null, 1-Copy (hemi), 2-Copy (homo) and 4-Copy).

TABLE 4

| Thermocycler conditions for PCR amplification. | | | |
|---|---|---|---|
| PCR Steps | Temp (° C.) | Time | No. of cycles |
| Step-1 | 95 | 10 minutes | 1 |
| Step-2 | 95 | 10 seconds | 40 |
| | 59 | 35 seconds | |
| | 72 | 1 second | |
| Step-3 | 40 | 10 seconds | 1 |

Results from the transgene copy number analysis of transgenic plants obtained via transformation with a bidirectional ZmUbi1 promoter construct (pDAB108706), and of transgenic plants obtained via transformation with a control unidirectional ZmUbi1 promoter YFP construct (pDAB101556) is shown in Table 5. Only plants with 1-2 copies of the yfp transgene were transferred to the greenhouse for further expression analyses.

TABLE 5

Transgene copy number estimation of the transgenic plants obtained from bidirectional promoter and control constructs.

| Construct | Number of Embryos Transformed | Number of Positive Events | 1-2 Copies of YFP |
|---|---|---|---|
| pDAB101566 | 100 | 31 | 13 |
| pDAB108708 | 113 | 26 | 16 |

Example 6

Whole Plant Stable Expression of Genes Operably Linked to a Synthetic Bidirectional SCBV Promoter Whole plants that contain a low copy number of the binary plasmid pDAB108708, and plants that contain a low copy number of the control binary plasmid pDAB101556, were grown in a greenhouse. These plants were analyzed using microscopy, where images could be observed showing YFP expression in $T_0$ *Z. mays* plants that are stably transformed with an exemplary nucleic acid construct comprising a YFP expression cassette operably linked to a synthetic SCBV bidirectional promoter (pDAB108708). Representative examples of stable expression of YFP in leaf and root tissue of transgenic $T_0$ maize plants obtained from *Z. mays* embryos transformed with pDAB108708 showed good YFP expression. The bidirectional SCBV promoter drove robust expression of the YFP coding sequences both in leaf tissues and root tissues. The microscopy analysis also confirmed that the Min-UbiP1 minimal promoter element in the bidirectional SCBV promoter drives YFP expression at similar expression levels as compared to *Z. mays* plants transformed with a control binary plasmid (pDAB101556) that contains a unidirectional ZmUbi1 promoter driving expression of the YFP coding sequence. The control plants showed stable YFP expression in leaf tissues and root tissues.

Example 7

Western Blot Analysis of Genes Operably Linked to a Synthetic Bidirectional SCBV Promoter Total Soluble Protein: Transformed $T_0$ maize plants were sampled at the V6 developmental stage. A total of four leaf punches from the youngest unfolded leaf were sampled into a matrix tube and placed into a matrix box. As a negative control, four leaf punches of two untransformed B104 maize plants at the V6 developmental stage were sampled into a matrix tube. A steel bead was placed into the matrix tubes with the samples, and then 400 μL PBST was added to each tube. The tubes were capped, and protein was extracted via bead beating at 1500 rpm for 5 minutes in a Kleco™ tissue grinder. Debris was pelleted via centrifugation.

A 5 μL sample from each tube was diluted to 25 μL with PBST in a 96-well microtiter plate. These samples were analyzed for total soluble protein using a BCA protein assay kit (Thermo Scientific Pierce, Rockford, Ill.) according to the manufacturer's directions. Bovine serum albumin (BSA) standards provided in the kit were analyzed in duplicate, and the average of the values was used to generate a standard curve that was subsequently used to calculate total soluble protein for each sample. The total soluble protein for each sample was then normalized to mg/μL.

TABLE 6

| Western blot protocol. | | |
|---|---|---|
| Step | Condition | Time |
| First Wash | PBST | 5 min. |
| Primary Hybridization | 2 μg/mL rabbit anti-PhiYFP (Axxora, San Diego, CA) in StartingBlock ™ T20 (Thermo Fisher Scientific Inc., Waltham, MA) | 60 min. |
| Rinse | PBST | 3 × 5 min. |
| Secondary Hybridization | horse radish peroxidase (HRP)-conjugated goat anti-rabbit IgG | 30 min. |
| Second Wash | PBST | 3 × 5 min. |
| Rinse | PBS | 3 × 2 min |

YFP/PhiYFP Western Blot Analysis: In the 96-well microtiter plate, each 5 μL sample of extracted protein was diluted with 5 μL 2× Laemmli Buffer+2-β-mercaptoethanol. Control samples of purified YFP/PhiYFP in HEPES buffer (50 mM HEPES, 200 mM KCl, 10% glycerol) were purchased from Axxora (San Diego, Calif.). The samples were prepared in the same plate by diluting 1:1 with Laemmli buffer to produce a standard curve of the following concentrations: 0.5 ng/μL, 0.25 ng/μL, and 0.125 ng/μL. Samples were heated in a Thermocycler at 95° C. for 30 minutes, and then cooled to 4° C. A Bio-Rad Criterion Gel™ was then assembled using MES/SDS buffer. The samples were allowed to warm to room temperature, and 10 μL of sample was loaded into each well of two gels. In addition, samples of purified YFP/PhiYFP used for a standard curve, and protein ladder marker, were loaded into wells of the gel. The gels were electrophoretically run at 150 V and 150 mA for 90 min. After the run, the gel casings were opened and the proteins were transferred to a nitrocellulose membrane using the iBlot System™ (Invitrogen). Protein was transferred from the gel to the membrane by running a current of 20 V for 10 minutes. The nitrocellulose membrane was removed and placed in StartingBlock T20™ blocking buffer overnight at 4° C. The blocking buffer was then discarded, and the membrane was processed using the protocol set forth in Table 6.

Antibody binding was detected using the Amersham ECL™ plus chemiluminescent detection system following the manufacturer's directions. Film was exposed at 10 minutes and 30 minutes. The 10 minute exposed film was used to quantify protein, and the 30 minute overexposure film was used to confirm the absence of protein in B104 and other control samples. The membrane was taped to the back of the exposed film, and protein was quantified via pixel density analysis. The pixel density of the purified protein standards was first used to generate a standard curve that was used to quantify protein in the samples. Though the membrane showed bands for a PhiYFP monomer and dimer even in the purified standard, only the PhiYFP monomer was used to quantify protein expression. Values for the protein were then normalized to ng/μL. The ratio of normalized total soluble protein (TSP) to PhiYFP was calculated to the units of ng YFP/mg TSP, or alternatively, parts per million (ppm).

GUS Western Blot Analysis: Expression of GUS protein was quantified in a similar manner to PhiYFP, with the following exception: a 10 μL sample of extract was diluted 1:1 with 2× Laemmli+2-β-mercaptoethanol, denatured at 95° C. for 30 minutes, and then 15 μL was loaded into the gel. Processed membranes with film (1 minute exposure) were overlayed with the membrane for pixel density analysis.

Results of a Western blot analysis of 12 transgenic $T_0$ maize plants obtained from *Z. mays* embryos transformed with the binary vector, pDAB108708, are shown in FIG. 16. The bidirectional SCBV promoter shows robust expression of the YFP and GUS coding sequences from leaf tissue. These observations confirmed that the Min-UbiP1 minimal promoter element isolated from a *Zea mays* Ubiquitin) Promoter and fused to the SCBV promoter drove expression of YFP at similar expression levels as compared to *Z. mays* callus transformed with a binary plasmid containing a unidirectional ZmUbi1 promoter driving the YFP coding sequence (pDAB101556; see FIG. 17).

Example 8

Construct of a Four-Gene Cassette Stack

A plasmid pDAB105806 construct was used as the starting plasmid to generate a four-gene cassette stack (AAD1-2A-PhiYFP and Cry34(8V6)-2A-Cry35) driven by a single SCBV bidirectional promoter. A representative map of plasmid pDAB105806 is shown in FIG. 6, which contains a SCBV bidirectional Promoter.

The AAD1-2A-PhiYFP fragment derived from plasmid pDAB105841 (FIG. 22) was cloned into the PstI and SacI cut vector backbone of the plasmid pDAB105806 using cloning methods commonly known in the art. This resulted in the intermediate plasmid pDAB105847 (FIG. 22). A NotI/XbaI digested Cry34(8V6)-2A-Cry35 fragment obtained from the plasmid pDAB105840 was cloned between NotI/SpeI sites of plasmid pDAB105847 to construct plasmid pDAB105849 (FIG. 23). The plasmid pDAB105849 contains Cry34(8V6)-2A-Cry35 and AAD1-2A-PhiYFP gene cassettes on each side of the SCBV bidirectional promoter.

A binary vector containing the SCBV bidirectional promoter, and gene expression cassettes Cry34(8V6)-2A-Cry35 and AAD1-2A-PhiYFP from plasmid pDAB105849 was generated via a GATEWAY L-R CLONASE reaction (Invitrogen, Carlsbad, Calif.) into a destination plasmid pDAB101917 (FIG. 24). The resulting vector, pDAB108719, contains the Cry34(8V6)-2A-Cry35, AAD1-2A-PhiYFP, and PAT gene expression cassettes within the T-DNA borders (FIG. 24).

Example 9

Construct of a Second Four-Gene Cassette Stack

A PhiYFP-2A-AAD1 fragment derived from plasmid pDAB105844 (FIG. 25) was cloned into the PstI and SacI cut vector backbone of the plasmid pDAB105806 using cloning methods commonly known in the art. This resulted in the intermediate plasmid pDAB105848 (FIG. 25). A NotI/XbaI digested Cry34(8V6)-2A-Cry35 fragment obtained from the plasmid pDAB105840 was cloned between NotI/SpeI sites of plasmid pDAB105848 to construct plasmid pDAB105865 (FIG. 26). The plasmid pDAB105865 contains Cry34(8V6)-2A-Cry35 and PhiYFP-2A-AAD1 gene cassettes on each side of the SCBV bidirectional promoter.

A binary vector containing the SCBV bidirectional promoter, and gene cassettes Cry34(8V6)-2A-Cry35 and PhiYFP-2A-AAD1 from plasmid pDAB105865 was generated via a GATEWAY L-R CLONASE reaction (Invitrogen, Carlsbad, Calif.) into a destination plasmid pDAB101917 (FIG. 24). The resulting vector, pDAB108720, contains the Cry34(8V6)-2A-Cry35, PhiYFP-2A-AAD1, and PAT gene expression cassettes within the T-DNA borders (FIG. 26).

Example 10

Transformation of *Agrobacterium tumefaciens* Strain DAt13192

The pDAB108719 and pDAB108720 binary vectors were transformed into *Agrobacterium tumefaciens* ternary strain DAt13192 (see U.S. Prov. Pat. App. No. 61/368,965, the content of which is hereby incorporated by reference in its entirety). Bacterial colonies were isolated and binary plasmid DNA was extracted and verified via restriction enzyme digestions.

Example 11

Transformation into Maize

Ear Sterilization and Embryo Isolation: To obtain maize immature embryos, plants of *Zea mays* (c.v. B104) were grown in the greenhouse and self or sib-pollinated to produce ears. The ears were harvested approximately 9-12 days post-pollination. On the day of the experiment, ears were surface-sterilized by immersion in a 20% solution of household bleach, which contains 5% sodium hypochlorite, and shaken for 20-30 minutes, followed by three rinses in sterile water. After sterilization, immature zygotic embryos (1.5-2.2 mm) were aseptically dissected from each ear and randomly distributed into micro-centrifuge tubes containing liquid infection media (LS Basal Medium, 4.43 g/L; N6 Vitamin Solution [1000×], 1.00 mL/L; L-proline, 700.0 mg/L; sucrose, 68.5 g/L; glucose, 36.0 g/L; 2,4-D, 1.50 mg/L. For a given set of experiments, pooled embryos from 2-3 ears were used for each treatment.

*Agrobacterium* Culture Initiation: Glycerol stocks of *Agrobacterium* strains containing the binary vectors described above were streaked on AB minimal medium plates containing appropriate antibiotics and were grown at 20° C. for 3-4 days. A single colony was picked and streaked onto YEP plates containing the same antibiotics and was incubated at 28° C. for 1-2 days.

*Agrobacterium* Culture and Co-cultivation: On the day of the experiment, *Agrobacterium* colonies were picked from the YEP plate, suspended in 10 mL of infection medium in a 50 mL disposable tube, and the cell density was adjusted to $OD_{600}$=0.2-0.4 nm using a spectrophotometer. The *Agrobacterium* cultures were placed on a rotary shaker at 115 rpm, room temperature, while embryo dissection was performed. Immature zygotic embryos between 1.5-2.2 mm in size were isolated from the sterilized maize kernels and placed in 1 mL of the infection medium and washed once in the same medium. The *Agrobacterium* suspension (2 mL) was added to each tube and the tubes were inverted for about 20 times then shaken for 10-15 minutes. The embryos were transferred onto co-cultivation media (MS Salts, 4.33 g/L; L-proline, 700.0 mg/L; myo-inositol, 100.0 mg/L; casein enzymatic hydrolysate 100.0 mg/L; Dicamba 3.30 mg/L; sucrose, 30.0 g/L; Gelzan™, 3.00 g/L; modified MS-Vitamin [1000×], 1.00 ml/L; $AgNo_3$, 15.0 mg/L; Acetosyringone, 100.0 μM), oriented with the scutellum facing up, and incubated for 3-4 days in the light at 25° C.

YFP/PhiYFP Transient expression: Transient YFP/PhiYFP expression was observed in transformed embryos after 3 days of co-cultivation with *Agrobacterium*. The embryos were observed under a stereomicroscope (Leica Microsystems, Buffalo Grove, Ill.) using YFP filter and 500 nm light source.

Callus Selection and Regeneration of Putative Events: Following the co-cultivation period, embryos were transferred to resting media (MS salts, 4.33 g/L; L-proline, 700.0 mg/L; myo-inositol, 100.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™, 2.30 g/L; modified MS-Vitamin [1000×], 1.00 ml/L; $AgNO_3$, 15.0 mg/L; Carbenicillin, 250.0 mg/L) without selective agent and incubated in 24 hours light with light intensity of 50 μmol $m^{-2}s^{-1}$ for 7 days at 28° C. Embryos were transferred onto selection 1 media (MS salts, 4.33 g/L; L-proline, 700.0 mg/L; myo-inositol, 100.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™, 2.30 g/L; modified MS-Vitamin [1000×], 1.00 ml/L; $AgNO_3$, 15.0 mg/L; Carbenicillin, 250.0 mg/L), containing 3 mg/L Bialaphos and incubated in 24 hours light with light intensity of 50 μmol $m^{-2}s^{-1}$ for 7 days at 28° C.

Embryos with proliferating embryogenic calli were transferred onto selection 2 media (MS salts, 4.33 g/L; myo-inositol, 100.0 mg/L; L-proline, 700.0 mg/L; MES [(2-(n-morpholino)-ethanesulfonic acid), free acid], 500.0 mg/L; casein enzymatic hydrolysate, 100.0 mg/L; Dicamba, 3.30 mg/L; sucrose, 30.0 g/L; Gelzan™ 2.30 g/L; modified MS-Vitamin [1000×], 1.00 ml/L; $AgNo_3$, 15.0 mg/L; Carbenicillin, 250.0 mg/L), containing 5 mg/L Bialaphos and were incubated in 24 hours light with light intensity of 50 μmol $m^{-2}s^{-1}$ for another 14 days at 28° C. This selection step allowed transgenic callus to further proliferate and differentiate. The callus selection period lasted for up to three weeks. Proliferating, embryogenic calli were transferred onto regeneration 1 media (MS salts, 4.33 g/L; myo-inositol, 100.0 mg/L; L-proline, 350.0 mg/L; MES [(2-(n-morpholino)-ethanesulfonic acid), free acid], 250.0 mg/L; casein enzymatic hydrolysate, 50.0 mg/L; NAA, 0.500 mg/L; ABA, 2.50 mg/L; BA, 1.00 mg/L; sucrose, 45.0 g/L; Gelzan™ 2.50 g/L; modified MS-Vitamin [1000×], 1.00 ml/L; $AgNO_3$, 1.00 mg/L; Carbenicillin, 250.0 mg/L), containing 3 mg/L Bialaphos and cultured in 24 hours light with light intensity of 50 μmol $m^{-2}s^{-1}$ for 7 days at 28° C.

Embryogenic calli with shoot/buds were transferred onto regeneration 2 media (MS salts, 4.33 g/L; modified MS-Vitamin [1000×], 1.00 ml/L; myo-inositol, 100.0 mg/L; sucrose, 60.0 g/L; Gellan Gum G434™, 3.00 g/L; Carbenicillin, 250.0 mg/L), containing 3 mg/L Bialaphos. The cultures were incubated under 24 hours light with light intensity of 50 μmol $m^{-2}s^{-1}$ for 7-10 days at 28° C. Small shoots with primary roots were transferred to shoot elongation and rooting media (MS salts, 4.33 g/L; N6 Vitamin Solution [1000×], 1.00 mL/L; myo-inositol, 100.0 mg/L; sucrose, 30.0 g/L; agar 5.50 g/L; in phytatrays, and were incubated under 16/8 hours light/dark at 90 μmol $m^{-2}s^{-1}$ for 7 days at 28° C. Healthy putative transgenic plantlets were selected then incubated in 16/8 hours light/dark at 200 μmol $m^{-2}s^{-1}$ for another 2-5 days at 25° C. and were analyzed for transgene copy number and transferred to the greenhouse.

Example 12

Transient PhiYFP Expression

Transient expression of PhiYFP from *Zea mays* embryos transformed with pDAB108719 was performed. The bidirectional SCBV promoter expressed PhiYFP from the AAD1-2A-PhiYFP gene expression cassette, where non-transformed embryos did not show any PhiYFP fluorescence. Similar level of PhiYFP expression could be observed from *Zea mays* embryos transformed with a binary plasmid pDAB105748 (FIG. 20) containing a uni-directional *Zea mays* (Zm) Ubi1 promoter driving a single PhiYFP coding sequence. Transient expression of PhiYFP could be observed from *Zea mays* embryos transformed with pDAB108720, where the bidirectional Zm Ubi1 promoter could express PhiYFP from the PhiYFP-2A-AAD1 gene expression cassette.

Example 13

PhiYFP Expression in Stably Transformed Maize

PhiYFP Expression in Stably Transformed *Zea mays* Callus Driven by a bidirectional Zm Ubi1 Promoter: *Zea mays* embryos transformed with the pDAB108719 binary vector containing the AAD1-2A-PhiYFP gene expression cassette showed good PhiYFP expression. The bidirectional SCBV promoter could drive robust expression of PhiYFP. These results confirmed that the Min-UbiP1 minimal promoter element of the bidirectional SCBV promoter is capable of expressing a reporter gene, for example PhiYFP or YFP. The levels of expression of the PhiYFP protein were similar as compared to *Zea mays* callus transformed with a control binary vector which contained the uni-directional Zm Ubi1 promoter driving the PhiYFP coding sequence (pDAB105748). Expression of PhiYFP was not detected in the negative control callus that was not transformed with a binary construct and did not contain the PhiYFP coding sequences.

*Zea mays* embryos transformed with the pDAB108720 binary vector that contains the PhiYFP-2A-AAD1 gene expression cassette showed good PhiYFP expression. The bidirectional SCBV promoter drove robust expression of PhiYFP. These results confirmed that the Min-UbiP1 minimal promoter element of the bidirectional SCBV promoter is capable of expressing a reporter gene, for example PhiYFP or YFP.

Example 14

Estimation of Transgene Copy Number

Transgene Copy Number Estimation Using Real Time TaqMan™ PCR: *Zea mays* plants were transformed with binary vectors containing a bidirectional SCBV promoter, pDAB108719 and pDAB108720, and other plants were transformed with a control binary vector, pDAB105748. The presence of coding sequence (PhiYFP, AAD1, Cry34, Cry35, Pat) within the genome of *Z. mays* plants transgenic to pDAB108719 and pDAB108720 was confirmed via a TaqMan hydrolysis probe assay. The plants transgenic to control vector pDAB105748 were analyzed for the presence of PhiYFP sequence. Stably transformed transgenic *Z. mays* plantlets that developed from the callus were obtained and analyzed to identify events that contain a low copy number (1-2 copies) of full-length T-strand inserts from the pDAB108719 and pDAB108720 binary vectors, and pDAB105748 control binary vector. Confirmed plantlets were advanced to the green house and grown.

The Roche Light Cycler 480™ system was used to determine the transgene copy number for events that were transformed with the pDAB108719 and pDAB108720 binary vector. The method utilized a biplex TAQMAN® reaction that employed oligonucleotides specific to the coding sequence and to the endogenous *Z. mays* reference gene, invertase (Genbank Accession No: U16123.1), in a single assay. Copy number and zygosity were determined by measuring the intensity of coding sequence-specific fluorescence, relative to the invertase-specific fluorescence, as compared to known copy number standards.

For *Z. mays* samples transformed with the pDAB108719 and pDAB108720 binary vectors, a coding sequence-specific DNA fragment is amplified with one TAQMAN® primer/probe set containing a probe labeled with FAM fluorescent dye, and invertase were amplified with a second TAQMAN® primer/probe set containing a probe labeled with HEX fluorescence (Table 7). The PCR reaction mixture was prepared as set forth in Table 8, and the gene-specific DNA fragments were amplified according to the conditions set forth in Table 9. Copy number and zygosity of the samples was determined by measuring the relative intensity of fluorescence specific for the coding sequence to fluorescence specific for the reference gene, invertase, as compared to known copy number standards.

Standards were created by diluting the vector (pDAB108719 or pDAB108720) into *Z. mays* B104 genomic DNA (gDNA) to obtain standards with a known relationship of vector:gDNA. For example, samples having one, two, and four cop(ies) of vector DNA per one copy of the *Z. mays* B104 gDNA were prepared. One and two copy dilutions of the vector mixed with the *Z. mays* B104 gDNA standard were validated against a control *Z. mays* event that is known to be hemizygous, and a control *Z. mays* event that is known to be homozygous (*Z. mays* event 278; See PCT International Patent Publication No. WO 2011/022469 A2, the content of which is hereby incorporated by reference in its entirety). A TAQMAN® biplex assay that utilizes oligonucleotides specific to the coding sequence gene and oligonucleotides specific to the endogenous *Z. mays* reference gene, invertase, was performed by amplifying and detecting

TABLE 7

Forward and reverse nucleotide primer and fluorescent probes (synthesized by Integrated DNA Technologies, Coralville, IA).

| Primer Name | Primer Sequence |
|---|---|
| YFP Forward Primer | GATGCCTCAGTGGGAAAGG (SEQ ID NO: 8) |
| YFP Reverse Primer | CCATAGGTGAGAGTGGTGACAA (SEQ ID NO: 9) |
| YFP Probe | ROCHE UPL Probe #125 CTTGGAGC (SEQ ID NO: 41) Cat # 04693604001 (Roche, Indianapolis, IN) |
| Invertase Forward Primer | TGGCGGACGACGACTTGT (SEQ ID NO: 10) |
| Invertase Reverse Primer | AAAGTTTGGAGGCTGCCGT (SEQ ID NO: 11) |
| Invertase Probe | 5'HEX/CGAGCAGACCGCCGTGTACTTCTACC/3BHQ_1/3' (SEQ ID NO: 12) |
| AAD1 Forward Primer | TGTTCGGTTCCCTCTACCAA (SEQ ID NO: 13) |
| AAD1 Reverse Primer | CAACATCCATCACCTTGACTGA (SEQ ID NO: 14) |
| AAD1 Probe | CACAGAACCGTCGCTTCAGCAACA (SEQ ID NO: 15) |
| Cry34 Forward Primer | GCCAACGACCAGATCAAGAC (SEQ ID NO: 42) |
| Cry34 Reverse Primer | GCCGTTGATGGAGTAGTAGATGG (SEQ ID NO: 43) |
| Cry34 Probe | CCGAATCCAACGGCTTCA (SEQ ID NO: 44) |
| Cry35 Forward Primer | CCTCATCCGCCTCACCG (SEQ ID NO: 45) |
| Cry35 Reverse Primer | GGTAGTCCTTGAGCTTGGTGTC (SEQ ID NO: 46) |
| Cry35 Probe | CAGCAATGGAACCTGACGT (SEQ ID NO: 47) |
| PAT Forward Primer | ACAAGAGTGGATTGATGATCTAGAGAGGT (SEQ ID NO: 48) |
| PAT Reverse Primer | CTTTGATGCCTATGTGACACGTAAACAGT (SEQ ID NO: 49) |
| PAT Probe | GGTGTTGTGGCTGGTATTGCTTACGCTGG (SEQ ID NO: 50) |

a gene-specific DNA fragment for coding sequence with one TAQMAN® primer/probe set containing a probe labeled with FAM fluorescent dye, and by amplifying and detecting a gene-specific DNA fragment for invertase with a second TAQMAN® primer/probe set containing a probe labeled with HEX fluorescence. According to Table 7, the coding sequence TAQMAN® reaction mixture was prepared as set forth in Table 8 and the specific fragments were amplified according to the conditions set forth in Table 9.

TABLE 8

TAQMAN ® PCR reaction mixture.

| Number of Reactions | μl each | Final Concentration |
|---|---|---|
| $H_2O$ | 0.5 μL | — |
| PVP (10%) | 0.1 μL | 0.1% |
| ROCHE 2X Master Mix | 5.0 μL | 1X |
| Coding sequence Forward Primer (10 μM) | 0.4 μL | 0.4 μM |
| Coding sequence Reverse Primer (10 μM) | 0.4 μL | 0.4 μM |
| Coding sequence Probe UPL#125 (5 μM) | 0.4 μL | 0.2 μM |
| Invertase Forward Primer (10 μM) | 0.4 μL | 0.4 μM |
| Invertase Reverse Primer (10 μM) | 0.4 μL | 0.4 μM |
| Invertase Probe (5 μM) | 0.4 μL | 0.2 μM |
| Template DNA | 2.0 μL | — |
| Total reaction volume | 10 μL | — |

The level of fluorescence generated for each reaction was analyzed using the Roche LightCycler 480™ Thermocycler according to the manufacturer's directions. The FAM fluorescent moiety was excited at an optical density of 465/510 nm, and the HEX fluorescent moiety was excited at an optical density of 533/580 nm. The copy number was determined by comparison of Target/Reference values for unknown samples (output by the LightCycler 480™) to Target/Reference values of four known copy number standards (for example, Null, 1-Copy (hemi), 2-Copy (homo), and 4-Copy).

TABLE 9

Thermocycler conditions for PCR amplification.

| PCR Steps | Temp (° C.) | Time | No. of cycles |
|---|---|---|---|
| Step-1 | 95 | 10 minutes | 1 |
| Step-2 | 95 | 10 seconds | 40 |
| | 59 | 35 seconds | |
| | 72 | 1 second | |
| Step-3 | 40 | 11 seconds | 1 |

Results from the transgene copy number analysis of transgenic plants obtained via transformation with a bidirectional SCBV promoter constructs (pDAB108719 and pDAB108720), and of transgenic plants obtained via transformation with a control unidirectional ZmUbi1 promoter PhiYFP construct (pDAB105748) are summarized in Table 10. Only plants with 1-2 copies of the all transgenes were transferred to the greenhouse for further expression analyses.

TABLE 10

Transgene copy number estimation of the transgenic plants obtained from bidirectional promoter and control constructs.

| Construct | Number of Embryos Transformed | Number of Positive Events | 1-2 Copies of all genes |
|---|---|---|---|
| pDAB108719 | 250 | 78 | 13 |
| pDAB108720 | 225 | 57 | 13 |
| pDAB105748 | 32 | 8 | 2 |

Example 15

Stable PhiYFP Expression in Maize T0 Plants

Stable PhiYFP Expression in *Zea mays* $T_0$ Plants Driven by bidirectional SCBV Promoter: *Zea mays* embryos transformed with the pDAB108719 binary vector containing the AAD1-2A-PhiYFP gene expression cassette could be observed. The bidirectional SCBV promoter drove robust expression of the PhiYFP both in shoot and root tissues. The results confirmed that the Min-UbiP1 minimal promoter element of the bidirectional SCBV promoter is capable of expressing a reporter gene, for example PhiYFP or YFP that is bicistronically fused with aad1 using a 2A sequence. The levels of expression of the PhiYFP protein was similar to *Z. mays* embryos transformed with a control binary vector which contained the uni-directional Zm Ubi1 promoter driving the PhiYFP coding sequence (pDAB105748). Expression of PhiYFP was not detected in the negative control plants that were not transformed with a binary construct and did not contain the PhiYFP coding sequences.

PhiYFP expression in leaf and root tissues of *Zea mays* T0 plants transgenic to pDAB108720 binary vector that contains the PhiYFP-2A-AAD1 gene expression cassette could be observed. The bidirectional SCBV promoter drove robust expression of PhiYFP. The results confirmed that the Min-UbiP1 minimal promoter element of the bidirectional SCBV promoter is capable of expressing a reporter gene, for example PhiYFP or YFP fused to aad1 with a 2A sequence or 2A-like sequence.

Example 16

Cry34, Cry35, and AAD1 Protein Analysis

Plants were sampled into columns 1-10 of a matrix box in 1.5 mL conical tubes to which 1 steel bead was added followed by PBST+0.5% BSA (0.6 mL). The box was then bead beated for sample grinding in a Geno Grinder for 5 minutes at 1500 rpm then centrifuged at 3700 rpm for 7 minutes at 4° C.

Cry34/35 ELISA assay: In a separate, 96 deep well plate, a sample of the extract was diluted 1:200 in PBST+1% blotto. Two volumes of 25 μL of the diluted sample were then transferred to separate 96-well plates that had been arrayed with anti-Cry34 and anti-Cry35 (Meso Scale Discovery). In the 11 and 12 columns of each plate standard concentrations of Cry34 and Cry35 in PBST+1% blotto were added (25 μL). The plates were then incubated while shaking at room temperature for one hour. The plates were then washed with PBST (3×300 μL). Then 25 μL of a solution of SulfoTAG conjugated anti-Cry34 and anti-Cry35 was added to each well and incubated with shaking at room temperature for one hour. The plates were then washed with PBST (3×300 μL). A volume of 150 μL Read Buffer T (Meso Scale Discovery) was then added and the plate was immediately read on a SECTOR® 6000 reader. Concentrations of proteins in the sample were calculated using the standard curve for the respective protein generated from the same plate.

AAD-1 ELISA assay: In a separate, 96 deep well plate, a sample of the extract was diluted 1:20 in PBST+0.5% BSA. Two volumes of 200 μl of the diluted sample were then transferred to separate 96 well plates that had been coated with anti-AAD1 (provided by Acadia Bioscience LLC). In the 11 and 12 columns of each plate standard concentrations of AAD1 in PBST+0.5% BSA were added (200 μL). A volume of 50 μL of biotinylated anti-AAD1 was then added to each well and the plates were incubated while shaking at room temperature for one hour. The plates were then washed with PBST (5×300 μL). Then 100 μL of a steptavidin-alkaline phosphate conjugate solution was added to each well and incubated with shaking at room temperature for 30 minutes. The plates were then washed with PBST (5×300 μL). A volume of 100 μL substrate (p-nitrophenylphosphate, PNPP) was then added and incubated with shaking at room temperature for 45 minutes. The plates were then read at A405 on a SpectraMax M5 plate reader (Molecular Devices). Concentrations of proteins in the sample were calculated using the standard curve generated from the same plate.

Example 17

Protein Analysis of Maize T0 Plants

Protein analysis of maize T0 plants driven by the bidirectional *Zea mays* SCBV Promoter construct (pDAB108719) was performed in this example.

TABLE 11

Cry34/Cry35/AAD1 expression in T0 maize pDAB108719 transgenic plants

| Plant ID | Cry34 ng/cm$^2$ | Cry35 ng/cm$^2$ | \|AAD1 ng/cm$^2$\| |
|---|---|---|---|
| 108719[2]-102.001 | 56 | 0 | 2 |
| 108719[3]-058.001 | 20 | 0 | 3 |
| 108719[3]-061.002 | 25 | 0 | 3 |
| 108719[3]-057.001 | 37 | 0 | 1 |
| 108719[3]-064.001 | 20 | 0 | 5 |
| 108719[1]-009.001 | 31 | 0 | 3 |
| 108719[1]-013.001 | 15 | 0 | 8 |
| 108719[1]-014.001 | 31 | 0 | 4 |
| 108719[1]-016.001 | 27 | 2 | 2 |
| 108719[1]-020.001 | 20 | 10 | 5 |
| 108719[2]-096.001 | 20 | 12 | 7 |
| 108719[2]-101.001 | 21 | 4 | 3 |

Results of a representative ELISA analysis of 12 transgenic T0 maize plants obtained from *Zea mays* embryos transformed with pDAB108719 that contains Cry34-2A-Cry35 gene expression cassette is summarized in Table 11. A bidirectional SCBV promoter drove robust expression of both Cry34 and Cry35 coding sequences in leaf. These observations showed that the single SCBV bidirectional promoter in construct pDAB108719 can express multiple genes (e.g., Cry34, Cry35, and AAD1).

Protein analysis of maize T0 plants driven by the bidirectional *Zea mays* Ubiquitin) Promoter construct (pDAB108720): Representative ELISA analysis of 9 transgenic T0 maize plants obtained from *Zea mays* embryos transformed with pDAB108720 that contained the Cry34-2A-Cry35 gene expression cassette is summarized in Table 12. The bidirectional SCBV promoter drove robust expression of both Cry34 and Cry35 coding sequences in leaf.

TABLE 12

Cry34/Cry35/AAD1 expression in T0 maize pDAB108720 transgenic plants

| Plant ID | Cry34 ng/cm$^2$ | Cry35 ng/cm$^2$ | \|AAD1 ng/cm$^2$\| |
|---|---|---|---|
| 108720[1]-017.001 | 19 | 24 | 10 |
| 108720[1]-024.001 | 21 | 0 | 9 |
| 108720[1]-027.001 | 20 | 2 | 8 |
| 108720[1]-032.001 | 32 | 12 | 8 |
| 108720[2]-085.001 | 16 | 0 | 8 |
| 108720[2]-086.001 | 30 | 0 | 5 |
| 108720[2]-088.001 | 0 | 26 | 4 |
| 108720[2]-092.001 | 0 | 0 | 13 |
| 108720[2]-105.001 | 26 | 0 | 2 |

Example 18

Transgene Stacking: Synthetic Bidirectional Promoters (T1 Data)

Gene expression of T1 plants driven by the bidirectional promoter constructs: ten to twelve single copy events per construct were selected for analysis, except that the control construct pDAB108716 had only one event. Five plants/events for the V6 stage were tested, and three plants/events for the V10-12 and/R3 stages were tested. Protein assays were performed using LCMS or ELISA.

The constructs used in this example are shown in FIG. 30. pDAB108708 (SCBV bidirectional (−200)) and pDAB108709 (SCBV bidirectional (−90)) are constructs with representative bidirectional promoter of the present invention in addition to constructs with maize Ubi1 bidirectional promoter (pDAB108706 [ZMUbi bidirectional (−200)) and pDAB108707 (ZMUbi bidirectional (−90))]; pDAB101556 (ZmUbi1-YFP control), pDAB108715 (SCBV without minimal promoter), and pDAB108716 (ZMUbi1 without minimal promoter) served as control constructs with uni-directional promoters.

Exemplary expression results (V6) from the seven constructs for YFP protein (LCMS) in ng/cm$^2$ are shown in FIG. 31A. Exemplary relative expression results (V6) from the seven constructs for YFP RNA are shown in FIG. 31B.

Exemplary expression results (V6) from the seven constructs for GUS protein (LCMS) in ng/cm$^2$ are shown in FIG. 32A. Exemplary relative expression results (V6) from the seven constructs for GUS RNA are shown in FIG. 32B.

Exemplary expression results (V6) from the seven constructs for AAD1 protein (LCMS) in ng/cm$^2$ are shown in FIG. 33A. Exemplary relative expression results (V6) from the seven constructs for AAD1 RNA are shown in FIG. 33B.

A statistical analysis of expression results (V6) from the seven constructs for YFP protein (LCMS) in ng/cm$^2$ is shown in FIG. 34A. A statistical analysis of relative expression results (V6) from the seven constructs for YFP RNA is shown in FIG. 34B. The mean values and statistical results are listed.

A statistical analysis of expression results (V6) from the seven constructs for GUS protein (LCMS) in ng/cm$^2$ is shown in FIG. 35A. A statistical analysis of relative expression results (V6) from the seven constructs for GUS RNA is shown in FIG. 35B. The mean values and statistical results are listed.

A statistical analysis of expression results (V6) from the seven constructs for AAD1 protein (LCMS) in ng/$cm^2$ is shown in FIG. 36A. A statistical analysis of relative expression results (V6) from the seven constructs for AAD1 RNA is shown in FIG. 36B. The mean values and statistical results are listed.

FIGS. 37A, 37B, and 37C show exemplary expression results (V10) from the seven constructs for YFP, AAD1, and GUS protein (LCMS) in ng/$cm^2$, respectively.

FIGS. 38A, 38B, and 38C show statistical analysis of expression results (V10) from the seven constructs for YFP, GUS, and AAD1 protein (LCMS) in ng/$cm^2$, respectively. The mean values and statistical results are listed.

FIGS. 39A, 39B, and 39C show exemplary expression results (R3) from the seven constructs for YFP, GUS, and AAD1 protein (LCMS) in ng/$cm^2$, respectively.

FIGS. 40A, 40B, and 40C show statistical analysis of expression results (R3) from the seven constructs for YFP, GUS, and AAD1 protein (LCMS) in ng/$cm^2$, respectively. The mean values and statistical results are listed.

The results show that both SCBV bidirectional promoters of the present invention and maize Ubi1 bidirectional promoters can drive robust expression of GUS and YFP. The YFP expression from Maize Ubi1 bidirectional promoter was similar to unidirectional maize Ubi1 driven YFP. The YFP expression from SCBV bidirectional promoter was significantly higher than unidirectional maize Ubi1 driven YFP or Maize Ubi1 bidirectional promoter. However, this difference became less significant at V10 stage. The results also suggest that bidirectional transcription has non-significant effect on GUS expression (GUS expression compared to the constructs lacking minimal promoter without YFP expression). SCBV bidirectional promoters also provided significantly higher GUS expression compared to maize Ubi1 bidirectional promoters.

Example 19

A Combination of Bidirectional Promoter and 2A Bicistronic Sequence to Drive Four Transgenes from One Single Promoter (T1 Data)

Gene expression of T1 plants driven by the bidirectional promoter constructs: ten to twelve single copy events per construct were selected for analysis, except that the control constructs had four or five events per construct. Five plants/events for the V6 stage were tested, and three plants/events for the V10-12 and/R3 stages were tested. Protein assays were performed using LCMS or ELISA.

pDAB108719 and pDAB108720 are shown in FIG. 19. pDAB105748 and pDAB105818 are shown in FIG. 20. Additional multi-transgene constructs using Ubi1 promoter, including pDAB108717 and pDAB108718 are shown in FIG. 41.

Exemplary relative expression results (V6) of Cry34 RNA from six constructs pDAB105748 (ZMUbi1-YFP), pDAB105818 (ZMUbi1-Cry34/ZMUbi1-Cry35/ZMUbi1-AAD1), pDAB108717 (YFP/AAD-1-ZMUbi1 bidirectional-Cry34-Cry35), pDAB108718 (AAD1/YFP-ZMUbi1 bidirectinal-Cry34-Cry35), pDAB108719 (YFP/AAD1-SCBV bidirectional-Cry34-Cry35), and pDAB108720 (AAD1/YFP-SCBV bidirectional-Cry34-Cry35) are shown in FIG. 42A. Exemplary relative expression results (V6) of Cry34 protein (LCMS) from the same six constructs pDAB105748, pDAB105818, pDAB108717, pDAB108718, pDAB108719, and pDAB108720 are shown in FIG. 42B.

Exemplary relative expression results (V6) of AAD1 RNA from the six constructs pDAB105748, pDAB105818, pDAB108717, pDAB108718, pDAB108719, and pDAB108720 are shown in FIG. 43A. Exemplary relative expression results (V6) of AAD1 protein (LCMS) from the same six constructs pDAB105748, pDAB105818, pDAB108717, pDAB108718, pDAB108719, and pDAB108720 are shown in FIG. 43B.

Exemplary relative expression results (V6) of YFP RNA from the six constructs pDAB105748, pDAB105818, pDAB108717, pDAB108718, pDAB108719, and pDAB108720 are shown in FIG. 44A. Exemplary relative expression results (V6) of YFP protein (LCMS) from the same six constructs pDAB105748, pDAB105818, pDAB108717, pDAB108718, pDAB108719, and pDAB108720 are shown in FIG. 44B.

Exemplary relative expression results (V6) of Cry35 RNA from the six constructs pDAB105748, pDAB105818, pDAB108717, pDAB108718, pDAB108719, and pDAB108720 are shown in FIG. 45A. Exemplary relative expression results (V6) of Cry35 protein (ELISA) from the same six constructs pDAB105748, pDAB105818, pDAB108717, pDAB108718, pDAB108719, and pDAB108720 are shown in FIG. 45B.

FIG. 46 shows exemplary relative expression results (V6) of PAT RNA from the six constructs pDAB105748, pDAB105818, pDAB108717, pDAB108718, pDAB108719, and pDAB108720.

A statistical analysis of expression results (V6) of Cry34 RNA from the six constructs pDAB105748, pDAB105818, pDAB108717, pDAB108718, pDAB108719, and pDAB108720 is shown in FIG. 47A. A statistical analysis of expression results (V6) of Cry34 protein from the same six constructs pDAB105748, pDAB105818, pDAB108717, pDAB108718, pDAB108719, and pDAB108720 is shown in FIG. 47B. The mean values and statistical results are listed.

A statistical analysis of expression results (V6) of AAD1 RNA from the six constructs pDAB105748, pDAB105818, pDAB108717, pDAB108718, pDAB108719, and pDAB108720 is shown in FIG. 48A. A statistical analysis of expression results (V6) of AAD1 protein from the same six constructs pDAB105748, pDAB105818, pDAB108717, pDAB108718, pDAB108719, and pDAB108720 is shown in FIG. 48B. The mean values and statistical results are listed.

A statistical analysis of expression results (V6) of YFP RNA from the six constructs pDAB105748, pDAB105818, pDAB108717, pDAB108718, pDAB108719, and pDAB108720 is shown in FIG. 49A. A statistical analysis of expression results (V6) of YFP protein from the same six constructs pDAB105748, pDAB105818, pDAB108717, pDAB108718, pDAB108719, and pDAB108720 is shown in FIG. 49B. The mean values and statistical results are listed.

A statistical analysis of expression results (V6) of Cry35 RNA from the six constructs pDAB105748, pDAB105818, pDAB108717, pDAB108718, pDAB108719, and pDAB108720 in FIG. 50A. A statistical analysis of expression results (V6) of Cry35 protein from the same six constructs pDAB105748, pDAB105818, pDAB108717, pDAB108718, pDAB108719, and pDAB108720 is shown in FIG. 50B. The mean values and statistical results are listed.

FIG. 51 shows a statistical analysis of expression results (V6) of PAT RNA from the six constructs pDAB105748, pDAB105818, pDAB108717, pDAB108718, pDAB108719, and pDAB108720. The mean values and statistical results are listed.

FIGS. 52A, 52B, 52C, and 52D show exemplary protein expression results (V10) of YFP, AAD1, Cry34, and Cry35 respectively from the six constructs pDAB105748, pDAB105818, pDAB108717, pDAB108718, pDAB108719, and pDAB108720.

FIGS. 53A, 53B, 53C, and 53D show statistical analysis of protein expression results (V10) of YFP, AAD1, Cry34, and Cry35 respectively from the six constructs pDAB105748, pDAB105818, pDAB108717, pDAB108718, pDAB108719, and pDAB108720. The mean values and statistical results are listed.

FIGS. 54A, 54B, 54C, and 54D show exemplary protein expression results (R3) of YFP, AAD1, Cry34, and Cry35 respectively from the six constructs pDAB105748, pDAB105818, pDAB108717, pDAB108718, pDAB108719, and pDAB108720.

FIGS. 55A, 55B, 55C, and 55D show statistical analysis of protein expression results (R3) of YFP, AAD1, Cry34, and Cry35 respectively from the six constructs pDAB105748, pDAB105818, pDAB108717, pDAB108718, pDAB108719, and pDAB108720. The mean values and statistical results are listed.

FIG. 56 shows exemplary results of Western blot for protein expression of Cry34, Cry35, and AAD1 from pDAB108718, pDAB108717, pDAB108719, and pDAB108720.

The results showed that all four transgenes in the single promoter-driven constructs were functional with good expression levels. Three genes (Cry34/Cry35/AAD1) in a Ubi1 bidirectional stack showed robust expression levels, similar to expression levels provided by the single Ubi1-driven gene stack (DExT).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A double-stranded nucleic acid construct for expressing multiple genes in a plant cell and/or a plant tissue, the construct comprising a bidirectional promoter comprising:

a first strand comprising a minimal core promoter element; and a second strand comprising a Sugar Cane Bacilloform Virus (SCBV) promoter, wherein the bidirectional promoter comprises the nucleotide sequence of SEQ ID NO:5, wherein the minimal core promoter element drives expression of a first gene expression cassette; and wherein the SCBV promoter drives expression of a second gene expression cassette.

2. A synthetic double-stranded polynucleotide comprising:

a first strand comprising a minimal core promoter element; and a second strand comprising a Sugar Cane Bacilliform Virus promoter, wherein the polynucleotide comprises the sequence of SEQ ID NO:5.

* * * * *

SEQUENCE LISTING

```
<160> NUMBER OF SEQ ID NOS: 53

<210> SEQ ID NO 1
<211> LENGTH: 215
<212> TYPE: DNA
<213> ORGANISM: Zea mays

<400> SEQUENCE: 1

ctggacccct ctcgagagtt ccgctccacc gttggacttg ctccgctgtc ggcatccaga      60

aattgcgtgg cggagcggca gacgtgagcc ggcacggcag gcggcctcct cctcctctca     120

cggcaccggc agctacgggg gattcctttc ccaccgctcc ttcgctttcc cttcctcgcc     180

cgccgtaata aatagacacc ccctccacac cctct                                215


<210> SEQ ID NO 2
<211> LENGTH: 1319
<212> TYPE: DNA
<213> ORGANISM: Artificial sequence
<220> FEATURE:
<223> OTHER INFORMATION: Reverse complement of polynucleotide comprising
      Z. mays minUbi1P minimal core promoter; Z. mays Ubi1 leader; and Z
      mays Ubi1 intron
<220> FEATURE:
<221> NAME/KEY: misc_feature
<222> LOCATION: (1)..(1015)
<223> OTHER INFORMATION: UbiI-Intron
<220> FEATURE:
<221> NAME/KEY: misc_feature
<222> LOCATION: (1016)..(1097)
<223> OTHER INFORMATION: Ubi1-leader
<220> FEATURE:
<221> NAME/KEY: misc_feature
<222> LOCATION: (1098)..(1319)
<223> OTHER INFORMATION: minUbi1P-min_core_promoter

<400> SEQUENCE: 2

ctgcagaagt aacaccaaac aacagggtga gcatcgacaa aagaaacagt accaagcaaa      60

taaatagcgt atgaaggcag ggctaaaaaa atccacatat agctgctgca tatgccatca     120

tccaagtata tcaagatcga aataattata aaacatactt gtttattata atagataggt     180

actcaaggtt agagcatatg aatagatgct gcatatgcca tcatgtatat gcatcagtaa     240

aacccacatc aacatgtata cctatcctag atcgatattt ccatccatct taaactcgta     300
```

```
actatgaaga tgtatgacac acacatacag ttccaaaatt aataaataca ccaggtagtt    360

tgaaacagta ttctactccg atctagaacg aatgaacgac cgcccaacca caccacatca    420

tcacaaccaa gcgaacaaaa agcatctctg tatatgcatc agtaaaaccc gcatcaacat    480

gtatacctat cctagatcga tatttccatc catcatcttc aattcgtaac tatgaatatg    540

tatggcacac acatacagat ccaaaattaa taaatccacc aggtagtttg aaacagaatt    600

ctactccgat ctagaacgac cgcccaacca gaccacatca tcacaaccaa gacaaaaaaa    660

agcatgaaaa gatgacccga caaacaagtg cacggcatat attgaaataa aggaaaaggg    720

caaaccaaac cctatgcaac gaaacaaaaa aaatcatgaa atcgatcccg tctgcggaac    780

ggctagagcc atcccaggat tccccaaaga gaaacactgg caagttagca atcagaacgt    840

gtctgacgta caggtcgcat ccgtgtacga acgctagcag cacggatcta acacaaacac    900

ggatctaaca caaacatgaa cagaagtaga actaccgggc cctaaccatg catggaccgg    960

aacgccgatc tagagaaggt agagaggggg gggggggga ggacgagcgg cgtaccttga   1020

agcggaggtg ccgacgggtg gatttggggg agatctggtt gtgtgtgtgt gcgctccgaa   1080

caacacgagg ttggggaggt accaagaggg tgtggagggg gtgtctattt attacggcgg   1140

gcgaggaagg gaaagcgaag gagcggtggg aaaggaatcc cccgtagctg ccggtgccgt   1200

gagaggagga ggaggccgcc tgccgtgccg gctcacgtct gccgctccgc cacgcaattt   1260

ctggatgccg acagcggagc aagtccaacg gtggagcgga actctcgaga ggggtccag    1319
```

<210> SEQ ID NO 3
<211> LENGTH: 3322
<212> TYPE: DNA
<213> ORGANISM: Artificial sequence
<220> FEATURE:
<223> OTHER INFORMATION: Exemplary synthetic Ubi1 bidirectional promoter
<220> FEATURE:
<221> NAME/KEY: misc_feature
<222> LOCATION: (1105)..(1319)
<223> OTHER INFORMATION: First_minUbi1P-reverse_complement
<220> FEATURE:
<221> NAME/KEY: misc_feature
<222> LOCATION: (2009)..(2244)
<223> OTHER INFORMATION: Second_minUbi1P-reverse_complement

<400> SEQUENCE: 3

```
ctgcagaagt aacaccaaac aacagggtga gcatcgacaa aagaaacagt accaagcaaa     60

taaatagcgt atgaaggcag ggctaaaaaa atccacatat agctgctgca tatgccatca    120

tccaagtata tcaagatcga aataattata aaacatactt gtttattata atagataggt    180

actcaaggtt agagcatatg aatagatgct gcatatgcca tcatgtatat gcatcagtaa    240

aacccacatc aacatgtata cctatcctag atcgatattt ccatccatct taaactcgta    300

actatgaaga tgtatgacac acacatacag ttccaaaatt aataaataca ccaggtagtt    360

tgaaacagta ttctactccg atctagaacg aatgaacgac cgcccaacca caccacatca    420

tcacaaccaa gcgaacaaaa agcatctctg tatatgcatc agtaaaaccc gcatcaacat    480

gtatacctat cctagatcga tatttccatc catcatcttc aattcgtaac tatgaatatg    540

tatggcacac acatacagat ccaaaattaa taaatccacc aggtagtttg aaacagaatt    600

ctactccgat ctagaacgac cgcccaacca gaccacatca tcacaaccaa gacaaaaaaa    660

agcatgaaaa gatgacccga caaacaagtg cacggcatat attgaaataa aggaaaaggg    720

caaaccaaac cctatgcaac gaaacaaaaa aaatcatgaa atcgatcccg tctgcggaac    780
```

```
ggctagagcc atcccaggat tccccaaaga gaaacactgg caagttagca atcagaacgt    840

gtctgacgta caggtcgcat ccgtgtacga acgctagcag cacggatcta acacaaacac    900

ggatctaaca caaacatgaa cagaagtaga actaccgggc cctaaccatg catggaccgg    960

aacgccgatc tagagaaggt agagaggggg ggggggggga ggacgagcgg cgtaccttga   1020

agcggaggtg ccgacgggtg gatttggggg agatctggtt gtgtgtgtgt gcgctccgaa   1080

caacacgagg ttggggaggt accaagaggg tgtggagggg gtgtctattt attacggcgg   1140

gcgaggaagg gaaagcgaag gagcggtggg aaaggaatcc cccgtagctg ccggtgccgt   1200

gagaggagga ggaggccgcc tgccgtgccg gctcacgtct gccgctccgc cacgcaattt   1260

ctggatgccg acagcggagc aagtccaacg gtggagcgga actctcgaga ggggtccagc   1320

cgcggagtgt gcagcgtgac ccggtcgtgc ccctctctag agataatgag cattgcatgt   1380

ctaagttata aaaaattacc acatattttt tttgtcacac ttgtttgaag tgcagtttat   1440

ctatctttat acatatattt aaactttact ctacgaataa tataatctat agtactacaa   1500

taatatcagt gttttagaga atcatataaa tgaacagtta gacatggtct aaaggacaat   1560

tgagtatttt gacaacagga ctctacagtt ttatcttttt agtgtgcatg tgttctcctt   1620

tttttttgca aatagcttca cctatataat acttcatcca ttttattagt acatccattt   1680

agggtttagg gttaatggtt tttatagact aattttttta gtacatctat tttattctat   1740

tttagcctct aaattaagaa aactaaaact ctattttagt tttttttattt aatagtttag   1800

atataaaata gaataaaata aagtgactaa aaattaaaca aataccctTT aagaaattaa   1860

aaaaactaag gaaacatttt tcttgtttcg agtagataat gccagcctgt taaacgccgt   1920

cgacgagtct aacggacacc aaccagcgaa ccagcagcgt cgcgtcgggc caagcgaagc   1980

agacggcacg gcatctctgt cgctgcctct ggacccctct cgagagttcc gctccaccgt   2040

tggacttgct ccgctgtcgg catccagaaa ttgcgtggcg gagcggcaga cgtgagccgg   2100

cacggcaggc ggcctcctcc tcctctcacg gcaccggcag ctacggggga ttccttttccc   2160

accgctcctt cgctttccct tcctcgcccg ccgtaataaa tagacacccc ctccacaccc   2220

tctttcccca acctcgtgtt gttcggagcg cacacacaca caaccagatc tcccccaaat   2280

ccacccgtcg gcacctccgc ttcaaggtac gccgctcgtc ctccccccccc ccccccctct   2340

ctaccttctc tagatcggcg ttccggtcca tgcatggtta gggcccggta gttctacttc   2400

tgttcatgtt tgtgttagat ccgtgtttgt gttagatccg tgctgctagc gttcgtacac   2460

ggatgcgacc tgtacgtcag acacgttctg attgctaact tgccagtgtt tctctttggg   2520

gaatcctggg atggctctag ccgttccgca gacgggatcg atttcatgat tttttttgtt   2580

tcgttgcata gggtttggtt tgccctttc ctttatttca atatatgccg tgcacttgtt   2640

tgtcgggtca tcttttcatg cttttttttg tcttggttgt gatgatgtgg tctggttggg   2700

cggtcgttct agatcggagt agaattctgt ttcaaactac ctggtggatt tattaatttt   2760

ggatctgtat gtgtgtgcca tacatattca tagttacgaa ttgaagatga tggatggaaa   2820

tatcgatcta ggataggtat acatgttgat gcgggtttta ctgatgcata tacagagatg   2880

cttttgttc gcttggttgt gatgatgtgg tgtggttggg cggtcgttca ttcgttctag   2940

atcggagtag aatactgttt caaactacct ggtgtattta ttaattttgg aactgtatgt   3000

gtgtgtcata catcttcata gttacgagtt taagatggat ggaaatatcg atctaggata   3060

ggtatacatg ttgatgtggg ttttactgat gcatatacat gatggcatat gcagcatcta   3120

ttcatatgct ctaaccttga gtacctatct attataataa acaagtatgt tttataatta   3180
```

tttcgatctt gatatacttg gatgatggca tatgcagcag ctatatgtgg attttttag 3240 ccctgccttc atacgctatt tatttgcttg gtactgtttc ttttgtcgat gctcaccctg 3300
ttgtttggtg ttacttctgc ag 3322

<210> SEQ ID NO 4
<211> LENGTH: 6698
<212> TYPE: DNA
<213> ORGANISM: Artificial sequence
<220> FEATURE:
<223> OTHER INFORMATION: Exemplary nucleic acid comprising yfp and GUS expression cassettes driven by a synthetic Ubi1 bidirectional promoter

<400> SEQUENCE: 4
agcacttaaa gatctttaga agaaagcaaa gcatttatta atacataaca atgtccaggt 60
agcccagctg aattacaata cgcaactgct cataataatt caacaaaccc aagtagtaca 120
caacatccag aagcaaataa agcccatacg taccaaagcc tacacaagca gcaacactca 180
ctgccagtgc cggtgggtct ttaaagcaca cgggccttga ccacgcgatc caccttgaaa 240
caaacttggt aaaattaaag caaaccagaa gcacacacac gccaacgcaa cgcttctgat 300
cgcgcgccca aggcccggcc ggccagaacg tacgacggac acgcacacgc tgcgaccgag 360
ctctaggtga ttaagctaac tactcaaagg taggtcttgc gacagtcaac agctctgaca 420
gtttctttca aggacatgtt gtctctgtgg tctgtcacat ctttggaaag tttcacatgg 480
taagacatgt gatgatactc tggaacatga actggacctc caccaatggg agtgttcatc 540
tgggtgtggt cagccactat gaagtcgcct ttgctgccag taatctcatg acagatcttg 600
aaggctgact tgagaccgtg gttggcttgg tcacccccaga tgtagaggca gtggggagtg 660
aagttgaact ccaagttctt tcccaacaca tgaccatctt tcttgaagcc ttgaccattg 720
agtttgaccc tattgtagac agacccattc tcaaaggtga cttcagccct agtcttgaag 780
ttgccatctc cttcaaaggt gattgtgcgc tcttgcacat agccatctgg catacaggac 840
ttgtagaagt ccttcaactc tggaccatac ttggcaaagc actgtgctcc ataggtgaga 900
gtggtgacaa gtgtgctcca aggcacagga acatcaccag ttgtgcagat gaactgtgca 960
tcaacctttc ccactgaggc atctccgtag cctttcccac gtatgctaaa ggtgtggcca 1020
tcaacattcc cttccatctc cacaacgtaa ggaatcttcc catgaaagag aagtgctcca 1080
gatgccatgg tgtcgtgtgg atccggtaca cacgtgccta ggaccggttc aactaactac 1140
tgcagaagta acaccaaaca acagggtgag catcgacaaa agaaacagta ccaagcaaat 1200
aaatagcgta tgaaggcagg gctaaaaaaa tccacatata gctgctgcat atgccatcat 1260
ccaagtatat caagatcgaa ataattataa aacatacttg tttattataa tagataggta 1320
ctcaaggtta gagcatatga atagatgctg catatgccat catgtatatg catcagtaaa 1380
acccacatca acatgtatac ctatcctaga tcgatatttc catccatctt aaactcgtaa 1440
ctatgaagat gtatgacaca cacatacagt tccaaaatta ataaatacac caggtagttt 1500
gaaacagtat tctactccga tctagaacga atgaacgacc gcccaaccac accacatcat 1560
cacaaccaag cgaacaaaaa gcatctctgt atatgcatca gtaaaacccg catcaacatg 1620
tatacctatc ctagatcgat atttccatcc atcatcttca attcgtaact atgaatatgt 1680
atggcacaca catacagatc caaaattaat aaatccacca ggtagtttga aacagaattc 1740
tactccgatc tagaacgacc gcccaaccag accacatcat cacaaccaag acaaaaaaaa 1800

-continued

```
gcatgaaaag atgacccgac aaacaagtgc acggcatata ttgaaataaa ggaaaagggc   1860
aaaccaaacc ctatgcaacg aaacaaaaaa aatcatgaaa tcgatcccgt ctgcggaacg   1920
gctagagcca tcccaggatt ccccaaagag aaacactggc aagttagcaa tcagaacgtg   1980
tctgacgtac aggtcgcatc cgtgtacgaa cgctagcagc acggatctaa cacaaacacg   2040
gatctaacac aaacatgaac agaagtagaa ctaccgggcc ctaaccatgc atggaccgga   2100
acgccgatct agagaaggta gagagggggg gggggggag gacgagcggc gtaccttgaa   2160
gcggaggtgc cgacgggtgg atttggggga gatctggttg tgtgtgtgtg cgctccgaac   2220
aacacgaggt tggggaggta ccaagagggt gtggaggggg tgtctattta ttacggcggg   2280
cgaggaaggg aaagcgaagg agcggtggga aaggaatccc ccgtagctgc cggtgccgtg   2340
agaggaggag gaggccgcct gccgtgccgg ctcacgtctg ccgctccgcc acgcaatttc   2400
tggatgccga cagcggagca agtccaacgg tggagcggaa ctctcgagag gggtccagcc   2460
gcggagtgtg cagcgtgacc cggtcgtgcc cctctctaga gataatgagc attgcatgtc   2520
taagttataa aaaattacca catatttttt ttgtcacact tgtttgaagt gcagtttatc   2580
tatctttata catatattta aactttactc tacgaataat ataatctata gtactacaat   2640
aatatcagtg ttttagagaa tcatataaat gaacagttag acatggtcta aaggacaatt   2700
gagtattttg acaacaggac tctacagttt tatcttttta gtgtgcatgt gttctccttt   2760
tttttgcaa atagcttcac ctatataata cttcatccat tttattagta catccattta   2820
gggtttaggg ttaatggttt ttatagacta atttttttag tacatctatt ttattctatt   2880
ttagcctcta aattaagaaa actaaaactc tattttagtt tttttattta atagtttaga   2940
tataaaatag aataaaataa agtgactaaa aattaaacaa ataccettta agaaattaaa   3000
aaaactaagg aaacattttt cttgtttcga gtagataatg ccagcctgtt aaacgccgtc   3060
gacgagtcta acggacacca accagcgaac cagcagcgtc gcgtcgggcc aagcgaagca   3120
gacggcacgg catctctgtc gctgcctctg gacccctctc gagagttccg ctccaccgtt   3180
ggacttgctc cgctgtcggc atccagaaat tgcgtggcgg agcggcagac gtgagccggc   3240
acggcaggcg gcctcctcct cctctcacgg caccggcagc tacgggggat tcctttccca   3300
ccgctccttc gctttccctt cctcgcccgc cgtaataaat agacaccccc tccacaccct   3360
ctttccccaa cctcgtgttg ttcggagcgc acacacacac aaccagatct cccccaaatc   3420
cacccgtcgg cacctccgct tcaaggtacg ccgctcgtcc tccccccccc ccccctctc   3480
taccttctct agatcggcgt tccggtccat gcatggttag ggcccggtag ttctacttct   3540
gttcatgttt gtgttagatc cgtgtttgtg ttagatccgt gctgctagcg ttcgtacacg   3600
gatgcgacct gtacgtcaga cacgttctga ttgctaactt gccagtgttt ctctttgggg   3660
aatcctggga tggctctagc cgttccgcag acgggatcga tttcatgatt ttttttgttt   3720
cgttgcatag ggtttggttt gccctttttcc tttatttcaa tatatgccgt gcacttgttt   3780
gtcgggtcat cttttcatgc ttttttttgt cttggttgtg atgatgtggt ctggttgggc   3840
ggtcgttcta gatcggagta gaattctgtt tcaaactacc tggtggattt attaattttg   3900
gatctgtatg tgtgtgccat acatattcat agttacgaat tgaagatgat ggatggaaat   3960
atcgatctag gataggtata catgttgatg cgggttttac tgatgcatat acagagatgc   4020
tttttgttcg cttggttgtg atgatgtggt gtggttgggc ggtcgttcat tcgttctaga   4080
tcggagtaga atactgtttc aaactacctg gtgtatttat taattttgga actgtatgtg   4140
tgtgtcatac atcttcatag ttacgagttt aagatggatg gaaatatcga tctaggatag   4200
```

```
gtatacatgt tgatgtgggt tttactgatg catatacatg atggcatatg cagcatctat   4260
tcatatgctc taaccttgag tacctatcta ttataataaa caagtatgtt ttataattat   4320
ttcgatcttg atatacttgg atgatggcat atgcagcagc tatatgtgga tttttttagc   4380
cctgccttca tacgctattt atttgcttgg tactgtttct tttgtcgatg ctcaccctgt   4440
tgtttggtgt tacttctgca ggtacagtag ttagttgagg tacagcggcc gcagggcacc   4500
atggtccgtc ctgtagaaac cccaacccgt gaaatcaaaa aactcgacgg cctgtgggca   4560
ttcagtctgg atcgcgaaaa ctgtggaatt gatcagcgtt ggtgggaaag cgcgttacaa   4620
gaaagccggg caattgctgt gccaggcagt tttaacgatc agttcgccga tgcagatatt   4680
cgtaattatg cgggcaacgt ctggtatcag cgcgaagtct ttataccgaa aggttgggca   4740
ggccagcgta tcgtgctgcg tttcgatgcg gtcactcatt acggcaaagt gtgggtcaat   4800
aatcaggaag tgatggagca tcagggcggc tatacgccat ttgaagccga tgtcacgccg   4860
tatgttattg ccgggaaaag tgtacgtatc accgtttgtg tgaacaacga actgaactgg   4920
cagactatcc cgccgggaat ggtgattacc gacgaaaacg gcaagaaaaa gcagtcttac   4980
ttccatgatt tctttaacta tgccggaatc catcgcagcg taatgctcta caccacgccg   5040
aacacctggg tggacgatat caccgtggtg acgcatgtcg cgcaagactg taaccacgcg   5100
tctgttgact ggcaggtggt ggccaatggt gatgtcagcg ttgaactgcg tgatgcggat   5160
caacaggtgg ttgcaactgg acaaggcact agcgggactt tgcaagtggt gaatccgcac   5220
ctctggcaac cgggtgaagg ttatctctat gaactgtgcg tcacagccaa aagccagaca   5280
gagtgtgata tctacccgct tcgcgtcggc atccggtcag tggcagtgaa gggcgaacag   5340
ttcctgatta accacaaacc gttctacttt actggctttg gtcgtcatga agatgcggac   5400
ttgcgtggca aaggattcga taacgtgctg atggtgcacg accacgcatt aatggactgg   5460
attggggcca actcctaccg tacctcgcat tacccttacg ctgaagagat gctcgactgg   5520
gcagatgaac atggcatcgt ggtgattgat gaaactgctg ctgtcggctt taacctctct   5580
ttaggcattg gtttcgaagc gggcaacaag ccgaaagaac tgtacagcga agaggcagtc   5640
aacggggaaa ctcagcaagc gcacttacag gcgattaaag agctgatagc gcgtgacaaa   5700
aaccacccaa gcgtggtgat gtggagtatt gccaacgaac cggatacccg tccgcaaggt   5760
gcacgggaat atttcgcgcc actggcggaa gcaacgcgta aactcgaccc gacgcgtccg   5820
atcacctgcg tcaatgtaat gttctgcgac gctcacaccg ataccatcag cgatctcttt   5880
gatgtgctgt gcctgaaccg ttattacgga tggtatgtcc aaagcggcga tttggaaacg   5940
gcagagaagg tactggaaaa agaacttctg gcctggcagg agaaactgca tcagccgatt   6000
atcatcaccg aatacggcgt ggatacgtta gccgggctgc actcaatgta caccgacatg   6060
tggagtgaag agtatcagtg tgcatggctg gatatgtatc accgcgtctt tgatcgcgtc   6120
agcgccgtcg tcggtgaaca ggtatggaat ttcgccgatt ttgcgacctc gcaaggcata   6180
ttgcgcgttg gcggtaacaa gaaagggatc ttcactcgcg accgcaaacc gaagtcggcg   6240
gcttttctgc tgcaaaaacg ctggactggc atgaacttcg gtgaaaaacc gcagcaggga   6300
ggcaaacaat gagacgtccg gtaaccttta aactgagggc actgaagtcg cttgatgtgc   6360
tgaattgttt gtgatgttgg tggcgtattt tgtttaaata agtaagcatg gctgtgattt   6420
tatcatatga tcgatctttg ggttttattt taacacattg taaaatgtgt atctattaat   6480
aactcaatgt ataagatgtg ttcattcttc ggttgccata gatctgctta tttgacctgt   6540
```

-continued

```
gatgttttga ctccaaaaac caaaatcaca actcaataaa ctcatggaat atgtccacct   6600

gtttcttgaa gagttcatct accattccag ttggcattta tcagtgttgc agcggcgctg   6660

tgctttgtaa cataacaatt gttacggcat atatccaa                           6698
```

<210> SEQ ID NO 5
<211> LENGTH: 3263
<212> TYPE: DNA
<213> ORGANISM: Artificial sequence
<220> FEATURE:
<223> OTHER INFORMATION: SCBV bidirectional promoter comprising a minUbi1P minimal core promoter
<220> FEATURE:
<221> NAME/KEY: misc_feature
<222> LOCATION: (1105)..(1319)
<223> OTHER INFORMATION: Reverse complement of the minUbi1P

<400> SEQUENCE: 5

```
ctgcagaagt aacaccaaac aacagggtga gcatcgacaa aagaaacagt accaagcaaa     60

taaatagcgt atgaaggcag ggctaaaaaa atccacatat agctgctgca tatgccatca    120

tccaagtata tcaagatcga aataattata aaacatactt gtttattata atagataggt    180

actcaaggtt agagcatatg aatagatgct gcatatgcca tcatgtatat gcatcagtaa    240

aacccacatc aacatgtata cctatcctag atcgatattt ccatccatct taaactcgta    300

actatgaaga tgtatgacac acacatacag ttccaaaatt aataaataca ccaggtagtt    360

tgaaacagta ttctactccg atctagaacg aatgaacgac cgcccaacca caccacatca    420

tcacaaccaa gcgaacaaaa agcatctctg tatatgcatc agtaaaaccc gcatcaacat    480

gtatacctat cctagatcga tatttccatc catcatcttc aattcgtaac tatgaatatg    540

tatggcacac acatacagat ccaaaattaa taaatccacc aggtagtttg aaacagaatt    600

ctactccgat ctagaacgac cgcccaacca gaccacatca tcacaaccaa gacaaaaaaa    660

agcatgaaaa gatgacccga caaacaagtg cacggcatat attgaaataa aggaaaaggg    720

caaaccaaac cctatgcaac gaaacaaaaa aaatcatgaa atcgatcccg tctgcggaac    780

ggctagagcc atcccaggat tccccaaaga gaaacactgg caagttagca atcagaacgt    840

gtctgacgta caggtcgcat ccgtgtacga acgctagcag cacggatcta acacaaacac    900

ggatctaaca caaacatgaa cagaagtaga actaccgggc cctaaccatg catggaccgg    960

aacgccgatc tagagaaggt agagaggggg ggggggggga ggacgagcgg cgtaccttga   1020

agcggaggtg ccgacgggtg gatttggggg agatctggtt gtgtgtgtgt gcgctccgaa   1080

caacacgagg ttggggaggt accaagaggg tgtggagggg gtgtctattt attacggcgg   1140

gcgaggaagg gaaagcgaag gagcggtggg aaaggaatcc cccgtagctg ccggtgccgt   1200

gagaggagga ggaggccgcc tgccgtgccg gctcacgtct gccgctccgc cacgcaattt   1260

ctggatgccg acagcggagc aagtccaacg gtggagcgga actctcgaga ggggtccagc   1320

cgcggagtat cggaagttga agacaaagaa ggtcttaaat cctggctagc aacactgaac   1380

tatgccagaa accacatcaa agcatatcgg caagcttctt ggcccattat atccaaagac   1440

ctcagagaaa ggtgagcgaa ggctcaattc agaagattgg aagctgatca ataggatcaa   1500

gacaatggtg agaacgcttc caaatctcac tattccacca gaagatgcat acattatcat   1560

tgaaacagat gcatgtgcaa ctggatgggg agcagtatgc aagtggaaga aaaacaaggc   1620

agacccaaga aatacagagc aaatctgtag gtatgccagt ggaaaatttg ataagccaaa   1680

aggaacctgt gatgcagaaa tctatggggt tatgaatggc ttagaaaaga tgagattgtt   1740
```

-continued

```
ctacttggac aaaagagaga tcacagtcag aactgacagt agtgcaatcg aaaggttcta   1800

caacaagagt gctgaacaca agccttctga gatcagatgg atcaggttca tggactacat   1860

cactggtgca ggaccagaga tagtcattga acacataaaa gggaagagca atggtttagc   1920

tgacatcttg tccaggctca aagccaaatt agctcagaat gaaccaacgg aagagatgat   1980

cctgcttaca caagccataa gggaagtaat tccttatcca gatcatccat acactgagca   2040

actcagagaa tggggaaaca aaattctgga tccattcccc acattcaaga aggacatgtt   2100

cgaaagaaca gagcaagctt ttatgctaac agaggaacca gttctactct gtgcatgcag   2160

gaagcctgca attcagttag tgtccagaac atctgccaac ccaggaagga aattcttcaa   2220

gtgcgcaatg aacaaatgcc attgctggta ctgggcagat ctcattgaag aacacattca   2280

agacagaatt gatgaatttc tcaagaatct tgaagttctg aagaccggtg gcgtgcaaac   2340

aatggaggag gaacttatga aggaagtcac caagctgaag atagaagagc aggagttcga   2400

ggaataccag gccacaccaa gggctatgtc gccagtagcc gcagaagatg tgctagatct   2460

ccaagacgta agcaatgacg attgaggagg cattgacgtc agggatgacc gcagcggaga   2520

gtactgggcc cattcagtgg atgctccact gagttgtatt attgtgtgct tttcggacaa   2580

gtgtgctgtc cactttcttt tggcacctgt gccactttat tccttgtctg ccacgatgcc   2640

tttgcttagc ttgtaagcaa ggatcgcagt gcgtgtgtga caccaccccc cttccgacgc   2700

tctgcctata taaggcaccg tctgtaagct cttacgatca tcggtagttc accaaggccc   2760

ggggtcggat ctagctgaag gctcgacaag gcagtccacg gaggagctga tatttggtgg   2820

acaagctgtg gataggagca accctatccc taatatacca gcaccaccaa gtcagggcaa   2880

tccccagatc accccagcag attcgaagaa ggtacagtac acacacatgt atatatgtat   2940

gatgtatccc ttcgatcgaa ggcatgcctt ggtataatca ctgagtagtc attttattac   3000

tttgttttga caagtcagta gttcatccat ttgtcccatt ttttcagctt ggaagtttgg   3060

ttgcactggc cttggtctaa taactgagta gtcattttat tacgttgttt cgacaagtca   3120

gtagctcatc catctgtccc attttttcag ctaggaagtt tggttgcact ggccttggac   3180

taataactga ttagtcattt tattacattg tttcgacaag tcagtagctc atccatctgt   3240

cccatttttc agctaggaag ttc                                            3263
```

<210> SEQ ID NO 6
<211> LENGTH: 1935
<212> TYPE: DNA
<213> ORGANISM: Artificial sequence
<220> FEATURE:
<223> OTHER INFORMATION: SCBV promoter containing ADH1 exon 6, intron 6, and exon 7
<220> FEATURE:
<221> NAME/KEY: misc_feature
<222> LOCATION: (1564)..(1583)
<223> OTHER INFORMATION: exon-6
<220> FEATURE:
<221> NAME/KEY: misc_feature
<222> LOCATION: (1584)..(1924)
<223> OTHER INFORMATION: intron-6
<220> FEATURE:
<221> NAME/KEY: misc_feature
<222> LOCATION: (1925)..(1935)
<223> OTHER INFORMATION: exon-7

<400> SEQUENCE: 6

```
atcggaagtt gaagacaaag aaggtcttaa atcctggcta gcaacactga actatgccag     60

aaaccacatc aaagcatatc ggcaagcttc ttggcccatt atatccaaag acctcagaga    120
```

-continued

```
aaggtgagcg aaggctcaat tcagaagatt ggaagctgat caataggatc aagacaatgg    180

tgagaacgct tccaaatctc actattccac cagaagatgc atacattatc attgaaacag    240

atgcatgtgc aactggatgg ggagcagtat gcaagtggaa gaaaaacaag gcagacccaa    300

gaaatacaga gcaaatctgt aggtatgcca gtggaaaatt tgataagcca aaaggaacct    360

gtgatgcaga aatctatggg gttatgaatg gcttagaaaa gatgagattg ttctacttgg    420

acaaaagaga gatcacagtc agaactgaca gtagtgcaat cgaaaggttc tacaacaaga    480

gtgctgaaca caagccttct gagatcagat ggatcaggtt catggactac atcactggtg    540

caggaccaga gatagtcatt gaacacataa aagggaagag caatggttta gctgacatct    600

tgtccaggct caaagccaaa ttagctcaga atgaaccaac ggaagagatg atcctgctta    660

cacaagccat aagggaagta attccttatc cagatcatcc atacactgag caactcagag    720

aatggggaaa caaaattctg gatccattcc ccacattcaa gaaggacatg ttcgaaagaa    780

cagagcaagc ttttatgcta acagaggaac cagttctact ctgtgcatgc aggaagcctg    840

caattcagtt agtgtccaga acatctgcca acccaggaag gaaattcttc aagtgcgcaa    900

tgaacaaatg ccattgctgg tactgggcag atctcattga agaacacatt caagacagaa    960

ttgatgaatt tctcaagaat cttgaagttc tgaagaccgg tggcgtgcaa acaatggagg   1020

aggaacttat gaaggaagtc accaagctga agatagaaga gcaggagttc gaggaatacc   1080

aggccacacc aagggctatg tcgccagtag ccgcagaaga tgtgctagat ctccaagacg   1140

taagcaatga cgattgagga ggcattgacg tcagggatga ccgcagcgga gagtactggg   1200

cccattcagt ggatgctcca ctgagttgta ttattgtgtg cttttcggac aagtgtgctg   1260

tccactttct tttggcacct gtgccacttt attccttgtc tgccacgatg cctttgctta   1320

gcttgtaagc aaggatcgca gtgcgtgtgt gacaccaccc cccttccgac gctctgccta   1380

tataaggcac cgtctgtaag ctcttacgat catcggtagt tcaccaaggc ccggggtcgg   1440

atctagctga aggctcgaca aggcagtcca cggaggagct gatatttggt ggacaagctg   1500

tggataggag caaccctatc cctaatatac cagcaccacc aagtcagggc aatccccaga   1560

tcaccccagc agattcgaag aaggtacagt acacacacat gtatatatgt atgatgtatc   1620

ccttcgatcg aaggcatgcc ttggtataat cactgagtag tcattttatt actttgtttt   1680

gacaagtcag tagttcatcc atttgtccca ttttttcagc ttggaagttt ggttgcactg   1740

gccttggtct aataactgag tagtcatttt attacgttgt ttcgacaagt cagtagctca   1800

tccatctgtc ccatttttttc agctaggaag tttggttgca ctggccttgg actaataact   1860

gattagtcat tttattacat tgtttcgaca agtcagtagc tcatccatct gtcccatttt   1920

tcagctagga agttc                                                    1935
```

<210> SEQ ID NO 7
<211> LENGTH: 6616
<212> TYPE: DNA
<213> ORGANISM: Artificial sequence
<220> FEATURE:
<223> OTHER INFORMATION: nucleic acid comprising YFP and GUS gene expression cassettes driven by an exemplary SCBV bidirectional promoter

<400> SEQUENCE: 7

```
agcacttaaa gatctttaga agaaagcaaa gcatttatta atacataaca atgtccaggt     60

agcccagctg aattacaata cgcaactgct cataataatt caacaaaccc aagtagtaca    120

caacatccag aagcaaataa agcccatacg taccaaagcc tacacaagca gcaacactca    180
```

-continued

```
ctgccagtgc cggtgggtct ttaaagcaca cgggccttga ccacgcgatc caccttgaaa    240
caaacttggt aaaattaaag caaaccagaa gcacacacac gccaacgcaa cgcttctgat    300
cgcgcgccca aggcccggcc ggccagaacg tacgacggac acgcacacgc tgcgaccgag    360
ctctaggtga ttaagctaac tactcaaagg taggtcttgc gacagtcaac agctctgaca    420
gtttctttca aggacatgtt gtctctgtgg tctgtcacat ctttggaaag tttcacatgg    480
taagacatgt gatgatactc tggaacatga actggacctc caccaatggg agtgttcatc    540
tgggtgtggt cagccactat gaagtcgcct ttgctgccag taatctcatg acagatcttg    600
aaggctgact tgagaccgtg gttggcttgg tcaccccaga tgtagaggca gtggggagtg    660
aagttgaact ccaagttctt tcccaacaca tgaccatctt tcttgaagcc ttgaccattg    720
agtttgaccc tattgtagac agacccattc tcaaaggtga cttcagccct agtcttgaag    780
ttgccatctc cttcaaaggt gattgtgcgc tcttgcacat agccatctgg catacaggac    840
ttgtagaagt ccttcaactc tggaccatac ttggcaaagc actgtgctcc ataggtgaga    900
gtggtgacaa gtgtgctcca aggcacagga acatcaccag ttgtgcagat gaactgtgca    960
tcaacctttc ccactgaggc atctccgtag cctttcccac gtatgctaaa ggtgtggcca   1020
tcaacattcc cttccatctc cacaacgtaa ggaatcttcc catgaaagag aagtgctcca   1080
gatgccatgg tgtcgtgtgg atccggtaca cacgtgccta ggaccggttc aactaactac   1140
tgcagaagta acaccaaaca acagggtgag catcgacaaa agaaacagta ccaagcaaat   1200
aaatagcgta tgaaggcagg gctaaaaaaa tccacatata gctgctgcat atgccatcat   1260
ccaagtatat caagatcgaa ataattataa aacatacttg tttattataa tagataggta   1320
ctcaaggtta gagcatatga atagatgctg catatgccat catgtatatg catcagtaaa   1380
acccacatca acatgtatac ctatcctaga tcgatatttc catccatctt aaactcgtaa   1440
ctatgaagat gtatgacaca cacatacagt tccaaaatta ataaatacac caggtagttt   1500
gaaacagtat tctactccga tctagaacga atgaacgacc gcccaaccac accacatcat   1560
cacaaccaag cgaacaaaaa gcatctctgt atatgcatca gtaaaacccg catcaacatg   1620
tatacctatc ctagatcgat atttccatcc atcatcttca attcgtaact atgaatatgt   1680
atggcacaca catacagatc caaaattaat aaatccacca ggtagtttga aacagaattc   1740
tactccgatc tagaacgacc gcccaaccag accacatcat cacaaccaag acaaaaaaaa   1800
gcatgaaaag atgacccgac aaacaagtgc acggcatata ttgaaataaa ggaaaagggc   1860
aaaccaaacc ctatgcaacg aaacaaaaaa aatcatgaaa tcgatcccgt ctgcggaacg   1920
gctagagcca tcccaggatt ccccaaagag aaacactggc aagttagcaa tcagaacgtg   1980
tctgacgtac aggtcgcatc cgtgtacgaa cgctagcagc acggatctaa cacaaacacg   2040
gatctaacac aaacatgaac agaagtagaa ctaccgggcc ctaaccatgc atggaccgga   2100
acgccgatct agagaaggta gagagggggg ggggggggag gacgagcggc gtaccttgaa   2160
gcggaggtgc cgacgggtgg atttggggga gatctggttg tgtgtgtgtg cgctccgaac   2220
aacacgaggt tggggaggta ccaagagggt gtggaggggg tgtctattta ttacggcggg   2280
cgaggaaggg aaagcgaagg agcggtggga aaggaatccc ccgtagctgc cggtgccgtg   2340
agaggaggag gaggccgcct gccgtgccgg ctcacgtctg ccgctccgcc acgcaatttc   2400
tggatgccga cagcggagca agtccaacgg tggagcggaa ctctcgagag gggtccagcc   2460
gcggagtatc ggaagttgaa gacaaagaag gtcttaaatc ctggctagca acactgaact   2520
```

-continued

```
atgccagaaa ccacatcaaa gcatatcggc aagcttcttg gcccattata tccaaagacc   2580
tcagagaaag gtgagcgaag gctcaattca gaagattgga agctgatcaa taggatcaag   2640
acaatggtga gaacgcttcc aaatctcact attccaccag aagatgcata cattatcatt   2700
gaaacagatg catgtgcaac tggatgggga gcagtatgca agtggaagaa aaacaaggca   2760
gacccaagaa atacagagca aatctgtagg tatgccagtg gaaaatttga taagccaaaa   2820
ggaacctgtg atgcagaaat ctatggggtt atgaatggct tagaaaagat gagattgttc   2880
tacttggaca aaagagagat cacagtcaga actgacagta gtgcaatcga aaggttctac   2940
aacaagagtg ctgaacacaa gccttctgag atcagatgga tcaggttcat ggactacatc   3000
actggtgcag gaccagagat agtcattgaa cacataaaag ggaagagcaa tggtttagct   3060
gacatcttgt ccaggctcaa agccaaatta gctcagaatg aaccaacgga agagatgatc   3120
ctgcttacac aagccataag ggaagtaatt ccttatccag atcatccata cactgagcaa   3180
ctcagagaat ggggaaacaa aattctggat ccattcccca cattcaagaa ggacatgttc   3240
gaaagaacag agcaagcttt tatgctaaca gaggaaccag ttctactctg tgcatgcagg   3300
aagcctgcaa ttcagttagt gtccagaaca tctgccaacc caggaaggaa attcttcaag   3360
tgcgcaatga acaaatgcca ttgctggtac tgggcagatc tcattgaaga acacattcaa   3420
gacagaattg atgaatttct caagaatctt gaagttctga agaccggtgg cgtgcaaaca   3480
atggaggagg aacttatgaa ggaagtcacc aagctgaaga tagaagagca ggagttcgag   3540
gaataccagg ccacaccaag ggctatgtcg ccagtagccg cagaagatgt gctagatctc   3600
caagacgtaa gcaatgacga ttgaggaggc attgacgtca gggatgaccg cagcggagag   3660
tactgggccc attcagtgga tgctccactg agttgtatta ttgtgtgctt ttcggacaag   3720
tgtgctgtcc actttctttt ggcacctgtg ccactttatt ccttgtctgc cacgatgcct   3780
ttgcttagct tgtaagcaag gatcgcagtg cgtgtgtgac accacccccc ttccgacgct   3840
ctgcctatat aaggcaccgt ctgtaagctc ttacgatcat cggtagttca ccaaggcccg   3900
gggtcggatc tagctgaagg ctcgacaagg cagtccacgg aggagctgat atttggtgga   3960
caagctgtgg ataggagcaa ccctatccct aatataccag caccaccaag tcagggcaat   4020
ccccagatca ccccagcaga ttcgaagaag gtacagtaca cacacatgta tatatgtatg   4080
atgtatccct tcgatcgaag gcatgccttg gtataatcac tgagtagtca ttttattact   4140
ttgttttgac aagtcagtag ttcatccatt tgtcccattt tttcagcttg gaagtttggt   4200
tgcactggcc ttggtctaat aactgagtag tcattttatt acgttgtttc gacaagtcag   4260
tagctcatcc atctgtccca ttttttcagc taggaagttt ggttgcactg gccttggact   4320
aataactgat tagtcatttt attacattgt ttcgacaagt cagtagctca tccatctgtc   4380
ccatttttca gctaggaagt tcgcggccgc agggcaccat ggtccgtcct gtagaaaccc   4440
caacccgtga aatcaaaaaa ctcgacggcc tgtgggcatt cagtctggat cgcgaaaact   4500
gtggaattga tcagcgttgg tgggaaagcg cgttacaaga aagccgggca attgctgtgc   4560
caggcagttt taacgatcag ttcgccgatg cagatattcg taattatgcg ggcaacgtct   4620
ggtatcagcg cgaagtcttt ataccgaaag gttgggcagg ccagcgtatc gtgctgcgtt   4680
tcgatgcggt cactcattac ggcaaagtgt gggtcaataa tcaggaagtg atggagcatc   4740
agggcggcta tacgccattt gaagccgatg tcacgccgta tgttattgcc gggaaaagtg   4800
tacgtatcac cgtttgtgtg aacaacgaac tgaactggca gactatcccg ccgggaatgg   4860
tgattaccga cgaaaacggc aagaaaaagc agtcttactt ccatgatttc tttaactatg   4920
```

ccggaatcca tcgcagcgta atgctctaca ccacgccgaa cacctgggtg gacgatatca 4980
ccgtggtgac gcatgtcgcg caagactgta accacgcgtc tgttgactgg caggtggtgg 5040
ccaatggtga tgtcagcgtt gaactgcgtg atgcggatca acaggtggtt gcaactggac 5100
aaggcactag cgggactttg caagtggtga atccgcacct ctggcaaccg ggtgaaggtt 5160
atctctatga actgtgcgtc acagccaaaa gccagacaga gtgtgatatc tacccgcttc 5220
gcgtcggcat ccggtcagtg gcagtgaagg gcgaacagtt cctgattaac cacaaaccgt 5280
tctactttac tggctttggt cgtcatgaag atgcggactt gcgtggcaaa ggattcgata 5340
acgtgctgat ggtgcacgac cacgcattaa tggactggat tggggccaac tcctaccgta 5400
cctcgcatta cccttacgct gaagagatgc tcgactgggc agatgaacat ggcatcgtgg 5460
tgattgatga aactgctgct gtcggcttta acctctcttt aggcattggt ttcgaagcgg 5520
gcaacaagcc gaaagaactg tacagcgaag aggcagtcaa cggggaaact cagcaagcgc 5580
acttacaggc gattaaagag ctgatagcgc gtgacaaaaa ccacccaagc gtggtgatgt 5640
ggagtattgc caacgaaccg gatacccgtc cgcaaggtgc acgggaatat ttcgcgccac 5700
tggcggaagc aacgcgtaaa ctcgacccga cgcgtccgat cacctgcgtc aatgtaatgt 5760
tctgcgacgc tcacaccgat accatcagcg atctctttga tgtgctgtgc ctgaaccgtt 5820
attacggatg gtatgtccaa agcggcgatt tggaaacggc agagaaggta ctggaaaaag 5880
aacttctggc ctggcaggag aaactgcatc agccgattat catcaccgaa tacggcgtgg 5940
atacgttagc cgggctgcac tcaatgtaca ccgacatgtg gagtgaagag tatcagtgtg 6000
catggctgga tatgtatcac cgcgtctttg atcgcgtcag cgccgtcgtc ggtgaacagg 6060
tatggaattt cgccgatttt gcgacctcgc aaggcatatt gcgcgttggc ggtaacaaga 6120
aagggatctt cactcgcgac cgcaaaccga agtcggcggc ttttctgctg caaaaacgct 6180
ggactggcat gaacttcggt gaaaaaccgc agcagggagg caaacaatga gacgtccggt 6240
aacctttaaa ctgagggcac tgaagtcgct tgatgtgctg aattgtttgt gatgttggtg 6300
gcgtattttg tttaaataag taagcatggc tgtgatttta tcatatgatc gatctttggg 6360
gttttattta acacattgta aaatgtgtat ctattaataa ctcaatgtat aagatgtgtt 6420
cattcttcgg ttgccataga tctgcttatt tgacctgtga tgttttgact ccaaaaacca 6480
aaatcacaac tcaataaact catggaatat gtccacctgt ttcttgaaga gttcatctac 6540
cattccagtt ggcatttatc agtgttgcag cggcgctgtg ctttgtaaca taacaattgt 6600
tacggcatat atccaa 6616

<210> SEQ ID NO 8
<211> LENGTH: 19
<212> TYPE: DNA
<213> ORGANISM: Artificial sequence
<220> FEATURE:
<223> OTHER INFORMATION: YFP Forward primer

<400> SEQUENCE: 8
gatgcctcag tgggaaagg 19

<210> SEQ ID NO 9
<211> LENGTH: 22
<212> TYPE: DNA
<213> ORGANISM: Artificial sequence
<220> FEATURE:
<223> OTHER INFORMATION: YFP Reverse primer -continued

<400> SEQUENCE: 9
ccataggtga gagtggtgac aa 22

<210> SEQ ID NO 10
<211> LENGTH: 18
<212> TYPE: DNA
<213> ORGANISM: Artificial sequence
<220> FEATURE:
<223> OTHER INFORMATION: Invertase forward primer

<400> SEQUENCE: 10
tggcggacga cgacttgt 18

<210> SEQ ID NO 11
<211> LENGTH: 19
<212> TYPE: DNA
<213> ORGANISM: Artificial sequence
<220> FEATURE:
<223> OTHER INFORMATION: Invertase Reverse primer

<400> SEQUENCE: 11
aaagtttgga ggctgccgt 19

<210> SEQ ID NO 12
<211> LENGTH: 26
<212> TYPE: DNA
<213> ORGANISM: Artificial sequence
<220> FEATURE:
<223> OTHER INFORMATION: Invertase probe

<400> SEQUENCE: 12
cgagcagacc gccgtgtact tctacc 26

<210> SEQ ID NO 13
<211> LENGTH: 20
<212> TYPE: DNA
<213> ORGANISM: Artificial sequence
<220> FEATURE:
<223> OTHER INFORMATION: AAD1 Forward primer

<400> SEQUENCE: 13
tgttcggttc cctctaccaa 20

<210> SEQ ID NO 14
<211> LENGTH: 22
<212> TYPE: DNA
<213> ORGANISM: Artificial sequence
<220> FEATURE:
<223> OTHER INFORMATION: AAD1 Reverse primer

<400> SEQUENCE: 14
caacatccat caccttgact ga 22

<210> SEQ ID NO 15
<211> LENGTH: 24
<212> TYPE: DNA
<213> ORGANISM: Artificial sequence
<220> FEATURE:
<223> OTHER INFORMATION: AAD1 probe

<400> SEQUENCE: 15
cacagaaccg tcgcttcagc aaca 24

<210> SEQ ID NO 16
<211> LENGTH: 215

```
<212> TYPE: DNA
<213> ORGANISM: Artificial sequence
<220> FEATURE:
<223> OTHER INFORMATION: min-Ubi1P or Ubi1-min P Minimal core promoter

<400> SEQUENCE: 16

ctggacccct ctcgagtgtt ccgcttcacc gttggacttg ctacgctgtc agcatcgaga      60

tgttgcgtgg cggagcggca gacttgagcc gtcacggcag gcggcctcct cctcctctca     120

cggcatctgt agctacgggg gattcctttc gcaccgctcg ttcgctttcc cttcctcgtc     180

tgccgaaata atgttacacc ccctccacag cctct                                215

<210> SEQ ID NO 17
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 2

<400> SEQUENCE: 17

ctggacccct ctcgagagtt ccgctccacc gttggactag ctctgctgtc ggcatccaga      60

aaatgcttgg cagtgcggca gacgtgagcc ggcacggcag ggggcctcct cctgctctca     120

cggcacatga agctacgggt gatagcttgc ccaccgctcc aacgctttcc cttactctca     180

cgccgtaata aatagacacc ccttccacaa cctct                                215

<210> SEQ ID NO 18
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 3

<400> SEQUENCE: 18

ctggacctct ctcgagagtt gcgctccacc gatggacttg ctccgctgtc ggcgtccata      60

atttgcgtgg cggagcggca gacgggagcc ggcacggcag ggagcctcgt cctcctctca     120

cggcacctgc aactacgggg gattcctatc ccaccgctcc ttcgctttca cttcttcgcc     180

ctccttaata agtagacacc ccatccgagc cctct                                215

<210> SEQ ID NO 19
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 4

<400> SEQUENCE: 19

caagacccct ctcgagagtt ccgcaccacc gttggacgtg ctccgctatc tgcatccaga      60

aattgcgtgg cggaacggta aacgtgagcc gtcacggcag gcggcctcct cctcctctca     120

cgacaccggc agctacgggg gatacctgtc acacagctcc ttcgcttttc tttcctcgcc     180

cgccgtaata tgtatacact ccctccgcac cctct                                215

<210> SEQ ID NO 20
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 5

<400> SEQUENCE: 20
```

-continued ctggacccct ctcgagggtt ccgttccacc gttggtcttg gtccgctgtc gggatccaga 60
aatagcgtgg cggagcggca gacgtgatcc ggcacggcat gcggcctcct agtcctatca 120
cagcaccggc agctatggga gattccattc ccaccgctcc tgcgctttca ctggctggcc 180
cgccgtgata gatagacacc ccctccacac cctct 215

<210> SEQ ID NO 21
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 6

<400> SEQUENCE: 21
gttggcttct cttgtgagtt ctgcttcacg gatggacttg gtcaacggac ggcatccaga 60
atttgcgtgg cgtagcggcg gacgtgatcc ggcgcggcag gcggcttcct cctcctctca 120
cttaagcgac agctacaggg gattcctttc ccaccgctcc ttcgcttgcc gtacctcgcc 180
cgccgtaata aatagacacc ccttccactc cctct 215

<210> SEQ ID NO 22
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 7

<400> SEQUENCE: 22
ctggatccct ctcgagagtg cggctccgac gttggacttg ctccgaagtc ggcatccaaa 60
aattgcgtgg tggagaggca gacttgagcc ggcacggcag gaggcctcgt cctactcgca 120
cggtatcggc agcaacggga gaatccttgc actctgctcc ttcgctgtac cttcctcgcc 180
cgctgatatt gatagacacc ccctgcatac cctct 215

<210> SEQ ID NO 23
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 8

<400> SEQUENCE: 23
atggaccctt ctcgagtgtt cggctccacc gttagacttg ctccacgatc gacatcaaga 60
aattgcgaga cggagctaca aacgtaagaa atctcggtag ggggcctcct cctcctctca 120
cggcaccggc agctacgggg gattcctgtc ccacctctcc ttcacgttcc ctacctcgcc 180
cgccataatt aataagcacc ccctccgcac cctct 215

<210> SEQ ID NO 24
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 9

<400> SEQUENCE: 24
ctggacccct ctaaagagtt ccacgccacc gttataatgg ctccgctgtc ggcatccaga 60
aattacttgg cggatcagca gacgtgagcc agcatggctg gcggcctcct cctcctctca 120
cgatgccgtc agctacgggg gattcctttc ccaacgctcc ttcgctttcc tatgcgcgcc 180
tgccggatta aataggcagc ttctcgtcac cctct 215

-continued

<210> SEQ ID NO 25
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
10

<400> SEQUENCE: 25
caagacacct ctcgattgtt ccgcttcacc gttggacttt ctcctcagtc ggcatacaga 60
aattgcttgg cgaagcggca gacatgagcc ggcacgacat gcgtcctcat tctcctctca 120
tggcaccggc agttactggt gaatcctatc gcaccgctcc ttcgctgtcc cttaatcgcc 180
cgccgaaaat aattgacacc ccatccacac cctct 215

<210> SEQ ID NO 26
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
11

<400> SEQUENCE: 26
gaggacccct ctcgtgtgta tcgctccacc tttggagttg gtccactatc ggcgtacaga 60
aaattcgttg cgaagcggca gacgtgagcc tacacggcag tcggcctcta cctcctgaca 120
aggcacgtgc agctacagat gatgcctttc ccaccactcc ttcgcgttcc tttcctcgcc 180
atcagtaatg aatggacacg tcctccagac tctct 215

<210> SEQ ID NO 27
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
12

<400> SEQUENCE: 27
ctgaacccat ctcgagtatg ccgcacgatc gattgacatg ctccactggc agcatccaga 60
aattgcattg gggagcatca ggcgtgagcc tgcacggcag gcggactatt cctcctcgcg 120
cggcaccggc aactacgggg gatgcttgac cgaccgctcc atcgatttcc caatctcgct 180
tgccgtatta aatagataac cccttcacac cctct 215

<210> SEQ ID NO 28
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
13

<400> SEQUENCE: 28
ctggactcct tacgggagat ccgctccacc gttggactag ctccgttttc ggcttcaata 60
aagggcgtgg gggagcggca gtcgggggca ggcacggcag tggtcctcat ccatatctca 120
cggggccggc agttgagggg gattcctgtc ccacctcacc tactctttcc ctacctcgtc 180
tgccatatta aatagtcacc ccctccacaa ccttt 215

<210> SEQ ID NO 29

-continued

<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
14

<400> SEQUENCE: 29
ttggacccct ctcgaaagtt aggctccgcc gttggactgg tttcgcggtc atcaatcagg 60
aattgcgggg cggagggtca gacgtgtgcc ggcacagcag gtggcctcct catcgtcaca 120
aggcactggc aactacgggt gattcatttc cttcagcacc tacgcttacc ctgccacgcc 180
ctccgtatta taatgacacc ccctccacac cttat 215

<210> SEQ ID NO 30
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
15

<400> SEQUENCE: 30
ctggacccca cgcggggttt tcgttcctcc gttgggatag ctccggtgtc agcatacaga 60
gaatatatgt cggagcggaa gacgtgagcc gacacggcgg gctgccgcct cctcctgtca 120
cgacaccggc aggtacgggg gattccgttc ccgccgcaca gtcactttcg cttccttgcc 180
ggtcgtatta aatagacacc gtgtccacag cctct 215

<210> SEQ ID NO 31
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
16

<400> SEQUENCE: 31
cttgagccca ctctagagtt ccgtttcacc gaatgactag ctccgctgtc ggtatccatt 60
aagtgggagg cagaacgtca tatgagagtc ggcacgggag gcgttcgcca cgtccgcgca 120
ctacagcggg agctgcggaa tatacctgtc ccaatgctgc tacgctttcc cttccgcgcc 180
caccgtagaa aaatgacagt cccttcacac cctct 215

<210> SEQ ID NO 32
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
17

<400> SEQUENCE: 32
taggaggcct ctcgaaaggt ccggaactcc gtaggacgtg ctccgctgac agcatccagg 60
aatatcatgg gggagctgca gacgagagcc tggacgacaa ggggtcacct cggccgctga 120
cagctgcggc agcaacggag tatgcttttc tcaccgctcc ggcgctttcc cttcgacgca 180
ggccagaata agtagacatc agcgccacac cctct 215

<210> SEQ ID NO 33
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
18

<400> SEQUENCE: 33
cttgtctcca ctctgatgtt ccgctccaac atttgatttg ctcctctgta ggcatacagt 60
tattggggga ctgatcggca gacgtgagcc agcactgcaa acggccaact cctcctctct 120
cgactaaggg attaattaag gataccttac ccgcggctcc ttctctttcc ctacctagcc 180
cgccttatta aatagagacc gcctccacag ccgct 215

<210> SEQ ID NO 34
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
19

<400> SEQUENCE: 34
ctgtaccctt cacaagggtt acacgctacc gatggacttg caccactgtg gggttccaat 60
aattgcgtgg ctgggcgtca gacatattcc ggcatggcaa gcggcctgct cctcctctgg 120
gagcaccggc aacaatgggg gattccaagc ccgcaggtcc ttcgttttac cgtcctcgcc 180
cgccgtagta tgtaggcatc ccagagacta cctct 215

<210> SEQ ID NO 35
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
20

<400> SEQUENCE: 35
caggaaccct aacgagggtt ccgcacgacc aaatgacttg atcttctgtc ggcatccaga 60
aatggggtgt cagagcggca tgcgtgagcc ggcggggcgt gcggcctcat gctgctctcg 120
cgggactagg agttacgggg gatacctgta ttgccgctcc gacactgtac catcctctcc 180
cgccggagta tagagacacc ccctcgacgc catat 215

<210> SEQ ID NO 36
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
21

<400> SEQUENCE: 36
ctgtgctcct gtatggggtt caactccacc gtgaaatttg cgcctctgtc gtcatccaga 60
aattgcgtgg ttgatctgct gacgttaaag ggctctgcag gcggcttcct tcggctatga 120
aggtactggc gtctgcaagt gatgcttttg ctaactcgcc ttcgatgtcc cttcctcgcg 180
tgctttaata ggttgtcagc cgctccagac cattt 215

<210> SEQ ID NO 37
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter
22

<400> SEQUENCE: 37
ctggtcccat cgctagtggt acgctccacc ggtggagtag ctcagatgtc tgaagggtgg 60
aatttagagg tggagagaca gacgtgagct agagcggcat gggacctggt ccaccgctcg 120
aggcaatggc aacgactgtt gaaaccttgc ccaccactcc tgcaattttc catcctcacc 180
ggccggaatg aattaaaacc cacgtcacaa cctct 215

<210> SEQ ID NO 38
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 23

<400> SEQUENCE: 38
cgtgacaggg ctcgggtgtt cggctccatc gtagtgcatg cgccgatgta agtatacaag 60
aagtacgtgg cttggcgtct gacgagggcc gtcaaggcag gcggcctcct tctaagctta 120
cggcgccggc aggttcgtag gttaccttac actcaactca tagtctatct attactcgta 180
ctgcgttata aattgtcacc ccctccacac cctct 215

<210> SEQ ID NO 39
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 24

<400> SEQUENCE: 39
aggaacgctt ctcgatggtt gcgcacatag gagggacttg atagtcggtg gaaatctaag 60
aattgcatat cagatctgca gacgttagcc gacatggcta gcagactact ccgcttcaca 120
cgtcagcgaa agcgacggag gatttcttgc caacggcgcc ttcgcgaacc cttcctcgcc 180
cgtcggaaga aagatactcc ccttgcacac cctct 215

<210> SEQ ID NO 40
<211> LENGTH: 215
<212> TYPE: DNA
<213> ORGANISM: Artificial sequence
<220> FEATURE:
<223> OTHER INFORMATION: min-Ubi1P or Ubi1-min P Minimal core promoter 25

<400> SEQUENCE: 40
cttgacttgg ctcgagagtt ctgcgcttcc attgtagttg cagcgatgtc ggagtccgag 60
ggttgcgtgg cggtgcggca gacgtgggca gatacgactg tatgccagca cctaaacata 120
cggtaccaga agctgcggtg gataccttc ccgacgcata tacgttttcc gtgcctctca 180
cgccgtagta aataaactcc ccctcctgtt ccttt 215

<210> SEQ ID NO 41
<211> LENGTH: 8
<212> TYPE: DNA
<213> ORGANISM: Artificial sequence
<220> FEATURE:
<223> OTHER INFORMATION: YFP probe

<400> SEQUENCE: 41 cttggagc 8

-continued

<210> SEQ ID NO 42
<211> LENGTH: 20
<212> TYPE: DNA
<213> ORGANISM: Artificial sequence
<220> FEATURE:
<223> OTHER INFORMATION: Cry34 Forward Primer

<400> SEQUENCE: 42
gccaacgacc agatcaagac 20

<210> SEQ ID NO 43
<211> LENGTH: 23
<212> TYPE: DNA
<213> ORGANISM: Artificial sequence
<220> FEATURE:
<223> OTHER INFORMATION: Cry34 Reverse Primer

<400> SEQUENCE: 43
gccgttgatg gagtagtaga tgg 23

<210> SEQ ID NO 44
<211> LENGTH: 18
<212> TYPE: DNA
<213> ORGANISM: Artificial sequence
<220> FEATURE:
<223> OTHER INFORMATION: Cry34 Probe

<400> SEQUENCE: 44
ccgaatccaa cggcttca 18

<210> SEQ ID NO 45
<211> LENGTH: 17
<212> TYPE: DNA
<213> ORGANISM: Artificial sequence
<220> FEATURE:
<223> OTHER INFORMATION: Cry35 Forward Primer

<400> SEQUENCE: 45
cctcatccgc ctcaccg 17

<210> SEQ ID NO 46
<211> LENGTH: 22
<212> TYPE: DNA
<213> ORGANISM: Artificial sequence
<220> FEATURE:
<223> OTHER INFORMATION: Cry35 Reverse Primer

<400> SEQUENCE: 46
ggtagtcctt gagcttggtg tc 22

<210> SEQ ID NO 47
<211> LENGTH: 19
<212> TYPE: DNA
<213> ORGANISM: Artificial sequence
<220> FEATURE:
<223> OTHER INFORMATION: Cry35 Probe

<400> SEQUENCE: 47
cagcaatgga acctgacgt 19

<210> SEQ ID NO 48
<211> LENGTH: 29
<212> TYPE: DNA
<213> ORGANISM: Artificial sequence
<220> FEATURE:

-continued

```
<223> OTHER INFORMATION: PAT Forward Primer

<400> SEQUENCE: 48

acaagagtgg attgatgatc tagagaggt                                       29


<210> SEQ ID NO 49
<211> LENGTH: 29
<212> TYPE: DNA
<213> ORGANISM: Artificial sequence
<220> FEATURE:
<223> OTHER INFORMATION: PAT Reverse Primer

<400> SEQUENCE: 49

ctttgatgcc tatgtgacac gtaaacagt                                       29


<210> SEQ ID NO 50
<211> LENGTH: 29
<212> TYPE: DNA
<213> ORGANISM: Artificial sequence
<220> FEATURE:
<223> OTHER INFORMATION: PAT Probe

<400> SEQUENCE: 50

ggtgttgtgg ctggtattgc ttacgctgg                                       29


<210> SEQ ID NO 51
<211> LENGTH: 234
<212> TYPE: PRT
<213> ORGANISM: Phialidium sp.

<400> SEQUENCE: 51

Met Ser Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
            20                  25                  30

Gly Tyr Gly Asp Ala Ser Val Gly Lys Val Asp Ala Gln Phe Ile Cys
        35                  40                  45

Thr Thr Gly Asp Val Pro Val Pro Trp Ser Thr Leu Val Thr Thr Leu
    50                  55                  60

Thr Tyr Gly Ala Gln Cys Phe Ala Lys Tyr Gly Pro Glu Leu Lys Asp
65                  70                  75                  80

Phe Tyr Lys Ser Cys Met Pro Glu Gly Tyr Val Gln Glu Arg Thr Ile
                85                  90                  95

Thr Phe Glu Gly Asp Gly Val Phe Lys Thr Arg Ala Glu Val Thr Phe
            100                 105                 110

Glu Asn Gly Ser Val Tyr Asn Arg Val Lys Leu Asn Gly Gln Gly Phe
        115                 120                 125

Lys Lys Asp Gly His Val Leu Gly Lys Asn Leu Glu Phe Asn Phe Thr
    130                 135                 140

Pro His Cys Leu Tyr Ile Trp Gly Asp Gln Ala Asn His Gly Leu Lys
145                 150                 155                 160

Ser Ala Phe Lys Ile Met His Glu Ile Thr Gly Ser Lys Glu Asp Phe
                165                 170                 175

Ile Val Ala Asp His Thr Gln Met Asn Thr Pro Ile Gly Gly Gly Pro
            180                 185                 190

Val His Val Pro Glu Tyr His His Ile Thr Tyr His Val Thr Leu Ser
        195                 200                 205

Lys Asp Val Thr Asp His Arg Asp Asn Met Ser Leu Val Glu Thr Val
    210                 215                 220
```

Arg Ala Val Asp Cys Arg Lys Thr Tyr Leu
225 230

<210> SEQ ID NO 52
<211> LENGTH: 234
<212> TYPE: PRT
<213> ORGANISM: Phialidium sp.

<400> SEQUENCE: 52

Met Ser Ser Gly Ala Leu Leu Phe His Gly Lys Ile Pro Tyr Val Val
1 5 10 15

Glu Met Glu Gly Asn Val Asp Gly His Thr Phe Ser Ile Arg Gly Lys
20 25 30

Gly Tyr Gly Asp Ala Ser Val Gly Lys Val Asp Ala Gln Phe Ile Cys
35 40 45

Thr Thr Gly Asp Val Pro Val Pro Trp Ser Thr Leu Val Thr Thr Leu
50 55 60

Thr Tyr Gly Ala Gln Cys Phe Ala Lys Tyr Gly Pro Glu Leu Lys Asp
65 70 75 80

Phe Tyr Lys Ser Cys Met Pro Asp Gly Tyr Val Gln Glu Arg Thr Ile
85 90 95

Thr Phe Glu Gly Asp Gly Asn Phe Lys Thr Arg Ala Glu Val Thr Phe
100 105 110

Glu Asn Gly Ser Val Tyr Asn Arg Val Lys Leu Asn Gly Gln Gly Phe
115 120 125

Lys Lys Asp Gly His Val Leu Gly Lys Asn Leu Glu Phe Asn Phe Thr
130 135 140

Pro His Cys Leu Tyr Ile Trp Gly Asp Gln Ala Asn His Gly Leu Lys
145 150 155 160

Ser Ala Phe Lys Ile Cys His Glu Ile Thr Gly Ser Lys Gly Asp Phe
165 170 175

Ile Val Ala Asp His Thr Gln Met Asn Thr Pro Ile Gly Gly Gly Pro
180 185 190

Val His Val Pro Glu Tyr His His Met Ser Tyr His Val Lys Leu Ser
195 200 205

Lys Asp Val Thr Asp His Arg Asp Asn Met Ser Leu Lys Glu Thr Val
210 215 220

Arg Ala Val Asp Cys Arg Lys Thr Tyr Leu
225 230

<210> SEQ ID NO 53
<211> LENGTH: 11406
<212> TYPE: DNA
<213> ORGANISM: Artificial
<220> FEATURE:
<223> OTHER INFORMATION: pDAB108719 gene expression cassette

<400> SEQUENCE: 53
aattacaacg gtatatatcc tgccagtcag catcatcaca ccaaaagtta ggcccgaata 60
gtttgaaatt agaaagctcg caattgaggt ctacaggcca aattcgctct tagccgtaca 120
atattactca ccagatccta accggtgtga tcatgggccg cgattaaaaa tctcaattat 180
atttggtcta atttagtttg gtattgagta aaacaaattc ggcgccatgc ccgggcaagc 240
ggccgcacaa gtttgtacaa aaaagcaggc tgagtattca ctacagtagt gcatcgatgg 300
agtcatcacg cagactatct cagcatgtgc gtagcacgtc tagacctagg taggttaatt 360

-continued

```
aagcttgcat gccggaggaa atatgaattc agcacttaaa gatctttaga agaaagcaaa    420
gcatttatta atacataaca atgtccaggt agcccagctg aattacaata cgcaactgct    480
cataataatt caacaaaccc aagtagtaca caacatccag aagcaaataa agcccatacg    540
taccaaagcc tacacaagca gcaacactca ctgccagtgc cggtgggtct ttaaagcaca    600
cgggccttga ccacgcgatc caccttgaaa caaacttggt aaaattaaag caaaccagaa    660
gcacacacac gccaacgcaa cgcttctgat cgcgcgccca aggcccggcc ggccagaacg    720
tacgacggac acgcacacgc tgcgaccgag ctctcaaagg taggtcttgc gacagtcaac    780
agctctgaca gtttctttca agctcatgtt gtctctgtgg tctgtcacat ctttggaaag    840
tttcacatgg taagacatat gatgatactc tggaacatga actggacctc caccaatggg    900
agtgttcatc tgggtgtggt cagccactat gaagtcgcct ttgctgccag taatctcatg    960
acatatcttg aaggctgact tgagaccgtg gttggcttgg tctccccaga tgtagaggca   1020
gtggggagtg aagttgaact ccaagttctt tcccaacacg tgaccatctt tcttgaagcc   1080
ttgaccattg agtttgaccc tattgtagac agacccattc tcaaaggtga cttcagccct   1140
agtcttgaag ttgccatctc cttcaaaggt gattgtgcgc tcttgcacat agccatctgg   1200
catacaggac ttgtagaagt ccttcaactc tggaccatac ttggcaaagc actgtgctcc   1260
ataggtgaga gtggtgacaa gtgtgctcca aggcacagga acatctccgg tagtacagat   1320
gaattgtgca tcaacctgca catcaccatg ttttggtcat atattagaaa agttataaat   1380
taaaatatac acacttataa actacagaaa agcaatagct atatactaca ttcttttatt   1440
ttgaaaaaaa tacttgaaat actatattac tactaattag tgataattat tatatatata   1500
tcaaaggtag aagcagaaac atacctttcc cactgaggca tctccgtagc ctttcccacg   1560
tatgctaaag gtgtggccat caacattccc ttccatctcc acaacgtaag gaatcttccc   1620
atgaaagaga agtgctccag atgacatagg gccgggattc tcctccacgt caccgcatgt   1680
tagaagactt cctctgccct cgcgggcagg cctaactcca ccaactgtgg tgcgagtcaa   1740
gtatctgaac ttgccagcat agtcaggaac agcacggtgc atggtgcaca agttgtccca   1800
gacaaggact tggtctttct tccacctcac acggcaagtg aagtcaaatc tggtggcatg   1860
ctcatagagg aactgaagca atggctttga ttctgcatct gtcatgccct caattctctg   1920
acagtagact tgattcacat aaaggccttt ccttccagag ccaggatgag tcacaaccaa   1980
gggatggact gtctctctgt caccagcatc aacatccatc accttgactg aggtgttgct   2040
gaagcgacgg ttctgtgctt ggtagaggga accgaacaca cgtgtggcag agtgcacaac   2100
gttgagccct tcgatggtgg cttgcatggt tggagacaag gtctcccaag ctgtgtacat   2160
tgaaaggaac ccagtgtctc cgccatgctc aggaacatct atggccctca tcacaacagc   2220
agctggaggt gcatcaagga aagtggagtc tgtgtgccag tcatcaccaa tcacccttcc   2280
agactcattg gcttctctgc ggatcatctg aacctctgga tagccttcaa tgctcttgag   2340
aagaggcact ggatcaactg gtccaaacct tcttgagaat gcaatgtgct gctcattggt   2400
gattgcttgg ccaggaaagt agatgacttg gtaagtgtgg aaggcatcca atatctcatt   2460
ccaggtgctg tcatcaagtg gttccctcaa gtccactcca gtgatctcag caccaaggac   2520
accagtgagt ggctggacag ctattctctc aaagcgttgg gagagagggc tgagggcagc   2580
atgagccatg gtgtcgtgtg gatccctgca gaagtaacac caaacaacag ggtgagcatc   2640
gacaaaagaa acagtaccaa gcaaataaat agcgtatgaa ggcagggcta aaaaaatcca   2700
catatagctg ctgcatatgc catcatccaa gtatatcaag atcgaaataa ttataaaaca   2760
```

```
tacttgttta ttataataga taggtactca aggttagagc atatgaatag atgctgcata   2820
tgccatcatg tatatgcatc agtaaaaccc acatcaacat gtatacctat cctagatcga   2880
tatttccatc catcttaaac tcgtaactat gaagatgtat gacacacaca tacagttcca   2940
aaattaataa atacaccagg tagtttgaaa cagtattcta ctccgatcta gaacgaatga   3000
acgaccgccc aaccacacca catcatcaca accaagcgaa caaaaagcat ctctgtatat   3060
gcatcagtaa aacccgcatc aacatgtata cctatcctag atcgatattt ccatccatca   3120
tcttcaattc gtaactatga atatgtatgg cacacacata cagatccaaa attaataaat   3180
ccaccaggta gtttgaaaca gaattctact ccgatctaga acgaccgccc aaccagacca   3240
catcatcaca accaagacaa aaaaaagcat gaaaagatga cccgacaaac aagtgcacgg   3300
catatattga aataaaggaa aagggcaaac caaaccctat gcaacgaaac aaaaaaaatc   3360
atgaaatcga tcccgtctgc ggaacggcta gagccatccc aggattcccc aaagagaaac   3420
actggcaagt tagcaatcag aacgtgtctg acgtacaggt cgcatccgtg tacgaacgct   3480
agcagcacgg atctaacaca aacacggatc taacacaaac atgaacagaa gtagaactac   3540
cgggccctaa ccatgcatgg accggaacgc cgatctagag aaggtagaga gggggggggg   3600
ggggaggacg agcggcgtac cttgaagcgg aggtgccgac gggtggattt gggggagatc   3660
tggttgtgtg tgtgtgcgct ccgaacaaca cgaggttggg gaggtaccaa gagggtgtgg   3720
agggggtgtc tatttattac ggcgggcgag gaagggaaag cgaaggagcg gtgggaaagg   3780
aatcccccgt agctgccggt gccgtgagag gaggaggagg ccgcctgccg tgccggctca   3840
cgtctgccgc tccgccacgc aatttctgga tgccgacagc ggagcaagtc caacggtgga   3900
gcggaactct cgagaggggt ccagccgcgg agtatcggaa gttgaagaca aagaaggtct   3960
taaatcctgg ctagcaacac tgaactatgc cagaaaccac atcaaagcat atcggcaagc   4020
ttcttggccc attatatcca aagacctcag agaaaggtga gcgaaggctc aattcagaag   4080
attggaagct gatcaatagg atcaagacaa tggtgagaac gcttccaaat ctcactattc   4140
caccagaaga tgcatacatt atcattgaaa cagatgcatg tgcaactgga tggggagcag   4200
tatgcaagtg gaagaaaaac aaggcagacc caagaaatac agagcaaatc tgtaggtatg   4260
ccagtggaaa atttgataag ccaaaaggaa cctgtgatgc agaaatctat ggggttatga   4320
atggcttaga aaagatgaga ttgttctact tggacaaaag agagatcaca gtcagaactg   4380
acagtagtgc aatcgaaagg ttctacaaca agagtgctga acacaagcct tctgagatca   4440
gatggatcag gttcatggac tacatcactg gtgcaggacc agagatagtc attgaacaca   4500
taaaagggaa gagcaatggt ttagctgaca tcttgtccag gctcaaagcc aaattagctc   4560
agaatgaacc aacggaagag atgatcctgc ttacacaagc cataagggaa gtaattcctt   4620
atccagatca tccatacact gagcaactca gagaatgggg aaacaaaatt ctggatccat   4680
tccccacatt caagaaggac atgttcgaaa gaacagagca agcttttatg ctaacagagg   4740
aaccagttct actctgtgca tgcaggaagc ctgcaattca gttagtgtcc agaacatctg   4800
ccaacccagg aaggaaattc ttcaagtgcg caatgaacaa atgccattgc tggtactggg   4860
cagatctcat tgaagaacac attcaagaca gaattgatga atttctcaag aatcttgaag   4920
ttctgaagac cggtggcgtg caaacaatgg aggaggaact tatgaaggaa gtcaccaagc   4980
tgaagataga agagcaggag ttcgaggaat accaggccac accaagggct atgtcgccag   5040
tagccgcaga agatgtgcta gatctccaag acgtaagcaa tgacgattga ggaggcattg   5100
```

-continued

```
acgtcaggga tgaccgcagc ggagagtact gggcccattc agtggatgct ccactgagtt   5160
gtattattgt gtgcttttcg gacaagtgtg ctgtccactt tcttttggca cctgtgccac   5220
tttattcctt gtctgccacg atgcctttgc ttagcttgta agcaaggatc gcagtgcgtg   5280
tgtgacacca ccccccttcc gacgctctgc ctatataagg caccgtctgt aagctcttac   5340
gatcatcggt agttcaccaa ggcccggggt cggatctagc tgaaggctcg acaaggcagt   5400
ccacggagga gctgatattt ggtggacaag ctgtggatag gagcaaccct atccctaata   5460
taccagcacc accaagtcag ggcaatcccc agatcacccc agcagattcg aagaaggtac   5520
agtacacaca catgtatata tgtatgatgt atcccttcga tcgaaggcat gccttggtat   5580
aatcactgag tagtcatttt attactttgt tttgacaagt cagtagttca tccatttgtc   5640
ccatttttc agcttggaag tttggttgca ctggccttgg tctaataact gagtagtcat   5700
tttattacgt tgtttcgaca agtcagtagc tcatccatct gtcccatttt ttcagctagg   5760
aagtttggtt gcactggcct tggactaata actgattagt cattttatta cattgtttcg   5820
acaagtcagt agctcatcca tctgtcccat ttttcagcta ggaagttcgc ggccgcacac   5880
gacaccatgt ccgcccgcga ggtgcacatc gacgtgaaca acaagaccgg ccacaccctc   5940
cagctggagg acaagaccaa gctcgacggc ggcaggtggc gcacctcccc gaccaacgtg   6000
gccaacgacc agatcaagac cttcgtggcc gaatccaacg gcttcatgac cggcaccgag   6060
ggcaccatct actactccat caacggcgag gccgagatca gcctctactt cgacaacccg   6120
ttcgccggct ccaacaaata cgacggccac tccaacaagt cccagtacga gatcatcacc   6180
cagggcggct ccggcaacca gtcccacgtg acctacacca tccagaccac ctcctcccgc   6240
tacggccaca agtccgaggg cagaggaagt cttctaacat gcggtgacgt ggaggagaat   6300
cccggcccta tgctcgacac caacaaggtg tacgagatca gcaaccacgc caacggcctc   6360
tacgccgcca cctacctctc cctcgacgac tccggcgtgt ccctcatgaa caagaacgac   6420
gacgacatcg acgactacaa cctcaagtgg ttcctcttcc cgatcgacga cgaccagtac   6480
atcatcacct cctacgccgc caacaactgc aaggtgtgga acgtgaacaa cgacaagatc   6540
aacgtgtcca cctactcctc caccaactcc atccagaagt ggcagatcaa ggccaacggc   6600
tcctcctacg tgatccagtc cgacaacggc aaggtgctca ccgccggcac cggccaggcc   6660
ctcggcctca tccgcctcac cgacgagtcc tccaacaacc cgaaccagca gtggaacctg   6720
acgtccgtgc agaccatcca gctcccgcag aagccgatca tcgacaccaa gctcaaggac   6780
tacccgaagt actccccgac cggcaacatc gacaacggca cctccccgca gctcatgggc   6840
tggaccctcg tgccgtgcat catggtgaac gacccgaaca tcgacaagaa cacccagatc   6900
aagaccaccc cgtactacat cctcaagaag taccagtact ggcagagggc cgtgggctcc   6960
aacgtcgcgc tccgcccgca cgagaagaag tcctacacct acgagtgggg caccgagatc   7020
gaccagaaga ccaccatcat caacaccctc ggcttccaga tcaacatcga cagcggcatg   7080
aagttcgaca tcccggaggt gggcggcggt accgacgaga tcaagaccca gctcaacgag   7140
gagctcaaga tcgagtactc ccacgagacg aagatcatgg agaagtacca ggagcagtcc   7200
gagatcgaca acccgaccga ccagtccatg aactccatcg gcttcctcac catcacctcc   7260
ctggagctct accgctacaa cggctccgag atccgcatca tgcagatcca gacctccgac   7320
aacgacacct acaacgtgac ctcctacccg aaccaccagc aggccctgct gtgagtagtt   7380
agcttaatca cctagaacct agacttgtcc atcttctgga ttggccaact taattaatgt   7440
atgaaataaa aggatgcaca catagtgaca tgctaatcac tataatgtgg gcatcaaagt   7500
```

```
tgtgtgttat gtgtaattac tagttatctg aataaaagag aaagagatca tccatatttc   7560
ttatcctaaa tgaatgtcac gtgtctttat aattctttga tgaaccagat gcatttcatt   7620
aaccaaatcc atatacatat aaatattaat catatataat taatatcaat tgggttagca   7680
aaacaaatct agtctaggtg tgttttgctc tagtgctagc ctcgaggtcg actctgatca   7740
tggatgctac gtcacggcag tacaggacta tcatcttgaa agtcgattga gcatcgaaac   7800
ccagctttct tgtacaaagt ggttgcggcc gcttaattaa atttaaatgt ttggggatcc   7860
tctagagtcg acctgcagtg cagcgtgacc cggtcgtgcc cctctctaga gataatgagc   7920
attgcatgtc taagttataa aaaattacca catatttttt ttgtcacact tgtttgaagt   7980
gcagtttatc tatctttata catatattta aactttactc tacgaataat ataatctata   8040
gtactacaat aatatcagtg ttttagagaa tcatataaat gaacagttag acatggtcta   8100
aaggacaatt gagtattttg acaacaggac tctacagttt tatcttttta gtgtgcatgt   8160
gttctccttt ttttttgcaa atagcttcac ctatataata cttcatccat tttattagta   8220
catccattta gggtttaggg ttaatggttt ttatagacta atttttttag tacatctatt   8280
ttattctatt ttagcctcta aattaagaaa actaaaactc tattttagtt tttttattta   8340
atagtttaga tataaaatag aataaaataa agtgactaaa aattaaacaa ataccettta   8400
agaaattaaa aaaactaagg aaacattttt cttgtttcga gtagataatg ccagcctgtt   8460
aaacgccgtc gacgagtcta acggacacca accagcgaac cagcagcgtc gcgtcgggcc   8520
aagcgaagca gacggcacgg catctctgtc gctgcctctg gacccctctc gagagttccg   8580
ctccaccgtt ggacttgctc cgctgtcggc atccagaaat tgcgtggcgg agcggcagac   8640
gtgagccggc acggcaggcg gcctcctcct cctctcacgg caccggcagc tacgggggat   8700
tcctttccca ccgctccttc gctttccctt cctcgcccgc cgtaataaat agacaccccc   8760
tccacaccct ctttccccaa cctcgtgttg ttcggagcgc acacacacac aaccagatct   8820
cccccaaatc cacccgtcgg cacctccgct tcaaggtacg ccgctcgtcc tccccccccc   8880
ccccccctctc taccttctct agatcggcgt tccggtccat gcatggttag ggcccggtag   8940
ttctacttct gttcatgttt gtgttagatc cgtgtttgtg ttagatccgt gctgctagcg   9000
ttcgtacacg gatgcgacct gtacgtcaga cacgttctga ttgctaactt gccagtgttt   9060
ctctttgggg aatcctggga tggctctagc cgttccgcag acgggatcga tttcatgatt   9120
tttttgttt cgttgcatag ggtttggttt gccctttcc tttatttcaa tatatgccgt   9180
gcacttgttt gtcgggtcat cttttcatgc ttttttttgt cttggttgtg atgatgtggt   9240
ctggttgggc ggtcgttcta gatcggagta gaattctgtt tcaaactacc tggtggattt   9300
attaattttg gatctgtatg tgtgtgccat acatattcat agttacgaat tgaagatgat   9360
ggatggaaat atcgatctag gataggtata catgttgatg cgggttttac tgatgcatat   9420
acagagatgc tttttgttcg cttggttgtg atgatgtggt gtggttgggc ggtcgttcat   9480
tcgttctaga tcggagtaga atactgtttc aaactacctg gtgtatttat taattttgga   9540
actgtatgtg tgtgtcatac atcttcatag ttacgagttt aagatggatg gaaatatcga   9600
tctaggatag gtatacatgt tgatgtgggt tttactgatg catatacatg atggcatatg   9660
cagcatctat tcatatgctc taaccttgag tacctatcta ttataataaa caagtatgtt   9720
ttataattat ttcgatcttg atatacttgg atgatggcat atgcagcagc tatatgtgga   9780
ttttttagc cctgccttca tacgctattt atttgcttgg tactgtttct tttgtcgatg   9840
```

-continued

```
ctcaccctgt tgtttggtgt tacttctgca gggtacagta gttagttgac acgacaccat    9900

gtctccggag aggagaccag ttgagattag gccagctaca gcagctgata tggccgcggt    9960

ttgtgatatc gttaaccatt acattgagac gtctacagtg aactttagga cagagccaca   10020

aacaccacaa gagtggattg atgatctaga gaggttgcaa gatagatacc cttggttggt   10080

tgctgaggtt gagggtgttg tggctggtat tgcttacgct gggccctgga aggctaggaa   10140

cgcttacgat tggacagttg agagtactgt ttacgtgtca cataggcatc aaaggttggg   10200

cctaggatcc acattgtaca cacatttgct taagtctatg gaggcgcaag gttttaagtc   10260

tgtggttgct gttataggcc ttccaaacga tccatctgtt aggttgcatg aggctttggg   10320

atacacagcc cgtggtacat tgcgcgcagc tggatacaag catggtggat ggcatgatgt   10380

tggtttttgg caaagggatt ttgagttgcc agctcctcca aggccagtta ggccagttac   10440

ccagatctga ctgagcttga gcttatgagc ttatgagctt agagctcggt cgcagcgtgt   10500

gcgtgtccgt cgtacgttct ggccggccgg gccttgggcg cgcgatcaga agcgttgcgt   10560

tggcgtgtgt gtgcttctgg tttgctttaa ttttaccaag tttgtttcaa ggtggatcgc   10620

gtggtcaagg cccgtgtgct ttaaagaccc accggcactg gcagtgagtg ttgctgcttg   10680

tgtaggcttt ggtacgtatg ggctttattt gcttctggat gttgtgtact acttgggttt   10740

gttgaattat tatgagcagt tgcgtattgt aattcagctg ggctacctgg acattgttat   10800

gtattaataa atgctttgct ttcttctaaa gatctttaag tgcttctaga gcatgcacat   10860

agacacacac atcatctcat tgatgcttgg taataattgt cattagattg tttttatgca   10920

tagatgcact cgaaatcagc caattttaga caagtatcaa acggatgtga cttcagtaca   10980

ttaaaaacgt ccgcaatgtg ttattaagtt gtctaagcgt caatttgatt tacaattgaa   11040

tatatcctgc cccagccagc caacagctcg atttacaatt gaatatatcc tgccggccgg   11100

cccacgcgtg tcgaggaatt ctgatctggc cccccatttgg acgtgaatgt agacacgtcg   11160

aaataaagat ttccgaatta gaataatttg tttattgctt tcgcctataa atacgacgga   11220

tcgtaatttg tcgttttatc aaaatgtact ttcattttat aataacgctg cggacatcta   11280

catttttgaa ttgaaaaaaa attggtaatt actctttctt tttctccata ttgaccatca   11340

tactcattgc tgatccatgt agatttcccg gacatgaagc catttacaat tgaatatatc   11400

ctgccg                                                              11406
```